US012012638B2

(12) United States Patent
Sudo et al.

(10) Patent No.: US 12,012,638 B2
(45) Date of Patent: Jun. 18, 2024

(54) ESOPHAGEAL CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Hiroko Sudo, Kamakura (JP); Hitoshi Nobumasa, Kamakura (JP); Satoko Kozono, Kamakura (JP); Satoshi Kondou, Kamakura (JP); Junpei Kawauchi, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 27 days.

(21) Appl. No.: 17/990,164

(22) Filed: Nov. 18, 2022

(65) Prior Publication Data

US 2023/0118787 A1 Apr. 20, 2023

Related U.S. Application Data

(62) Division of application No. 16/803,390, filed on Feb. 27, 2020, now Pat. No. 11,542,558, which is a division of application No. 15/317,857, filed as application No. PCT/JP2015/067580 on Jun. 18, 2015, now Pat. No. 10,619,212.

(30) Foreign Application Priority Data

Jun. 18, 2014 (JP) .................................. 2014-125036
Mar. 30, 2015 (JP) .................................. 2015-070379

(51) Int. Cl.
| | | |
|---|---|---|
| C12Q 1/68 | (2018.01) | |
| C12N 15/09 | (2006.01) | |
| C12P 19/34 | (2006.01) | |
| C12Q 1/6886 | (2018.01) | |
| G01N 33/53 | (2006.01) | |
| G01N 33/574 | (2006.01) | |

(52) U.S. Cl.
CPC ........... *C12Q 1/6886* (2013.01); *C12N 15/09* (2013.01); *C12Q 1/68* (2013.01); *G01N 33/53* (2013.01); *G01N 33/574* (2013.01); *C12Q 2600/158* (2013.01); *C12Q 2600/178* (2013.01)

(58) Field of Classification Search
CPC .. C12Q 1/68; C12Q 1/6886; C12Q 2600/158; C12Q 2600/178; C12Q 1/6837
See application file for complete search history.

(56) References Cited

U.S. PATENT DOCUMENTS

| | | |
|---|---|---|
| 2010/0285471 A1 | 11/2010 | Croce et al. |
| 2014/0031246 A1 | 1/2014 | Meltzer et al. |
| 2014/0256562 A1 | 9/2014 | Umansky et al. |

FOREIGN PATENT DOCUMENTS

| | | |
|---|---|---|
| CN | 101316935 A | 12/2008 |
| CN | 101851682 A | 10/2010 |
| CN | 101861401 A | 10/2010 |
| CN | 102399870 A | 4/2012 |
| CN | 103620019 A | 3/2014 |
| JP | 2010-510769 A | 4/2010 |
| JP | 2011-501943 A | 1/2011 |
| WO | WO 2008/064519 A1 | 6/2008 |
| WO | WO 2009/049129 A1 | 4/2009 |

OTHER PUBLICATIONS

Naomi S. Sakai, et al. "A review of the current understanding and clinical utility of miRNAs in esophageal cancer" Semin Cancer Biol. Dec. 2013;23(6 Pt B):512-21 (Year: 2013).*
Kenneth K. Lai, et al "Circulating Biomarkers for Esophageal Squamous Cell Carcinoma" New Advances on Disease Biomarkers and Molecular Targets in Biomedicine (2013): 85-103. (Year: 2013).*
American Cancer Society, "Esophagus Cancer", 2014, pp. 2-8, 19-20, and 29-41.
Berillo et al., "Binding of intronic miRNAs to the mRNAs of host genes encoding intronic miRNAs and proteins that participate in tumourigenesis," Computers in Biology and Medicine (2013), Vo. 43, pp. 1374-1381.
Cheung et al., "Natural variation in human gene expression assessed in lymphoblastoid cells", Nature Genetics, vol. 33, Mar. 2003, pp. 422-425.
Chinese Office Action and Search Report for Chinese Application No. 201580031909.6, dated Jul. 30, 2018.
Cobb et al., "Sepsis gene expression profiling: Murine splenic compared with hepatic responses determined by using complementary DNA microarrays", Critical Care Medicine, vol. 30, No. 12, 2002, pp. 2711-2721.
Cui et al., "Growth inhibition of hepatocellular carcinoma tumor endothelial cells by miR-204-3p and underlying mechanism," World Journal of Gastroenterology, vol. 20, No. 18, May 14, 2014, pp. 5493-5504 (13 pages total).
Eto et al., "Prospect of microRNA toward laboratory medicine Gastrointestinal Cancer and microRNA", Clinical Chemistry, 2014, vol. 43, No. 2, pp. 99-105.

(Continued)

*Primary Examiner* — Stephen T Kapushoc
(74) *Attorney, Agent, or Firm* — Birch, Stewart, Kolasch & Birch, LLP

(57) ABSTRACT

It is intended to provide a kit or a device for the detection of esophageal cancer and a method for detecting esophageal cancer. The present invention provides a kit or a device for the detection of esophageal cancer, comprising nucleic acid(s) capable of specifically binding to miRNA(s) in a sample of a subject, and a method for detecting esophageal cancer, comprising measuring the miRNA in vitro.

6 Claims, 4 Drawing Sheets

Specification includes a Sequence Listing.

(56) References Cited

OTHER PUBLICATIONS

Gen Bank Locus N R_029621 (2013) obtained from https://www.ncbi.nlm.nih.gov/nuccore/262206275?sat=18&satkey=2740935 on Aug. 7, 19; three pages.

Hoshikawa et al., "Hypoxia induces different genes in the lungs of rats compared with mice", Physiological Genomics, vol. 12, 2003, pp. 209-219.

International Search Report, issued in PCT/JP2015/067580, PCT/ISA/210, dated Sep. 15, 2015.

Ito et al., "Cancer and MicroRNA as a Diagnostic and Therapeutic Market", Yamaguchi Medical Journal, 2013, vol. 62, No. 4, pp. 191-197.

Japanese Office Action dated May 28, 2019 for Application No. 2016-529504.

Kano et al., "miR-145, miR-133a and miR-133b: tumor suppressive miRNAs target FSCN1 in esophageal squamous cell carcinoma," Int. J. Cancer (2010), vol. 127, pp. 2804-2814.

Kitaya, "Reproductive Immuno-Dysfunctional Diseases", American Journal of Reproductive Immunology, vol. 70, No. 1, 2013, pp. 21-27.

MiScript™ miRNA PCR Array (384-well, 384HC) Human miRBase Profiler HC Plate 5, Qiagen, 2012, 10 pages.

NCBI GEO Accession Display for Platform GPL7766, public on May 14, 2009. Kyoto Univ. 3D-Gene Human miRNA Oligo chip v11.0. Obtained from https://www.ncbi.nlm.nih.gov/geo/query/acc.cgi?acc=GPL7766 on Aug. 22, 2018. Including full Data Table. 2009 12 pages.

Office Action dated Mar. 22, 2022, in Republic of Korea Patent Application No. 10-2017-7000803.

Office Action dated Sep. 24, 2021, in Korean Patent Application No. 10-2017-7000803.

Partial European Search Report dated Mar. 5, 2021, in European Patent Application No. 20207038.9.

Partial Supplementary European Search Report for European Application No. 15809775.8, dated Dec. 15, 2017.

Qiagen Prodcut sheet for "miScript™ miRNA PCR Array (384-well, 384HC) Human miRBase Profiler HC Plate 7" from https://b2b.qiagen.com/-/media/genetable/mi/hs/34/mihs-3407a, document 1073798, Aug. 2012 (Year: 2012).

Sakai et al., "A review of the current understanding and clinical utility of miRNAs in esophageal cancer"; Seminars in Cancer Biology, 2013; vol. 23P, pp. 512-521.

Shen et al., "Exploration of Genome-Wide Circulating MicroRNA in Hepatocellular Carcinoma: MiR-483-5p as a Potential Biomarker", Cancer Epidemiology, Biomarkers and Prevention, vol. 22, No. 12, Dec. 2013, pp. 2364-2373.

Sobin et al., "TNM Classification of Malignant Tumours, the 7th edition, Japanese version", 2009, pp. 63-68.

Terada et al., "Epstein-Barr virus associated lymphoepithelial carcinoma of the esophagus", International Journal of Clinical and Experimental Medicine, 2013, vol. 6, No. 3, pp. 219-226.

Third Party Submission filed Jan. 20, 2022, in U.S. Appl. No. 16/803,390.

Written Opinion of the International Searching Authority; issued in PCT/JP2015/067580, PCT/ISA/237, dated Sep. 15, 2015.

Xie et al., "Salivary MicroRNAs as Promising Biomarkers for Detection of Esophageal Cancer," PLOS ONE (2013), vol. 8, Issue 4, e57502, pp. 1-12.

Chinese Office Action and Search Report for Chinese Application No. 202010760220.X, dated Mar. 21, 2023.

Zhu et al., "Correlations Between miRNAs and TGF-β1 in Tumor Microenvironment of Esophageal Squamous Cell Cancer", Chinese Journal of Cellular and Molecular Immunology, vol. 29, No. 5, 2013. pp. 524-528, with an English abstract.

\* cited by examiner

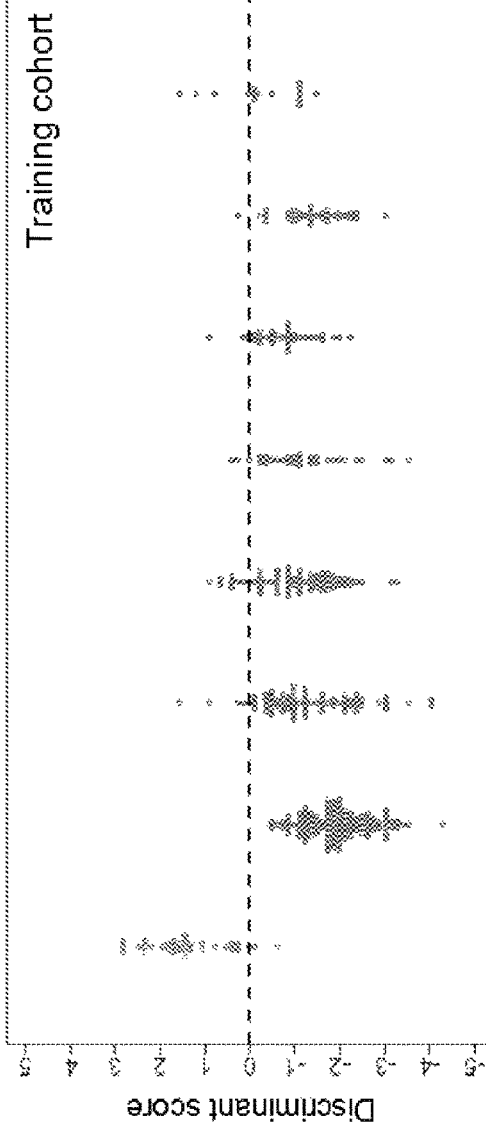
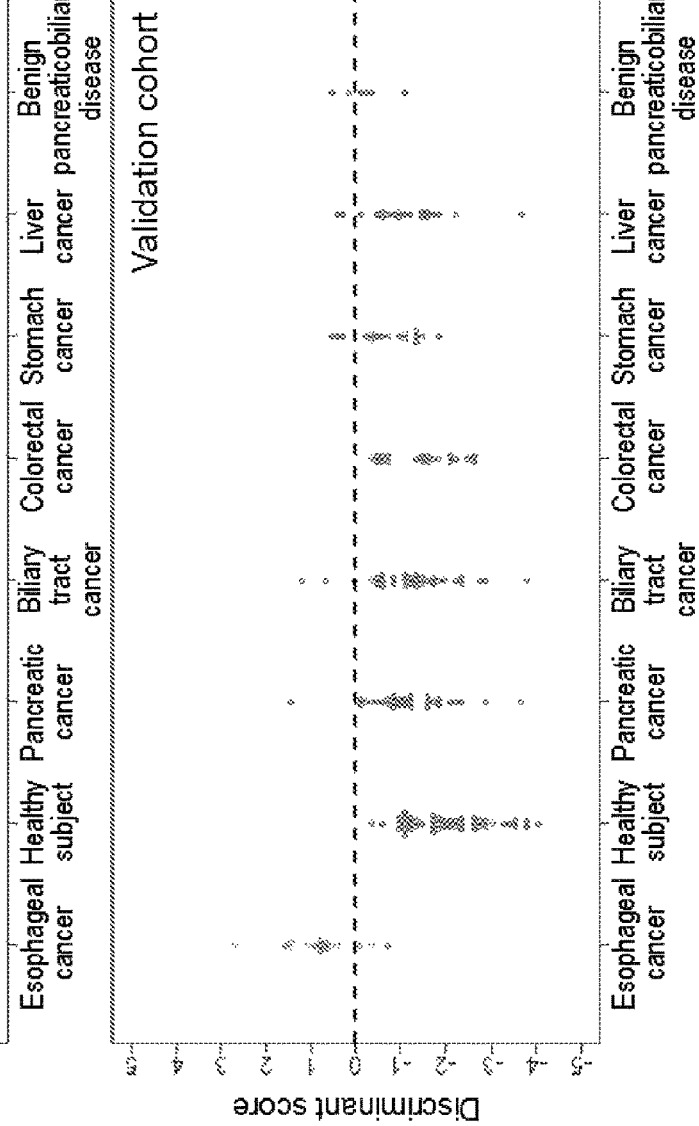
Fig. 4A
Fig. 4B

```
                            SEQUENCE LISTING

Sequence total quantity: 700
SEQ ID NO: 1            moltype = RNA  length = 21
FEATURE                 Location/Qualifiers
source                  1..21
                        mol_type = unassigned RNA
                        organism = Homo sapiens
SEQUENCE: 1
gctgggaagg caaagggacg t                                                   21

SEQ ID NO: 2            moltype = RNA  length = 24
FEATURE                 Location/Qualifiers
source                  1..24
                        mol_type = unassigned RNA
                        organism = Homo sapiens
SEQUENCE: 2
ccccgggaac gtcgagactg gagc                                                24

SEQ ID NO: 3            moltype = RNA  length = 21
FEATURE                 Location/Qualifiers
source                  1..21
                        mol_type = unassigned RNA
                        organism = Homo sapiens
SEQUENCE: 3
tgagggaccc aggacaggag a                                                   21

SEQ ID NO: 4            moltype = RNA  length = 22
FEATURE                 Location/Qualifiers
source                  1..22
                        mol_type = unassigned RNA
                        organism = Homo sapiens
SEQUENCE: 4
ttgggattg ggtcaggcca gt                                                   22

SEQ ID NO: 5            moltype = RNA  length = 21
FEATURE                 Location/Qualifiers
source                  1..21
                        mol_type = unassigned RNA
                        organism = Homo sapiens
SEQUENCE: 5
cgggagctgg ggtctgcagg t                                                   21

SEQ ID NO: 6            moltype = RNA  length = 23
FEATURE                 Location/Qualifiers
source                  1..23
                        mol_type = unassigned RNA
                        organism = Homo sapiens
SEQUENCE: 6
agaggctttg tgcggatacg ggg                                                 23

SEQ ID NO: 7            moltype = RNA  length = 23
FEATURE                 Location/Qualifiers
source                  1..23
                        mol_type = unassigned RNA
                        organism = Homo sapiens
SEQUENCE: 7
ggatggttgg gggcggtcgg cgt                                                 23

SEQ ID NO: 8            moltype = RNA  length = 18
FEATURE                 Location/Qualifiers
source                  1..18
                        mol_type = unassigned RNA
                        organism = Homo sapiens
```

```
SEQUENCE: 8
ccagaggtgg ggactgag                                                    18

SEQ ID NO: 9          moltype = RNA   length = 22
FEATURE               Location/Qualifiers
source                1..22
                      mol_type = unassigned RNA
                      organism = Homo sapiens
SEQUENCE: 9
ctcctggggc ccgcactctc gc                                               22

SEQ ID NO: 10         moltype = RNA   length = 21
FEATURE               Location/Qualifiers
source                1..21
                      mol_type = unassigned RNA
                      organism = Homo sapiens
SEQUENCE: 10
gtgtggccgg caggcgggtg g                                                21

SEQ ID NO: 11         moltype = RNA   length = 22
FEATURE               Location/Qualifiers
source                1..22
                      mol_type = unassigned RNA
                      organism = Homo sapiens
SEQUENCE: 11
tggggaggtg tggagtcagc at                                               22

SEQ ID NO: 12         moltype = RNA   length = 19
FEATURE               Location/Qualifiers
source                1..19
                      mol_type = unassigned RNA
                      organism = Homo sapiens
SEQUENCE: 12
ttgatctcgg aagctaagc                                                   19

SEQ ID NO: 13         moltype = RNA   length = 23
FEATURE               Location/Qualifiers
source                1..23
                      mol_type = unassigned RNA
                      organism = Homo sapiens
SEQUENCE: 13
agaagaaggc ggtcggtctg cgg                                              23

SEQ ID NO: 14         moltype = RNA   length = 21
FEATURE               Location/Qualifiers
source                1..21
                      mol_type = unassigned RNA
                      organism = Homo sapiens
SEQUENCE: 14
agcggtgctc ctgcgggccg a                                                21

SEQ ID NO: 15         moltype = RNA   length = 22
FEATURE               Location/Qualifiers
source                1..22
                      mol_type = unassigned RNA
                      organism = Homo sapiens
SEQUENCE: 15
cccctggggc tgggcaggcg ga                                               22

SEQ ID NO: 16         moltype = RNA   length = 21
FEATURE               Location/Qualifiers
source                1..21
                      mol_type = unassigned RNA
                      organism = Homo sapiens
SEQUENCE: 16
caggcaggtg tagggtggag c                                                21

SEQ ID NO: 17         moltype = RNA   length = 21
FEATURE               Location/Qualifiers
source                1..21
                      mol_type = unassigned RNA
                      organism = Homo sapiens
SEQUENCE: 17
caggagtggg gggtgggacg t                                                21

SEQ ID NO: 18         moltype = RNA   length = 22
FEATURE               Location/Qualifiers
source                1..22
                      mol_type = unassigned RNA
```

```
                               organism = Homo sapiens
SEQUENCE: 18
ggctggagcg agtgcagtgg tg                                            22

SEQ ID NO: 19          moltype = RNA  length = 21
FEATURE                Location/Qualifiers
source                 1..21
                       mol_type = unassigned RNA
                       organism = Homo sapiens
SEQUENCE: 19
cgggccggag gtcaagggcg t                                             21

SEQ ID NO: 20          moltype = RNA  length = 21
FEATURE                Location/Qualifiers
source                 1..21
                       mol_type = unassigned RNA
                       organism = Homo sapiens
SEQUENCE: 20
cggcggggac ggcgattggt c                                             21

SEQ ID NO: 21          moltype = RNA  length = 18
FEATURE                Location/Qualifiers
source                 1..18
                       mol_type = unassigned RNA
                       organism = Homo sapiens
SEQUENCE: 21
cggtgagcgc tcgctggc                                                 18

SEQ ID NO: 22          moltype = RNA  length = 21
FEATURE                Location/Qualifiers
source                 1..21
                       mol_type = unassigned RNA
                       organism = Homo sapiens
SEQUENCE: 22
aagggacagg gagggtcgtg g                                             21

SEQ ID NO: 23          moltype = RNA  length = 18
FEATURE                Location/Qualifiers
source                 1..18
                       mol_type = unassigned RNA
                       organism = Homo sapiens
SEQUENCE: 23
ggtgggcttc ccggaggg                                                 18

SEQ ID NO: 24          moltype = RNA  length = 24
FEATURE                Location/Qualifiers
source                 1..24
                       mol_type = unassigned RNA
                       organism = Homo sapiens
SEQUENCE: 24
tgaggggcct cagaccgagc tttt                                          24

SEQ ID NO: 25          moltype = RNA  length = 22
FEATURE                Location/Qualifiers
source                 1..22
                       mol_type = unassigned RNA
                       organism = Homo sapiens
SEQUENCE: 25
gtgggtacgg cccagtgggg gg                                            22

SEQ ID NO: 26          moltype = RNA  length = 20
FEATURE                Location/Qualifiers
source                 1..20
                       mol_type = unassigned RNA
                       organism = Homo sapiens
SEQUENCE: 26
gtgtctgggc ggacagctgc                                               20

SEQ ID NO: 27          moltype = RNA  length = 22
FEATURE                Location/Qualifiers
source                 1..22
                       mol_type = unassigned RNA
                       organism = Homo sapiens
SEQUENCE: 27
tgagcccctg tgccgccccc ag                                            22

SEQ ID NO: 28          moltype = RNA  length = 22
FEATURE                Location/Qualifiers
source                 1..22
```

```
                        mol_type = unassigned RNA
                        organism = Homo sapiens
SEQUENCE: 28
ctggtacagg cctgggggac ag                                              22

SEQ ID NO: 29           moltype = RNA  length = 21
FEATURE                 Location/Qualifiers
source                  1..21
                        mol_type = unassigned RNA
                        organism = Homo sapiens
SEQUENCE: 29
acaggagtgg gggtgggaca t                                               21

SEQ ID NO: 30           moltype = RNA  length = 20
FEATURE                 Location/Qualifiers
source                  1..20
                        mol_type = unassigned RNA
                        organism = Homo sapiens
SEQUENCE: 30
gcggaaggcg gagcggcgga                                                 20

SEQ ID NO: 31           moltype = RNA  length = 22
FEATURE                 Location/Qualifiers
source                  1..22
                        mol_type = unassigned RNA
                        organism = Homo sapiens
SEQUENCE: 31
agactgacgg ctggaggccc at                                              22

SEQ ID NO: 32           moltype = RNA  length = 22
FEATURE                 Location/Qualifiers
source                  1..22
                        mol_type = unassigned RNA
                        organism = Homo sapiens
SEQUENCE: 32
tggcggggt agagctggct gc                                               22

SEQ ID NO: 33           moltype = RNA  length = 20
FEATURE                 Location/Qualifiers
source                  1..20
                        mol_type = unassigned RNA
                        organism = Homo sapiens
SEQUENCE: 33
gccggggctt tgggtgaggg                                                 20

SEQ ID NO: 34           moltype = RNA  length = 22
FEATURE                 Location/Qualifiers
source                  1..22
                        mol_type = unassigned RNA
                        organism = Homo sapiens
SEQUENCE: 34
gggggtcccc ggtgctcgga tc                                              22

SEQ ID NO: 35           moltype = RNA  length = 21
FEATURE                 Location/Qualifiers
source                  1..21
                        mol_type = unassigned RNA
                        organism = Homo sapiens
SEQUENCE: 35
tcacctggct ggcccgccca g                                               21

SEQ ID NO: 36           moltype = RNA  length = 21
FEATURE                 Location/Qualifiers
source                  1..21
                        mol_type = unassigned RNA
                        organism = Homo sapiens
SEQUENCE: 36
gttggggtgc agggtctgc t                                                21

SEQ ID NO: 37           moltype = RNA  length = 22
FEATURE                 Location/Qualifiers
source                  1..22
                        mol_type = unassigned RNA
                        organism = Homo sapiens
SEQUENCE: 37
tgggggtggt ctctagccaa gg                                              22

SEQ ID NO: 38           moltype = RNA  length = 22
FEATURE                 Location/Qualifiers
```

```
source                  1..22
                        mol_type = unassigned RNA
                        organism = Homo sapiens
SEQUENCE: 38
tcaaaatcag gagtcggggc tt                                                  22

SEQ ID NO: 39           moltype = RNA  length = 23
FEATURE                 Location/Qualifiers
source                  1..23
                        mol_type = unassigned RNA
                        organism = Homo sapiens
SEQUENCE: 39
tggggaaggc ttggcaggga aga                                                 23

SEQ ID NO: 40           moltype = RNA  length = 22
FEATURE                 Location/Qualifiers
source                  1..22
                        mol_type = unassigned RNA
                        organism = Homo sapiens
SEQUENCE: 40
ggctacaaca caggacccgg gc                                                  22

SEQ ID NO: 41           moltype = RNA  length = 23
FEATURE                 Location/Qualifiers
source                  1..23
                        mol_type = unassigned RNA
                        organism = Homo sapiens
SEQUENCE: 41
cggggccgta gcactgtctg aga                                                 23

SEQ ID NO: 42           moltype = RNA  length = 22
FEATURE                 Location/Qualifiers
source                  1..22
                        mol_type = unassigned RNA
                        organism = Homo sapiens
SEQUENCE: 42
tgggcgaggg cggctgagcg gc                                                  22

SEQ ID NO: 43           moltype = RNA  length = 22
FEATURE                 Location/Qualifiers
source                  1..22
                        mol_type = unassigned RNA
                        organism = Homo sapiens
SEQUENCE: 43
gtgggtgctg gtgggagccg tg                                                  22

SEQ ID NO: 44           moltype = RNA  length = 22
FEATURE                 Location/Qualifiers
source                  1..22
                        mol_type = unassigned RNA
                        organism = Homo sapiens
SEQUENCE: 44
tagggatggg aggccaggat ga                                                  22

SEQ ID NO: 45           moltype = RNA  length = 21
FEATURE                 Location/Qualifiers
source                  1..21
                        mol_type = unassigned RNA
                        organism = Homo sapiens
SEQUENCE: 45
tgggggtgtg gggagagaga g                                                   21

SEQ ID NO: 46           moltype = RNA  length = 18
FEATURE                 Location/Qualifiers
source                  1..18
                        mol_type = unassigned RNA
                        organism = Homo sapiens
SEQUENCE: 46
atcctagtca cggcacca                                                       18

SEQ ID NO: 47           moltype = RNA  length = 22
FEATURE                 Location/Qualifiers
source                  1..22
                        mol_type = unassigned RNA
                        organism = Homo sapiens
SEQUENCE: 47
agtgggaggc cagggcacgg ca                                                  22

SEQ ID NO: 48           moltype = RNA  length = 19
```

```
FEATURE                 Location/Qualifiers
source                  1..19
                        mol_type = unassigned RNA
                        organism = Homo sapiens
SEQUENCE: 48
cggggccaga gcagagagc                                                 19

SEQ ID NO: 49           moltype = RNA   length = 23
FEATURE                 Location/Qualifiers
source                  1..23
                        mol_type = unassigned RNA
                        organism = Homo sapiens
SEQUENCE: 49
acaggcggct gtagcaatgg ggg                                            23

SEQ ID NO: 50           moltype = RNA   length = 22
FEATURE                 Location/Qualifiers
source                  1..22
                        mol_type = unassigned RNA
                        organism = Homo sapiens
SEQUENCE: 50
tggcggcggt agttatgggc tt                                             22

SEQ ID NO: 51           moltype = RNA   length = 21
FEATURE                 Location/Qualifiers
source                  1..21
                        mol_type = unassigned RNA
                        organism = Homo sapiens
SEQUENCE: 51
ctgggggagg gagaccctgc t                                              21

SEQ ID NO: 52           moltype = RNA   length = 20
FEATURE                 Location/Qualifiers
source                  1..20
                        mol_type = unassigned RNA
                        organism = Homo sapiens
SEQUENCE: 52
agagatgaag cggggggggcg                                               20

SEQ ID NO: 53           moltype = RNA   length = 25
FEATURE                 Location/Qualifiers
source                  1..25
                        mol_type = unassigned RNA
                        organism = Homo sapiens
SEQUENCE: 53
tagggtgggg ggaattcagg ggtgt                                          25

SEQ ID NO: 54           moltype = RNA   length = 21
FEATURE                 Location/Qualifiers
source                  1..21
                        mol_type = unassigned RNA
                        organism = Homo sapiens
SEQUENCE: 54
atccagttct ctgagggggc t                                              21

SEQ ID NO: 55           moltype = RNA   length = 20
FEATURE                 Location/Qualifiers
source                  1..20
                        mol_type = unassigned RNA
                        organism = Homo sapiens
SEQUENCE: 55
ggatccgagt cacggcacca                                                20

SEQ ID NO: 56           moltype = RNA   length = 23
FEATURE                 Location/Qualifiers
source                  1..23
                        mol_type = unassigned RNA
                        organism = Homo sapiens
SEQUENCE: 56
ctgggcccgc ggcgggcgtg ggg                                            23

SEQ ID NO: 57           moltype = RNA   length = 20
FEATURE                 Location/Qualifiers
source                  1..20
                        mol_type = unassigned RNA
                        organism = Homo sapiens
SEQUENCE: 57
ggcggcgggg aggtaggcag                                                20
```

```
SEQ ID NO: 58            moltype = RNA   length = 17
FEATURE                  Location/Qualifiers
source                   1..17
                         mol_type = unassigned RNA
                         organism = Homo sapiens
SEQUENCE: 58
gggagaaggg tcggggc                                                      17

SEQ ID NO: 59            moltype = RNA   length = 23
FEATURE                  Location/Qualifiers
source                   1..23
                         mol_type = unassigned RNA
                         organism = Homo sapiens
SEQUENCE: 59
agggtggggc tggaggtggg gct                                               23

SEQ ID NO: 60            moltype = RNA   length = 26
FEATURE                  Location/Qualifiers
source                   1..26
                         mol_type = unassigned RNA
                         organism = Homo sapiens
SEQUENCE: 60
ctcggccgcg gcgcgtagcc cccgcc                                            26

SEQ ID NO: 61            moltype = RNA   length = 23
FEATURE                  Location/Qualifiers
source                   1..23
                         mol_type = unassigned RNA
                         organism = Homo sapiens
SEQUENCE: 61
tcaataggaa agaggtggga cct                                               23

SEQ ID NO: 62            moltype = RNA   length = 19
FEATURE                  Location/Qualifiers
source                   1..19
                         mol_type = unassigned RNA
                         organism = Homo sapiens
SEQUENCE: 62
tgcggcagag ctggggtca                                                    19

SEQ ID NO: 63            moltype = RNA   length = 23
FEATURE                  Location/Qualifiers
source                   1..23
                         mol_type = unassigned RNA
                         organism = Homo sapiens
SEQUENCE: 63
tgggggggaca gatggagagg aca                                              23

SEQ ID NO: 64            moltype = RNA   length = 23
FEATURE                  Location/Qualifiers
source                   1..23
                         mol_type = unassigned RNA
                         organism = Homo sapiens
SEQUENCE: 64
tgaggatatg gcagggaagg gga                                               23

SEQ ID NO: 65            moltype = RNA   length = 21
FEATURE                  Location/Qualifiers
source                   1..21
                         mol_type = unassigned RNA
                         organism = Homo sapiens
SEQUENCE: 65
cgtggaggac gaggaggagg c                                                 21

SEQ ID NO: 66            moltype = RNA   length = 23
FEATURE                  Location/Qualifiers
source                   1..23
                         mol_type = unassigned RNA
                         organism = Homo sapiens
SEQUENCE: 66
tgggcagggg cttattgtag gag                                               23

SEQ ID NO: 67            moltype = RNA   length = 22
FEATURE                  Location/Qualifiers
source                   1..22
                         mol_type = unassigned RNA
                         organism = Homo sapiens
SEQUENCE: 67
caggcacggg agctcaggtg ag                                                22
```

```
SEQ ID NO: 68            moltype = RNA    length = 24
FEATURE                  Location/Qualifiers
source                   1..24
                         mol_type = unassigned RNA
                         organism = Homo sapiens
SEQUENCE: 68
tggggagctg aggctctggg ggtg                                                24

SEQ ID NO: 69            moltype = RNA    length = 23
FEATURE                  Location/Qualifiers
source                   1..23
                         mol_type = unassigned RNA
                         organism = Homo sapiens
SEQUENCE: 69
gacacgggcg acagctgcgg ccc                                                 23

SEQ ID NO: 70            moltype = RNA    length = 18
FEATURE                  Location/Qualifiers
source                   1..18
                         mol_type = unassigned RNA
                         organism = Homo sapiens
SEQUENCE: 70
ttcccagcca acgcacca                                                       18

SEQ ID NO: 71            moltype = RNA    length = 22
FEATURE                  Location/Qualifiers
source                   1..22
                         mol_type = unassigned RNA
                         organism = Homo sapiens
SEQUENCE: 71
tcgggcctgg ggttggggga gc                                                  22

SEQ ID NO: 72            moltype = RNA    length = 22
FEATURE                  Location/Qualifiers
source                   1..22
                         mol_type = unassigned RNA
                         organism = Homo sapiens
SEQUENCE: 72
ggaggggtcc cgcactggga gg                                                  22

SEQ ID NO: 73            moltype = RNA    length = 20
FEATURE                  Location/Qualifiers
source                   1..20
                         mol_type = unassigned RNA
                         organism = Homo sapiens
SEQUENCE: 73
cggggtgggt gaggtcgggc                                                     20

SEQ ID NO: 74            moltype = RNA    length = 22
FEATURE                  Location/Qualifiers
source                   1..22
                         mol_type = unassigned RNA
                         organism = Homo sapiens
SEQUENCE: 74
caggaggcag tgggcgagca gg                                                  22

SEQ ID NO: 75            moltype = RNA    length = 23
FEATURE                  Location/Qualifiers
source                   1..23
                         mol_type = unassigned RNA
                         organism = Homo sapiens
SEQUENCE: 75
tgggggctgg gatgggccat ggt                                                 23

SEQ ID NO: 76            moltype = RNA    length = 20
FEATURE                  Location/Qualifiers
source                   1..20
                         mol_type = unassigned RNA
                         organism = Homo sapiens
SEQUENCE: 76
tcacacctgc ctcgccccc                                                      20

SEQ ID NO: 77            moltype = RNA    length = 22
FEATURE                  Location/Qualifiers
source                   1..22
                         mol_type = unassigned RNA
                         organism = Homo sapiens
SEQUENCE: 77
```

```
agacacattt ggagagggac cc                                              22

SEQ ID NO: 78          moltype = RNA   length = 22
FEATURE                Location/Qualifiers
source                 1..22
                       mol_type = unassigned RNA
                       organism = Homo sapiens
SEQUENCE: 78
ccgggagaag gaggtggcct gg                                              22

SEQ ID NO: 79          moltype = RNA   length = 22
FEATURE                Location/Qualifiers
source                 1..22
                       mol_type = unassigned RNA
                       organism = Homo sapiens
SEQUENCE: 79
gtgggctggg ctgggctggg cc                                              22

SEQ ID NO: 80          moltype = RNA   length = 23
FEATURE                Location/Qualifiers
source                 1..23
                       mol_type = unassigned RNA
                       organism = Homo sapiens
SEQUENCE: 80
tcgaggactg gtggaagggc ctt                                             23

SEQ ID NO: 81          moltype = RNA   length = 20
FEATURE                Location/Qualifiers
source                 1..20
                       mol_type = unassigned RNA
                       organism = Homo sapiens
SEQUENCE: 81
taggggtgg caggctggcc                                                  20

SEQ ID NO: 82          moltype = RNA   length = 23
FEATURE                Location/Qualifiers
source                 1..23
                       mol_type = unassigned RNA
                       organism = Homo sapiens
SEQUENCE: 82
cctccctgcc cgcctctctg cag                                             23

SEQ ID NO: 83          moltype = RNA   length = 21
FEATURE                Location/Qualifiers
source                 1..21
                       mol_type = unassigned RNA
                       organism = Homo sapiens
SEQUENCE: 83
atcacattgc cagggatttc c                                               21

SEQ ID NO: 84          moltype = RNA   length = 22
FEATURE                Location/Qualifiers
source                 1..22
                       mol_type = unassigned RNA
                       organism = Homo sapiens
SEQUENCE: 84
cagaaggga gttgggagca ga                                               22

SEQ ID NO: 85          moltype = RNA   length = 24
FEATURE                Location/Qualifiers
source                 1..24
                       mol_type = unassigned RNA
                       organism = Homo sapiens
SEQUENCE: 85
tgggggagcc atgagataag agca                                            24

SEQ ID NO: 86          moltype = RNA   length = 23
FEATURE                Location/Qualifiers
source                 1..23
                       mol_type = unassigned RNA
                       organism = Homo sapiens
SEQUENCE: 86
tgagcaccac acaggccggg cgc                                             23

SEQ ID NO: 87          moltype = RNA   length = 22
FEATURE                Location/Qualifiers
source                 1..22
                       mol_type = unassigned RNA
                       organism = Homo sapiens
```

```
SEQUENCE: 87
gctgcgggct gcggtcaggg cg                                              22

SEQ ID NO: 88            moltype = RNA   length = 21
FEATURE                  Location/Qualifiers
source                   1..21
                         mol_type = unassigned RNA
                         organism = Homo sapiens
SEQUENCE: 88
tggggcgggg caggtccctg c                                               21

SEQ ID NO: 89            moltype = RNA   length = 17
FEATURE                  Location/Qualifiers
source                   1..17
                         mol_type = unassigned RNA
                         organism = Homo sapiens
SEQUENCE: 89
gccggacaag agggagg                                                    17

SEQ ID NO: 90            moltype = RNA   length = 22
FEATURE                  Location/Qualifiers
source                   1..22
                         mol_type = unassigned RNA
                         organism = Homo sapiens
SEQUENCE: 90
caggaaggat ttagggacag gc                                              22

SEQ ID NO: 91            moltype = RNA   length = 23
FEATURE                  Location/Qualifiers
source                   1..23
                         mol_type = unassigned RNA
                         organism = Homo sapiens
SEQUENCE: 91
tgaggggcag agagcgagac ttt                                             23

SEQ ID NO: 92            moltype = RNA   length = 22
FEATURE                  Location/Qualifiers
source                   1..22
                         mol_type = unassigned RNA
                         organism = Homo sapiens
SEQUENCE: 92
acgcccttcc cccccttctt ca                                              22

SEQ ID NO: 93            moltype = RNA   length = 20
FEATURE                  Location/Qualifiers
source                   1..20
                         mol_type = unassigned RNA
                         organism = Homo sapiens
SEQUENCE: 93
tctcttcatc tacccccag                                                  20

SEQ ID NO: 94            moltype = RNA   length = 22
FEATURE                  Location/Qualifiers
source                   1..22
                         mol_type = unassigned RNA
                         organism = Homo sapiens
SEQUENCE: 94
gtgaacgggc gccatcccga gg                                              22

SEQ ID NO: 95            moltype = RNA   length = 23
FEATURE                  Location/Qualifiers
source                   1..23
                         mol_type = unassigned RNA
                         organism = Homo sapiens
SEQUENCE: 95
cgggctgtcc ggaggggtcg gct                                             23

SEQ ID NO: 96            moltype = RNA   length = 22
FEATURE                  Location/Qualifiers
source                   1..22
                         mol_type = unassigned RNA
                         organism = Homo sapiens
SEQUENCE: 96
tgattgtctt cccccaccct ca                                              22

SEQ ID NO: 97            moltype = RNA   length = 22
FEATURE                  Location/Qualifiers
source                   1..22
                         mol_type = unassigned RNA
```

```
                                 organism = Homo sapiens
SEQUENCE: 97
tccaggcagg agccggactg ga                                              22

SEQ ID NO: 98           moltype = RNA  length = 21
FEATURE                 Location/Qualifiers
source                  1..21
                        mol_type = unassigned RNA
                        organism = Homo sapiens
SEQUENCE: 98
ctgggagggg ctgggtttgg c                                               21

SEQ ID NO: 99           moltype = RNA  length = 25
FEATURE                 Location/Qualifiers
source                  1..25
                        mol_type = unassigned RNA
                        organism = Homo sapiens
SEQUENCE: 99
agcggggagg aagtgggcgc tgctt                                           25

SEQ ID NO: 100          moltype = RNA  length = 20
FEATURE                 Location/Qualifiers
source                  1..20
                        mol_type = unassigned RNA
                        organism = Homo sapiens
SEQUENCE: 100
cgggcgtggt ggtgggggtg                                                 20

SEQ ID NO: 101          moltype = RNA  length = 23
FEATURE                 Location/Qualifiers
source                  1..23
                        mol_type = unassigned RNA
                        organism = Homo sapiens
SEQUENCE: 101
gagggcagcg tgggtgtggc gga                                             23

SEQ ID NO: 102          moltype = RNA  length = 23
FEATURE                 Location/Qualifiers
source                  1..23
                        mol_type = unassigned RNA
                        organism = Homo sapiens
SEQUENCE: 102
ggaggcgcag gctcggaaag gcg                                             23

SEQ ID NO: 103          moltype = RNA  length = 23
FEATURE                 Location/Qualifiers
source                  1..23
                        mol_type = unassigned RNA
                        organism = Homo sapiens
SEQUENCE: 103
ccaggggat gggcgagctt ggg                                              23

SEQ ID NO: 104          moltype = RNA  length = 22
FEATURE                 Location/Qualifiers
source                  1..22
                        mol_type = unassigned RNA
                        organism = Homo sapiens
SEQUENCE: 104
gggacccagg gagagacgta ag                                              22

SEQ ID NO: 105          moltype = RNA  length = 22
FEATURE                 Location/Qualifiers
source                  1..22
                        mol_type = unassigned RNA
                        organism = Homo sapiens
SEQUENCE: 105
gcccaggact ttgtgcgggg tg                                              22

SEQ ID NO: 106          moltype = RNA  length = 19
FEATURE                 Location/Qualifiers
source                  1..19
                        mol_type = unassigned RNA
                        organism = Homo sapiens
SEQUENCE: 106
ctggggagtg gctggggag                                                  19

SEQ ID NO: 107          moltype = RNA  length = 23
FEATURE                 Location/Qualifiers
source                  1..23
```

```
                         mol_type = unassigned RNA
                         organism = Homo sapiens
SEQUENCE: 107
ctcggggcag gcggctggga gcg                                          23

SEQ ID NO: 108           moltype = RNA  length = 20
FEATURE                  Location/Qualifiers
source                   1..20
                         mol_type = unassigned RNA
                         organism = Homo sapiens
SEQUENCE: 108
actcaaactg tgggggcact                                              20

SEQ ID NO: 109           moltype = RNA  length = 22
FEATURE                  Location/Qualifiers
source                   1..22
                         mol_type = unassigned RNA
                         organism = Homo sapiens
SEQUENCE: 109
gtagggagg ttgggccagg ga                                            22

SEQ ID NO: 110           moltype = RNA  length = 20
FEATURE                  Location/Qualifiers
source                   1..20
                         mol_type = unassigned RNA
                         organism = Homo sapiens
SEQUENCE: 110
tgtgggactg caaatgggag                                              20

SEQ ID NO: 111           moltype = RNA  length = 17
FEATURE                  Location/Qualifiers
source                   1..17
                         mol_type = unassigned RNA
                         organism = Homo sapiens
SEQUENCE: 111
gtggggccag gcggtgg                                                 17

SEQ ID NO: 112           moltype = RNA  length = 19
FEATURE                  Location/Qualifiers
source                   1..19
                         mol_type = unassigned RNA
                         organism = Homo sapiens
SEQUENCE: 112
aggcacggtg tcagcaggc                                               19

SEQ ID NO: 113           moltype = RNA  length = 22
FEATURE                  Location/Qualifiers
source                   1..22
                         mol_type = unassigned RNA
                         organism = Homo sapiens
SEQUENCE: 113
cttcccccca gtaatcttca tc                                           22

SEQ ID NO: 114           moltype = RNA  length = 19
FEATURE                  Location/Qualifiers
source                   1..19
                         mol_type = unassigned RNA
                         organism = Homo sapiens
SEQUENCE: 114
ggggcctggc ggtgggcgg                                               19

SEQ ID NO: 115           moltype = RNA  length = 21
FEATURE                  Location/Qualifiers
source                   1..21
                         mol_type = unassigned RNA
                         organism = Homo sapiens
SEQUENCE: 115
ttggggtggt cggccctgga g                                            21

SEQ ID NO: 116           moltype = RNA  length = 19
FEATURE                  Location/Qualifiers
source                   1..19
                         mol_type = unassigned RNA
                         organism = Homo sapiens
SEQUENCE: 116
gagccagttg gacaggagc                                               19

SEQ ID NO: 117           moltype = RNA  length = 22
FEATURE                  Location/Qualifiers
```

```
source                  1..22
                        mol_type = unassigned RNA
                        organism = Homo sapiens
SEQUENCE: 117
tggggaaggc gtcagtgtcg gg                                                  22

SEQ ID NO: 118          moltype = RNA   length = 20
FEATURE                 Location/Qualifiers
source                  1..20
                        mol_type = unassigned RNA
                        organism = Homo sapiens
SEQUENCE: 118
tgggaatggg ggtaagggcc                                                     20

SEQ ID NO: 119          moltype = RNA   length = 22
FEATURE                 Location/Qualifiers
source                  1..22
                        mol_type = unassigned RNA
                        organism = Homo sapiens
SEQUENCE: 119
ggggctgtga ttgaccagca gg                                                  22

SEQ ID NO: 120          moltype = RNA   length = 20
FEATURE                 Location/Qualifiers
source                  1..20
                        mol_type = unassigned RNA
                        organism = Homo sapiens
SEQUENCE: 120
ccccagggcg acgcggcggg                                                     20

SEQ ID NO: 121          moltype = RNA   length = 23
FEATURE                 Location/Qualifiers
source                  1..23
                        mol_type = unassigned RNA
                        organism = Homo sapiens
SEQUENCE: 121
aggaagccct ggaggggctg gag                                                 23

SEQ ID NO: 122          moltype = RNA   length = 17
FEATURE                 Location/Qualifiers
source                  1..17
                        mol_type = unassigned RNA
                        organism = Homo sapiens
SEQUENCE: 122
ggcgggtgcg ggggtgg                                                        17

SEQ ID NO: 123          moltype = RNA   length = 22
FEATURE                 Location/Qualifiers
source                  1..22
                        mol_type = unassigned RNA
                        organism = Homo sapiens
SEQUENCE: 123
tgcaggggtc gggtgggcca gg                                                  22

SEQ ID NO: 124          moltype = RNA   length = 23
FEATURE                 Location/Qualifiers
source                  1..23
                        mol_type = unassigned RNA
                        organism = Homo sapiens
SEQUENCE: 124
gccccggcgc gggcgggttc tgg                                                 23

SEQ ID NO: 125          moltype = RNA   length = 22
FEATURE                 Location/Qualifiers
source                  1..22
                        mol_type = unassigned RNA
                        organism = Homo sapiens
SEQUENCE: 125
cgtcccgggg ctgcgcgagg ca                                                  22

SEQ ID NO: 126          moltype = RNA   length = 21
FEATURE                 Location/Qualifiers
source                  1..21
                        mol_type = unassigned RNA
                        organism = Homo sapiens
SEQUENCE: 126
gtgccagctg cagtggggga g                                                   21

SEQ ID NO: 127          moltype = RNA   length = 24
```

-continued

```
FEATURE                 Location/Qualifiers
source                  1..24
                        mol_type = unassigned RNA
                        organism = Homo sapiens
SEQUENCE: 127
tgggcgaggg gtgggctctc agag                                           24

SEQ ID NO: 128          moltype = RNA   length = 22
FEATURE                 Location/Qualifiers
source                  1..22
                        mol_type = unassigned RNA
                        organism = Homo sapiens
SEQUENCE: 128
tgcggggcta gggctaacag ca                                             22

SEQ ID NO: 129          moltype = RNA   length = 22
FEATURE                 Location/Qualifiers
source                  1..22
                        mol_type = unassigned RNA
                        organism = Homo sapiens
SEQUENCE: 129
agacacattt ggagagggaa cc                                             22

SEQ ID NO: 130          moltype = RNA   length = 22
FEATURE                 Location/Qualifiers
source                  1..22
                        mol_type = unassigned RNA
                        organism = Homo sapiens
SEQUENCE: 130
aaaccgttac cattactgag tt                                             22

SEQ ID NO: 131          moltype = RNA   length = 19
FEATURE                 Location/Qualifiers
source                  1..19
                        mol_type = unassigned RNA
                        organism = Homo sapiens
SEQUENCE: 131
tgggggagat ggggttga                                                  19

SEQ ID NO: 132          moltype = RNA   length = 17
FEATURE                 Location/Qualifiers
source                  1..17
                        mol_type = unassigned RNA
                        organism = Homo sapiens
SEQUENCE: 132
ttggaggcgt gggtttt                                                   17

SEQ ID NO: 133          moltype = RNA   length = 22
FEATURE                 Location/Qualifiers
source                  1..22
                        mol_type = unassigned RNA
                        organism = Homo sapiens
SEQUENCE: 133
caggcaggga ggtgggacca tg                                             22

SEQ ID NO: 134          moltype = RNA   length = 23
FEATURE                 Location/Qualifiers
source                  1..23
                        mol_type = unassigned RNA
                        organism = Homo sapiens
SEQUENCE: 134
tgggagggga gaggcagcaa gca                                            23

SEQ ID NO: 135          moltype = RNA   length = 20
FEATURE                 Location/Qualifiers
source                  1..20
                        mol_type = unassigned RNA
                        organism = Homo sapiens
SEQUENCE: 135
gtgagtcagg gtgggctgg                                                 20

SEQ ID NO: 136          moltype = RNA   length = 22
FEATURE                 Location/Qualifiers
source                  1..22
                        mol_type = unassigned RNA
                        organism = Homo sapiens
SEQUENCE: 136
tatagggatt ggagccgtgg cg                                             22
```

```
SEQ ID NO: 137          moltype = RNA   length = 22
FEATURE                 Location/Qualifiers
source                  1..22
                        mol_type = unassigned RNA
                        organism = Homo sapiens
SEQUENCE: 137
ggtggcccgg ccgtgcctga gg                                                  22

SEQ ID NO: 138          moltype = RNA   length = 22
FEATURE                 Location/Qualifiers
source                  1..22
                        mol_type = unassigned RNA
                        organism = Homo sapiens
SEQUENCE: 138
tggggagcgg cccccgggtg gg                                                  22

SEQ ID NO: 139          moltype = RNA   length = 20
FEATURE                 Location/Qualifiers
source                  1..20
                        mol_type = unassigned RNA
                        organism = Homo sapiens
SEQUENCE: 139
cagggaacca gttggggctt                                                     20

SEQ ID NO: 140          moltype = RNA   length = 22
FEATURE                 Location/Qualifiers
source                  1..22
                        mol_type = unassigned RNA
                        organism = Homo sapiens
SEQUENCE: 140
ctgggggtgg ggggctgggc gt                                                  22

SEQ ID NO: 141          moltype = RNA   length = 23
FEATURE                 Location/Qualifiers
source                  1..23
                        mol_type = unassigned RNA
                        organism = Homo sapiens
SEQUENCE: 141
ttgctctgct ccccgcccc cag                                                  23

SEQ ID NO: 142          moltype = RNA   length = 23
FEATURE                 Location/Qualifiers
source                  1..23
                        mol_type = unassigned RNA
                        organism = Homo sapiens
SEQUENCE: 142
gggggccgat acactgtacg aga                                                 23

SEQ ID NO: 143          moltype = RNA   length = 23
FEATURE                 Location/Qualifiers
source                  1..23
                        mol_type = unassigned RNA
                        organism = Homo sapiens
SEQUENCE: 143
tgggccaggg agcagctggt ggg                                                 23

SEQ ID NO: 144          moltype = RNA   length = 22
FEATURE                 Location/Qualifiers
source                  1..22
                        mol_type = unassigned RNA
                        organism = Homo sapiens
SEQUENCE: 144
ctcggcgcgg ggcgcgggct cc                                                  22

SEQ ID NO: 145          moltype = RNA   length = 22
FEATURE                 Location/Qualifiers
source                  1..22
                        mol_type = unassigned RNA
                        organism = Homo sapiens
SEQUENCE: 145
gggtggggat ttgttgcatt ac                                                  22

SEQ ID NO: 146          moltype = RNA   length = 20
FEATURE                 Location/Qualifiers
source                  1..20
                        mol_type = unassigned RNA
                        organism = Homo sapiens
SEQUENCE: 146
gtgggttggg gcgggctctg                                                     20
```

```
SEQ ID NO: 147          moltype = RNA   length = 18
FEATURE                 Location/Qualifiers
source                  1..18
                        mol_type = unassigned RNA
                        organism = Homo sapiens
SEQUENCE: 147
gggtcccggg gagggggg                                                        18

SEQ ID NO: 148          moltype = RNA   length = 19
FEATURE                 Location/Qualifiers
source                  1..19
                        mol_type = unassigned RNA
                        organism = Homo sapiens
SEQUENCE: 148
atcccaccac tgccaccat                                                       19

SEQ ID NO: 149          moltype = RNA   length = 23
FEATURE                 Location/Qualifiers
source                  1..23
                        mol_type = unassigned RNA
                        organism = Homo sapiens
SEQUENCE: 149
gtgagtggga gccggtgggg ctg                                                  23

SEQ ID NO: 150          moltype = RNA   length = 22
FEATURE                 Location/Qualifiers
source                  1..22
                        mol_type = unassigned RNA
                        organism = Homo sapiens
SEQUENCE: 150
accttgcctt gctgcccggg cc                                                   22

SEQ ID NO: 151          moltype = RNA   length = 24
FEATURE                 Location/Qualifiers
source                  1..24
                        mol_type = unassigned RNA
                        organism = Homo sapiens
SEQUENCE: 151
agggctggac tcagcggcgg agct                                                 24

SEQ ID NO: 152          moltype = RNA   length = 17
FEATURE                 Location/Qualifiers
source                  1..17
                        mol_type = unassigned RNA
                        organism = Homo sapiens
SEQUENCE: 152
accccactcc tggtacc                                                         17

SEQ ID NO: 153          moltype = RNA   length = 18
FEATURE                 Location/Qualifiers
source                  1..18
                        mol_type = unassigned RNA
                        organism = Homo sapiens
SEQUENCE: 153
gtgaaggccc ggcggaga                                                        18

SEQ ID NO: 154          moltype = RNA   length = 24
FEATURE                 Location/Qualifiers
source                  1..24
                        mol_type = unassigned RNA
                        organism = Homo sapiens
SEQUENCE: 154
gtagggcgt cccgggcgcg cggg                                                  24

SEQ ID NO: 155          moltype = RNA   length = 22
FEATURE                 Location/Qualifiers
source                  1..22
                        mol_type = unassigned RNA
                        organism = Homo sapiens
SEQUENCE: 155
ccaggaggcg gaggaggtgg ag                                                   22

SEQ ID NO: 156          moltype = RNA   length = 18
FEATURE                 Location/Qualifiers
source                  1..18
                        mol_type = unassigned RNA
                        organism = Homo sapiens
SEQUENCE: 156
```

-continued

```
cgggcgtggt ggtggggg                                              18

SEQ ID NO: 157         moltype = RNA   length = 22
FEATURE                Location/Qualifiers
source                 1..22
                       mol_type = unassigned RNA
                       organism = Homo sapiens
SEQUENCE: 157
gggggtgtg gagccagggg gc                                          22

SEQ ID NO: 158         moltype = RNA   length = 19
FEATURE                Location/Qualifiers
source                 1..19
                       mol_type = unassigned RNA
                       organism = Homo sapiens
SEQUENCE: 158
ggctggtcag atgggagtg                                             19

SEQ ID NO: 159         moltype = RNA   length = 21
FEATURE                Location/Qualifiers
source                 1..21
                       mol_type = unassigned RNA
                       organism = Homo sapiens
SEQUENCE: 159
gtaggtgaca gtcagggcg g                                           21

SEQ ID NO: 160         moltype = RNA   length = 17
FEATURE                Location/Qualifiers
source                 1..17
                       mol_type = unassigned RNA
                       organism = Homo sapiens
SEQUENCE: 160
ccccggggag cccggcg                                               17

SEQ ID NO: 161         moltype = RNA   length = 21
FEATURE                Location/Qualifiers
source                 1..21
                       mol_type = unassigned RNA
                       organism = Homo sapiens
SEQUENCE: 161
cccatgcctc ctgccgcggt c                                          21

SEQ ID NO: 162         moltype = RNA   length = 21
FEATURE                Location/Qualifiers
source                 1..21
                       mol_type = unassigned RNA
                       organism = Homo sapiens
SEQUENCE: 162
cttccgcccc gccgggcgtc g                                          21

SEQ ID NO: 163         moltype = RNA   length = 21
FEATURE                Location/Qualifiers
source                 1..21
                       mol_type = unassigned RNA
                       organism = Homo sapiens
SEQUENCE: 163
aggtgggtat ggaggagccc t                                          21

SEQ ID NO: 164         moltype = RNA   length = 22
FEATURE                Location/Qualifiers
source                 1..22
                       mol_type = unassigned RNA
                       organism = Homo sapiens
SEQUENCE: 164
agcccgcccc agccgaggtt ct                                         22

SEQ ID NO: 165         moltype = RNA   length = 25
FEATURE                Location/Qualifiers
source                 1..25
                       mol_type = unassigned RNA
                       organism = Homo sapiens
SEQUENCE: 165
gtgaggcggg gccaggaggg tgtgt                                      25

SEQ ID NO: 166         moltype = RNA   length = 25
FEATURE                Location/Qualifiers
source                 1..25
                       mol_type = unassigned RNA
                       organism = Homo sapiens
```

```
SEQUENCE: 166
aagggaggag gagcggaggg gccct                                              25

SEQ ID NO: 167           moltype = RNA   length = 21
FEATURE                  Location/Qualifiers
source                   1..21
                         mol_type = unassigned RNA
                         organism = Homo sapiens
SEQUENCE: 167
gggggatgt gcatgctggt t                                                   21

SEQ ID NO: 168           moltype = RNA   length = 20
FEATURE                  Location/Qualifiers
source                   1..20
                         mol_type = unassigned RNA
                         organism = Homo sapiens
SEQUENCE: 168
tcagggagtc aggggagggc                                                    20

SEQ ID NO: 169           moltype = RNA   length = 17
FEATURE                  Location/Qualifiers
source                   1..17
                         mol_type = unassigned RNA
                         organism = Homo sapiens
SEQUENCE: 169
ggatggagga ggggtct                                                       17

SEQ ID NO: 170           moltype = RNA   length = 22
FEATURE                  Location/Qualifiers
source                   1..22
                         mol_type = unassigned RNA
                         organism = Homo sapiens
SEQUENCE: 170
tgggagggcg tggatgatgg tg                                                 22

SEQ ID NO: 171           moltype = RNA   length = 22
FEATURE                  Location/Qualifiers
source                   1..22
                         mol_type = unassigned RNA
                         organism = Homo sapiens
SEQUENCE: 171
gtgcggaacg ctggccgggg cg                                                 22

SEQ ID NO: 172           moltype = RNA   length = 22
FEATURE                  Location/Qualifiers
source                   1..22
                         mol_type = unassigned RNA
                         organism = Homo sapiens
SEQUENCE: 172
aggggcgca gtcactgacg tg                                                  22

SEQ ID NO: 173           moltype = RNA   length = 18
FEATURE                  Location/Qualifiers
source                   1..18
                         mol_type = unassigned RNA
                         organism = Homo sapiens
SEQUENCE: 173
atcccacctc tgccacca                                                      18

SEQ ID NO: 174           moltype = RNA   length = 17
FEATURE                  Location/Qualifiers
source                   1..17
                         mol_type = unassigned RNA
                         organism = Homo sapiens
SEQUENCE: 174
gctgggcgag gctggca                                                       17

SEQ ID NO: 175           moltype = RNA   length = 22
FEATURE                  Location/Qualifiers
source                   1..22
                         mol_type = unassigned RNA
                         organism = Homo sapiens
SEQUENCE: 175
tggtggagga agagggcagc tc                                                 22

SEQ ID NO: 176           moltype = RNA   length = 20
FEATURE                  Location/Qualifiers
source                   1..20
                         mol_type = unassigned RNA
```

```
                                 organism = Homo sapiens
SEQUENCE: 176
ctaggtgggg ggcttgaagc                                                      20

SEQ ID NO: 177           moltype = RNA   length = 22
FEATURE                  Location/Qualifiers
source                   1..22
                         mol_type = unassigned RNA
                         organism = Homo sapiens
SEQUENCE: 177
actgggtagg tggggctcca gg                                                   22

SEQ ID NO: 178           moltype = RNA   length = 22
FEATURE                  Location/Qualifiers
source                   1..22
                         mol_type = unassigned RNA
                         organism = Homo sapiens
SEQUENCE: 178
agggacggga cgcggtgcag tg                                                   22

SEQ ID NO: 179           moltype = RNA   length = 23
FEATURE                  Location/Qualifiers
source                   1..23
                         mol_type = unassigned RNA
                         organism = Homo sapiens
SEQUENCE: 179
gtgagtggga gccccagtgt gtg                                                  23

SEQ ID NO: 180           moltype = RNA   length = 23
FEATURE                  Location/Qualifiers
source                   1..23
                         mol_type = unassigned RNA
                         organism = Homo sapiens
SEQUENCE: 180
aggaggtggt actaggggcc agc                                                  23

SEQ ID NO: 181           moltype = RNA   length = 19
FEATURE                  Location/Qualifiers
source                   1..19
                         mol_type = unassigned RNA
                         organism = Homo sapiens
SEQUENCE: 181
cggggtcggc ggcgacgtg                                                       19

SEQ ID NO: 182           moltype = RNA   length = 21
FEATURE                  Location/Qualifiers
source                   1..21
                         mol_type = unassigned RNA
                         organism = Homo sapiens
SEQUENCE: 182
agggagggac gggggctgtg c                                                    21

SEQ ID NO: 183           moltype = RNA   length = 22
FEATURE                  Location/Qualifiers
source                   1..22
                         mol_type = unassigned RNA
                         organism = Homo sapiens
SEQUENCE: 183
ttgaggagac atggtggggg cc                                                   22

SEQ ID NO: 184           moltype = RNA   length = 22
FEATURE                  Location/Qualifiers
source                   1..22
                         mol_type = unassigned RNA
                         organism = Homo sapiens
SEQUENCE: 184
tagggcagc agaggacctg gg                                                    22

SEQ ID NO: 185           moltype = RNA   length = 22
FEATURE                  Location/Qualifiers
source                   1..22
                         mol_type = unassigned RNA
                         organism = Homo sapiens
SEQUENCE: 185
acaggtgagg ttcttgggag cc                                                   22

SEQ ID NO: 186           moltype = RNA   length = 21
FEATURE                  Location/Qualifiers
source                   1..21
```

```
                        mol_type = unassigned RNA
                        organism = Homo sapiens
SEQUENCE: 186
atcacattgc cagggattac c                                              21

SEQ ID NO: 187          moltype = RNA   length = 23
FEATURE                 Location/Qualifiers
source                  1..23
                        mol_type = unassigned RNA
                        organism = Homo sapiens
SEQUENCE: 187
gaacgcctgt tcttgccagg tgg                                            23

SEQ ID NO: 188          moltype = RNA   length = 22
FEATURE                 Location/Qualifiers
source                  1..22
                        mol_type = unassigned RNA
                        organism = Homo sapiens
SEQUENCE: 188
tctgccccct ccgctgctgc ca                                             22

SEQ ID NO: 189          moltype = RNA   length = 22
FEATURE                 Location/Qualifiers
source                  1..22
                        mol_type = unassigned RNA
                        organism = Homo sapiens
SEQUENCE: 189
tagcagcacg taaatattgg cg                                             22

SEQ ID NO: 190          moltype = RNA   length = 23
FEATURE                 Location/Qualifiers
source                  1..23
                        mol_type = unassigned RNA
                        organism = Homo sapiens
SEQUENCE: 190
tggtgcggag agggcccaca gtg                                            23

SEQ ID NO: 191          moltype = RNA   length = 21
FEATURE                 Location/Qualifiers
source                  1..21
                        mol_type = unassigned RNA
                        organism = Homo sapiens
SEQUENCE: 191
cggggcagct cagtacagga t                                              21

SEQ ID NO: 192          moltype = RNA   length = 23
FEATURE                 Location/Qualifiers
source                  1..23
                        mol_type = unassigned RNA
                        organism = Homo sapiens
SEQUENCE: 192
acggggagtc aggcagtggt gga                                            23

SEQ ID NO: 193          moltype = RNA   length = 17
FEATURE                 Location/Qualifiers
source                  1..17
                        mol_type = unassigned RNA
                        organism = Homo sapiens
SEQUENCE: 193
ctccgggacg gctgggc                                                   17

SEQ ID NO: 194          moltype = RNA   length = 22
FEATURE                 Location/Qualifiers
source                  1..22
                        mol_type = unassigned RNA
                        organism = Homo sapiens
SEQUENCE: 194
gagggttggg tggaggctct cc                                             22

SEQ ID NO: 195          moltype = RNA   length = 23
FEATURE                 Location/Qualifiers
source                  1..23
                        mol_type = unassigned RNA
                        organism = Homo sapiens
SEQUENCE: 195
cgaggggtag aagagcacag ggg                                            23

SEQ ID NO: 196          moltype = RNA   length = 22
FEATURE                 Location/Qualifiers
```

```
source                  1..22
                        mol_type = unassigned RNA
                        organism = Homo sapiens
SEQUENCE: 196
tgctgggggc cacatgagtg tg                                               22

SEQ ID NO: 197          moltype = RNA   length = 23
FEATURE                 Location/Qualifiers
source                  1..23
                        mol_type = unassigned RNA
                        organism = Homo sapiens
SEQUENCE: 197
tcggggagtc tggggtccgg aat                                              23

SEQ ID NO: 198          moltype = RNA   length = 21
FEATURE                 Location/Qualifiers
source                  1..21
                        mol_type = unassigned RNA
                        organism = Homo sapiens
SEQUENCE: 198
gcggtggggc cggaggggcg t                                                21

SEQ ID NO: 199          moltype = RNA   length = 22
FEATURE                 Location/Qualifiers
source                  1..22
                        mol_type = unassigned RNA
                        organism = Homo sapiens
SEQUENCE: 199
tattgcactt gtcccggcct gt                                               22

SEQ ID NO: 200          moltype = RNA   length = 17
FEATURE                 Location/Qualifiers
source                  1..17
                        mol_type = unassigned RNA
                        organism = Homo sapiens
SEQUENCE: 200
gggagtctac agcaggg                                                     17

SEQ ID NO: 201          moltype = RNA   length = 24
FEATURE                 Location/Qualifiers
source                  1..24
                        mol_type = unassigned RNA
                        organism = Homo sapiens
SEQUENCE: 201
aggcaggggc tggtgctggg cggg                                             24

SEQ ID NO: 202          moltype = RNA   length = 21
FEATURE                 Location/Qualifiers
source                  1..21
                        mol_type = unassigned RNA
                        organism = Homo sapiens
SEQUENCE: 202
agcatgacag aggagaggtg g                                                21

SEQ ID NO: 203          moltype = RNA   length = 22
FEATURE                 Location/Qualifiers
source                  1..22
                        mol_type = unassigned RNA
                        organism = Homo sapiens
SEQUENCE: 203
aggcggggcg ccgcgggacc gc                                               22

SEQ ID NO: 204          moltype = RNA   length = 20
FEATURE                 Location/Qualifiers
source                  1..20
                        mol_type = unassigned RNA
                        organism = Homo sapiens
SEQUENCE: 204
cggctctggg tctgtgggga                                                  20

SEQ ID NO: 205          moltype = RNA   length = 22
FEATURE                 Location/Qualifiers
source                  1..22
                        mol_type = unassigned RNA
                        organism = Homo sapiens
SEQUENCE: 205
actggggagc agaaggagaa cc                                               22

SEQ ID NO: 206          moltype = RNA   length = 19
```

```
FEATURE                 Location/Qualifiers
source                  1..19
                        mol_type = unassigned RNA
                        organism = Homo sapiens
SEQUENCE: 206
ggggagcgag gggcggggc                                                  19

SEQ ID NO: 207          moltype = RNA   length = 23
FEATURE                 Location/Qualifiers
source                  1..23
                        mol_type = unassigned RNA
                        organism = Homo sapiens
SEQUENCE: 207
ctggcggagc ccattccatg cca                                             23

SEQ ID NO: 208          moltype = RNA   length = 20
FEATURE                 Location/Qualifiers
source                  1..20
                        mol_type = unassigned RNA
                        organism = Homo sapiens
SEQUENCE: 208
tgggaggagg ggatcttggg                                                 20

SEQ ID NO: 209          moltype = RNA   length = 18
FEATURE                 Location/Qualifiers
source                  1..18
                        mol_type = unassigned RNA
                        organism = Homo sapiens
SEQUENCE: 209
cggggcggca gggccctc                                                   18

SEQ ID NO: 210          moltype = RNA   length = 22
FEATURE                 Location/Qualifiers
source                  1..22
                        mol_type = unassigned RNA
                        organism = Homo sapiens
SEQUENCE: 210
tgggggagtg cagtgattgt gg                                              22

SEQ ID NO: 211          moltype = RNA   length = 18
FEATURE                 Location/Qualifiers
source                  1..18
                        mol_type = unassigned RNA
                        organism = Homo sapiens
SEQUENCE: 211
tgaggcgggg gggcgagc                                                   18

SEQ ID NO: 212          moltype = RNA   length = 23
FEATURE                 Location/Qualifiers
source                  1..23
                        mol_type = unassigned RNA
                        organism = Homo sapiens
SEQUENCE: 212
ctgggggacg cgtgagcgcg agc                                             23

SEQ ID NO: 213          moltype = RNA   length = 22
FEATURE                 Location/Qualifiers
source                  1..22
                        mol_type = unassigned RNA
                        organism = Homo sapiens
SEQUENCE: 213
ggggaactgt agatgaaaag gc                                              22

SEQ ID NO: 214          moltype = RNA   length = 22
FEATURE                 Location/Qualifiers
source                  1..22
                        mol_type = unassigned RNA
                        organism = Homo sapiens
SEQUENCE: 214
cagggcaggg aaggtgggag ag                                              22

SEQ ID NO: 215          moltype = RNA   length = 110
FEATURE                 Location/Qualifiers
source                  1..110
                        mol_type = unassigned RNA
                        organism = Homo sapiens
SEQUENCE: 215
ggctacagtc tttcttcatg tgactcgtgg acttcccttt gtcatcctat gcctgagaat     60
atatgaagga ggctgggaag gcaaagggac gttcaattgt catcactggc                110
```

```
SEQ ID NO: 216           moltype = RNA   length = 136
FEATURE                  Location/Qualifiers
source                   1..136
                         mol_type = unassigned RNA
                         organism = Homo sapiens
SEQUENCE: 216
ccgcttgcct cgcccagcgc agccccggcc gctgggcgca cccgtcccgt tcgtcccccgg    60
acgttgctct ctaccccggg aacgtcgaga ctggagcgcc cgaactgagc caccttcgcg   120
gaccccgaga gcggcg                                                    136

SEQ ID NO: 217           moltype = RNA   length = 72
FEATURE                  Location/Qualifiers
source                   1..72
                         mol_type = unassigned RNA
                         organism = Homo sapiens
SEQUENCE: 217
gagtctgagg gacccaggac aggagaaggc ctatggtgat ttgcattctt cctgccctgg    60
ctccatcctc ag                                                        72

SEQ ID NO: 218           moltype = RNA   length = 93
FEATURE                  Location/Qualifiers
source                   1..93
                         mol_type = unassigned RNA
                         organism = Homo sapiens
SEQUENCE: 218
gcttgttggg gattgggtca ggccagtgtt caagggcccc tcctctagta ctccctgttt    60
gtgttctgcc actgactgag cttctcccca cag                                 93

SEQ ID NO: 219           moltype = RNA   length = 61
FEATURE                  Location/Qualifiers
source                   1..61
                         mol_type = unassigned RNA
                         organism = Homo sapiens
SEQUENCE: 219
gggggcggga gctggggtct gcaggttcgc actgatgcct gctcgccctg tctcccgcta    60
g                                                                    61

SEQ ID NO: 220           moltype = RNA   length = 85
FEATURE                  Location/Qualifiers
source                   1..85
                         mol_type = unassigned RNA
                         organism = Homo sapiens
SEQUENCE: 220
ggcgcctcct gctctgctgt gccgccaggg cctccctag cgcgccttct ggagaggctt     60
tgtgcggata cggggctgga ggcct                                          85

SEQ ID NO: 221           moltype = RNA   length = 86
FEATURE                  Location/Qualifiers
source                   1..86
                         mol_type = unassigned RNA
                         organism = Homo sapiens
SEQUENCE: 221
cgcctgagcg tgcagcagga catcttcctg acctggtaat aattaggtga gaaggatggt    60
tgggggcggt cggcgtaact caggga                                         86

SEQ ID NO: 222           moltype = RNA   length = 86
FEATURE                  Location/Qualifiers
source                   1..86
                         mol_type = unassigned RNA
                         organism = Homo sapiens
SEQUENCE: 222
ggcttagaaa cagtccctag gtaggatttg gggaggagct aagaagcccc tacagggccc    60
agaggtgggg actgagcctt agttgg                                         86

SEQ ID NO: 223           moltype = RNA   length = 84
FEATURE                  Location/Qualifiers
source                   1..84
                         mol_type = unassigned RNA
                         organism = Homo sapiens
SEQUENCE: 223
gctggcgtcg gtgctgggga gcggcccccg ggtgggcctc tgctctggcc cctcctgggg    60
cccgcactct cgctctgggc ccgc                                           84

SEQ ID NO: 224           moltype = RNA   length = 87
FEATURE                  Location/Qualifiers
source                   1..87
                         mol_type = unassigned RNA
                         organism = Homo sapiens
```

```
SEQUENCE: 224
gtgtggccgg caggcgggtg ggcggggcg ccggtggga accccgcccc gccccgcgcc   60
cgcactcacc cgcccgtctc cccacag                                    87

SEQ ID NO: 225          moltype = RNA   length = 66
FEATURE                 Location/Qualifiers
source                  1..66
                        mol_type = unassigned RNA
                        organism = Homo sapiens
SEQUENCE: 225
gggcatgggg aggtgtggag tcagcatggg gctaggaggc cccgcgctga cccgccttct   60
ccgcag                                                             66

SEQ ID NO: 226          moltype = RNA   length = 61
FEATURE                 Location/Qualifiers
source                  1..61
                        mol_type = unassigned RNA
                        organism = Homo sapiens
SEQUENCE: 226
tctcgtttga tctcggaagc taagcagggt tgggcctggt tagtacttgg atgggaaact   60
t                                                                  61

SEQ ID NO: 227          moltype = RNA   length = 53
FEATURE                 Location/Qualifiers
source                  1..53
                        mol_type = unassigned RNA
                        organism = Homo sapiens
SEQUENCE: 227
gtttgatctc ggaagctaag cagggtcggg cctggttagt acttggatgg gag          53

SEQ ID NO: 228          moltype = RNA   length = 68
FEATURE                 Location/Qualifiers
source                  1..68
                        mol_type = unassigned RNA
                        organism = Homo sapiens
SEQUENCE: 228
gaatggaaga agaaggcggt cggtctgcgg gagccaggcc gcagagccat ccgccttctg   60
tccatgtc                                                           68

SEQ ID NO: 229          moltype = RNA   length = 71
FEATURE                 Location/Qualifiers
source                  1..71
                        mol_type = unassigned RNA
                        organism = Homo sapiens
SEQUENCE: 229
gtgtctgtgc cggtcccagg agaacctgca gaggcatcgg gtcagcggtg ctcctgcggg   60
ccgacactca c                                                       71

SEQ ID NO: 230          moltype = RNA   length = 67
FEATURE                 Location/Qualifiers
source                  1..67
                        mol_type = unassigned RNA
                        organism = Homo sapiens
SEQUENCE: 230
ccagacccct ggggctgggc aggcggaaag aggtctgaac tgcctctgcc tccttggtct   60
ccggcag                                                            67

SEQ ID NO: 231          moltype = RNA   length = 69
FEATURE                 Location/Qualifiers
source                  1..69
                        mol_type = unassigned RNA
                        organism = Homo sapiens
SEQUENCE: 231
ccgggcaggc aggtgtaggg tggagcccac tgtggctcct gactcagccc tgctgccttc   60
acctgccag                                                          69

SEQ ID NO: 232          moltype = RNA   length = 102
FEATURE                 Location/Qualifiers
source                  1..102
                        mol_type = unassigned RNA
                        organism = Homo sapiens
SEQUENCE: 232
tgtgttccct atcctcctta tgtcccaccc ccactcctgt ttgaatattt caccagaaac   60
aggagtgggg ggtgggacgt aaggaggatg ggggaaagaa ca                    102

SEQ ID NO: 233          moltype = RNA   length = 68
FEATURE                 Location/Qualifiers
source                  1..68
                        mol_type = unassigned RNA
```

```
                         organism = Homo sapiens
SEQUENCE: 233
tgcccaggct ggagcgagtg cagtggtgca gtcagtccta gctcactgca gcctcgaact    60
cctgggct                                                             68

SEQ ID NO: 234           moltype = RNA  length = 64
FEATURE                  Location/Qualifiers
source                   1..64
                         mol_type = unassigned RNA
                         organism = Homo sapiens
SEQUENCE: 234
aaccccgggc cggaggtcaa gggcgtcgct tctccctaat gttgcctctt ttccacggcc    60
tcag                                                                 64

SEQ ID NO: 235           moltype = RNA  length = 80
FEATURE                  Location/Qualifiers
source                   1..80
                         mol_type = unassigned RNA
                         organism = Homo sapiens
SEQUENCE: 235
cgggaatgcc gcggcgggga cggcgattgg tccgtatgtg tggtgccacc ggccgccggc    60
tccgccccgg ccccgcccc                                                 80

SEQ ID NO: 236           moltype = RNA  length = 74
FEATURE                  Location/Qualifiers
source                   1..74
                         mol_type = unassigned RNA
                         organism = Homo sapiens
SEQUENCE: 236
gcagcccggt gagcgctcgc tggcctggca gtgcgtcgga agaacagggc gggtggggcc    60
gcgcacatct ctgc                                                      74

SEQ ID NO: 237           moltype = RNA  length = 99
FEATURE                  Location/Qualifiers
source                   1..99
                         mol_type = unassigned RNA
                         organism = Homo sapiens
SEQUENCE: 237
gcaagggaca gggagggtcg tggcgacact cgcgccagct cccgggacgg ctgggctcgg    60
gctggtcgcc gacctccgac cctccactag atgcctggc                           99

SEQ ID NO: 238           moltype = RNA  length = 73
FEATURE                  Location/Qualifiers
source                   1..73
                         mol_type = unassigned RNA
                         organism = Homo sapiens
SEQUENCE: 238
gaaaacaacc aggtgggctt cccggagggc ggaacaccca gccccagcat ccagggctca    60
cctaccacgt ttg                                                       73

SEQ ID NO: 239           moltype = RNA  length = 75
FEATURE                  Location/Qualifiers
source                   1..75
                         mol_type = unassigned RNA
                         organism = Homo sapiens
SEQUENCE: 239
aagcaagact gagggcctc agaccgagct tttggaaaat agaaaagtct cgctctctgc     60
ccctcagcct aactt                                                     75

SEQ ID NO: 240           moltype = RNA  length = 90
FEATURE                  Location/Qualifiers
source                   1..90
                         mol_type = unassigned RNA
                         organism = Homo sapiens
SEQUENCE: 240
gtgggtacgg cccagtgggg gggagaggga cacgccctgg gctctgccca gggtgcagcc    60
ggactgactg agccctgtg ccgccccag                                       90

SEQ ID NO: 241           moltype = RNA  length = 92
FEATURE                  Location/Qualifiers
source                   1..92
                         mol_type = unassigned RNA
                         organism = Homo sapiens
SEQUENCE: 241
gtcagtgtct gggcggacag ctgcaggaaa gggaagacca aggcttgctg tctgtccagt    60
ctgccaccct accctgtctg ttcttgccac ag                                  92

SEQ ID NO: 242           moltype = RNA  length = 84
FEATURE                  Location/Qualifiers
```

```
source                  1..84
                        mol_type = unassigned RNA
                        organism = Homo sapiens
SEQUENCE: 242
ctccccatgg ccctgtctcc caacccttgt accagtgctg ggctcagacc ctggtacagg    60
cctggggac agggacctgg ggac                                            84

SEQ ID NO: 243          moltype = RNA  length = 81
FEATURE                 Location/Qualifiers
source                  1..81
                        mol_type = unassigned RNA
                        organism = Homo sapiens
SEQUENCE: 243
catcctcctt acgtcccacc ccccactcct gtttctggtg aaatattcaa acaggagtgg    60
gggtgggaca taaggaggat a                                              81

SEQ ID NO: 244          moltype = RNA  length = 96
FEATURE                 Location/Qualifiers
source                  1..96
                        mol_type = unassigned RNA
                        organism = Homo sapiens
SEQUENCE: 244
gctctgggc gtgccgccgc cgtcgctgcc acctcccta ccgctagtgg aagaagatgg      60
cggaaggcgg agcggcggat ctggacaccc agcggt                              96

SEQ ID NO: 245          moltype = RNA  length = 86
FEATURE                 Location/Qualifiers
source                  1..86
                        mol_type = unassigned RNA
                        organism = Homo sapiens
SEQUENCE: 245
attctaggtg gggagactga cggctggagg cccataagct gtctaaaact tcggccccca    60
gatttctggt ctccccactt cagaac                                         86

SEQ ID NO: 246          moltype = RNA  length = 61
FEATURE                 Location/Qualifiers
source                  1..61
                        mol_type = unassigned RNA
                        organism = Homo sapiens
SEQUENCE: 246
tcggctggcg ggggtagagc tggctgcagg cccggcccct ctcagctgct gccctctcca    60
g                                                                    61

SEQ ID NO: 247          moltype = RNA  length = 67
FEATURE                 Location/Qualifiers
source                  1..67
                        mol_type = unassigned RNA
                        organism = Homo sapiens
SEQUENCE: 247
tacaggccgg ggctttgggt gagggacccc cggagtctgt cacggtctca ccccaactct    60
gccccag                                                              67

SEQ ID NO: 248          moltype = RNA  length = 96
FEATURE                 Location/Qualifiers
source                  1..96
                        mol_type = unassigned RNA
                        organism = Homo sapiens
SEQUENCE: 248
ctcgggaggg gcgggagggg ggtccccggt gctcggatct cgagggtgct tattgttcgg    60
tccgagcctg ggtctccctc ttcccccaa cccccc                               96

SEQ ID NO: 249          moltype = RNA  length = 87
FEATURE                 Location/Qualifiers
source                  1..87
                        mol_type = unassigned RNA
                        organism = Homo sapiens
SEQUENCE: 249
gtgaggcggg gccaggaggg tgtgtggcgt gggtgctgcg gggccgtcag ggtgcctgcg    60
ggacgctcac ctggctggcc cgcccag                                        87

SEQ ID NO: 250          moltype = RNA  length = 137
FEATURE                 Location/Qualifiers
source                  1..137
                        mol_type = unassigned RNA
                        organism = Homo sapiens
SEQUENCE: 250
agccagacaa gagggtcatg gggagtcact gtcaacccag agcaggcact gcccctgcga    60
ccagcctggg gcatcggttg gggtgcaggg gtctgctggt gatgctttcc atctctttgc   120
tttgtcctga ttgtagc                                                  137
```

-continued

```
SEQ ID NO: 251          moltype = RNA   length = 65
FEATURE                 Location/Qualifiers
source                  1..65
                        mol_type = unassigned RNA
                        organism = Homo sapiens
SEQUENCE: 251
agccctgggg gtggtctcta gccaaggctc tggggtctca cccttggctg gtctctgctc    60
cgcag                                                                65

SEQ ID NO: 252          moltype = RNA   length = 81
FEATURE                 Location/Qualifiers
source                  1..81
                        mol_type = unassigned RNA
                        organism = Homo sapiens
SEQUENCE: 252
tagaggcagt ttcaacagat gtgtagactt ttgatatgag aaattggttt caaaatcagg    60
agtcggggct ttactgcttt t                                              81

SEQ ID NO: 253          moltype = RNA   length = 79
FEATURE                 Location/Qualifiers
source                  1..79
                        mol_type = unassigned RNA
                        organism = Homo sapiens
SEQUENCE: 253
cagcctgggg aaggcttggc agggaagaca catgagcagt gcctccactt cacgcctctc    60
ccttgtctcc tttccctag                                                 79

SEQ ID NO: 254          moltype = RNA   length = 109
FEATURE                 Location/Qualifiers
source                  1..109
                        mol_type = unassigned RNA
                        organism = Homo sapiens
SEQUENCE: 254
ggtcgggctc accatgacac agtgtgagac ctcgggctac aacacaggac ccgggcgctg    60
ctctgacccc tcgtgtcttg tgttgcagcc ggagggacgc aggtccgca              109

SEQ ID NO: 255          moltype = RNA   length = 82
FEATURE                 Location/Qualifiers
source                  1..82
                        mol_type = unassigned RNA
                        organism = Homo sapiens
SEQUENCE: 255
tgagctgttg gattcggggc cgtagcactg tctgagaggt ttacatttct cacagtgaac    60
cggtctcttt ttcagctgct tc                                             82

SEQ ID NO: 256          moltype = RNA   length = 65
FEATURE                 Location/Qualifiers
source                  1..65
                        mol_type = unassigned RNA
                        organism = Homo sapiens
SEQUENCE: 256
gagggtgggc gagggcggct gagcggctcc atccccggc ctgctcatcc ccctcgccct     60
ctcag                                                                65

SEQ ID NO: 257          moltype = RNA   length = 63
FEATURE                 Location/Qualifiers
source                  1..63
                        mol_type = unassigned RNA
                        organism = Homo sapiens
SEQUENCE: 257
aatgggtggg tgctggtggg agccgtgccc tggccactca ttcggctctc tccctcaccc    60
tag                                                                  63

SEQ ID NO: 258          moltype = RNA   length = 69
FEATURE                 Location/Qualifiers
source                  1..69
                        mol_type = unassigned RNA
                        organism = Homo sapiens
SEQUENCE: 258
gggcttaggg atgggaggcc aggatgaaga ttaatcccta atccccaaca ctggccttgc    60
tatccccag                                                            69

SEQ ID NO: 259          moltype = RNA   length = 86
FEATURE                 Location/Qualifiers
source                  1..86
                        mol_type = unassigned RNA
                        organism = Homo sapiens
SEQUENCE: 259
```

```
ggggctgggg gtgtggggag agagagtgca cagccagctc aggattaaa gctctttctc   60
tctctctctc tcccacttcc ctgcag                                       86

SEQ ID NO: 260          moltype = RNA   length = 68
FEATURE                 Location/Qualifiers
source                  1..68
                        mol_type = unassigned RNA
                        organism = Homo sapiens
SEQUENCE: 260
gtgcaaagag caggaggaca ggggatttat ctcccaaggg aggtccctg atcctagtca    60
cggcacca                                                           68

SEQ ID NO: 261          moltype = RNA   length = 82
FEATURE                 Location/Qualifiers
source                  1..82
                        mol_type = unassigned RNA
                        organism = Homo sapiens
SEQUENCE: 261
gtgagtggga ggccagggca cggcaggggg agctgcaggg ctatgggagg ggccccagcg   60
tctgagccct gtcctcccgc ag                                           82

SEQ ID NO: 262          moltype = RNA   length = 82
FEATURE                 Location/Qualifiers
source                  1..82
                        mol_type = unassigned RNA
                        organism = Homo sapiens
SEQUENCE: 262
gtgagtggga ggccagggca cggcaggggg agctgcaggg ctatgggagg ggccccagcg   60
tctgagccct gtcctcccgc ag                                           82

SEQ ID NO: 263          moltype = RNA   length = 61
FEATURE                 Location/Qualifiers
source                  1..61
                        mol_type = unassigned RNA
                        organism = Homo sapiens
SEQUENCE: 263
aactgcgggg ccagagcaga gagcccttgc acaccaccag cctctcctcc ctgtgcccca   60
g                                                                  61

SEQ ID NO: 264          moltype = RNA   length = 106
FEATURE                 Location/Qualifiers
source                  1..106
                        mol_type = unassigned RNA
                        organism = Homo sapiens
SEQUENCE: 264
agaagaatgc ccaaccagcc ctcagttgct acagttccct gttgtttcag ctcgacaaca   60
acaggcggct gtagcaatgg ggggctggat gggcatctca atgtgc                106

SEQ ID NO: 265          moltype = RNA   length = 63
FEATURE                 Location/Qualifiers
source                  1..63
                        mol_type = unassigned RNA
                        organism = Homo sapiens
SEQUENCE: 265
tggtggcggc ggtagttatg ggcttctctt tctcaccagc agccctggg ccgccgcctc    60
cct                                                                63

SEQ ID NO: 266          moltype = RNA   length = 65
FEATURE                 Location/Qualifiers
source                  1..65
                        mol_type = unassigned RNA
                        organism = Homo sapiens
SEQUENCE: 266
gtctcctggg gggaggagac cctgctctcc ctggcagcaa gcctctcctg cccttccaga   60
ttagc                                                              65

SEQ ID NO: 267          moltype = RNA   length = 51
FEATURE                 Location/Qualifiers
source                  1..51
                        mol_type = unassigned RNA
                        organism = Homo sapiens
SEQUENCE: 267
agagatgaag cggggggggcg gggtcttgct ctattgccta cgctgatctc a          51

SEQ ID NO: 268          moltype = RNA   length = 69
FEATURE                 Location/Qualifiers
source                  1..69
                        mol_type = unassigned RNA
                        organism = Homo sapiens
```

```
SEQUENCE: 268
tggggtaggg gtgggggaat tcagggg tgt cgaactcatg gctgccacct ttgtgtcccc    60
atcctgcag                                                             69

SEQ ID NO: 269          moltype = RNA   length = 115
FEATURE                 Location/Qualifiers
source                  1..115
                        mol_type = unassigned RNA
                        organism = Homo sapiens
SEQUENCE: 269
gagcaaaaac cagagaacaa catgggagcg ttcctaaccc ctaaggcaac tggatgggag    60
acctgaccca tccagttctc tgaggggggct cttgtgtgtt ctacaaggtt gttca        115

SEQ ID NO: 270          moltype = RNA   length = 55
FEATURE                 Location/Qualifiers
source                  1..55
                        mol_type = unassigned RNA
                        organism = Homo sapiens
SEQUENCE: 270
ccggatccga gtcacggcac caaatttcat gcgtgtccgt gtgaagagac cacca          55

SEQ ID NO: 271          moltype = RNA   length = 92
FEATURE                 Location/Qualifiers
source                  1..92
                        mol_type = unassigned RNA
                        organism = Homo sapiens
SEQUENCE: 271
cgctgcgctt ctgggcccgc ggcgggcgtg gggctgcccg ggccggtcga ccagcgcgcc    60
gtagctcccg aggcccgagc cgcgacccgc gg                                   92

SEQ ID NO: 272          moltype = RNA   length = 80
FEATURE                 Location/Qualifiers
source                  1..80
                        mol_type = unassigned RNA
                        organism = Homo sapiens
SEQUENCE: 272
gcgtcaagat ggcggcgggg aggtaggcag agcaggacgc cgctgctgcc gccgccaccg    60
ccgcctccgc tccagtcgcc                                                 80

SEQ ID NO: 273          moltype = RNA   length = 86
FEATURE                 Location/Qualifiers
source                  1..86
                        mol_type = unassigned RNA
                        organism = Homo sapiens
SEQUENCE: 273
agggagaagg gtcgggcag ggagggcagg gcaggctctg gggtgggggg tctgtgagtc      60
agccacggct ctgcccacgt ctcccc                                          86

SEQ ID NO: 274          moltype = RNA   length = 63
FEATURE                 Location/Qualifiers
source                  1..63
                        mol_type = unassigned RNA
                        organism = Homo sapiens
SEQUENCE: 274
accctagggt ggggctggag gtggggctga ggctgagtct cctcccctt cctccctgcc      60
cag                                                                   63

SEQ ID NO: 275          moltype = RNA   length = 79
FEATURE                 Location/Qualifiers
source                  1..79
                        mol_type = unassigned RNA
                        organism = Homo sapiens
SEQUENCE: 275
ctcgaggtgc tggggacgc gtgagcgcga gccgcttcct cacggctcgg ccgcggcgcg      60
tagccccgc cacatcggg                                                   79

SEQ ID NO: 276          moltype = RNA   length = 98
FEATURE                 Location/Qualifiers
source                  1..98
                        mol_type = unassigned RNA
                        organism = Homo sapiens
SEQUENCE: 276
cttggtcaat aggaaagagg tgggacctcc tggcttttcc tctgcagcat ggctcggacc    60
tagtgcaatg tttaagctcc cctctctttc ctgttcag                             98

SEQ ID NO: 277          moltype = RNA   length = 62
FEATURE                 Location/Qualifiers
source                  1..62
                        mol_type = unassigned RNA
```

```
                    organism = Homo sapiens
SEQUENCE: 277
ccttctgcgg cagagctggg gtcaccagcc ctcatgtact tgtgacttct cccctgccac    60
ag                                                                  62

SEQ ID NO: 278          moltype = RNA  length = 65
FEATURE                 Location/Qualifiers
source                  1..65
                        mol_type = unassigned RNA
                        organism = Homo sapiens
SEQUENCE: 278
gagaatgggg ggacagatgg agaggacaca ggctggcact gaggtcccct ccactttcct    60
cctag                                                               65

SEQ ID NO: 279          moltype = RNA  length = 68
FEATURE                 Location/Qualifiers
source                  1..68
                        mol_type = unassigned RNA
                        organism = Homo sapiens
SEQUENCE: 279
cgtggtgagg atatggcagg gaagggagt ttccctctat tcccttcccc ccagtaatct     60
tcatcatg                                                            68

SEQ ID NO: 280          moltype = RNA  length = 103
FEATURE                 Location/Qualifiers
source                  1..103
                        mol_type = unassigned RNA
                        organism = Homo sapiens
SEQUENCE: 280
gtgtcggctg tggcgtgact gtccctctgt gtcccccact aggcccactg ctcagtggag    60
cgtggaggac gaggaggagg ccgtccacga gcaatgccag cat                    103

SEQ ID NO: 281          moltype = RNA  length = 87
FEATURE                 Location/Qualifiers
source                  1..87
                        mol_type = unassigned RNA
                        organism = Homo sapiens
SEQUENCE: 281
ccctcatctc tgggcagggg cttattgtag gagtctctga agagagctgt ggactgacct    60
gctttaaccc ttccccaggt tcccatt                                       87

SEQ ID NO: 282          moltype = RNA  length = 83
FEATURE                 Location/Qualifiers
source                  1..83
                        mol_type = unassigned RNA
                        organism = Homo sapiens
SEQUENCE: 282
aatagagggt gcacaggcac gggagctcag gtgaggcagg gagctgagct cacctgacct    60
cccatgcctg tgcaccctct att                                           83

SEQ ID NO: 283          moltype = RNA  length = 82
FEATURE                 Location/Qualifiers
source                  1..82
                        mol_type = unassigned RNA
                        organism = Homo sapiens
SEQUENCE: 283
tgtgggcagg gccctgggga gctgaggctc tggggtggc cggggctgac cctgggcctc     60
tgctccccag tgtctgaccg cg                                            82

SEQ ID NO: 284          moltype = RNA  length = 98
FEATURE                 Location/Qualifiers
source                  1..98
                        mol_type = unassigned RNA
                        organism = Homo sapiens
SEQUENCE: 284
ttctcacccc cgcctgacac gggcgacagc tgcggcccgc tgtgttcact cgggccgagt    60
gcgtctcctg tcaggcaagg gagagcagag cccccctg                           98

SEQ ID NO: 285          moltype = RNA  length = 49
FEATURE                 Location/Qualifiers
source                  1..49
                        mol_type = unassigned RNA
                        organism = Homo sapiens
SEQUENCE: 285
ttcccagcca acgcaccaaa aatgatatgg gtctgttgtc tggagaaac                49

SEQ ID NO: 286          moltype = RNA  length = 69
FEATURE                 Location/Qualifiers
source                  1..69
```

```
                        mol_type = unassigned RNA
                        organism = Homo sapiens
SEQUENCE: 286
ggccctcggg cctggggttg ggggagctct gtcctgtctc actcattgct cctccctgc    60
ctggcccag                                                           69

SEQ ID NO: 287          moltype = RNA   length = 80
FEATURE                 Location/Qualifiers
source                  1..80
                        mol_type = unassigned RNA
                        organism = Homo sapiens
SEQUENCE: 287
cgtgtgagcc cgccctgtgc ccggcccact tctgcttcct cttagcgcag gaggggtccc    60
gcactgggag gggccctcac                                                80

SEQ ID NO: 288          moltype = RNA   length = 73
FEATURE                 Location/Qualifiers
source                  1..73
                        mol_type = unassigned RNA
                        organism = Homo sapiens
SEQUENCE: 288
cggcgacggc ggggtgggtg aggtcgggcc ccaagactcg gggtttgccg ggcgcctcag    60
ttcaccgcgg ccg                                                       73

SEQ ID NO: 289          moltype = RNA   length = 74
FEATURE                 Location/Qualifiers
source                  1..74
                        mol_type = unassigned RNA
                        organism = Homo sapiens
SEQUENCE: 289
cctgcaggag gcagtgggcg agcaggcggg gcagcccaat gccatgggcc tgatctcacc    60
gctgcctcct tccc                                                      74

SEQ ID NO: 290          moltype = RNA   length = 70
FEATURE                 Location/Qualifiers
source                  1..70
                        mol_type = unassigned RNA
                        organism = Homo sapiens
SEQUENCE: 290
gtccctgggg gctgggatgg gccatggtgt gctctgatcc ccctgtggtc tcttggcccc    60
caggaactcc                                                           70

SEQ ID NO: 291          moltype = RNA   length = 73
FEATURE                 Location/Qualifiers
source                  1..73
                        mol_type = unassigned RNA
                        organism = Homo sapiens
SEQUENCE: 291
gtgggcgggg gcaggtgtgt ggtgggtggt ggcctgcggt gagcagggcc ctcacacctg    60
cctcgccccc cag                                                       73

SEQ ID NO: 292          moltype = RNA   length = 77
FEATURE                 Location/Qualifiers
source                  1..77
                        mol_type = unassigned RNA
                        organism = Homo sapiens
SEQUENCE: 292
gagttgggag gttccctctc caaatgtgtc ttgatccccc accccaagac acatttggag    60
agggaccctc ccaactc                                                   77

SEQ ID NO: 293          moltype = RNA   length = 63
FEATURE                 Location/Qualifiers
source                  1..63
                        mol_type = unassigned RNA
                        organism = Homo sapiens
SEQUENCE: 293
cttgcccggg agaaggaggt ggcctggaga gctgctgtct ccagccgccg cctgtctcca    60
cag                                                                  63

SEQ ID NO: 294          moltype = RNA   length = 79
FEATURE                 Location/Qualifiers
source                  1..79
                        mol_type = unassigned RNA
                        organism = Homo sapiens
SEQUENCE: 294
gtgaggtggg ggccagcagg gagtgggctg ggctgggctg ggccaaggta caaggcctca    60
ccctgcatcc cgcacccag                                                 79

SEQ ID NO: 295          moltype = RNA   length = 63
```

```
FEATURE                 Location/Qualifiers
source                  1..63
                        mol_type = unassigned RNA
                        organism = Homo sapiens
SEQUENCE: 295
gagtcgagga ctggtggaag ggcctttccc ctcagaccaa ggccctggcc ccagcttctt    60
ctc                                                                  63

SEQ ID NO: 296          moltype = RNA   length = 60
FEATURE                 Location/Qualifiers
source                  1..60
                        mol_type = unassigned RNA
                        organism = Homo sapiens
SEQUENCE: 296
aggcctaggg ggtggcaggc tggccatcag tgtgggctaa ccctgtcctc tccctcccag    60

SEQ ID NO: 297          moltype = RNA   length = 59
FEATURE                 Location/Qualifiers
source                  1..59
                        mol_type = unassigned RNA
                        organism = Homo sapiens
SEQUENCE: 297
ctccagggag acagtgtgtg aggcctcttg ccatggcctc cctgcccgcc tctctgcag     59

SEQ ID NO: 298          moltype = RNA   length = 73
FEATURE                 Location/Qualifiers
source                  1..73
                        mol_type = unassigned RNA
                        organism = Homo sapiens
SEQUENCE: 298
ggccggctgg ggttcctggg gatgggattt gcttcctgtc acaaatcaca ttgccaggga    60
tttccaaccg acc                                                       73

SEQ ID NO: 299          moltype = RNA   length = 84
FEATURE                 Location/Qualifiers
source                  1..84
                        mol_type = unassigned RNA
                        organism = Homo sapiens
SEQUENCE: 299
ggcccctcct tctcagcccc agctcccgct caccccctgcc acgtcaaagg aggcagaagg    60
ggagttggga gcagagaggg gacc                                           84

SEQ ID NO: 300          moltype = RNA   length = 81
FEATURE                 Location/Qualifiers
source                  1..81
                        mol_type = unassigned RNA
                        organism = Homo sapiens
SEQUENCE: 300
agttggtggg ggagccatga gataagagca cctcctagag aatgttgaac taaaggtgcc    60
ctctctggct cctccccaaa g                                              81

SEQ ID NO: 301          moltype = RNA   length = 97
FEATURE                 Location/Qualifiers
source                  1..97
                        mol_type = unassigned RNA
                        organism = Homo sapiens
SEQUENCE: 301
cccgggacct tggtccaggc gctggtctgc gtggtgctcg ggtggataag tctgatctga    60
gcaccacaca ggccgggcgc cgggaccaag ggggctc                             97

SEQ ID NO: 302          moltype = RNA   length = 70
FEATURE                 Location/Qualifiers
source                  1..70
                        mol_type = unassigned RNA
                        organism = Homo sapiens
SEQUENCE: 302
ctcgggcccg accgcgccgg cccgcacctc ccggcccgga gctgcgggct gcggtcaggg    60
cgatcccggg                                                           70

SEQ ID NO: 303          moltype = RNA   length = 66
FEATURE                 Location/Qualifiers
source                  1..66
                        mol_type = unassigned RNA
                        organism = Homo sapiens
SEQUENCE: 303
ccgagtgggg cggggcaggt ccctgcaggg actgtgacac tgaaggacct gcaccttcgc    60
ccacag                                                               66

SEQ ID NO: 304          moltype = RNA   length = 67
```

```
FEATURE              Location/Qualifiers
source               1..67
                     mol_type = unassigned RNA
                     organism = Homo sapiens
SEQUENCE: 304
gcgccctccc tctctccccg gtgtgcaaat gtgtgtgtgc ggtgttatgc cggacaagag    60
ggaggtg                                                              67

SEQ ID NO: 305       moltype = RNA   length = 70
FEATURE              Location/Qualifiers
source               1..70
                     mol_type = unassigned RNA
                     organism = Homo sapiens
SEQUENCE: 305
aaaagcctgt ccctaagtcc ctcccagcct tccagagttg gtgccaggaa ggatttaggg    60
acaggctttg                                                           70

SEQ ID NO: 306       moltype = RNA   length = 94
FEATURE              Location/Qualifiers
source               1..94
                     mol_type = unassigned RNA
                     organism = Homo sapiens
SEQUENCE: 306
ataaaggaag ttaggctgag gggcagagag cgagactttt ctattttcca aaagctcggt    60
ctgaggcccc tcagtcttgc ttcctaaccc gcgc                                94

SEQ ID NO: 307       moltype = RNA   length = 66
FEATURE              Location/Qualifiers
source               1..66
                     mol_type = unassigned RNA
                     organism = Homo sapiens
SEQUENCE: 307
gggaggaggg aggagatggg ccaagttccc tctggctgga acgcccttcc cccccttctt    60
cacctg                                                               66

SEQ ID NO: 308       moltype = RNA   length = 57
FEATURE              Location/Qualifiers
source               1..57
                     mol_type = unassigned RNA
                     organism = Homo sapiens
SEQUENCE: 308
cattggaggg tgtggaagac atctgggcca actctgatct cttcatctac cccccag       57

SEQ ID NO: 309       moltype = RNA   length = 79
FEATURE              Location/Qualifiers
source               1..79
                     mol_type = unassigned RNA
                     organism = Homo sapiens
SEQUENCE: 309
gtgcagatcc ttgggagccc tgttagactc tggattttac acttggagtg aacgggcgcc    60
atcccgaggc tttgcacag                                                 79

SEQ ID NO: 310       moltype = RNA   length = 90
FEATURE              Location/Qualifiers
source               1..90
                     mol_type = unassigned RNA
                     organism = Homo sapiens
SEQUENCE: 310
cgggcggggc gggtccggcc gcctccgagc ccggccggca gccccggcc ttaaagcgcg     60
ggctgtccgg aggggtcggc tttcccaccg                                     90

SEQ ID NO: 311       moltype = RNA   length = 72
FEATURE              Location/Qualifiers
source               1..72
                     mol_type = unassigned RNA
                     organism = Homo sapiens
SEQUENCE: 311
atgagcgggt gggagcagat cttattgaga gttccttctc ctgctcctga ttgtcttccc    60
ccaccctcac ag                                                        72

SEQ ID NO: 312       moltype = RNA   length = 59
FEATURE              Location/Qualifiers
source               1..59
                     mol_type = unassigned RNA
                     organism = Homo sapiens
SEQUENCE: 312
gtccaggcag gagccggact ggacctcagg gaagaggctg accggcccc tcttgcggc      59

SEQ ID NO: 313       moltype = RNA   length = 64
```

| FEATURE | Location/Qualifiers |
|---|---|
| source | 1..64 |
| | mol_type = unassigned RNA |
| | organism = Homo sapiens |

SEQUENCE: 313
gagctctggg aggggctggg tttggcagga cagtttccaa gccctgtctc ctcccatctt 60
ccag 64

| SEQ ID NO: 314 | moltype = RNA length = 82 |
|---|---|
| FEATURE | Location/Qualifiers |
| source | 1..82 |
| | mol_type = unassigned RNA |
| | organism = Homo sapiens |

SEQUENCE: 314
gctacgggga gcggggagga agtgggcgct gcttctgcgt tatctggaag gagcagccca 60
ctcctgtcct gggctctgtg gt 82

| SEQ ID NO: 315 | moltype = RNA length = 50 |
|---|---|
| FEATURE | Location/Qualifiers |
| source | 1..50 |
| | mol_type = unassigned RNA |
| | organism = Homo sapiens |

SEQUENCE: 315
acccgggcgt ggtggtgggg gtgggtgcct gtaattccag ctagttggga 50

| SEQ ID NO: 316 | moltype = RNA length = 61 |
|---|---|
| FEATURE | Location/Qualifiers |
| source | 1..61 |
| | mol_type = unassigned RNA |
| | organism = Homo sapiens |

SEQUENCE: 316
gagggcagcg tgggtgtggc ggaggcaggc gtgaccgttt gccgccctct cgctgctcta 60
g 61

| SEQ ID NO: 317 | moltype = RNA length = 73 |
|---|---|
| FEATURE | Location/Qualifiers |
| source | 1..73 |
| | mol_type = unassigned RNA |
| | organism = Homo sapiens |

SEQUENCE: 317
ggcgagggga ggcgcaggct cggaaaggcg cgcgaggctc caggctcctt cccgatccac 60
cgctctcctc gct 73

| SEQ ID NO: 318 | moltype = RNA length = 67 |
|---|---|
| FEATURE | Location/Qualifiers |
| source | 1..67 |
| | mol_type = unassigned RNA |
| | organism = Homo sapiens |

SEQUENCE: 318
ggcagccagg gggatgggcg agcttgggcc cattcctttc cttaccctac cccccatccc 60
cctgtag 67

| SEQ ID NO: 319 | moltype = RNA length = 76 |
|---|---|
| FEATURE | Location/Qualifiers |
| source | 1..76 |
| | mol_type = unassigned RNA |
| | organism = Homo sapiens |

SEQUENCE: 319
actgactttg agtctctcct cagggtgctg caggcaaagc tggggaccca gggagagacg 60
taagtgaggg gagatg 76

| SEQ ID NO: 320 | moltype = RNA length = 71 |
|---|---|
| FEATURE | Location/Qualifiers |
| source | 1..71 |
| | mol_type = unassigned RNA |
| | organism = Homo sapiens |

SEQUENCE: 320
tgaccacccc cgggcaaaga cctgcagatc ccctgttaga gacgggccca ggactttgtg 60
cggggtgccc a 71

| SEQ ID NO: 321 | moltype = RNA length = 65 |
|---|---|
| FEATURE | Location/Qualifiers |
| source | 1..65 |
| | mol_type = unassigned RNA |
| | organism = Homo sapiens |

SEQUENCE: 321
ttctcctggg gagtggctgg ggagcagaca gacccaacct catgctcccc ggcctctgcc 60
cccag 65

```
SEQ ID NO: 322           moltype = RNA   length = 65
FEATURE                  Location/Qualifiers
source                   1..65
                         mol_type = unassigned RNA
                         organism = Homo sapiens
SEQUENCE: 322
gggtgctcgg ggcaggcggc tgggagcggc cctcacattg atggctcctg ccacctcctc     60
cgcag                                                                 65

SEQ ID NO: 323           moltype = RNA   length = 67
FEATURE                  Location/Qualifiers
source                   1..67
                         mol_type = unassigned RNA
                         organism = Homo sapiens
SEQUENCE: 323
gtggcactca aactgtgggg gcactttctg ctctctggtg aaagtgccgc catcttttga     60
gtgttac                                                               67

SEQ ID NO: 324           moltype = RNA   length = 63
FEATURE                  Location/Qualifiers
source                   1..63
                         mol_type = unassigned RNA
                         organism = Homo sapiens
SEQUENCE: 324
gaggtgtagg ggaggttggg ccagggatgc cttcactgtg tctctctggt cttgccaccc     60
cag                                                                   63

SEQ ID NO: 325           moltype = RNA   length = 72
FEATURE                  Location/Qualifiers
source                   1..72
                         mol_type = unassigned RNA
                         organism = Homo sapiens
SEQUENCE: 325
tgtgggactg caaatgggag ctcagcacct gcctgccacc cacgcagacc agccctgct      60
ctgttcccac ag                                                         72

SEQ ID NO: 326           moltype = RNA   length = 88
FEATURE                  Location/Qualifiers
source                   1..88
                         mol_type = unassigned RNA
                         organism = Homo sapiens
SEQUENCE: 326
gtggggccag gcggtggtgg gcactgctgg ggtgggcaca gcagccatgc agagcgggca     60
tttgaccccg tgccaccctt ttccccag                                        88

SEQ ID NO: 327           moltype = RNA   length = 94
FEATURE                  Location/Qualifiers
source                   1..94
                         mol_type = unassigned RNA
                         organism = Homo sapiens
SEQUENCE: 327
cgggcagcgg gtgccaggca cggtgtcagc aggcaacatg gccgagaggc cggggcctcc     60
gggcggcgcc gtgtccgcga ccgcgtaccc tgac                                 94

SEQ ID NO: 328           moltype = RNA   length = 90
FEATURE                  Location/Qualifiers
source                   1..90
                         mol_type = unassigned RNA
                         organism = Homo sapiens
SEQUENCE: 328
ggcgcctctg cagctccggc tccccctggc ctctcgggaa ctacaagtcc caggggcct      60
ggcggtgggc ggcgggcgga agaggcgggg                                      90

SEQ ID NO: 329           moltype = RNA   length = 70
FEATURE                  Location/Qualifiers
source                   1..70
                         mol_type = unassigned RNA
                         organism = Homo sapiens
SEQUENCE: 329
ttgggttggg gtggtcggcc ctggaggggg tttgtttgct tattccctc tgtgcttcac      60
ccctacccag                                                            70

SEQ ID NO: 330           moltype = RNA   length = 94
FEATURE                  Location/Qualifiers
source                   1..94
                         mol_type = unassigned RNA
                         organism = Homo sapiens
SEQUENCE: 330
aattcagccc tgccactggc ttatgtcatg accttgggct actcaggctg tctgcacaat     60
```

```
gagccagttg acaggagca gtgccactca actc                                    94

SEQ ID NO: 331          moltype = RNA   length = 90
FEATURE                 Location/Qualifiers
source                  1..90
                        mol_type = unassigned RNA
                        organism = Homo sapiens
SEQUENCE: 331
gtgtctctct ggagaccctg cagccttccc acccaccagg gagctttcca tgggctgtgg       60
ggaaggcgtc agtgtcgggt gagggaacac                                        90

SEQ ID NO: 332          moltype = RNA   length = 80
FEATURE                 Location/Qualifiers
source                  1..80
                        mol_type = unassigned RNA
                        organism = Homo sapiens
SEQUENCE: 332
gagaggccaa gaccttggga atggggtaa gggccttctg agcccaggtc cgaactctcc        60
attcctctgc agagcgctct                                                   80

SEQ ID NO: 333          moltype = RNA   length = 77
FEATURE                 Location/Qualifiers
source                  1..77
                        mol_type = unassigned RNA
                        organism = Homo sapiens
SEQUENCE: 333
catgagaaat cctgctggtc aaccatagcc ctggtcagac tctccggggc tgtgattgac       60
cagcaggact tctcatg                                                      77

SEQ ID NO: 334          moltype = RNA   length = 80
FEATURE                 Location/Qualifiers
source                  1..80
                        mol_type = unassigned RNA
                        organism = Homo sapiens
SEQUENCE: 334
tgagaggccg caccttgcct tgctgcccgg gccgtgcacc cgtgggcccc agggcgacgc       60
ggcggggcg gccctagcga                                                    80

SEQ ID NO: 335          moltype = RNA   length = 118
FEATURE                 Location/Qualifiers
source                  1..118
                        mol_type = unassigned RNA
                        organism = Homo sapiens
SEQUENCE: 335
gcaggtgaac tggcaggcca ggaagaggag gaagccctgg aggggctgga ggtgatggat       60
gttttcctcc ggttctcagg gctccacctc tttcgggccg tagagccagg gctggtgc        118

SEQ ID NO: 336          moltype = RNA   length = 69
FEATURE                 Location/Qualifiers
source                  1..69
                        mol_type = unassigned RNA
                        organism = Homo sapiens
SEQUENCE: 336
ctttcggcca gcgggacggc atccgaggtg ggctaggctc gggcccgtgg cgggtgcggg       60
ggtgggagg                                                               69

SEQ ID NO: 337          moltype = RNA   length = 78
FEATURE                 Location/Qualifiers
source                  1..78
                        mol_type = unassigned RNA
                        organism = Homo sapiens
SEQUENCE: 337
ggcctcaggc aggcgcaccc gaccacatgc atggctggtg gcggcgtgca ggggtcgggt       60
gggccaggct gtggggcg                                                     78

SEQ ID NO: 338          moltype = RNA   length = 80
FEATURE                 Location/Qualifiers
source                  1..80
                        mol_type = unassigned RNA
                        organism = Homo sapiens
SEQUENCE: 338
ggttccggag ccccggcgcg ggcggggttct ggggtgtaga cgctgctggc cagcccgccc      60
cagccgaggt tctcggcacc                                                   80

SEQ ID NO: 339          moltype = RNA   length = 66
FEATURE                 Location/Qualifiers
source                  1..66
                        mol_type = unassigned RNA
                        organism = Homo sapiens
```

```
SEQUENCE: 339
agcagccctc ggcggcccgg ggggcgggcg gcggtgcccg tcccggggct gcgcgaggca    60
caggcg                                                                66

SEQ ID NO: 340           moltype = RNA   length = 83
FEATURE                  Location/Qualifiers
source                   1..83
                         mol_type = unassigned RNA
                         organism = Homo sapiens
SEQUENCE: 340
cctgctgcag aggtgccagc tgcagtgggg gaggcactgc cagggctgcc cactctgctt    60
agccagcagg tgccaagaac agg                                             83

SEQ ID NO: 341           moltype = RNA   length = 64
FEATURE                  Location/Qualifiers
source                   1..64
                         mol_type = unassigned RNA
                         organism = Homo sapiens
SEQUENCE: 341
tctgggcgag gggtgggctc tcagaggggc tggcagtact gctctgaggc ctgcctctcc    60
ccag                                                                  64

SEQ ID NO: 342           moltype = RNA   length = 98
FEATURE                  Location/Qualifiers
source                   1..98
                         mol_type = unassigned RNA
                         organism = Homo sapiens
SEQUENCE: 342
ttgggcaagg tgcggggcta gggctaacag cagtcttact gaaggtttcc tggaaaccac    60
gcacatgctg ttgccactaa cctcaacctt actcggtc                             98

SEQ ID NO: 343           moltype = RNA   length = 97
FEATURE                  Location/Qualifiers
source                   1..97
                         mol_type = unassigned RNA
                         organism = Homo sapiens
SEQUENCE: 343
atctgagttg ggagggtccc tctccaaatg tgtcttgggg tgggggatca agacacattt    60
ggagagggaa cctcccaact cggcctctgc catcatt                              97

SEQ ID NO: 344           moltype = RNA   length = 72
FEATURE                  Location/Qualifiers
source                   1..72
                         mol_type = unassigned RNA
                         organism = Homo sapiens
SEQUENCE: 344
cttgggaatg gcaaggaaac cgttaccatt actgagttta gtaatggtaa tggttctctt    60
gctataccca ga                                                         72

SEQ ID NO: 345           moltype = RNA   length = 60
FEATURE                  Location/Qualifiers
source                   1..60
                         mol_type = unassigned RNA
                         organism = Homo sapiens
SEQUENCE: 345
caaggtgggg gagatggggg ttgaacttca tttctcatgc tcatcccat ctcctttcag      60

SEQ ID NO: 346           moltype = RNA   length = 53
FEATURE                  Location/Qualifiers
source                   1..53
                         mol_type = unassigned RNA
                         organism = Homo sapiens
SEQUENCE: 346
ggtgggggtt ggaggcgtgg gttttagaac ctatcccttt ctagccctga gca             53

SEQ ID NO: 347           moltype = RNA   length = 59
FEATURE                  Location/Qualifiers
source                   1..59
                         mol_type = unassigned RNA
                         organism = Homo sapiens
SEQUENCE: 347
ggggccaggc agggaggtgg gaccatgggg gccttgctgt gtgaccaccg ttcctgcag      59

SEQ ID NO: 348           moltype = RNA   length = 67
FEATURE                  Location/Qualifiers
source                   1..67
                         mol_type = unassigned RNA
                         organism = Homo sapiens
SEQUENCE: 348
```

```
gtgggagggg agaggcagca agcacacagg gcctgggact agcatgctga cctccctcct   60
gccccag                                                              67

SEQ ID NO: 349         moltype = RNA   length = 86
FEATURE                Location/Qualifiers
source                 1..86
                       mol_type = unassigned RNA
                       organism = Homo sapiens
SEQUENCE: 349
agcactgccc ccggtgagtc agggtggggc tggcccctg cttcgtgccc atccgcgctc    60
tgactctctg cccacctgca ggagct                                         86

SEQ ID NO: 350         moltype = RNA   length = 90
FEATURE                Location/Qualifiers
source                 1..90
                       mol_type = unassigned RNA
                       organism = Homo sapiens
SEQUENCE: 350
aggcctcgct gttctctatg gcttttatt cctatgtgat tctactgctc actcatatag    60
ggattggagc cgtggcgcac ggcggggaca                                    90

SEQ ID NO: 351         moltype = RNA   length = 115
FEATURE                Location/Qualifiers
source                 1..115
                       mol_type = unassigned RNA
                       organism = Homo sapiens
SEQUENCE: 351
ggtgccgagg gccgtccggc atcctaggcg ggtcgctgcg gtacctccct cctgtctgtg    60
gcggtgggat cccgtggccg tgttttcctg gtgcccggc cgtgcctgag gtttc         115

SEQ ID NO: 352         moltype = RNA   length = 61
FEATURE                Location/Qualifiers
source                 1..61
                       mol_type = unassigned RNA
                       organism = Homo sapiens
SEQUENCE: 352
tggcccaggg aaccagttgg ggcttccgct ctgcagaggc tctaactggc tttccctgca    60
g                                                                    61

SEQ ID NO: 353         moltype = RNA   length = 65
FEATURE                Location/Qualifiers
source                 1..65
                       mol_type = unassigned RNA
                       organism = Homo sapiens
SEQUENCE: 353
ctcctctggg ggtgggggc tgggcgtggt ggacagcgat gcatccctcg ccttctcacc    60
ctcag                                                                65

SEQ ID NO: 354         moltype = RNA   length = 62
FEATURE                Location/Qualifiers
source                 1..62
                       mol_type = unassigned RNA
                       organism = Homo sapiens
SEQUENCE: 354
tggcctaggg ggcggcttgt ggagtgtatg ggctgagcct tgctctgctc cccgccccc    60
ag                                                                   62

SEQ ID NO: 355         moltype = RNA   length = 84
FEATURE                Location/Qualifiers
source                 1..84
                       mol_type = unassigned RNA
                       organism = Homo sapiens
SEQUENCE: 355
tgtgcagtgg aaggggggc cgatacactg tacgagagtg agtagcaggt ctcacagtga    60
accggtctct ttccctactg tgtc                                           84

SEQ ID NO: 356         moltype = RNA   length = 90
FEATURE                Location/Qualifiers
source                 1..90
                       mol_type = unassigned RNA
                       organism = Homo sapiens
SEQUENCE: 356
ctgtgggctg ggccagggag cagctggtgg gtgggaagta agatctgacc tggactccat    60
cccacccacc ccctgtttcc tggcccacag                                    90

SEQ ID NO: 357         moltype = RNA   length = 47
FEATURE                Location/Qualifiers
source                 1..47
                       mol_type = unassigned RNA
```

```
                              -continued organism = Homo sapiens
SEQUENCE: 357
ctcggcgcgg ggcgcgggct ccgggttggg gcgagccaac gccgggg              47

SEQ ID NO: 358          moltype = RNA   length = 75
FEATURE                 Location/Qualifiers
source                  1..75
                        mol_type = unassigned RNA
                        organism = Homo sapiens
SEQUENCE: 358
tcatccctgg gtggggatttt gttgcattac ttgtgttcta tataaagtat tgcacttgtc  60
ccggcctgtg aaga                                                    75

SEQ ID NO: 359          moltype = RNA   length = 102
FEATURE                 Location/Qualifiers
source                  1..102
                        mol_type = unassigned RNA
                        organism = Homo sapiens
SEQUENCE: 359
gcttatcgag gaaaagatcg aggtgggttg gggcgggctc tggggatttg gtctcacagc   60
ccggatccca gcccacttac cttggttact ctccttcctt ct                    102

SEQ ID NO: 360          moltype = RNA   length = 62
FEATURE                 Location/Qualifiers
source                  1..62
                        mol_type = unassigned RNA
                        organism = Homo sapiens
SEQUENCE: 360
gctggggtc ccccgacagt gtggagctgg ggccgggtcc cggggagggg ggttctgggc    60
ag                                                                 62

SEQ ID NO: 361          moltype = RNA   length = 89
FEATURE                 Location/Qualifiers
source                  1..89
                        mol_type = unassigned RNA
                        organism = Homo sapiens
SEQUENCE: 361
tctccgttta tcccaccact gccaccatta ttgctactgt tcagcaggtg ctgctggtgg   60
tgatggtgat agtctggtgg gggcggtgg                                    89

SEQ ID NO: 362          moltype = RNA   length = 71
FEATURE                 Location/Qualifiers
source                  1..71
                        mol_type = unassigned RNA
                        organism = Homo sapiens
SEQUENCE: 362
ggtgagtggg agccggtggg gctggagtaa gggcacgccc ggggctgccc cacctgctga   60
ccaccctccc c                                                       71

SEQ ID NO: 363          moltype = RNA   length = 100
FEATURE                 Location/Qualifiers
source                  1..100
                        mol_type = unassigned RNA
                        organism = Homo sapiens
SEQUENCE: 363
agctcagggc ggctgcgcag agggctggac tcagcggcgg agctggctgc tggcctcagt   60
tctgcctctg tccaggtcct tgtgacccgc ccgctctcct                       100

SEQ ID NO: 364          moltype = RNA   length = 93
FEATURE                 Location/Qualifiers
source                  1..93
                        mol_type = unassigned RNA
                        organism = Homo sapiens
SEQUENCE: 364
tacttatggc accccactcc tggtaccata gtcataagtt aggagatgtt agagctgtga   60
gtaccatgac ttaagtgtgg tggcttaaac atg                               93

SEQ ID NO: 365          moltype = RNA   length = 89
FEATURE                 Location/Qualifiers
source                  1..89
                        mol_type = unassigned RNA
                        organism = Homo sapiens
SEQUENCE: 365
agcctgtggg aaagagaaga gcagggcagg gtgaaggccc ggcggagaca ctctgcccac   60
cccacaccct gcctatgggc cacacagct                                    89

SEQ ID NO: 366          moltype = RNA   length = 98
FEATURE                 Location/Qualifiers
source                  1..98
```

```
                        mol_type = unassigned RNA
                        organism = Homo sapiens
SEQUENCE: 366
cgaggtaggg gcgtcccggg cgcgcgggcg ggtcccaggc tgggcccctc ggaggccggg      60
tgctcactgc cccgtccggg cgcccgtgtc tcctccag                             98

SEQ ID NO: 367          moltype = RNA  length = 66
FEATURE                 Location/Qualifiers
source                  1..66
                        mol_type = unassigned RNA
                        organism = Homo sapiens
SEQUENCE: 367
acccaggagg cggaggaggt ggaggttgca gtgagccaag atcgtggcac tgactccagc      60
ctgggg                                                                66

SEQ ID NO: 368          moltype = RNA  length = 52
FEATURE                 Location/Qualifiers
source                  1..52
                        mol_type = unassigned RNA
                        organism = Homo sapiens
SEQUENCE: 368
tagccgggcg tggtggtggg ggcctgtggt cccagctact ttggaggctg ag              52

SEQ ID NO: 369          moltype = RNA  length = 71
FEATURE                 Location/Qualifiers
source                  1..71
                        mol_type = unassigned RNA
                        organism = Homo sapiens
SEQUENCE: 369
atggaggggg gtgtggagcc aggggcccca ggtctacagc ttctcccgc tccctgcccc       60
catactccca g                                                          71

SEQ ID NO: 370          moltype = RNA  length = 109
FEATURE                 Location/Qualifiers
source                  1..109
                        mol_type = unassigned RNA
                        organism = Homo sapiens
SEQUENCE: 370
tcccgcattc cctctgcttt ggtcaggtgg tgccctcctt ccatgggtag agccagagat      60
ggtgggttct ggctggtcag atgggagtgg acagagaccc gggtcctc                  109

SEQ ID NO: 371          moltype = RNA  length = 82
FEATURE                 Location/Qualifiers
source                  1..82
                        mol_type = unassigned RNA
                        organism = Homo sapiens
SEQUENCE: 371
acctgtaggt gacagtcagg ggcggggtgt ggtgggctg gggctggccc cctcctcaca       60
cctctcctgg catcgccccc ag                                              82

SEQ ID NO: 372          moltype = RNA  length = 51
FEATURE                 Location/Qualifiers
source                  1..51
                        mol_type = unassigned RNA
                        organism = Homo sapiens
SEQUENCE: 372
acagacccg gggagccgg cggtgaagct cctggtatcc tgggtgtctg a                 51

SEQ ID NO: 373          moltype = RNA  length = 62
FEATURE                 Location/Qualifiers
source                  1..62
                        mol_type = unassigned RNA
                        organism = Homo sapiens
SEQUENCE: 373
gtgggtctcg catcaggagg caaggccagg acccgctgac ccatgcctcc tgccgcggtc      60
ag                                                                    62

SEQ ID NO: 374          moltype = RNA  length = 70
FEATURE                 Location/Qualifiers
source                  1..70
                        mol_type = unassigned RNA
                        organism = Homo sapiens
SEQUENCE: 374
ggccgcggcg cgcaagatgg cggcgggccc gggcaccgcc ccttccgccc cgcgggcgt       60
cgcacgaggc                                                            70

SEQ ID NO: 375          moltype = RNA  length = 73
FEATURE                 Location/Qualifiers
source                  1..73
```

```
                         mol_type = unassigned RNA
                         organism = Homo sapiens
SEQUENCE: 375
aggccaggtg ggtatggagg agccctcata tggcagttgg cgagggccca gtgagccct    60
ctctgctctc cag                                                      73

SEQ ID NO: 376           moltype = RNA    length = 74
FEATURE                  Location/Qualifiers
source                   1..74
                         mol_type = unassigned RNA
                         organism = Homo sapiens
SEQUENCE: 376
gggaggaaga agggaggagg agcggagggg cccttgtctt cccagagcct ctcccttcct    60
cccctccccc tccc                                                     74

SEQ ID NO: 377           moltype = RNA    length = 75
FEATURE                  Location/Qualifiers
source                   1..75
                         mol_type = unassigned RNA
                         organism = Homo sapiens
SEQUENCE: 377
gtcagagggg ggatgtgcat gctggttggg gtgggctgcc tgtggaccaa tcagcgtgca    60
cttcccacc ctgaa                                                     75

SEQ ID NO: 378           moltype = RNA    length = 70
FEATURE                  Location/Qualifiers
source                   1..70
                         mol_type = unassigned RNA
                         organism = Homo sapiens
SEQUENCE: 378
acaaatagct tcagggagtc aggggagggc agaaatagat ggccttcccc tgctgggaag    60
aaagtgggtc                                                          70

SEQ ID NO: 379           moltype = RNA    length = 60
FEATURE                  Location/Qualifiers
source                   1..60
                         mol_type = unassigned RNA
                         organism = Homo sapiens
SEQUENCE: 379
tgtgaatgac cccttccag agccaaaatc accaggatg gaggaggggt cttgggtact      60

SEQ ID NO: 380           moltype = RNA    length = 81
FEATURE                  Location/Qualifiers
source                   1..81
                         mol_type = unassigned RNA
                         organism = Homo sapiens
SEQUENCE: 380
ctccctggga gggcgtggat gatggtggga gaggagcccc actgtggaag tctgacccc     60
acatcgcccc accttcccca g                                             81

SEQ ID NO: 381           moltype = RNA    length = 61
FEATURE                  Location/Qualifiers
source                   1..61
                         mol_type = unassigned RNA
                         organism = Homo sapiens
SEQUENCE: 381
gtgcggaacg ctggccgggg cgggagggga agggacgccc ggccggaacg ccgcactcac    60
g                                                                   61

SEQ ID NO: 382           moltype = RNA    length = 78
FEATURE                  Location/Qualifiers
source                   1..78
                         mol_type = unassigned RNA
                         organism = Homo sapiens
SEQUENCE: 382
gggcccagaa gggggcgcag tcactgacgt gaagggacca catcccgctt catgtcagtg    60
actcctgccc cttggtct                                                 78

SEQ ID NO: 383           moltype = RNA    length = 73
FEATURE                  Location/Qualifiers
source                   1..73
                         mol_type = unassigned RNA
                         organism = Homo sapiens
SEQUENCE: 383
acctttccag ctcatcccac ctctgccacc aaaacactca tcgcggggtc agagggagtg    60
ccaaaaaagg taa                                                      73

SEQ ID NO: 384           moltype = RNA    length = 63
FEATURE                  Location/Qualifiers
```

```
source                          1..63
                                mol_type = unassigned RNA
                                organism = Homo sapiens
SEQUENCE: 384
gcatgctggg cgaggctggc atctagcaca ggcggtagat gcttgctctt gccattgcaa    60
tga                                                                  63

SEQ ID NO: 385                  moltype = RNA   length = 62
FEATURE                         Location/Qualifiers
source                          1..62
                                mol_type = unassigned RNA
                                organism = Homo sapiens
SEQUENCE: 385
gagggtggtg gaggaagagg gcagctccca tgactgcctg accgccttct ctcctccccc    60
ag                                                                   62

SEQ ID NO: 386                  moltype = RNA   length = 65
FEATURE                         Location/Qualifiers
source                          1..65
                                mol_type = unassigned RNA
                                organism = Homo sapiens
SEQUENCE: 386
gagggctagg tggggggctt gaagcccga gatgcctcac gtcttcaccc ctctcaccta     60
agcag                                                                65

SEQ ID NO: 387                  moltype = RNA   length = 64
FEATURE                         Location/Qualifiers
source                          1..64
                                mol_type = unassigned RNA
                                organism = Homo sapiens
SEQUENCE: 387
gaggcactgg gtaggtgggg ctccagggct cctgacacct ggacctctcc tccccaggcc    60
caca                                                                 64

SEQ ID NO: 388                  moltype = RNA   length = 96
FEATURE                         Location/Qualifiers
source                          1..96
                                mol_type = unassigned RNA
                                organism = Homo sapiens
SEQUENCE: 388
cgggccccgg gcgggcggga gggacgggac gcggtgcagt gttgtttttt ccccgccaa     60
tattgcactc gtcccggcct ccggccccc cggccc                               96

SEQ ID NO: 389                  moltype = RNA   length = 83
FEATURE                         Location/Qualifiers
source                          1..83
                                mol_type = unassigned RNA
                                organism = Homo sapiens
SEQUENCE: 389
gtgagtggga gccccagtgt gtggttgggg ccatggcggg tggcagccc agcctctgag     60
ccttcctcgt ctgtctgccc cag                                            83

SEQ ID NO: 390                  moltype = RNA   length = 67
FEATURE                         Location/Qualifiers
source                          1..67
                                mol_type = unassigned RNA
                                organism = Homo sapiens
SEQUENCE: 390
cagggaggag gtggtactag gggccagcaa cctgattacc cctctttggc cctttgtacc    60
cctccag                                                              67

SEQ ID NO: 391                  moltype = RNA   length = 59
FEATURE                         Location/Qualifiers
source                          1..59
                                mol_type = unassigned RNA
                                organism = Homo sapiens
SEQUENCE: 391
cggggtcggc ggcgacgtgc tcagcttggc acccaagttc tgccgctccg acgcccggc     59

SEQ ID NO: 392                  moltype = RNA   length = 89
FEATURE                         Location/Qualifiers
source                          1..89
                                mol_type = unassigned RNA
                                organism = Homo sapiens
SEQUENCE: 392
gccggcgccc gagctctggc tccgtgtctt cactcccgtg cttgtccgag gagggaggga    60
gggacggggg ctgtgctggg gcagctgga                                      89

SEQ ID NO: 393                  moltype = RNA   length = 70
```

```
FEATURE                 Location/Qualifiers
source                  1..70
                        mol_type = unassigned RNA
                        organism = Homo sapiens
SEQUENCE: 393
ggtttctcct tgaggagaca tggtggggc cggtcaggca gcccatgcca tgtgtcctca    60
tggagaggcc                                                          70

SEQ ID NO: 394          moltype = RNA  length = 83
FEATURE                 Location/Qualifiers
source                  1..83
                        mol_type = unassigned RNA
                        organism = Homo sapiens
SEQUENCE: 394
gtctactccc agggtgccaa gctgtttcgt gttccctccc tagggatcc caggtagggg    60
cagcagagga cctgggcctg gac                                           83

SEQ ID NO: 395          moltype = RNA  length = 86
FEATURE                 Location/Qualifiers
source                  1..86
                        mol_type = unassigned RNA
                        organism = Homo sapiens
SEQUENCE: 395
tgccagtctc taggtccctg agacccttta acctgtgagg acatccaggg tcacaggtga    60
ggttcttggg agcctggcgt ctggcc                                         86

SEQ ID NO: 396          moltype = RNA  length = 97
FEATURE                 Location/Qualifiers
source                  1..97
                        mol_type = unassigned RNA
                        organism = Homo sapiens
SEQUENCE: 396
ctcaggtgct ctggctgctt gggttcctgg catgctgatt tgtgacttaa gattaaaatc    60
acattgccag ggattaccac gcaaccacga ccttggc                             97

SEQ ID NO: 397          moltype = RNA  length = 90
FEATURE                 Location/Qualifiers
source                  1..90
                        mol_type = unassigned RNA
                        organism = Homo sapiens
SEQUENCE: 397
tctaagaaac gcagtggtct ctgaagcctg caggggcagg ccagccctgc actgaacgcc    60
tgttcttgcc aggtggcaga aggttgctgc                                     90

SEQ ID NO: 398          moltype = RNA  length = 80
FEATURE                 Location/Qualifiers
source                  1..80
                        mol_type = unassigned RNA
                        organism = Homo sapiens
SEQUENCE: 398
acctctacct cccggcagag gaggctgcag aggctggctt tccaaaactc tgcccctcc    60
gctgctgcca agtggctggt                                               80

SEQ ID NO: 399          moltype = RNA  length = 89
FEATURE                 Location/Qualifiers
source                  1..89
                        mol_type = unassigned RNA
                        organism = Homo sapiens
SEQUENCE: 399
gtcagcagtg ccttagcagc acgtaaatat tggcgttaag attctaaaat tatctccagt    60
attaactgtg ctgctgaagt aaggttgac                                      89

SEQ ID NO: 400          moltype = RNA  length = 81
FEATURE                 Location/Qualifiers
source                  1..81
                        mol_type = unassigned RNA
                        organism = Homo sapiens
SEQUENCE: 400
gttccactct agcagcacgt aaatattggc gtagtgaaat atatattaaa caccaatatt    60
actgtgctgc tttagtgtga c                                              81

SEQ ID NO: 401          moltype = RNA  length = 73
FEATURE                 Location/Qualifiers
source                  1..73
                        mol_type = unassigned RNA
                        organism = Homo sapiens
SEQUENCE: 401
cccagggtct ggtgcggaga gggcccacag tggacttggt gacgctgtat gccctcaccg    60
ctcagcccct ggg                                                       73
```

```
SEQ ID NO: 402          moltype = RNA   length = 68
FEATURE                 Location/Qualifiers
source                  1..68
                        mol_type = unassigned RNA
                        organism = Homo sapiens
SEQUENCE: 402
gcatcctgta ctgagctgcc ccgaggccct tcatgctgcc cagctcgggg cagctcagta    60
caggatac                                                             68

SEQ ID NO: 403          moltype = RNA   length = 64
FEATURE                 Location/Qualifiers
source                  1..64
                        mol_type = unassigned RNA
                        organism = Homo sapiens
SEQUENCE: 403
tcctgtactg agctgccccg agctgggcag catgaagggc ctcggggcag ctcagtacag    60
gatg                                                                 64

SEQ ID NO: 404          moltype = RNA   length = 66
FEATURE                 Location/Qualifiers
source                  1..66
                        mol_type = unassigned RNA
                        organism = Homo sapiens
SEQUENCE: 404
tcaagacggg gagtcaggca gtggtggaga tggagagccc tgagcctcca ctctcctggc    60
ccccag                                                               66

SEQ ID NO: 405          moltype = RNA   length = 89
FEATURE                 Location/Qualifiers
source                  1..89
                        mol_type = unassigned RNA
                        organism = Homo sapiens
SEQUENCE: 405
acctccggga cggctgggcg ccggcggccg ggagatccgc gcttcctgaa tcccggccgg    60
cccgcccggc gcccgtccgc ccgcgggtc                                      89

SEQ ID NO: 406          moltype = RNA   length = 80
FEATURE                 Location/Qualifiers
source                  1..80
                        mol_type = unassigned RNA
                        organism = Homo sapiens
SEQUENCE: 406
aggacccttc cagagggccc ccctcaatc ctgttgtgcc taattcagag ggttgggtgg     60
aggctctcct gaagggctct                                                80

SEQ ID NO: 407          moltype = RNA   length = 64
FEATURE                 Location/Qualifiers
source                  1..64
                        mol_type = unassigned RNA
                        organism = Homo sapiens
SEQUENCE: 407
gaaggcgagg ggtagaagag cacaggggtt ctgataaacc cttctgcctg cattctactc    60
ccag                                                                 64

SEQ ID NO: 408          moltype = RNA   length = 70
FEATURE                 Location/Qualifiers
source                  1..70
                        mol_type = unassigned RNA
                        organism = Homo sapiens
SEQUENCE: 408
ccctgccagt gctgggggcc acatgagtgt gcagtcatcc acacacaagt ggcccccaac    60
actggcaggg                                                           70

SEQ ID NO: 409          moltype = RNA   length = 59
FEATURE                 Location/Qualifiers
source                  1..59
                        mol_type = unassigned RNA
                        organism = Homo sapiens
SEQUENCE: 409
ctgtgtcggg gagtctgggg tccggaattc tccagagcct ctgtgcccct acttcccag     59

SEQ ID NO: 410          moltype = RNA   length = 113
FEATURE                 Location/Qualifiers
source                  1..113
                        mol_type = unassigned RNA
                        organism = Homo sapiens
SEQUENCE: 410
gccgggtggg gcggggcggc ctcaggaggg gcccagctcc cctggatgtg ctgcggtggg    60
```

```
gccggagggg cgtcacgtgc acccaagtga cgccccttct gattctgcct cag          113

SEQ ID NO: 411         moltype = RNA   length = 78
FEATURE                Location/Qualifiers
source                 1..78
                       mol_type = unassigned RNA
                       organism = Homo sapiens
SEQUENCE: 411
ctttctacac aggttgggat cggttgcaat gctgtgtttc tgtatggtat tgcacttgtc   60
ccggcctgtt gagtttgg                                                 78

SEQ ID NO: 412         moltype = RNA   length = 76
FEATURE                Location/Qualifiers
source                 1..76
                       mol_type = unassigned RNA
                       organism = Homo sapiens
SEQUENCE: 412
ccgatgcctc gggagtctac agcagggcca tgtctgtgag ggcccaaggg tgcatgtgtc   60
tcccaggttt cggtgc                                                   76

SEQ ID NO: 413         moltype = RNA   length = 92
FEATURE                Location/Qualifiers
source                 1..92
                       mol_type = unassigned RNA
                       organism = Homo sapiens
SEQUENCE: 413
cctgtccctc ctgccctgcg cctgcccagc cctcctgctc tggtgactga ggaccgccag   60
gcaggggctg gtgctgggcg gggggcggcg gg                                 92

SEQ ID NO: 414         moltype = RNA   length = 113
FEATURE                Location/Qualifiers
source                 1..113
                       mol_type = unassigned RNA
                       organism = Homo sapiens
SEQUENCE: 414
agcatgacag aggagaggtg gaggtaggcg agagtaatat aatttctcca ggagaacatc   60
tgagagggga agttgctttc ctgccctggc cctttcaccc tcctgagttt ggg          113

SEQ ID NO: 415         moltype = RNA   length = 93
FEATURE                Location/Qualifiers
source                 1..93
                       mol_type = unassigned RNA
                       organism = Homo sapiens
SEQUENCE: 415
ccttccggcg tcccaggcgg ggcgccgcgg gaccgccctc gtgtctgtgg cggtgggatc   60
ccgcggccgt gttttcctgg tggcccggcc atg                                93

SEQ ID NO: 416         moltype = RNA   length = 80
FEATURE                Location/Qualifiers
source                 1..80
                       mol_type = unassigned RNA
                       organism = Homo sapiens
SEQUENCE: 416
ggcgcgtcgc ccccctcagt ccaccagagc ccggatacct cagaaattcg gctctgggtc   60
tgtggggagc gaaatgcaac                                               80

SEQ ID NO: 417         moltype = RNA   length = 66
FEATURE                Location/Qualifiers
source                 1..66
                       mol_type = unassigned RNA
                       organism = Homo sapiens
SEQUENCE: 417
tgactgggga gcagaaggag aacccaagaa aagctgactt ggaggtccct ccttctgtcc   60
ccacag                                                              66

SEQ ID NO: 418         moltype = RNA   length = 60
FEATURE                Location/Qualifiers
source                 1..60
                       mol_type = unassigned RNA
                       organism = Homo sapiens
SEQUENCE: 418
cgctgggtcc gcgcgccctg ggccgggcga tgtccgcttg ggggagcgag gggcggggcg   60

SEQ ID NO: 419         moltype = RNA   length = 76
FEATURE                Location/Qualifiers
source                 1..76
                       mol_type = unassigned RNA
                       organism = Homo sapiens
SEQUENCE: 419
```

```
cgcaggcctc tggcggagcc cattccatgc cagatgctga gcgatggctg gtgtgtgctg    60
ctccacaggc ctggtg                                                    76

SEQ ID NO: 420          moltype = RNA   length = 65
FEATURE                 Location/Qualifiers
source                  1..65
                        mol_type = unassigned RNA
                        organism = Homo sapiens
SEQUENCE: 420
gcttctggga ggaggggatc ttgggagtga tcccaacagc tgagctccct gaatccctgt    60
cccag                                                                65

SEQ ID NO: 421          moltype = RNA   length = 64
FEATURE                 Location/Qualifiers
source                  1..64
                        mol_type = unassigned RNA
                        organism = Homo sapiens
SEQUENCE: 421
gggtggggc ggggcggcag gggcctcccc cagtgccagg ccccattctg cttctctccc     60
agct                                                                 64

SEQ ID NO: 422          moltype = RNA   length = 72
FEATURE                 Location/Qualifiers
source                  1..72
                        mol_type = unassigned RNA
                        organism = Homo sapiens
SEQUENCE: 422
ctgtgcacct gggggagtgc agtgattgtg gaatgcaaag tcccacaatc actgtactcc    60
ccaggtgcac ag                                                        72

SEQ ID NO: 423          moltype = RNA   length = 49
FEATURE                 Location/Qualifiers
source                  1..49
                        mol_type = unassigned RNA
                        organism = Homo sapiens
SEQUENCE: 423
ggtgaggcgg gggggcgagc cctgaggggc tctcgcttct ggcgccaag               49

SEQ ID NO: 424          moltype = RNA   length = 81
FEATURE                 Location/Qualifiers
source                  1..81
                        mol_type = unassigned RNA
                        organism = Homo sapiens
SEQUENCE: 424
tacaggtgca ggggaactgt agatgaaaag gcttggcact tgagggaaag cctcagttca    60
ttctcatttt gctcacctgt t                                              81

SEQ ID NO: 425          moltype = RNA   length = 66
FEATURE                 Location/Qualifiers
source                  1..66
                        mol_type = unassigned RNA
                        organism = Homo sapiens
SEQUENCE: 425
cagagcaggg cagggaaggt gggagagggg cccagctgac cctcctgtca cccgctcctt    60
gcccag                                                               66

SEQ ID NO: 426          moltype = RNA   length = 24
FEATURE                 Location/Qualifiers
source                  1..24
                        mol_type = unassigned RNA
                        organism = Homo sapiens
SEQUENCE: 426
gaggctggga aggcaaaggg acgt                                           24

SEQ ID NO: 427          moltype = RNA   length = 15
FEATURE                 Location/Qualifiers
source                  1..15
                        mol_type = unassigned RNA
                        organism = Homo sapiens
SEQUENCE: 427
gaaggaggct gggaa                                                     15

SEQ ID NO: 428          moltype = RNA   length = 22
FEATURE                 Location/Qualifiers
source                  1..22
                        mol_type = unassigned RNA
                        organism = Homo sapiens
SEQUENCE: 428
ccgggaacgt cgagactgga gc                                             22
```

```
SEQ ID NO: 429          moltype = RNA  length = 15
FEATURE                 Location/Qualifiers
source                  1..15
                        mol_type = unassigned RNA
                        organism = Homo sapiens
SEQUENCE: 429
cgggaacgtc gagac                                                      15

SEQ ID NO: 430          moltype = RNA  length = 26
FEATURE                 Location/Qualifiers
source                  1..26
                        mol_type = unassigned RNA
                        organism = Homo sapiens
SEQUENCE: 430
ccttctggag aggctttgtg cggata                                          26

SEQ ID NO: 431          moltype = RNA  length = 15
FEATURE                 Location/Qualifiers
source                  1..15
                        mol_type = unassigned RNA
                        organism = Homo sapiens
SEQUENCE: 431
ccttctggag aggct                                                      15

SEQ ID NO: 432          moltype = RNA  length = 23
FEATURE                 Location/Qualifiers
source                  1..23
                        mol_type = unassigned RNA
                        organism = Homo sapiens
SEQUENCE: 432
ctcctggggc ccgcactctc gct                                             23

SEQ ID NO: 433          moltype = RNA  length = 18
FEATURE                 Location/Qualifiers
source                  1..18
                        mol_type = unassigned RNA
                        organism = Homo sapiens
SEQUENCE: 433
ctcctggggc ccgcactc                                                   18

SEQ ID NO: 434          moltype = RNA  length = 23
FEATURE                 Location/Qualifiers
source                  1..23
                        mol_type = unassigned RNA
                        organism = Homo sapiens
SEQUENCE: 434
agaagaaggc ggtcggtctg cgg                                             23

SEQ ID NO: 435          moltype = RNA  length = 21
FEATURE                 Location/Qualifiers
source                  1..21
                        mol_type = unassigned RNA
                        organism = Homo sapiens
SEQUENCE: 435
aagaaggcgg tcggtctgcg g                                               21

SEQ ID NO: 436          moltype = RNA  length = 21
FEATURE                 Location/Qualifiers
source                  1..21
                        mol_type = unassigned RNA
                        organism = Homo sapiens
SEQUENCE: 436
cccaggctgg agcgagtgca g                                               21

SEQ ID NO: 437          moltype = RNA  length = 15
FEATURE                 Location/Qualifiers
source                  1..15
                        mol_type = unassigned RNA
                        organism = Homo sapiens
SEQUENCE: 437
agctcactgc agcct                                                      15

SEQ ID NO: 438          moltype = RNA  length = 22
FEATURE                 Location/Qualifiers
source                  1..22
                        mol_type = unassigned RNA
                        organism = Homo sapiens
SEQUENCE: 438
```

```
cgcggcgggg acggcgattg gt                                          22

SEQ ID NO: 439          moltype = RNA   length = 17
FEATURE                 Location/Qualifiers
source                  1..17
                        mol_type = unassigned RNA
                        organism = Homo sapiens
SEQUENCE: 439
cggcggggac ggcgatt                                                17

SEQ ID NO: 440          moltype = RNA   length = 17
FEATURE                 Location/Qualifiers
source                  1..17
                        mol_type = unassigned RNA
                        organism = Homo sapiens
SEQUENCE: 440
ggtgagcgct cgctggc                                                17

SEQ ID NO: 441          moltype = RNA   length = 15
FEATURE                 Location/Qualifiers
source                  1..15
                        mol_type = unassigned RNA
                        organism = Homo sapiens
SEQUENCE: 441
cggtgagcgc tcgct                                                  15

SEQ ID NO: 442          moltype = RNA   length = 18
FEATURE                 Location/Qualifiers
source                  1..18
                        mol_type = unassigned RNA
                        organism = Homo sapiens
SEQUENCE: 442
ggtgggcttc ccggaggg                                               18

SEQ ID NO: 443          moltype = RNA   length = 15
FEATURE                 Location/Qualifiers
source                  1..15
                        mol_type = unassigned RNA
                        organism = Homo sapiens
SEQUENCE: 443
ggtgggcttc ccgga                                                  15

SEQ ID NO: 444          moltype = RNA   length = 24
FEATURE                 Location/Qualifiers
source                  1..24
                        mol_type = unassigned RNA
                        organism = Homo sapiens
SEQUENCE: 444
ctggtacagg cctgggggac aggg                                        24

SEQ ID NO: 445          moltype = RNA   length = 18
FEATURE                 Location/Qualifiers
source                  1..18
                        mol_type = unassigned RNA
                        organism = Homo sapiens
SEQUENCE: 445
ctggtacagg cctggggg                                               18

SEQ ID NO: 446          moltype = RNA   length = 23
FEATURE                 Location/Qualifiers
source                  1..23
                        mol_type = unassigned RNA
                        organism = Homo sapiens
SEQUENCE: 446
acaggagtgg gggtgggaca taa                                         23

SEQ ID NO: 447          moltype = RNA   length = 20
FEATURE                 Location/Qualifiers
source                  1..20
                        mol_type = unassigned RNA
                        organism = Homo sapiens
SEQUENCE: 447
acaggagtgg gggtgggaca                                             20

SEQ ID NO: 448          moltype = RNA   length = 23
FEATURE                 Location/Qualifiers
source                  1..23
                        mol_type = unassigned RNA
                        organism = Homo sapiens
```

-continued

```
SEQUENCE: 448
ctagtggaag aagatggcgg aag                                            23

SEQ ID NO: 449         moltype = RNA   length = 15
FEATURE                Location/Qualifiers
source                 1..15
                       mol_type = unassigned RNA
                       organism = Homo sapiens
SEQUENCE: 449
tagtggaaga agatg                                                     15

SEQ ID NO: 450         moltype = RNA   length = 18
FEATURE                Location/Qualifiers
source                 1..18
                       mol_type = unassigned RNA
                       organism = Homo sapiens
SEQUENCE: 450
tctaggtggg gagactga                                                  18

SEQ ID NO: 451         moltype = RNA   length = 16
FEATURE                Location/Qualifiers
source                 1..16
                       mol_type = unassigned RNA
                       organism = Homo sapiens
SEQUENCE: 451
gtggggagac tgacgg                                                    16

SEQ ID NO: 452         moltype = RNA   length = 23
FEATURE                Location/Qualifiers
source                 1..23
                       mol_type = unassigned RNA
                       organism = Homo sapiens
SEQUENCE: 452
gggggtcccc ggtgctcgga tct                                            23

SEQ ID NO: 453         moltype = RNA   length = 16
FEATURE                Location/Qualifiers
source                 1..16
                       mol_type = unassigned RNA
                       organism = Homo sapiens
SEQUENCE: 453
tcgggagggg cgggag                                                    16

SEQ ID NO: 454         moltype = RNA   length = 16
FEATURE                Location/Qualifiers
source                 1..16
                       mol_type = unassigned RNA
                       organism = Homo sapiens
SEQUENCE: 454
tgctggtgat gctttc                                                    16

SEQ ID NO: 455         moltype = RNA   length = 16
FEATURE                Location/Qualifiers
source                 1..16
                       mol_type = unassigned RNA
                       organism = Homo sapiens
SEQUENCE: 455
tgctggtgat gctttc                                                    16

SEQ ID NO: 456         moltype = RNA   length = 23
FEATURE                Location/Qualifiers
source                 1..23
                       mol_type = unassigned RNA
                       organism = Homo sapiens
SEQUENCE: 456
ggctacaaca caggacccgg gcg                                            23

SEQ ID NO: 457         moltype = RNA   length = 21
FEATURE                Location/Qualifiers
source                 1..21
                       mol_type = unassigned RNA
                       organism = Homo sapiens
SEQUENCE: 457
ggctacaaca caggacccgg g                                              21

SEQ ID NO: 458         moltype = RNA   length = 23
FEATURE                Location/Qualifiers
source                 1..23
                       mol_type = unassigned RNA
```

```
                                organism = Homo sapiens
SEQUENCE: 458
cggggccgta gcactgtctg aga                                                     23

SEQ ID NO: 459              moltype = RNA  length = 20
FEATURE                     Location/Qualifiers
source                      1..20
                            mol_type = unassigned RNA
                            organism = Homo sapiens
SEQUENCE: 459
cggggccgta gcactgtctg                                                         20

SEQ ID NO: 460              moltype = RNA  length = 17
FEATURE                     Location/Qualifiers
source                      1..17
                            mol_type = unassigned RNA
                            organism = Homo sapiens
SEQUENCE: 460
tcctagtcac ggcacca                                                            17

SEQ ID NO: 461              moltype = RNA  length = 17
FEATURE                     Location/Qualifiers
source                      1..17
                            mol_type = unassigned RNA
                            organism = Homo sapiens
SEQUENCE: 461
tcctagtcac ggcacca                                                            17

SEQ ID NO: 462              moltype = RNA  length = 19
FEATURE                     Location/Qualifiers
source                      1..19
                            mol_type = unassigned RNA
                            organism = Homo sapiens
SEQUENCE: 462
agtgggaggc cagggcacg                                                          19

SEQ ID NO: 463              moltype = RNA  length = 15
FEATURE                     Location/Qualifiers
source                      1..15
                            mol_type = unassigned RNA
                            organism = Homo sapiens
SEQUENCE: 463
aggggagct gcagg                                                               15

SEQ ID NO: 464              moltype = RNA  length = 25
FEATURE                     Location/Qualifiers
source                      1..25
                            mol_type = unassigned RNA
                            organism = Homo sapiens
SEQUENCE: 464
tggcggcggt agttatgggc ttctc                                                   25

SEQ ID NO: 465              moltype = RNA  length = 25
FEATURE                     Location/Qualifiers
source                      1..25
                            mol_type = unassigned RNA
                            organism = Homo sapiens
SEQUENCE: 465
tggcggcggt agttatgggc ttctc                                                   25

SEQ ID NO: 466              moltype = RNA  length = 15
FEATURE                     Location/Qualifiers
source                      1..15
                            mol_type = unassigned RNA
                            organism = Homo sapiens
SEQUENCE: 466
tgaagcgggg gggcg                                                              15

SEQ ID NO: 467              moltype = RNA  length = 15
FEATURE                     Location/Qualifiers
source                      1..15
                            mol_type = unassigned RNA
                            organism = Homo sapiens
SEQUENCE: 467
tgaagcgggg gggcg                                                              15

SEQ ID NO: 468              moltype = RNA  length = 21
FEATURE                     Location/Qualifiers
source                      1..21
```

```
                          mol_type = unassigned RNA
                          organism = Homo sapiens
SEQUENCE: 468
atccagttct ctgaggggc t                                          21

SEQ ID NO: 469            moltype = RNA   length = 21
FEATURE                   Location/Qualifiers
source                    1..21
                          mol_type = unassigned RNA
                          organism = Homo sapiens
SEQUENCE: 469
atccagttct ctgaggggc t                                          21

SEQ ID NO: 470            moltype = RNA   length = 21
FEATURE                   Location/Qualifiers
source                    1..21
                          mol_type = unassigned RNA
                          organism = Homo sapiens
SEQUENCE: 470
cggatccgag tcacggcacc a                                         21

SEQ ID NO: 471            moltype = RNA   length = 15
FEATURE                   Location/Qualifiers
source                    1..15
                          mol_type = unassigned RNA
                          organism = Homo sapiens
SEQUENCE: 471
ggatccgagt cacgg                                                15

SEQ ID NO: 472            moltype = RNA   length = 25
FEATURE                   Location/Qualifiers
source                    1..25
                          mol_type = unassigned RNA
                          organism = Homo sapiens
SEQUENCE: 472
ttctgggccc gcggcgggcg tgggg                                     25

SEQ ID NO: 473            moltype = RNA   length = 15
FEATURE                   Location/Qualifiers
source                    1..15
                          mol_type = unassigned RNA
                          organism = Homo sapiens
SEQUENCE: 473
cgcggcgggc gtggg                                                15

SEQ ID NO: 474            moltype = RNA   length = 23
FEATURE                   Location/Qualifiers
source                    1..23
                          mol_type = unassigned RNA
                          organism = Homo sapiens
SEQUENCE: 474
agggtcgggg cagggagggc agg                                       23

SEQ ID NO: 475            moltype = RNA   length = 15
FEATURE                   Location/Qualifiers
source                    1..15
                          mol_type = unassigned RNA
                          organism = Homo sapiens
SEQUENCE: 475
gggagaaggg tcggg                                                15

SEQ ID NO: 476            moltype = RNA   length = 23
FEATURE                   Location/Qualifiers
source                    1..23
                          mol_type = unassigned RNA
                          organism = Homo sapiens
SEQUENCE: 476
tgaggatatg gcagggaagg gga                                       23

SEQ ID NO: 477            moltype = RNA   length = 19
FEATURE                   Location/Qualifiers
source                    1..19
                          mol_type = unassigned RNA
                          organism = Homo sapiens
SEQUENCE: 477
tgaggatatg gcagggaag                                            19

SEQ ID NO: 478            moltype = RNA   length = 25
FEATURE                   Location/Qualifiers
```

```
source                  1..25
                        mol_type = unassigned RNA
                        organism = Homo sapiens
SEQUENCE: 478
tgggcagggg cttattgtag gagtc                                          25

SEQ ID NO: 479          moltype = RNA   length = 19
FEATURE                 Location/Qualifiers
source                  1..19
                        mol_type = unassigned RNA
                        organism = Homo sapiens
SEQUENCE: 479
tgggcagggg cttattgta                                                 19

SEQ ID NO: 480          moltype = RNA   length = 22
FEATURE                 Location/Qualifiers
source                  1..22
                        mol_type = unassigned RNA
                        organism = Homo sapiens
SEQUENCE: 480
caggcacggg agctcaggtg ag                                             22

SEQ ID NO: 481          moltype = RNA   length = 17
FEATURE                 Location/Qualifiers
source                  1..17
                        mol_type = unassigned RNA
                        organism = Homo sapiens
SEQUENCE: 481
caggcacggg agctcag                                                   17

SEQ ID NO: 482          moltype = RNA   length = 24
FEATURE                 Location/Qualifiers
source                  1..24
                        mol_type = unassigned RNA
                        organism = Homo sapiens
SEQUENCE: 482
tggggagctg aggctctggg ggtg                                           24

SEQ ID NO: 483          moltype = RNA   length = 15
FEATURE                 Location/Qualifiers
source                  1..15
                        mol_type = unassigned RNA
                        organism = Homo sapiens
SEQUENCE: 483
ggccctgggg agctg                                                     15

SEQ ID NO: 484          moltype = RNA   length = 23
FEATURE                 Location/Qualifiers
source                  1..23
                        mol_type = unassigned RNA
                        organism = Homo sapiens
SEQUENCE: 484
aggagggtc ccgcactggg agg                                             23

SEQ ID NO: 485          moltype = RNA   length = 15
FEATURE                 Location/Qualifiers
source                  1..15
                        mol_type = unassigned RNA
                        organism = Homo sapiens
SEQUENCE: 485
tgggaggggc cctca                                                     15

SEQ ID NO: 486          moltype = RNA   length = 23
FEATURE                 Location/Qualifiers
source                  1..23
                        mol_type = unassigned RNA
                        organism = Homo sapiens
SEQUENCE: 486
ggtgggtgag gtcgggcccc aag                                            23

SEQ ID NO: 487          moltype = RNA   length = 20
FEATURE                 Location/Qualifiers
source                  1..20
                        mol_type = unassigned RNA
                        organism = Homo sapiens
SEQUENCE: 487
cggggtgggt gaggtcgggc                                                20

SEQ ID NO: 488          moltype = RNA   length = 21
```

```
                           -continued

FEATURE                 Location/Qualifiers
source                  1..21
                        mol_type = unassigned RNA
                        organism = Homo sapiens
SEQUENCE: 488
aggaggcagt gggcgagcag g                                              21

SEQ ID NO: 489          moltype = RNA   length = 21
FEATURE                 Location/Qualifiers
source                  1..21
                        mol_type = unassigned RNA
                        organism = Homo sapiens
SEQUENCE: 489
aggaggcagt gggcgagcag g                                              21

SEQ ID NO: 490          moltype = RNA   length = 22
FEATURE                 Location/Qualifiers
source                  1..22
                        mol_type = unassigned RNA
                        organism = Homo sapiens
SEQUENCE: 490
cctcacacct gcctcgcccc cc                                             22

SEQ ID NO: 491          moltype = RNA   length = 15
FEATURE                 Location/Qualifiers
source                  1..15
                        mol_type = unassigned RNA
                        organism = Homo sapiens
SEQUENCE: 491
tcacacctgc ctcgc                                                     15

SEQ ID NO: 492          moltype = RNA   length = 20
FEATURE                 Location/Qualifiers
source                  1..20
                        mol_type = unassigned RNA
                        organism = Homo sapiens
SEQUENCE: 492
aagacacatt tggagaggga                                                20

SEQ ID NO: 493          moltype = RNA   length = 16
FEATURE                 Location/Qualifiers
source                  1..16
                        mol_type = unassigned RNA
                        organism = Homo sapiens
SEQUENCE: 493
agacacattt ggagag                                                    16

SEQ ID NO: 494          moltype = RNA   length = 23
FEATURE                 Location/Qualifiers
source                  1..23
                        mol_type = unassigned RNA
                        organism = Homo sapiens
SEQUENCE: 494
gtgggctggg ctgggctggg cca                                            23

SEQ ID NO: 495          moltype = RNA   length = 15
FEATURE                 Location/Qualifiers
source                  1..15
                        mol_type = unassigned RNA
                        organism = Homo sapiens
SEQUENCE: 495
gggctgggct gggct                                                     15

SEQ ID NO: 496          moltype = RNA   length = 24
FEATURE                 Location/Qualifiers
source                  1..24
                        mol_type = unassigned RNA
                        organism = Homo sapiens
SEQUENCE: 496
tcgaggactg gtggaagggc cttt                                           24

SEQ ID NO: 497          moltype = RNA   length = 16
FEATURE                 Location/Qualifiers
source                  1..16
                        mol_type = unassigned RNA
                        organism = Homo sapiens
SEQUENCE: 497
tcgaggactg gtggaa                                                    16
```

| | | |
|---|---|---|
| SEQ ID NO: 498 | moltype = RNA length = 27 | |
| FEATURE | Location/Qualifiers | |
| source | 1..27 | |
| | mol_type = unassigned RNA | |
| | organism = Homo sapiens | |
| SEQUENCE: 498 | | |
| atcacattgc cagggatttc caaccga | | 27 |
| | | |
| SEQ ID NO: 499 | moltype = RNA length = 15 | |
| FEATURE | Location/Qualifiers | |
| source | 1..15 | |
| | mol_type = unassigned RNA | |
| | organism = Homo sapiens | |
| SEQUENCE: 499 | | |
| aatcacattg ccagg | | 15 |
| | | |
| SEQ ID NO: 500 | moltype = RNA length = 22 | |
| FEATURE | Location/Qualifiers | |
| source | 1..22 | |
| | mol_type = unassigned RNA | |
| | organism = Homo sapiens | |
| SEQUENCE: 500 | | |
| cagaagggga gttgggagca ga | | 22 |
| | | |
| SEQ ID NO: 501 | moltype = RNA length = 16 | |
| FEATURE | Location/Qualifiers | |
| source | 1..16 | |
| | mol_type = unassigned RNA | |
| | organism = Homo sapiens | |
| SEQUENCE: 501 | | |
| gaagggagt tgggag | | 16 |
| | | |
| SEQ ID NO: 502 | moltype = RNA length = 25 | |
| FEATURE | Location/Qualifiers | |
| source | 1..25 | |
| | mol_type = unassigned RNA | |
| | organism = Homo sapiens | |
| SEQUENCE: 502 | | |
| gggggagcca tgagataaga gcacc | | 25 |
| | | |
| SEQ ID NO: 503 | moltype = RNA length = 20 | |
| FEATURE | Location/Qualifiers | |
| source | 1..20 | |
| | mol_type = unassigned RNA | |
| | organism = Homo sapiens | |
| SEQUENCE: 503 | | |
| tggggagcc atgagataag | | 20 |
| | | |
| SEQ ID NO: 504 | moltype = RNA length = 24 | |
| FEATURE | Location/Qualifiers | |
| source | 1..24 | |
| | mol_type = unassigned RNA | |
| | organism = Homo sapiens | |
| SEQUENCE: 504 | | |
| gctgcgggct gcggtcaggg cgat | | 24 |
| | | |
| SEQ ID NO: 505 | moltype = RNA length = 20 | |
| FEATURE | Location/Qualifiers | |
| source | 1..20 | |
| | mol_type = unassigned RNA | |
| | organism = Homo sapiens | |
| SEQUENCE: 505 | | |
| gctgcgggct gcggtcaggg | | 20 |
| | | |
| SEQ ID NO: 506 | moltype = RNA length = 20 | |
| FEATURE | Location/Qualifiers | |
| source | 1..20 | |
| | mol_type = unassigned RNA | |
| | organism = Homo sapiens | |
| SEQUENCE: 506 | | |
| ctccccggtg tgcaaatgtg | | 20 |
| | | |
| SEQ ID NO: 507 | moltype = RNA length = 15 | |
| FEATURE | Location/Qualifiers | |
| source | 1..15 | |
| | mol_type = unassigned RNA | |
| | organism = Homo sapiens | |
| SEQUENCE: 507 | | |
| gtgtgcggtg ttatg | | 15 |

```
SEQ ID NO: 508          moltype = RNA   length = 25
FEATURE                 Location/Qualifiers
source                  1..25
                        mol_type = unassigned RNA
                        organism = Homo sapiens
SEQUENCE: 508
caggaaggat ttagggacag gcttt                                               25

SEQ ID NO: 509          moltype = RNA   length = 19
FEATURE                 Location/Qualifiers
source                  1..19
                        mol_type = unassigned RNA
                        organism = Homo sapiens
SEQUENCE: 509
caggaaggat ttagggaca                                                      19

SEQ ID NO: 510          moltype = RNA   length = 30
FEATURE                 Location/Qualifiers
source                  1..30
                        mol_type = unassigned RNA
                        organism = Homo sapiens
SEQUENCE: 510
tgaggggcag agagcgagac ttttctattt                                          30

SEQ ID NO: 511          moltype = RNA   length = 15
FEATURE                 Location/Qualifiers
source                  1..15
                        mol_type = unassigned RNA
                        organism = Homo sapiens
SEQUENCE: 511
tgaggggcag agagc                                                          15

SEQ ID NO: 512          moltype = RNA   length = 26
FEATURE                 Location/Qualifiers
source                  1..26
                        mol_type = unassigned RNA
                        organism = Homo sapiens
SEQUENCE: 512
aggagggagg agatgggcca agttcc                                              26

SEQ ID NO: 513          moltype = RNA   length = 15
FEATURE                 Location/Qualifiers
source                  1..15
                        mol_type = unassigned RNA
                        organism = Homo sapiens
SEQUENCE: 513
gggaggaggg aggag                                                          15

SEQ ID NO: 514          moltype = RNA   length = 21
FEATURE                 Location/Qualifiers
source                  1..21
                        mol_type = unassigned RNA
                        organism = Homo sapiens
SEQUENCE: 514
caactctgat ctcttcatct a                                                   21

SEQ ID NO: 515          moltype = RNA   length = 20
FEATURE                 Location/Qualifiers
source                  1..20
                        mol_type = unassigned RNA
                        organism = Homo sapiens
SEQUENCE: 515
tctcttcatc tacccccag                                                      20

SEQ ID NO: 516          moltype = RNA   length = 27
FEATURE                 Location/Qualifiers
source                  1..27
                        mol_type = unassigned RNA
                        organism = Homo sapiens
SEQUENCE: 516
gtgaacgggc gccatcccga ggctttg                                             27

SEQ ID NO: 517          moltype = RNA   length = 16
FEATURE                 Location/Qualifiers
source                  1..16
                        mol_type = unassigned RNA
                        organism = Homo sapiens
SEQUENCE: 517
```

```
gtgaacgggc gccatc                                                   16

SEQ ID NO: 518         moltype = RNA   length = 26
FEATURE                Location/Qualifiers
source                 1..26
                       mol_type = unassigned RNA
                       organism = Homo sapiens
SEQUENCE: 518
gcgggctgtc cggaggggtc ggcttt                                        26

SEQ ID NO: 519         moltype = RNA   length = 16
FEATURE                Location/Qualifiers
source                 1..16
                       mol_type = unassigned RNA
                       organism = Homo sapiens
SEQUENCE: 519
gctgtccgga ggggtc                                                   16

SEQ ID NO: 520         moltype = RNA   length = 24
FEATURE                Location/Qualifiers
source                 1..24
                       mol_type = unassigned RNA
                       organism = Homo sapiens
SEQUENCE: 520
caggcaggag ccggactgga cctc                                          24

SEQ ID NO: 521         moltype = RNA   length = 21
FEATURE                Location/Qualifiers
source                 1..21
                       mol_type = unassigned RNA
                       organism = Homo sapiens
SEQUENCE: 521
tccaggcagg agccggactg g                                             21

SEQ ID NO: 522         moltype = RNA   length = 25
FEATURE                Location/Qualifiers
source                 1..25
                       mol_type = unassigned RNA
                       organism = Homo sapiens
SEQUENCE: 522
agcggggagg aagtgggcgc tgctt                                         25

SEQ ID NO: 523         moltype = RNA   length = 21
FEATURE                Location/Qualifiers
source                 1..21
                       mol_type = unassigned RNA
                       organism = Homo sapiens
SEQUENCE: 523
agcggggagg aagtgggcgc t                                             21

SEQ ID NO: 524         moltype = RNA   length = 24
FEATURE                Location/Qualifiers
source                 1..24
                       mol_type = unassigned RNA
                       organism = Homo sapiens
SEQUENCE: 524
cgggcgtggt ggtggggtg ggtg                                           24

SEQ ID NO: 525         moltype = RNA   length = 15
FEATURE                Location/Qualifiers
source                 1..15
                       mol_type = unassigned RNA
                       organism = Homo sapiens
SEQUENCE: 525
cgggcgtggt ggtgg                                                    15

SEQ ID NO: 526         moltype = RNA   length = 21
FEATURE                Location/Qualifiers
source                 1..21
                       mol_type = unassigned RNA
                       organism = Homo sapiens
SEQUENCE: 526
gagggcagcg tgggtgtggc g                                             21

SEQ ID NO: 527         moltype = RNA   length = 21
FEATURE                Location/Qualifiers
source                 1..21
                       mol_type = unassigned RNA
                       organism = Homo sapiens
```

```
SEQUENCE: 527
gagggcagcg tgggtgtggc g                                                 21

SEQ ID NO: 528          moltype = RNA   length = 23
FEATURE                 Location/Qualifiers
source                  1..23
                        mol_type = unassigned RNA
                        organism = Homo sapiens
SEQUENCE: 528
ggaggcgcag gctcggaaag gcg                                               23

SEQ ID NO: 529          moltype = RNA   length = 15
FEATURE                 Location/Qualifiers
source                  1..15
                        mol_type = unassigned RNA
                        organism = Homo sapiens
SEQUENCE: 529
gcaggctcgg aaagg                                                        15

SEQ ID NO: 530          moltype = RNA   length = 16
FEATURE                 Location/Qualifiers
source                  1..16
                        mol_type = unassigned RNA
                        organism = Homo sapiens
SEQUENCE: 530
ggacccaggg agagac                                                       16

SEQ ID NO: 531          moltype = RNA   length = 16
FEATURE                 Location/Qualifiers
source                  1..16
                        mol_type = unassigned RNA
                        organism = Homo sapiens
SEQUENCE: 531
ggacccaggg agagac                                                       16

SEQ ID NO: 532          moltype = RNA   length = 22
FEATURE                 Location/Qualifiers
source                  1..22
                        mol_type = unassigned RNA
                        organism = Homo sapiens
SEQUENCE: 532
actcaaactg tggggcact tt                                                 22

SEQ ID NO: 533          moltype = RNA   length = 19
FEATURE                 Location/Qualifiers
source                  1..19
                        mol_type = unassigned RNA
                        organism = Homo sapiens
SEQUENCE: 533
actcaaactg tggggcac                                                     19

SEQ ID NO: 534          moltype = RNA   length = 22
FEATURE                 Location/Qualifiers
source                  1..22
                        mol_type = unassigned RNA
                        organism = Homo sapiens
SEQUENCE: 534
tgtgggactg caaatgggag ct                                                22

SEQ ID NO: 535          moltype = RNA   length = 22
FEATURE                 Location/Qualifiers
source                  1..22
                        mol_type = unassigned RNA
                        organism = Homo sapiens
SEQUENCE: 535
tgtgggactg caaatgggag ct                                                22

SEQ ID NO: 536          moltype = RNA   length = 18
FEATURE                 Location/Qualifiers
source                  1..18
                        mol_type = unassigned RNA
                        organism = Homo sapiens
SEQUENCE: 536
ctccgggcgg cgccgtgt                                                     18

SEQ ID NO: 537          moltype = RNA   length = 18
FEATURE                 Location/Qualifiers
source                  1..18
                        mol_type = unassigned RNA
```

```
                             organism = Homo sapiens
SEQUENCE: 537
ctccgggcgg cgccgtgt                                                      18

SEQ ID NO: 538           moltype = RNA   length = 21
FEATURE                  Location/Qualifiers
source                   1..21
                         mol_type = unassigned RNA
                         organism = Homo sapiens
SEQUENCE: 538
cttcccccca gtaatcttca t                                                  21

SEQ ID NO: 539           moltype = RNA   length = 21
FEATURE                  Location/Qualifiers
source                   1..21
                         mol_type = unassigned RNA
                         organism = Homo sapiens
SEQUENCE: 539
cttcccccca gtaatcttca t                                                  21

SEQ ID NO: 540           moltype = RNA   length = 16
FEATURE                  Location/Qualifiers
source                   1..16
                         mol_type = unassigned RNA
                         organism = Homo sapiens
SEQUENCE: 540
ggcggtgggc ggcggg                                                        16

SEQ ID NO: 541           moltype = RNA   length = 15
FEATURE                  Location/Qualifiers
source                   1..15
                         mol_type = unassigned RNA
                         organism = Homo sapiens
SEQUENCE: 541
ggcctctcgg gaact                                                         15

SEQ ID NO: 542           moltype = RNA   length = 23
FEATURE                  Location/Qualifiers
source                   1..23
                         mol_type = unassigned RNA
                         organism = Homo sapiens
SEQUENCE: 542
tggggaaggc gtcagtgtcg ggt                                                23

SEQ ID NO: 543           moltype = RNA   length = 16
FEATURE                  Location/Qualifiers
source                   1..16
                         mol_type = unassigned RNA
                         organism = Homo sapiens
SEQUENCE: 543
tggggaaggc gtcagt                                                        16

SEQ ID NO: 544           moltype = RNA   length = 21
FEATURE                  Location/Qualifiers
source                   1..21
                         mol_type = unassigned RNA
                         organism = Homo sapiens
SEQUENCE: 544
tgggaatggg ggtaagggcc t                                                  21

SEQ ID NO: 545           moltype = RNA   length = 15
FEATURE                  Location/Qualifiers
source                   1..15
                         mol_type = unassigned RNA
                         organism = Homo sapiens
SEQUENCE: 545
cttctgagcc caggt                                                         15

SEQ ID NO: 546           moltype = RNA   length = 20
FEATURE                  Location/Qualifiers
source                   1..20
                         mol_type = unassigned RNA
                         organism = Homo sapiens
SEQUENCE: 546
ccccagggcg acgcggcggg                                                    20

SEQ ID NO: 547           moltype = RNA   length = 15
FEATURE                  Location/Qualifiers
source                   1..15
```

```
                    mol_type = unassigned RNA
                    organism = Homo sapiens
SEQUENCE: 547
cgcggcgggg gcggc                                                   15

SEQ ID NO: 548      moltype = RNA   length = 25
FEATURE             Location/Qualifiers
source              1..25
                    mol_type = unassigned RNA
                    organism = Homo sapiens
SEQUENCE: 548
aggaagccct ggaggggctg gaggt                                        25

SEQ ID NO: 549      moltype = RNA   length = 15
FEATURE             Location/Qualifiers
source              1..15
                    mol_type = unassigned RNA
                    organism = Homo sapiens
SEQUENCE: 549
aggaagagga ggaag                                                   15

SEQ ID NO: 550      moltype = RNA   length = 19
FEATURE             Location/Qualifiers
source              1..19
                    mol_type = unassigned RNA
                    organism = Homo sapiens
SEQUENCE: 550
tggcgggtgc gggggtggg                                               19

SEQ ID NO: 551      moltype = RNA   length = 15
FEATURE             Location/Qualifiers
source              1..15
                    mol_type = unassigned RNA
                    organism = Homo sapiens
SEQUENCE: 551
tggcgggtgc ggggg                                                   15

SEQ ID NO: 552      moltype = RNA   length = 23
FEATURE             Location/Qualifiers
source              1..23
                    mol_type = unassigned RNA
                    organism = Homo sapiens
SEQUENCE: 552
gccccggcgc gggcgggttc tgg                                          23

SEQ ID NO: 553      moltype = RNA   length = 16
FEATURE             Location/Qualifiers
source              1..16
                    mol_type = unassigned RNA
                    organism = Homo sapiens
SEQUENCE: 553
ggagccccgg cgcggg                                                  16

SEQ ID NO: 554      moltype = RNA   length = 26
FEATURE             Location/Qualifiers
source              1..26
                    mol_type = unassigned RNA
                    organism = Homo sapiens
SEQUENCE: 554
gtcccggggc tgcgcgaggc acaggc                                       26

SEQ ID NO: 555      moltype = RNA   length = 15
FEATURE             Location/Qualifiers
source              1..15
                    mol_type = unassigned RNA
                    organism = Homo sapiens
SEQUENCE: 555
ggcccggggg gcggg                                                   15

SEQ ID NO: 556      moltype = RNA   length = 16
FEATURE             Location/Qualifiers
source              1..16
                    mol_type = unassigned RNA
                    organism = Homo sapiens
SEQUENCE: 556
agctgcagtg ggggag                                                  16

SEQ ID NO: 557      moltype = RNA   length = 15
FEATURE             Location/Qualifiers
```

```
source                  1..15
                        mol_type = unassigned RNA
                        organism = Homo sapiens
SEQUENCE: 557
gctgcagtgg gggag                                                          15

SEQ ID NO: 558          moltype = RNA   length = 15
FEATURE                 Location/Qualifiers
source                  1..15
                        mol_type = unassigned RNA
                        organism = Homo sapiens
SEQUENCE: 558
tctgggcgag gggtg                                                          15

SEQ ID NO: 559          moltype = RNA   length = 15
FEATURE                 Location/Qualifiers
source                  1..15
                        mol_type = unassigned RNA
                        organism = Homo sapiens
SEQUENCE: 559
tctgggcgag gggtg                                                          15

SEQ ID NO: 560          moltype = RNA   length = 25
FEATURE                 Location/Qualifiers
source                  1..25
                        mol_type = unassigned RNA
                        organism = Homo sapiens
SEQUENCE: 560
tgcggggcta gggctaacag cagtc                                               25

SEQ ID NO: 561          moltype = RNA   length = 15
FEATURE                 Location/Qualifiers
source                  1..15
                        mol_type = unassigned RNA
                        organism = Homo sapiens
SEQUENCE: 561
tgcggggcta gggct                                                          15

SEQ ID NO: 562          moltype = RNA   length = 24
FEATURE                 Location/Qualifiers
source                  1..24
                        mol_type = unassigned RNA
                        organism = Homo sapiens
SEQUENCE: 562
agacacattt ggagagggaa cctc                                                24

SEQ ID NO: 563          moltype = RNA   length = 16
FEATURE                 Location/Qualifiers
source                  1..16
                        mol_type = unassigned RNA
                        organism = Homo sapiens
SEQUENCE: 563
agacacattt ggagag                                                         16

SEQ ID NO: 564          moltype = RNA   length = 27
FEATURE                 Location/Qualifiers
source                  1..27
                        mol_type = unassigned RNA
                        organism = Homo sapiens
SEQUENCE: 564
aaaccgttac cattactgag tttagta                                             27

SEQ ID NO: 565          moltype = RNA   length = 15
FEATURE                 Location/Qualifiers
source                  1..15
                        mol_type = unassigned RNA
                        organism = Homo sapiens
SEQUENCE: 565
gaaaccgtta ccatt                                                          15

SEQ ID NO: 566          moltype = RNA   length = 21
FEATURE                 Location/Qualifiers
source                  1..21
                        mol_type = unassigned RNA
                        organism = Homo sapiens
SEQUENCE: 566
gttggaggcg tgggttttag a                                                   21

SEQ ID NO: 567          moltype = RNA   length = 15
```

```
FEATURE                 Location/Qualifiers
source                  1..15
                        mol_type = unassigned RNA
                        organism = Homo sapiens
SEQUENCE: 567
gttggaggcg tgggt                                                        15

SEQ ID NO: 568          moltype = RNA   length = 22
FEATURE                 Location/Qualifiers
source                  1..22
                        mol_type = unassigned RNA
                        organism = Homo sapiens
SEQUENCE: 568
tgggagggga gaggcagcaa gc                                                22

SEQ ID NO: 569          moltype = RNA   length = 22
FEATURE                 Location/Qualifiers
source                  1..22
                        mol_type = unassigned RNA
                        organism = Homo sapiens
SEQUENCE: 569
tgggagggga gaggcagcaa gc                                                22

SEQ ID NO: 570          moltype = RNA   length = 21
FEATURE                 Location/Qualifiers
source                  1..21
                        mol_type = unassigned RNA
                        organism = Homo sapiens
SEQUENCE: 570
gtgagtcagg gtggggctgg c                                                 21

SEQ ID NO: 571          moltype = RNA   length = 21
FEATURE                 Location/Qualifiers
source                  1..21
                        mol_type = unassigned RNA
                        organism = Homo sapiens
SEQUENCE: 571
gtgagtcagg gtggggctgg c                                                 21

SEQ ID NO: 572          moltype = RNA   length = 22
FEATURE                 Location/Qualifiers
source                  1..22
                        mol_type = unassigned RNA
                        organism = Homo sapiens
SEQUENCE: 572
atatagggat tggagccgtg gc                                                22

SEQ ID NO: 573          moltype = RNA   length = 20
FEATURE                 Location/Qualifiers
source                  1..20
                        mol_type = unassigned RNA
                        organism = Homo sapiens
SEQUENCE: 573
atatagggat tggagccgtg                                                   20

SEQ ID NO: 574          moltype = RNA   length = 23
FEATURE                 Location/Qualifiers
source                  1..23
                        mol_type = unassigned RNA
                        organism = Homo sapiens
SEQUENCE: 574
ggcccggccg tgcctgaggt ttc                                               23

SEQ ID NO: 575          moltype = RNA   length = 15
FEATURE                 Location/Qualifiers
source                  1..15
                        mol_type = unassigned RNA
                        organism = Homo sapiens
SEQUENCE: 575
ggcggtggga tcccg                                                        15

SEQ ID NO: 576          moltype = RNA   length = 23
FEATURE                 Location/Qualifiers
source                  1..23
                        mol_type = unassigned RNA
                        organism = Homo sapiens
SEQUENCE: 576
gggggccgat acactgtacg aga                                               23
```

```
SEQ ID NO: 577         moltype = RNA   length = 20
FEATURE                Location/Qualifiers
source                 1..20
                       mol_type = unassigned RNA
                       organism = Homo sapiens
SEQUENCE: 577
gggggccgat acactgtacg                                                   20

SEQ ID NO: 578         moltype = RNA   length = 25
FEATURE                Location/Qualifiers
source                 1..25
                       mol_type = unassigned RNA
                       organism = Homo sapiens
SEQUENCE: 578
ctgggccagg gagcagctgg tgggt                                             25

SEQ ID NO: 579         moltype = RNA   length = 20
FEATURE                Location/Qualifiers
source                 1..20
                       mol_type = unassigned RNA
                       organism = Homo sapiens
SEQUENCE: 579
tgggccaggg agcagctggt                                                   20

SEQ ID NO: 580         moltype = RNA   length = 25
FEATURE                Location/Qualifiers
source                 1..25
                       mol_type = unassigned RNA
                       organism = Homo sapiens
SEQUENCE: 580
gggtggggat ttgttgcatt acttg                                             25

SEQ ID NO: 581         moltype = RNA   length = 20
FEATURE                Location/Qualifiers
source                 1..20
                       mol_type = unassigned RNA
                       organism = Homo sapiens
SEQUENCE: 581
gggtggggat ttgttgcatt                                                   20

SEQ ID NO: 582         moltype = RNA   length = 19
FEATURE                Location/Qualifiers
source                 1..19
                       mol_type = unassigned RNA
                       organism = Homo sapiens
SEQUENCE: 582
gtgggttggg gcgggctct                                                    19

SEQ ID NO: 583         moltype = RNA   length = 19
FEATURE                Location/Qualifiers
source                 1..19
                       mol_type = unassigned RNA
                       organism = Homo sapiens
SEQUENCE: 583
gtgggttggg gcgggctct                                                    19

SEQ ID NO: 584         moltype = RNA   length = 16
FEATURE                Location/Qualifiers
source                 1..16
                       mol_type = unassigned RNA
                       organism = Homo sapiens
SEQUENCE: 584
ctgggggtcc cccgac                                                       16

SEQ ID NO: 585         moltype = RNA   length = 15
FEATURE                Location/Qualifiers
source                 1..15
                       mol_type = unassigned RNA
                       organism = Homo sapiens
SEQUENCE: 585
gtgtggagct ggggc                                                        15

SEQ ID NO: 586         moltype = RNA   length = 20
FEATURE                Location/Qualifiers
source                 1..20
                       mol_type = unassigned RNA
                       organism = Homo sapiens
SEQUENCE: 586
atcccaccac tgccaccatt                                                   20
```

```
SEQ ID NO: 587           moltype = RNA   length = 15
FEATURE                  Location/Qualifiers
source                   1..15
                         mol_type = unassigned RNA
                         organism = Homo sapiens
SEQUENCE: 587
atcccaccac tgcca                                                          15

SEQ ID NO: 588           moltype = RNA   length = 24
FEATURE                  Location/Qualifiers
source                   1..24
                         mol_type = unassigned RNA
                         organism = Homo sapiens
SEQUENCE: 588
gtgagtggga gccggtgggg ctgg                                                24

SEQ ID NO: 589           moltype = RNA   length = 15
FEATURE                  Location/Qualifiers
source                   1..15
                         mol_type = unassigned RNA
                         organism = Homo sapiens
SEQUENCE: 589
ggggctggag taagg                                                          15

SEQ ID NO: 590           moltype = RNA   length = 23
FEATURE                  Location/Qualifiers
source                   1..23
                         mol_type = unassigned RNA
                         organism = Homo sapiens
SEQUENCE: 590
caccttgcct tgctgcccgg gcc                                                 23

SEQ ID NO: 591           moltype = RNA   length = 22
FEATURE                  Location/Qualifiers
source                   1..22
                         mol_type = unassigned RNA
                         organism = Homo sapiens
SEQUENCE: 591
caccttgcct tgctgcccgg gc                                                  22

SEQ ID NO: 592           moltype = RNA   length = 26
FEATURE                  Location/Qualifiers
source                   1..26
                         mol_type = unassigned RNA
                         organism = Homo sapiens
SEQUENCE: 592
agggctggac tcagcggcgg agctgg                                              26

SEQ ID NO: 593           moltype = RNA   length = 17
FEATURE                  Location/Qualifiers
source                   1..17
                         mol_type = unassigned RNA
                         organism = Homo sapiens
SEQUENCE: 593
gcggcggagc tggctgc                                                        17

SEQ ID NO: 594           moltype = RNA   length = 22
FEATURE                  Location/Qualifiers
source                   1..22
                         mol_type = unassigned RNA
                         organism = Homo sapiens
SEQUENCE: 594
accccactcc tggtaccata gt                                                  22

SEQ ID NO: 595           moltype = RNA   length = 15
FEATURE                  Location/Qualifiers
source                   1..15
                         mol_type = unassigned RNA
                         organism = Homo sapiens
SEQUENCE: 595
accccactcc tggta                                                          15

SEQ ID NO: 596           moltype = RNA   length = 16
FEATURE                  Location/Qualifiers
source                   1..16
                         mol_type = unassigned RNA
                         organism = Homo sapiens
SEQUENCE: 596
```

-continued

| | | |
|---|---|---|
| gtgaaggccc ggcgga | | 16 |
| SEQ ID NO: 597<br>FEATURE<br>source<br><br>SEQUENCE: 597 | moltype = RNA  length = 15<br>Location/Qualifiers<br>1..15<br>mol_type = unassigned RNA<br>organism = Homo sapiens | |
| gtgaaggccc ggcgg | | 15 |
| SEQ ID NO: 598<br>FEATURE<br>source<br><br>SEQUENCE: 598 | moltype = RNA  length = 23<br>Location/Qualifiers<br>1..23<br>mol_type = unassigned RNA<br>organism = Homo sapiens | |
| ccaggaggcg gaggaggtgg agg | | 23 |
| SEQ ID NO: 599<br>FEATURE<br>source<br><br>SEQUENCE: 599 | moltype = RNA  length = 15<br>Location/Qualifiers<br>1..15<br>mol_type = unassigned RNA<br>organism = Homo sapiens | |
| acccaggagg cggag | | 15 |
| SEQ ID NO: 600<br>FEATURE<br>source<br><br>SEQUENCE: 600 | moltype = RNA  length = 21<br>Location/Qualifiers<br>1..21<br>mol_type = unassigned RNA<br>organism = Homo sapiens | |
| gccgggcgtg gtggtggggg c | | 21 |
| SEQ ID NO: 601<br>FEATURE<br>source<br><br>SEQUENCE: 601 | moltype = RNA  length = 15<br>Location/Qualifiers<br>1..15<br>mol_type = unassigned RNA<br>organism = Homo sapiens | |
| tagccgggcg tggtg | | 15 |
| SEQ ID NO: 602<br>FEATURE<br>source<br><br>SEQUENCE: 602 | moltype = RNA  length = 20<br>Location/Qualifiers<br>1..20<br>mol_type = unassigned RNA<br>organism = Homo sapiens | |
| ggctggtcag atgggagtgg | | 20 |
| SEQ ID NO: 603<br>FEATURE<br>source<br><br>SEQUENCE: 603 | moltype = RNA  length = 20<br>Location/Qualifiers<br>1..20<br>mol_type = unassigned RNA<br>organism = Homo sapiens | |
| ggctggtcag atgggagtgg | | 20 |
| SEQ ID NO: 604<br>FEATURE<br>source<br><br>SEQUENCE: 604 | moltype = RNA  length = 20<br>Location/Qualifiers<br>1..20<br>mol_type = unassigned RNA<br>organism = Homo sapiens | |
| ccccggggag cccggcggtg | | 20 |
| SEQ ID NO: 605<br>FEATURE<br>source<br><br>SEQUENCE: 605 | moltype = RNA  length = 15<br>Location/Qualifiers<br>1..15<br>mol_type = unassigned RNA<br>organism = Homo sapiens | |
| accccgggga gcccg | | 15 |
| SEQ ID NO: 606<br>FEATURE<br>source | moltype = RNA  length = 15<br>Location/Qualifiers<br>1..15<br>mol_type = unassigned RNA<br>organism = Homo sapiens | |

```
SEQUENCE: 606
ggcggcgggc ccggg                                                        15

SEQ ID NO: 607        moltype = RNA   length = 15
FEATURE               Location/Qualifiers
source                1..15
                      mol_type = unassigned RNA
                      organism = Homo sapiens
SEQUENCE: 607
ggcggcgggc ccggg                                                        15

SEQ ID NO: 608        moltype = RNA   length = 23
FEATURE               Location/Qualifiers
source                1..23
                      mol_type = unassigned RNA
                      organism = Homo sapiens
SEQUENCE: 608
cagcccgccc cagccgaggt tct                                               23

SEQ ID NO: 609        moltype = RNA   length = 17
FEATURE               Location/Qualifiers
source                1..17
                      mol_type = unassigned RNA
                      organism = Homo sapiens
SEQUENCE: 609
agcccgcccc agccgag                                                      17

SEQ ID NO: 610        moltype = RNA   length = 23
FEATURE               Location/Qualifiers
source                1..23
                      mol_type = unassigned RNA
                      organism = Homo sapiens
SEQUENCE: 610
aagggaggag gagcggaggg gcc                                               23

SEQ ID NO: 611        moltype = RNA   length = 15
FEATURE               Location/Qualifiers
source                1..15
                      mol_type = unassigned RNA
                      organism = Homo sapiens
SEQUENCE: 611
gggaggagga gcgga                                                        15

SEQ ID NO: 612        moltype = RNA   length = 23
FEATURE               Location/Qualifiers
source                1..23
                      mol_type = unassigned RNA
                      organism = Homo sapiens
SEQUENCE: 612
gggggatgt gcatgctggt tgg                                                23

SEQ ID NO: 613        moltype = RNA   length = 15
FEATURE               Location/Qualifiers
source                1..15
                      mol_type = unassigned RNA
                      organism = Homo sapiens
SEQUENCE: 613
atcagcgtgc acttc                                                        15

SEQ ID NO: 614        moltype = RNA   length = 20
FEATURE               Location/Qualifiers
source                1..20
                      mol_type = unassigned RNA
                      organism = Homo sapiens
SEQUENCE: 614
atcccacctc tgccaccaaa                                                   20

SEQ ID NO: 615        moltype = RNA   length = 15
FEATURE               Location/Qualifiers
source                1..15
                      mol_type = unassigned RNA
                      organism = Homo sapiens
SEQUENCE: 615
atcccacctc tgcca                                                        15

SEQ ID NO: 616        moltype = RNA   length = 19
FEATURE               Location/Qualifiers
source                1..19
                      mol_type = unassigned RNA
```

```
                          organism = Homo sapiens
SEQUENCE: 616
gctgggcgag gctggcatc                                                19

SEQ ID NO: 617          moltype = RNA  length = 17
FEATURE                 Location/Qualifiers
source                  1..17
                        mol_type = unassigned RNA
                        organism = Homo sapiens
SEQUENCE: 617
gctgggcgag gctggca                                                  17

SEQ ID NO: 618          moltype = RNA  length = 26
FEATURE                 Location/Qualifiers
source                  1..26
                        mol_type = unassigned RNA
                        organism = Homo sapiens
SEQUENCE: 618
agggacggga cgcggtgcag tgttgt                                        26

SEQ ID NO: 619          moltype = RNA  length = 15
FEATURE                 Location/Qualifiers
source                  1..15
                        mol_type = unassigned RNA
                        organism = Homo sapiens
SEQUENCE: 619
ggcgggcggg aggga                                                    15

SEQ ID NO: 620          moltype = RNA  length = 23
FEATURE                 Location/Qualifiers
source                  1..23
                        mol_type = unassigned RNA
                        organism = Homo sapiens
SEQUENCE: 620
gagggaggga cgggggctgt gct                                           23

SEQ ID NO: 621          moltype = RNA  length = 15
FEATURE                 Location/Qualifiers
source                  1..15
                        mol_type = unassigned RNA
                        organism = Homo sapiens
SEQUENCE: 621
gaggagggag ggagg                                                    15

SEQ ID NO: 622          moltype = RNA  length = 21
FEATURE                 Location/Qualifiers
source                  1..21
                        mol_type = unassigned RNA
                        organism = Homo sapiens
SEQUENCE: 622
ttgaggagac atggtggggg c                                             21

SEQ ID NO: 623          moltype = RNA  length = 15
FEATURE                 Location/Qualifiers
source                  1..15
                        mol_type = unassigned RNA
                        organism = Homo sapiens
SEQUENCE: 623
ttgaggagac atggt                                                    15

SEQ ID NO: 624          moltype = RNA  length = 23
FEATURE                 Location/Qualifiers
source                  1..23
                        mol_type = unassigned RNA
                        organism = Homo sapiens
SEQUENCE: 624
tagggcagc agaggacctg ggc                                            23

SEQ ID NO: 625          moltype = RNA  length = 20
FEATURE                 Location/Qualifiers
source                  1..20
                        mol_type = unassigned RNA
                        organism = Homo sapiens
SEQUENCE: 625
tagggcagc agaggacctg                                                20

SEQ ID NO: 626          moltype = RNA  length = 23
FEATURE                 Location/Qualifiers
source                  1..23
```

```
                        mol_type = unassigned RNA
                        organism = Homo sapiens
SEQUENCE: 626
cacaggtgag gttcttggga gcc                                           23

SEQ ID NO: 627          moltype = RNA length = 15
FEATURE                 Location/Qualifiers
source                  1..15
                        mol_type = unassigned RNA
                        organism = Homo sapiens
SEQUENCE: 627
acaggtgagg ttctt                                                    15

SEQ ID NO: 628          moltype = RNA length = 26
FEATURE                 Location/Qualifiers
source                  1..26
                        mol_type = unassigned RNA
                        organism = Homo sapiens
SEQUENCE: 628
aaaatcacat tgccagggat taccac                                        26

SEQ ID NO: 629          moltype = RNA length = 15
FEATURE                 Location/Qualifiers
source                  1..15
                        mol_type = unassigned RNA
                        organism = Homo sapiens
SEQUENCE: 629
aatcacattg ccagg                                                    15

SEQ ID NO: 630          moltype = RNA length = 17
FEATURE                 Location/Qualifiers
source                  1..17
                        mol_type = unassigned RNA
                        organism = Homo sapiens
SEQUENCE: 630
tgcaggggca ggccagc                                                  17

SEQ ID NO: 631          moltype = RNA length = 17
FEATURE                 Location/Qualifiers
source                  1..17
                        mol_type = unassigned RNA
                        organism = Homo sapiens
SEQUENCE: 631
tgcaggggca ggccagc                                                  17

SEQ ID NO: 632          moltype = RNA length = 22
FEATURE                 Location/Qualifiers
source                  1..22
                        mol_type = unassigned RNA
                        organism = Homo sapiens
SEQUENCE: 632
ccggcagagg aggctgcaga gg                                            22

SEQ ID NO: 633          moltype = RNA length = 19
FEATURE                 Location/Qualifiers
source                  1..19
                        mol_type = unassigned RNA
                        organism = Homo sapiens
SEQUENCE: 633
ccggcagagg aggctgcag                                                19

SEQ ID NO: 634          moltype = RNA length = 27
FEATURE                 Location/Qualifiers
source                  1..27
                        mol_type = unassigned RNA
                        organism = Homo sapiens
SEQUENCE: 634
tagcagcacg taaatattgg cgttaag                                       27

SEQ ID NO: 635          moltype = RNA length = 15
FEATURE                 Location/Qualifiers
source                  1..15
                        mol_type = unassigned RNA
                        organism = Homo sapiens
SEQUENCE: 635
tagcagcacg taaat                                                    15

SEQ ID NO: 636          moltype = RNA length = 23
FEATURE                 Location/Qualifiers
```

```
source                  1..23
                        mol_type = unassigned RNA
                        organism = Homo sapiens
SEQUENCE: 636
tggtgcggag agggcccaca gtg                                              23

SEQ ID NO: 637          moltype = RNA   length = 15
FEATURE                 Location/Qualifiers
source                  1..15
                        mol_type = unassigned RNA
                        organism = Homo sapiens
SEQUENCE: 637
gggtctggtg cggag                                                       15

SEQ ID NO: 638          moltype = RNA   length = 23
FEATURE                 Location/Qualifiers
source                  1..23
                        mol_type = unassigned RNA
                        organism = Homo sapiens
SEQUENCE: 638
cggggcagct cagtacagga tac                                              23

SEQ ID NO: 639          moltype = RNA   length = 15
FEATURE                 Location/Qualifiers
source                  1..15
                        mol_type = unassigned RNA
                        organism = Homo sapiens
SEQUENCE: 639
agctcagtac aggat                                                       15

SEQ ID NO: 640          moltype = RNA   length = 17
FEATURE                 Location/Qualifiers
source                  1..17
                        mol_type = unassigned RNA
                        organism = Homo sapiens
SEQUENCE: 640
cctccgggac ggctggg                                                     17

SEQ ID NO: 641          moltype = RNA   length = 15
FEATURE                 Location/Qualifiers
source                  1..15
                        mol_type = unassigned RNA
                        organism = Homo sapiens
SEQUENCE: 641
ctccgggacg gctgg                                                       15

SEQ ID NO: 642          moltype = RNA   length = 22
FEATURE                 Location/Qualifiers
source                  1..22
                        mol_type = unassigned RNA
                        organism = Homo sapiens
SEQUENCE: 642
gagggttggg tggaggctct cc                                               22

SEQ ID NO: 643          moltype = RNA   length = 15
FEATURE                 Location/Qualifiers
source                  1..15
                        mol_type = unassigned RNA
                        organism = Homo sapiens
SEQUENCE: 643
gagggttggg tggag                                                       15

SEQ ID NO: 644          moltype = RNA   length = 21
FEATURE                 Location/Qualifiers
source                  1..21
                        mol_type = unassigned RNA
                        organism = Homo sapiens
SEQUENCE: 644
tgctgggggc cacatgagtg t                                                21

SEQ ID NO: 645          moltype = RNA   length = 20
FEATURE                 Location/Qualifiers
source                  1..20
                        mol_type = unassigned RNA
                        organism = Homo sapiens
SEQUENCE: 645
gctgggggcc acatgagtgt                                                  20

SEQ ID NO: 646          moltype = RNA   length = 28
```

```
FEATURE                 Location/Qualifiers
source                  1..28
                        mol_type = unassigned RNA
                        organism = Homo sapiens
SEQUENCE: 646
gtatggtatt gcacttgtcc cggcctgt                                          28

SEQ ID NO: 647          moltype = RNA   length = 15
FEATURE                 Location/Qualifiers
source                  1..15
                        mol_type = unassigned RNA
                        organism = Homo sapiens
SEQUENCE: 647
tattgcactt gtccc                                                        15

SEQ ID NO: 648          moltype = RNA   length = 24
FEATURE                 Location/Qualifiers
source                  1..24
                        mol_type = unassigned RNA
                        organism = Homo sapiens
SEQUENCE: 648
aggcaggggc tggtgctggg cggg                                              24

SEQ ID NO: 649          moltype = RNA   length = 15
FEATURE                 Location/Qualifiers
source                  1..15
                        mol_type = unassigned RNA
                        organism = Homo sapiens
SEQUENCE: 649
gggcgggggg cggcg                                                        15

SEQ ID NO: 650          moltype = RNA   length = 26
FEATURE                 Location/Qualifiers
source                  1..26
                        mol_type = unassigned RNA
                        organism = Homo sapiens
SEQUENCE: 650
cggtgggatc ccgcggccgt gttttc                                            26

SEQ ID NO: 651          moltype = RNA   length = 15
FEATURE                 Location/Qualifiers
source                  1..15
                        mol_type = unassigned RNA
                        organism = Homo sapiens
SEQUENCE: 651
ggggcgccgc gggac                                                        15

SEQ ID NO: 652          moltype = RNA   length = 23
FEATURE                 Location/Qualifiers
source                  1..23
                        mol_type = unassigned RNA
                        organism = Homo sapiens
SEQUENCE: 652
tcggctctgg gtctgtgggg agc                                               23

SEQ ID NO: 653          moltype = RNA   length = 15
FEATURE                 Location/Qualifiers
source                  1..15
                        mol_type = unassigned RNA
                        organism = Homo sapiens
SEQUENCE: 653
gcccggatac ctcag                                                        15

SEQ ID NO: 654          moltype = RNA   length = 24
FEATURE                 Location/Qualifiers
source                  1..24
                        mol_type = unassigned RNA
                        organism = Homo sapiens
SEQUENCE: 654
tgactgggga gcagaaggag aacc                                              24

SEQ ID NO: 655          moltype = RNA   length = 15
FEATURE                 Location/Qualifiers
source                  1..15
                        mol_type = unassigned RNA
                        organism = Homo sapiens
SEQUENCE: 655
gactggggag cagaa                                                        15
```

| | | |
|---|---|---|
| SEQ ID NO: 656 | moltype = RNA length = 22 | |
| FEATURE | Location/Qualifiers | |
| source | 1..22 | |
| | mol_type = unassigned RNA | |
| | organism = Homo sapiens | |
| SEQUENCE: 656 | | |
| tggcggagcc cattccatgc ca | | 22 |
| | | |
| SEQ ID NO: 657 | moltype = RNA length = 21 | |
| FEATURE | Location/Qualifiers | |
| source | 1..21 | |
| | mol_type = unassigned RNA | |
| | organism = Homo sapiens | |
| SEQUENCE: 657 | | |
| ctggcggagc ccattccatg c | | 21 |
| | | |
| SEQ ID NO: 658 | moltype = RNA length = 17 | |
| FEATURE | Location/Qualifiers | |
| source | 1..17 | |
| | mol_type = unassigned RNA | |
| | organism = Homo sapiens | |
| SEQUENCE: 658 | | |
| gcggggcggc aggggcc | | 17 |
| | | |
| SEQ ID NO: 659 | moltype = RNA length = 15 | |
| FEATURE | Location/Qualifiers | |
| source | 1..15 | |
| | mol_type = unassigned RNA | |
| | organism = Homo sapiens | |
| SEQUENCE: 659 | | |
| gggggcgggg cggca | | 15 |
| | | |
| SEQ ID NO: 660 | moltype = RNA length = 24 | |
| FEATURE | Location/Qualifiers | |
| source | 1..24 | |
| | mol_type = unassigned RNA | |
| | organism = Homo sapiens | |
| SEQUENCE: 660 | | |
| tgggggagtg cagtgattgt ggaa | | 24 |
| | | |
| SEQ ID NO: 661 | moltype = RNA length = 19 | |
| FEATURE | Location/Qualifiers | |
| source | 1..19 | |
| | mol_type = unassigned RNA | |
| | organism = Homo sapiens | |
| SEQUENCE: 661 | | |
| tgggggagtg cagtgattg | | 19 |
| | | |
| SEQ ID NO: 662 | moltype = RNA length = 26 | |
| FEATURE | Location/Qualifiers | |
| source | 1..26 | |
| | mol_type = unassigned RNA | |
| | organism = Homo sapiens | |
| SEQUENCE: 662 | | |
| gaggggctct cgcttctggc gccaag | | 26 |
| | | |
| SEQ ID NO: 663 | moltype = RNA length = 15 | |
| FEATURE | Location/Qualifiers | |
| source | 1..15 | |
| | mol_type = unassigned RNA | |
| | organism = Homo sapiens | |
| SEQUENCE: 663 | | |
| ggtgaggcgg ggggg | | 15 |
| | | |
| SEQ ID NO: 664 | moltype = RNA length = 23 | |
| FEATURE | Location/Qualifiers | |
| source | 1..23 | |
| | mol_type = unassigned RNA | |
| | organism = Homo sapiens | |
| SEQUENCE: 664 | | |
| ctggggacg cgtgagcgcg agc | | 23 |
| | | |
| SEQ ID NO: 665 | moltype = RNA length = 21 | |
| FEATURE | Location/Qualifiers | |
| source | 1..21 | |
| | mol_type = unassigned RNA | |
| | organism = Homo sapiens | |
| SEQUENCE: 665 | | |
| ctggggacg cgtgagcgcg a | | 21 |

```
SEQ ID NO: 666          moltype = RNA   length = 22
FEATURE                 Location/Qualifiers
source                  1..22
                        mol_type = unassigned RNA
                        organism = Homo sapiens
SEQUENCE: 666
aggcgatgtg gggatgtaga ga                                                  22

SEQ ID NO: 667          moltype = RNA   length = 21
FEATURE                 Location/Qualifiers
source                  1..21
                        mol_type = unassigned RNA
                        organism = Homo sapiens
SEQUENCE: 667
agccgcgggg atcgccgagg g                                                   21

SEQ ID NO: 668          moltype = RNA   length = 23
FEATURE                 Location/Qualifiers
source                  1..23
                        mol_type = unassigned RNA
                        organism = Homo sapiens
SEQUENCE: 668
ttagggagta aagggtggg gag                                                  23

SEQ ID NO: 669          moltype = RNA   length = 22
FEATURE                 Location/Qualifiers
source                  1..22
                        mol_type = unassigned RNA
                        organism = Homo sapiens
SEQUENCE: 669
cgcaggggcc gggtgctcac cg                                                  22

SEQ ID NO: 670          moltype = RNA   length = 22
FEATURE                 Location/Qualifiers
source                  1..22
                        mol_type = unassigned RNA
                        organism = Homo sapiens
SEQUENCE: 670
acctggcagc agggagcgtc gt                                                  22

SEQ ID NO: 671          moltype = RNA   length = 23
FEATURE                 Location/Qualifiers
source                  1..23
                        mol_type = unassigned RNA
                        organism = Homo sapiens
SEQUENCE: 671
tggtgggtgg ggaggagaag tgc                                                 23

SEQ ID NO: 672          moltype = RNA   length = 21
FEATURE                 Location/Qualifiers
source                  1..21
                        mol_type = unassigned RNA
                        organism = Homo sapiens
SEQUENCE: 672
atgcctcccc cggccccgca g                                                   21

SEQ ID NO: 673          moltype = RNA   length = 20
FEATURE                 Location/Qualifiers
source                  1..20
                        mol_type = unassigned RNA
                        organism = Homo sapiens
SEQUENCE: 673
aaaaggcggg agaagcccca                                                     20

SEQ ID NO: 674          moltype = RNA   length = 22
FEATURE                 Location/Qualifiers
source                  1..22
                        mol_type = unassigned RNA
                        organism = Homo sapiens
SEQUENCE: 674
ttggggtgga gggccaagga gc                                                  22

SEQ ID NO: 675          moltype = RNA   length = 20
FEATURE                 Location/Qualifiers
source                  1..20
                        mol_type = unassigned RNA
                        organism = Homo sapiens
SEQUENCE: 675
```

```
caggggggact gggggtgagc                                                    20

SEQ ID NO: 676          moltype = RNA   length = 22
FEATURE                 Location/Qualifiers
source                  1..22
                        mol_type = unassigned RNA
                        organism = Homo sapiens
SEQUENCE: 676
tggctcagtt cagcaggaac ag                                                  22

SEQ ID NO: 677          moltype = RNA   length = 73
FEATURE                 Location/Qualifiers
source                  1..73
                        mol_type = unassigned RNA
                        organism = Homo sapiens
SEQUENCE: 677
ctggtgtttg aggcgatgtg gggatgtaga gacaacttcc cagtctcatt tcctcatcct         60
gccaggccac cat                                                            73

SEQ ID NO: 678          moltype = RNA   length = 180
FEATURE                 Location/Qualifiers
source                  1..180
                        mol_type = unassigned RNA
                        organism = Homo sapiens
SEQUENCE: 678
cgcgactgcg gcgcggtgg tgggggagc cgcggggatc gccgagggcc ggtcggccgc           60
cccgggtgcc gcgcggtgcc gccggcggcg gtgaggcccc gcgcgtgtgt cccggctgcg         120
gtcggccgcg ctcgagggggt ccccgtggcg tccccttccc cgccggccgc ctttctcgcg       180

SEQ ID NO: 679          moltype = RNA   length = 82
FEATURE                 Location/Qualifiers
source                  1..82
                        mol_type = unassigned RNA
                        organism = Homo sapiens
SEQUENCE: 679
ctgacttttt tagggagtag aagggtgggg agcatgaaca atgtttctca ctccctaccc         60
ctccactccc caaaaaagtc ag                                                  82

SEQ ID NO: 680          moltype = RNA   length = 80
FEATURE                 Location/Qualifiers
source                  1..80
                        mol_type = unassigned RNA
                        organism = Homo sapiens
SEQUENCE: 680
catccaggac aatggtgagt gccggtgcct gccctggggc cgtccctgcg caggggccgg         60
gtgctcaccg catctgcccc                                                     80

SEQ ID NO: 681          moltype = RNA   length = 72
FEATURE                 Location/Qualifiers
source                  1..72
                        mol_type = unassigned RNA
                        organism = Homo sapiens
SEQUENCE: 681
gatttcagtg acctggcagc agggagcgtc gtcagtgttt gactgtttat ggtatgtcag         60
ggagctggtt cc                                                             72

SEQ ID NO: 682          moltype = RNA   length = 62
FEATURE                 Location/Qualifiers
source                  1..62
                        mol_type = unassigned RNA
                        organism = Homo sapiens
SEQUENCE: 682
cttcctggtg ggtggggagg agaagtgccg tcctcatgag cccctctctg tcccacccat         60
ag                                                                        62

SEQ ID NO: 683          moltype = RNA   length = 63
FEATURE                 Location/Qualifiers
source                  1..63
                        mol_type = unassigned RNA
                        organism = Homo sapiens
SEQUENCE: 683
ggctccgcag ggccctggcg caggcatcca gacagcgggc gaatgcctcc cccggccccg         60
cag                                                                       63

SEQ ID NO: 684          moltype = RNA   length = 83
FEATURE                 Location/Qualifiers
source                  1..83
                        mol_type = unassigned RNA
                        organism = Homo sapiens
```

-continued

```
SEQUENCE: 684
gggtttcctc tgcctttttt tccaatgaaa ataacgaaac ctgttatttc ccattgaggg    60
ggaaaaaggc gggagaagcc cca                                           83

SEQ ID NO: 685          moltype = RNA   length = 61
FEATURE                 Location/Qualifiers
source                  1..61
                        mol_type = unassigned RNA
                        organism = Homo sapiens
SEQUENCE: 685
gagggttggg gtggagggcc aaggagctgg gtggggtgcc aagcctctgt ccccacccca    60
g                                                                   61

SEQ ID NO: 686          moltype = RNA   length = 68
FEATURE                 Location/Qualifiers
source                  1..68
                        mol_type = unassigned RNA
                        organism = Homo sapiens
SEQUENCE: 686
gggcgcaggg ggactggggg tgagcaggcc cagaacccag ctcgtgctca ctctcagtcc    60
ctccctag                                                            68

SEQ ID NO: 687          moltype = RNA   length = 68
FEATURE                 Location/Qualifiers
source                  1..68
                        mol_type = unassigned RNA
                        organism = Homo sapiens
SEQUENCE: 687
ctccggtgcc tactgagctg atatcagttc tcattttaca cactggctca gttcagcagg    60
aacaggag                                                            68

SEQ ID NO: 688          moltype = RNA   length = 73
FEATURE                 Location/Qualifiers
source                  1..73
                        mol_type = unassigned RNA
                        organism = Homo sapiens
SEQUENCE: 688
ctctgcctcc cgtgcctact gagctgaaac acagttggtt tgtgtacact ggctcagttc    60
agcaggaaca ggg                                                      73

SEQ ID NO: 689          moltype = RNA   length = 21
FEATURE                 Location/Qualifiers
source                  1..21
                        mol_type = unassigned RNA
                        organism = Homo sapiens
SEQUENCE: 689
gaggcgatgt gggatgtag a                                              21

SEQ ID NO: 690          moltype = RNA   length = 20
FEATURE                 Location/Qualifiers
source                  1..20
                        mol_type = unassigned RNA
                        organism = Homo sapiens
SEQUENCE: 690
cccagtctca tttcctcatc                                               20

SEQ ID NO: 691          moltype = RNA   length = 29
FEATURE                 Location/Qualifiers
source                  1..29
                        mol_type = unassigned RNA
                        organism = Homo sapiens
SEQUENCE: 691
gggagccgcg gggatcgccg agggccggt                                     29

SEQ ID NO: 692          moltype = RNA   length = 15
FEATURE                 Location/Qualifiers
source                  1..15
                        mol_type = unassigned RNA
                        organism = Homo sapiens
SEQUENCE: 692
ggcggcggtg gtggg                                                    15

SEQ ID NO: 693          moltype = RNA   length = 23
FEATURE                 Location/Qualifiers
source                  1..23
                        mol_type = unassigned RNA
                        organism = Homo sapiens
SEQUENCE: 693
agggagtaga agggtgggga gca                                           23
```

```
SEQ ID NO: 694          moltype = RNA  length = 16
FEATURE                 Location/Qualifiers
source                  1..16
                        mol_type = unassigned RNA
                        organism = Homo sapiens
SEQUENCE: 694
tagggagtag aagggt                                                         16

SEQ ID NO: 695          moltype = RNA  length = 23
FEATURE                 Location/Qualifiers
source                  1..23
                        mol_type = unassigned RNA
                        organism = Homo sapiens
SEQUENCE: 695
tgcgcagggg ccgggtgctc acc                                                 23

SEQ ID NO: 696          moltype = RNA  length = 19
FEATURE                 Location/Qualifiers
source                  1..19
                        mol_type = unassigned RNA
                        organism = Homo sapiens
SEQUENCE: 696
cgcaggggcc gggtgctca                                                      19

SEQ ID NO: 697          moltype = RNA  length = 22
FEATURE                 Location/Qualifiers
source                  1..22
                        mol_type = unassigned RNA
                        organism = Homo sapiens
SEQUENCE: 697
gaaaaaggcg ggagaagccc ca                                                  22

SEQ ID NO: 698          moltype = RNA  length = 15
FEATURE                 Location/Qualifiers
source                  1..15
                        mol_type = unassigned RNA
                        organism = Homo sapiens
SEQUENCE: 698
gaaaaaggcg ggaga                                                          15

SEQ ID NO: 699          moltype = RNA  length = 24
FEATURE                 Location/Qualifiers
source                  1..24
                        mol_type = unassigned RNA
                        organism = Homo sapiens
SEQUENCE: 699
actggctcag ttcagcagga acag                                                24

SEQ ID NO: 700          moltype = RNA  length = 15
FEATURE                 Location/Qualifiers
source                  1..15
                        mol_type = unassigned RNA
                        organism = Homo sapiens
SEQUENCE: 700
tggctcagtt cagca                                                          15
```

ESOPHAGEAL CANCER DETECTION KIT OR DEVICE, AND DETECTION METHOD

CROSS-REFERENCE TO RELATED APPLICATIONS

This application is a Divisional of application Ser. No. 16/803,390 filed Feb. 27, 2020, which is a Divisional of application Ser. No. 15/317,857, filed on Dec. 9, 2016 (now U.S. Pat. No. 10,619,212 B2), which is the National Phase under 35 U.S.C. § 371 of International Application No. PCT/JP2015/067580, filed on Jun. 18, 2015, and under 35 U.S.C. § 119(a) to Patent Application No. 2014-125036, filed in Japan on Jun. 18, 2014 and to Patent Application No. 2015-070379, filed in Japan on Mar. 30, 2015, all of which are hereby expressly incorporated by reference into the present application.

REFERENCE TO ELECTRONIC SEQUENCE LISTING

The application contains a Sequence Listing which has been submitted electronically in .XML format and is hereby incorporated by reference in its entirety. Said .XML copy, created on Oct. 3, 2022, is named "PH-6237-PCT Sequence Listing ST26.xml" and is 629,631 bytes in size. The sequence listing contained in this .XML file is part of the specification and is hereby incorporated by reference herein in its entirety.

TECHNICAL FIELD

The present invention relates to a kit or a device for the detection of esophageal cancer, comprising a nucleic acid capable of specifically binding to a particular miRNA, which is used for examining the presence or absence of esophageal cancer in a subject, and a method for detecting esophageal cancer, comprising measuring an expression level of the miRNA using the nucleic acid.

BACKGROUND ART

The esophagus is a tubular organ that conveys food from the mouth to the stomach, and is positioned between the trachea and the backbone. The wall of the esophagus is divided into 4 layers: mucosa, submucosa, proper muscular layer, and outer membrane from inside toward outside. These layers have their respective functions of conveying food from the mouth to the stomach (Non-Patent Literature 1). According to the 2012 statistics of cancer type in Japan disclosed by the Center for Cancer Control and Information Services, National Cancer Center, the number of esophageal cancer deaths climbed to 11,592 people, and esophageal cancer is the 10th leading cause of cancer type-specific mortality. Japanese men have 5.6 times higher risk of mortality due to esophageal cancer than women, and smoking and alcohol intake are reported risk factors for esophageal cancer (Non-Patent Literature 1). Also, it is estimated that one out of 125 American men and one out of 435 American women experience esophageal cancer. The estimated number of individuals affected by esophageal cancer in 2014 climbed to 18,170 people, among which approximately 15,450 people reportedly died (Non-Patent Literature 1).

The progressed stages of esophageal cancer are defined in Non-Patent Literature 2 and classified into stage 0 (Tis/N0/M0), stage IA (T1/N0M0), stage IB (T2/N0/M0), stage IIA (T3/N0/M0), stage IIB (T1 to T2/N1/M0s), stage IIIA (T4a/N0/M0, T3/N1M0, and T1 to T2/N2M0), stage IIIB (T3/N2/M0), stage IIIC (T4a/N1 to N2M0, T4b/M0, and N3/M0), and stage IV (M1) according to tumor size (Tis, T1 to T3, and T4a to T4b), lymph node metastasis (N1 to N3), distant metastasis (M0 to M1), etc.

The 5-year relative survival rate of esophageal cancer largely depends on the stages of cancer progression and is reportedly 39% for tumors limited to esophageal tissues, 21% for tumors limited to esophageal and adjacent tissues, and 4% for tumors that have metastasized distantly (Non-Patent Literature 1). Thus, the early detection of esophageal cancer leads to drastic improvement in the survival rate. Therefore, the provision of an approach that permits the early detection is strongly desired.

The method for treating esophageal cancer is determined in view of the stages of cancer progression and general conditions and mainly includes endoscopic therapy, surgery, radiotherapy, and anticancer agents. Esophageal cancer that has progressed to some extent is treated by multimodality therapy which combines these treatment methods to exert synergistic effects by exploiting their respective features (Non-Patent Literature 1). Early esophageal cancer at stage 0, 1, or the like may be adaptable to endoscopic therapy or photo dynamic therapy, which places less burden on patients (Non-Patent Literature 1).

According to Non-Patent Literature 1, initial diagnostic tests of esophageal cancer are X-ray esophagography and endoscopy. In addition, CT scan, MRI scan, endosonography, ultrasonography, or the like is performed in order to examine the degree of cancer spread. When there are findings on suspected esophageal cancer by these initial tests, pathological examination which involves inserting a needle into a lesion and collecting cells or tissues to be examined under a microscope is carried out as a secondary test. For example, CEA and SCC are known as tumor markers in blood for the detection of esophageal cancer (Non-Patent Literature 3).

As shown in Patent Literature 1, there is a report, albeit at a research stage, on the detection of esophageal cancer using the expression levels of microRNAs (miRNAs) or combinations of the expression levels of miRNAs and the expression levels of additional protein markers in biological samples including blood.

Patent Literature 1 discloses a method for detecting esophageal cancer by measuring miRNAs such as miR-663a, miR-92a-3p, and miR-575 in serum.

CITATION LIST

Patent Literature

Patent Literature 1: Published U.S. Patent Application No. 2014/031246

Non-Patent Literature

Non-Patent Literature 1: American Cancer Society, "Esophagus Cancer", 2014, p. 2 to 8, 19 to 20, and 29 to 41

Non-Patent Literature 2: Sobin, L. et al., "TNM Classification of Malignant Tumours, the 7th edition, Japanese version", 2009, p. 63 to 68

Non-Patent Literature 3: Terada, T. et al., 2013, International Journal of Clinical and Experimental Medicine, Vol. 6 (3), p. 219-26

SUMMARY OF INVENTION

Technical Problem

An object of the present invention is to find a novel tumor marker for esophageal cancer and to provide a method that can effectively detect esophageal cancer using a nucleic acid capable of specifically binding to the marker.

As described in Non-Patent Literature 1, general tests of esophageal cancer are X-ray esophagography and endoscopy. However, ordinary medical checkup places emphasis on stomach cancer screening and often insufficiently observes the esophagus. Although these tests are now popularized, the number of esophageal cancer deaths in Japan is still increasing. Thus, such diagnostic imaging cannot always serve as a deterrent against esophageal cancer. In addition, CT scan or MRI scan is capable of detecting esophageal cancer with high performance, but requires a special apparatus and high examination costs. Therefore, these tests are not suitable for widely used as primary tests for esophageal cancer.

For example, CEA and SCC are known as tumor markers in blood for the detection of esophageal cancer (Non-Patent Literature 3). These markers, however, present problems associated with accuracy in such a way that the markers also elevate in cancers other than esophageal cancer. Therefore, their usefulness has not yet been established. If use of these markers causes false diagnosis of other cancers as esophageal cancer, this wastes appropriate therapeutic opportunity or places unnecessary economical and physical burdens on patients due to the application of wrong medicine. Hence, the esophageal cancer guidebook provided by the American Cancer Society makes no mention about these markers (Non-Patent Literature 1).

As described below, there is a report, albeit at a research stage, on the determination of esophageal cancer using the expression levels of microRNAs (miRNAs) in biological samples including blood, none of which, however, have yet to be brought into the practical use.

Patent Literature 1 discloses a method for detecting esophageal cancer by measuring miRNAs such as miR-663a, miR-92a-3p, and miR-575 in serum. Specifically, this literature shows a list of miRNAs that vary in serum in 16 esophageal cancer patients compared with 12 healthy subjects, and the presence or absence of esophageal cancer is determined by measuring the expression levels of these miRNAs. This detection method, however, includes few Examples or statements regarding specific detection performance such as accuracy, sensitivity, or specificity for determining esophageal cancer, and is thus industrially less practical. hsa-miR-345, which was only one miRNA validated therein, had AUC of 0.814 and is difficult to use alone for determining esophageal cancer according to the description.

As mentioned above, the existing tumor markers exhibit low performance in the detection of esophageal cancer, or neither performance nor detection methods are specifically shown as to the markers at a research stage. Therefore, use of these markers might lead to carrying out needless extra examination due to the false detection of healthy subjects as being esophageal cancer patients, or might waste therapeutic opportunity because of overlooking esophageal cancer patients. In addition, the measurement of dozens of miRNAs increases examination costs and is therefore difficult to use in large-scale screening such as medical checkup. Furthermore, the collection of esophageal tissues for measuring the tumor markers is highly invasive to patients and is not favorable. Hence, there is a demand for a highly accurate esophageal cancer marker that is detectable from blood, which can be collected with limited invasiveness, and is capable of correctly identifying an esophageal cancer patient as an esophageal cancer patient and a healthy subject as a healthy subject. Particularly, the early detection and treatment of esophageal cancer can drastically improve survival rates. In addition, endoscopic therapy or photo dynamic therapy which places less burden on patients can be applied as a therapeutic choice. Therefore, a highly sensitive esophageal cancer marker capable of detecting esophageal cancer even at an early progressed stage is desired.

Solution to Problem

The present inventors have conducted diligent studies to attain the object and consequently completed the present invention by finding multiple genes usable as markers for the detection of esophageal cancer from blood and finding that esophageal cancer can be significantly detected by using nucleic acids capable of specifically binding to any of these markers.

SUMMARY OF INVENTION

The present invention has the following features:

(1) A kit for the detection of esophageal cancer, comprising nucleic acid(s) capable of specifically binding to at least one polynucleotide selected from the group consisting of the following esophageal cancer markers: miR-204-3p, miR-1247-3p, miR-6875-5p, miR-6857-5p, miR-6726-5p, miR-3188, miR-8069, miR-4257, miR-1343-3p, miR-7108-5p, miR-6825-5p, miR-7641, miR-3185, miR-4746-3p, miR-6791-5p, miR-6893-5p, miR-4433b-3p, miR-3135b, miR-6781-5p, miR-1908-5p, miR-4792, miR-7845-5p, miR-4417, miR-3184-5p, miR-1225-5p, miR-1231, miR-1225-3p, miR-150-3p, miR-4433-3p, miR-6125, miR-4513, miR-6787-5p, miR-6784-5p, miR-615-5p, miR-6765-3p, miR-5572, miR-6842-5p, miR-8063, miR-6780b-5p, miR-187-5p, miR-128-1-5p, miR-6729-5p, miR-6741-5p, miR-6757-5p, miR-7110-5p, miR-7975, miR-1233-5p, miR-6845-5p, miR-3937, miR-4467, miR-7109-5p, miR-6088, miR-6782-5p, miR-5195-3p, miR-4454, miR-6724-5p, miR-8072, miR-4516, miR-6756-5p, miR-4665-3p, miR-6826-5p, miR-6820-5p, miR-6887-5p, miR-3679-5p, miR-7847-3p, miR-6721-5p, miR-3622a-5p, miR-939-5p, miR-602, miR-7977, miR-6749-5p, miR-1914-3p, miR-4651, miR-4695-5p, miR-6848-5p, miR-1228-3p, miR-642b-3p, miR-6746-5p, miR-3620-5p, miR-3131, miR-6732-5p, miR-7113-3p, miR-23a-3p, miR-3154, miR-4723-5p, miR-3663-3p, miR-4734, miR-6816-5p, miR-4442, miR-4476, miR-423-5p, miR-1249, miR-6515-3p, miR-887-3p, miR-4741, miR-6766-3p, miR-4673, miR-6779-5p, miR-4706, miR-1268b, miR-4632-5p, miR-3197, miR-6798-5p, miR-711, miR-6840-3p, miR-6763-5p, miR-6727-5p, miR-371a-5p, miR-6824-5p, miR-4648, miR-1227-5p, miR-564, miR-3679-3p, miR-2861, miR-6737-5p, miR-4725-3p, miR-6716-5p, miR-4675, miR-1915-3p, miR-671-5p, miR-3656, miR-6722-3p, miR-4707-5p, miR-4449, miR-1202, miR-4649-5p, miR-744-5p, miR-642a-3p, miR-451a, miR-6870-5p, miR-4443, miR-6808-5p, miR-4728-5p, miR-937-5p, miR-135a-3p, miR-663b, miR-1343-5p, miR-6822-5p, miR-6803-5p, miR-6805-3p, miR-128-2-5p, miR-4640-5p, miR-1469, miR-92a-2-5p, miR-3940-5p, miR-4281, miR-1260b, miR-4758-5p, miR-1915-5p, miR-5001-5p, miR-4286, miR-6126, miR-6789-5p, miR-4459, miR-1268a, miR-6752-5p, miR-6131, miR-6800-5p, miR-4532, miR-6872-

3p, miR-718, miR-6769a-5p, miR-4707-3p, miR-6765-5p, miR-4739, miR-4525, miR-4270, miR-4534, miR-6785-5p, miR-6850-5p, miR-4697-5p, miR-1260a, miR-4486, miR-6880-5p, miR-6802-5p, miR-6861-5p, miR-92b-5p, miR-1238-5p, miR-6851-5p, miR-7704, miR-149-3p, miR-4689, miR-4688, miR-125a-3p, miR-23b-3p, miR-614, miR-1913, miR-16-5p, miR-6717-5p, miR-3648, miR-3162-5p, miR-1909-3p, miR-8073, miR-6769b-5p, miR-6836-3p, miR-4484, miR-6819-5p and miR-6794-5p.

(2) The kit according to (1), wherein miR-204-3p is hsa-miR-204-3p, miR-1247-3p is hsa-miR-1247-3p, miR-6875-5p is hsa-miR-6875-5p, miR-6857-5p is hsa-miR-6857-5p, miR-6726-5p is hsa-miR-6726-5p, miR-3188 is hsa-miR-3188, miR-8069 is hsa-miR-8069, miR-4257 is hsa-miR-4257, miR-1343-3p is hsa-miR-1343-3p, miR-7108-5p is hsa-miR-7108-5p, miR-6825-5p is hsa-miR-6825-5p, miR-7641 is hsa-miR-7641, miR-3185 is hsa-miR-3185, miR-4746-3p is hsa-miR-4746-3p, miR-6791-5p is hsa-miR-6791-5p, miR-6893-5p is hsa-miR-6893-5p, miR-4433b-3p is hsa-miR-4433b-3p, miR-3135b is hsa-miR-3135b, miR-6781-5p is hsa-miR-6781-5p, miR-1908-5p is hsa-miR-1908-5p, miR-4792 is hsa-miR-4792, miR-7845-5p is hsa-miR-7845-5p, miR-4417 is hsa-miR-4417, miR-3184-5p is hsa-miR-3184-5p, miR-1225-5p is hsa-miR-1225-5p, miR-1231 is hsa-miR-1231, miR-1225-3p is hsa-miR-1225-3p, miR-150-3p is hsa-miR-150-3p, miR-4433-3p is hsa-miR-4433-3p, miR-6125 is hsa-miR-6125, miR-4513 is hsa-miR-4513, miR-6787-5p is hsa-miR-6787-5p, miR-6784-5p is hsa-miR-6784-5p, miR-615-5p is hsa-miR-615-5p, miR-6765-3p is hsa-miR-6765-3p, miR-5572 is hsa-miR-5572, miR-6842-5p is hsa-miR-6842-5p, miR-8063 is hsa-miR-8063, miR-6780b-5p is hsa-miR-6780b-5p, miR-187-5p is hsa-miR-187-5p, miR-128-1-5p is hsa-miR-128-1-5p, miR-6729-5p is hsa-miR-6729-5p, miR-6741-5p is hsa-miR-6741-5p, miR-6757-5p is hsa-miR-6757-5p, miR-7110-5p is hsa-miR-7110-5p, miR-7975 is hsa-miR-7975, miR-1233-5p is hsa-miR-1233-5p, miR-6845-5p is hsa-miR-6845-5p, miR-3937 is hsa-miR-3937, miR-4467 is hsa-miR-4467, miR-7109-5p is hsa-miR-7109-5p, miR-6088 is hsa-miR-6088, miR-6782-5p is hsa-miR-6782-5p, miR-5195-3p is hsa-miR-5195-3p, miR-4454 is hsa-miR-4454, miR-6724-5p is hsa-miR-6724-5p, miR-8072 is hsa-miR-8072, miR-4516 is hsa-miR-4516, miR-6756-5p is hsa-miR-6756-5p, miR-4665-3p is hsa-miR-4665-3p, miR-6826-5p is hsa-miR-6826-5p, miR-6820-5p is hsa-miR-6820-5p, miR-6887-5p is hsa-miR-6887-5p, miR-3679-5p is hsa-miR-3679-5p, miR-7847-3p is hsa-miR-7847-3p, miR-6721-5p is hsa-miR-6721-5p, miR-3622a-5p is hsa-miR-3622a-5p, miR-939-5p is hsa-miR-939-5p, miR-602 is hsa-miR-602, miR-7977 is hsa-miR-7977, miR-6749-5p is hsa-miR-6749-5p, miR-1914-3p is hsa-miR-1914-3p, miR-4651 is hsa-miR-4651, miR-4695-5p is hsa-miR-4695-5p, miR-6848-5p is hsa-miR-6848-5p, miR-1228-3p is hsa-miR-1228-3p, miR-642b-3p is hsa-miR-642b-3p, miR-6746-5p is hsa-miR-6746-5p, miR-3620-5p is hsa-miR-3620-5p, miR-3131 is hsa-miR-3131, miR-6732-5p is hsa-miR-6732-5p, miR-7113-3p is hsa-miR-7113-3p, miR-23a-3p is hsa-miR-23a-3p, miR-3154 is hsa-miR-3154, miR-4723-5p is hsa-miR-4723-5p, miR-3663-3p is hsa-miR-3663-3p, miR-4734 is hsa-miR-4734, miR-6816-5p is hsa-miR-6816-5p, miR-4442 is hsa-miR-4442, miR-4476 is hsa-miR-4476, miR-423-5p is hsa-miR-423-5p, miR-1249 is hsa-miR-1249, miR-6515-3p is hsa-miR-6515-3p, miR-887-3p is hsa-miR-887-3p, miR-4741 is hsa-miR-4741, miR-6766-3p is hsa-miR-6766-3p, miR-4673 is hsa-miR-4673, miR-6779-5p is hsa-miR-6779-5p, miR-4706 is hsa-miR-4706, miR-1268b is hsa-miR-1268b, miR-4632-5p is hsa-miR-4632-5p, miR-3197 is hsa-miR-3197, miR-6798-5p is hsa-miR-6798-5p, miR-711 is hsa-miR-711, miR-6840-3p is hsa-miR-6840-3p, miR-6763-5p is hsa-miR-6763-5p, miR-6727-5p is hsa-miR-6727-5p, miR-371a-5p is hsa-miR-371a-5p, miR-6824-5p is hsa-miR-6824-5p, miR-4648 is hsa-miR-4648, miR-1227-5p is hsa-miR-1227-5p, miR-564 is hsa-miR-564, miR-3679-3p is hsa-miR-3679-3p, miR-2861 is hsa-miR-2861, miR-6737-5p is hsa-miR-6737-5p, miR-4725-3p is hsa-miR-4725-3p, miR-6716-5p is hsa-miR-6716-5p, miR-4675 is hsa-miR-4675, miR-1915-3p is hsa-miR-1915-3p, miR-671-5p is hsa-miR-671-5p, miR-3656 is hsa-miR-3656, miR-6722-3p is hsa-miR-6722-3p, miR-4707-5p is hsa-miR-4707-5p, miR-4449 is hsa-miR-4449, miR-1202 is hsa-miR-1202, miR-4649-5p is hsa-miR-4649-5p, miR-744-5p is hsa-miR-744-5p, miR-642a-3p is hsa-miR-642a-3p, miR-451a is hsa-miR-451a, miR-6870-5p is hsa-miR-6870-5p, miR-4443 is hsa-miR-4443, miR-6808-5p is hsa-miR-6808-5p, miR-4728-5p is hsa-miR-4728-5p, miR-937-5p is hsa-miR-937-5p, miR-135a-3p is hsa-miR-135a-3p, miR-663b is hsa-miR-663b, miR-1343-5p is hsa-miR-1343-5p, miR-6822-5p is hsa-miR-6822-5p, miR-6803-5p is hsa-miR-6803-5p, miR-6805-3p is hsa-miR-6805-3p, miR-128-2-5p is hsa-miR-128-2-5p, miR-4640-5p is hsa-miR-4640-5p, miR-1469 is hsa-miR-1469, miR-92a-2-5p is hsa-miR-92a-2-5p, miR-3940-5p is hsa-miR-3940-5p, miR-4281 is hsa-miR-4281, miR-1260b is hsa-miR-1260b, miR-4758-5p is hsa-miR-4758-5p, miR-1915-5p is hsa-miR-1915-5p, miR-5001-5p is hsa-miR-5001-5p, miR-4286 is hsa-miR-4286, miR-6126 is hsa-miR-6126, miR-6789-5p is hsa-miR-6789-5p, miR-4459 is hsa-miR-4459, miR-1268a is hsa-miR-1268a, miR-6752-5p is hsa-miR-6752-5p, miR-6131 is hsa-miR-6131, miR-6800-5p is hsa-miR-6800-5p, miR-4532 is hsa-miR-4532, miR-6872-3p is hsa-miR-6872-3p, miR-718 is hsa-miR-718, miR-6769a-5p is hsa-miR-6769a-5p, miR-4707-3p is hsa-miR-4707-3p, miR-6765-5p is hsa-miR-6765-5p, miR-4739 is hsa-miR-4739, miR-4525 is hsa-miR-4525, miR-4270 is hsa-miR-4270, miR-4534 is hsa-miR-4534, miR-6785-5p is hsa-miR-6785-5p, miR-6850-5p is hsa-miR-6850-5p, miR-4697-5p is hsa-miR-4697-5p, miR-1260a is hsa-miR-1260a, miR-4486 is hsa-miR-4486, miR-6880-5p is hsa-miR-6880-5p, miR-6802-5p is hsa-miR-6802-5p, miR-6861-5p is hsa-miR-6861-5p, miR-92b-5p is hsa-miR-92b-5p, miR-1238-5p is hsa-miR-1238-5p, miR-6851-5p is hsa-miR-6851-5p, miR-7704 is hsa-miR-7704, miR-149-3p is hsa-miR-149-3p, miR-4689 is hsa-miR-4689, miR-4688 is hsa-miR-4688, miR-125a-3p is hsa-miR-125a-3p, miR-23b-3p is hsa-miR-23b-3p, miR-614 is hsa-miR-614, miR-1913 is hsa-miR-1913, miR 5p is hsa-miR-16-5p, miR-6717-5p is hsa-miR-6717-5p, miR-3648 is hsa-miR-3648, miR-3162-5p is hsa-miR-3162-5p, miR-1909-3p is hsa-miR-1909-3p, miR-8073 is hsa-miR-8073, miR-6769b-5p is hsa-miR-6769b-5p, miR-6836-3p is hsa-miR-6836-3p, miR-4484 is hsa-miR-4484, miR-6819-5p is hsa-miR-6819-5p, and miR-6794-5p is hsa-miR-6794-5p.

(3) The kit according to (1) or (2), wherein the nucleic acid(s) is/are polynucleotide(s) selected from the group consisting of the following polynucleotides (a) to (e):
  (a) a polynucleotide consisting of a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides,
  (b) a polynucleotide comprising a nucleotide sequence represented by any of SEQ ID NOs: 1 to 115, 117 to 189, and 666 to 675, (c) a polynucleotide consisting of a nucleotide sequence complementary to a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 115, 117 to 189, and 666 to 675 or a nucleotide sequence from the nucleotide sequence by the replacement of u with t, and (e) a polynucleotide hybridizing under stringent conditions to any of the polynucleotides (a) to (d).

(4) The kit according to any of (1) to (3), wherein the kit further comprises a nucleic acid capable of specifically binding to polynucleotide(s) selected from other esophageal cancer markers miR-575 and miR-24-3p.

(5) The kit according to (4), wherein miR-575 is hsa-miR-575, and miR-24-3p is hsa-miR-24-3p.

(6) The kit according to (4) or (5), wherein the nucleic acid(s) is/are polynucleotide(s) selected from the group consisting of the following polynucleotides (f) to (j):

(f) a polynucleotide consisting of a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 116 and 676, (h) a polynucleotide consisting of a nucleotide sequence complementary to a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 116 and 676 or a nucleotide sequence from the nucleotide sequence by the replacement of u with t, and (j) a polynucleotide hybridizing under stringent conditions to any of the polynucleotides (f) to (i).

(7) The kit according to any of (1) to (6), wherein the kit further comprises a nucleic acid capable of specifically binding to at least one polynucleotide selected from the group consisting of the following other esophageal cancer markers: miR-675-5p, miR-486-3p, miR-6777-5p, miR-4497, miR-296-3p, miR-6738-5p, miR-4731-5p, miR-6889-5p, miR-6786-5p, miR-92a-3p, miR-4294, miR-4763-3p, miR-6076, miR-663a, miR-760, miR-4667-5p, miR-6090, miR-4730, miR-7106-5p, miR-3196, miR-5698, miR-6087, miR-4665-5p, miR-8059 and miR-6879-5p.

(8) The kit according to (7), wherein miR-675-5p is hsa-miR-675-5p, miR-486-3p is hsa-miR-486-3p, miR-6777-5p is hsa-miR-6777-5p, miR-4497 is hsa-miR-4497, miR-296-3p is hsa-miR-296-3p, miR-6738-5p is hsa-miR-6738-5p, miR-4731-5p is hsa-miR-4731-5p, miR-6889-5p is hsa-miR-6889-5p, miR-6786-5p is hsa-miR-6786-5p, miR-92a-3p is hsa-miR-92a-3p, miR-4294 is hsa-miR-4294, miR-4763-3p is hsa-miR-4763-3p, miR-6076 is hsa-miR-6076, miR-663a is hsa-miR-663a, miR-760 is hsa-miR-760, miR-4667-5p is hsa-miR-4667-5p, miR-6090 is hsa-miR-6090, miR-4730 is hsa-miR-4730, miR-7106-5p is hsa-miR-7106-5p, miR-3196 is hsa-miR-3196, miR-5698 is hsa-miR-5698, miR-6087 is hsa-miR-6087, miR-4665-5p is hsa-miR-4665-5p, miR-8059 is hsa-miR-8059, and miR-6879-5p is hsa-miR-6879-5p.

(9) The kit according to (7) or (8), wherein the nucleic acid(s) is/are polynucleotide(s) selected from the group consisting of the following polynucleotides (k) to (o):

(k) a polynucleotide consisting of a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 190 to 214, (m) a polynucleotide consisting of a nucleotide sequence complementary to a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 190 to 214 or a nucleotide sequence from the nucleotide sequence by the replacement of u with t, and (o) a polynucleotide hybridizing under stringent conditions to any of the polynucleotides (k) to (n).

(10) The kit according to any of (1) to (9), wherein the kit comprises at least two nucleic acids capable of specifically binding to at least two polynucleotides, respectively, selected from all of the esophageal cancer markers according to (1) or (2).

(11) A device for the detection of esophageal cancer, comprising nucleic acid(s) capable of specifically binding to at least one polynucleotide selected from the group consisting of the following esophageal cancer markers: miR-204-3p, miR-1247-3p, miR-6875-5p, miR-6857-5p, miR-6726-5p, miR-3188, miR-8069, miR-4257, miR-1343-3p, miR-7108-5p, miR-6825-5p, miR-7641, miR-3185, miR-4746-3p, miR-6791-5p, miR-6893-5p, miR-4433b-3p, miR-3135b, miR-6781-5p, miR-1908-5p, miR-4792, miR-7845-5p, miR-4417, miR-3184-5p, miR-1225-5p, miR-1231, miR-1225-3p, miR-150-3p, miR-4433-3p, miR-6125, miR-4513, miR-6787-5p, miR-6784-5p, miR-615-5p, miR-6765-3p, miR-5572, miR-6842-5p, miR-8063, miR-6780b-5p, miR-187-5p, miR-128-1-5p, miR-6729-5p, miR-6741-5p, miR-6757-5p, miR-7110-5p, miR-7975, miR-1233-5p, miR-6845-5p, miR-3937, miR-4467, miR-7109-5p, miR-6088, miR-6782-5p, miR-5195-3p, miR-4454, miR-6724-5p, miR-8072, miR-4516, miR-6756-5p, miR-4665-3p, miR-6826-5p, miR-6820-5p, miR-6887-5p, miR-3679-5p, miR-7847-3p, miR-6721-5p, miR-3622a-5p, miR-939-5p, miR-602, miR-7977, miR-6749-5p, miR-1914-3p, miR-4651, miR-4695-5p, miR-6848-5p, miR-1228-3p, miR-642b-3p, miR-6746-5p, miR-3620-5p, miR-3131, miR-6732-5p, miR-7113-3p, miR-23a-3p, miR-3154, miR-4723-5p, miR-3663-3p, miR-4734, miR-6816-5p, miR-4442, miR-4476, miR-423-5p, miR-1249, miR-6515-3p, miR-887-3p, miR-4741, miR-6766-3p, miR-4673, miR-6779-5p, miR-4706, miR-1268b, miR-4632-5p, miR-3197, miR-6798-5p, miR-711, miR-6840-3p, miR-6763-5p, miR-6727-5p, miR-371a-5p, miR-6824-5p, miR-4648, miR-1227-5p, miR-564, miR-3679-3p, miR-2861, miR-6737-5p, miR-4725-3p, miR-6716-5p, miR-4675, miR-1915-3p, miR-671-5p, miR-3656, miR-6722-3p, miR-4707-5p, miR-4449, miR-1202, miR-4649-5p, miR-744-5p, miR-642a-3p, miR- 451a, miR-6870-5p, miR-4443, miR-6808-5p, miR-4728-5p, miR-937-5p, miR-135a-3p, miR-663b, miR-1343-5p, miR-6822-5p, miR-6803-5p, miR-6805-3p, miR-128-2-5p, miR-4640-5p, miR-1469, miR-92a-2-5p, miR-3940-5p, miR-4281, miR-1260b, miR-4758-5p, miR-1915-5p, miR-5001-5p, miR-4286, miR-6126, miR-6789-5p, miR-4459, miR-1268a, miR-6752-5p, miR-6131, miR-6800-5p, miR-4532, miR-6872-3p, miR-718, miR-6769a-5p, miR-4707-3p, miR-6765-5p, miR-4739, miR-4525, miR-4270, miR-4534, miR-6785-5p, miR-6850-5p, miR-4697-5p, miR-1260a, miR-4486, miR-6880-5p, miR-6802-5p, miR-6861-5p, miR-92b-5p, miR-1238-5p, miR-6851-5p, miR-7704, miR-149-3p, miR-4689, miR-4688, miR-125a-3p, miR-23b-3p, miR-614, miR-1913, miR-16-5p, miR-6717-5p, miR-3648, miR-3162-5p, miR-1909-3p, miR-8073, miR-6769b-5p, miR-6836-3p, miR-4484, miR-6819-5p and miR-6794-5p.

(12) The device according to (11), wherein miR-204-3p is hsa-miR-204-3p, miR-1247-3p is hsa-miR-1247-3p, miR-6875-5p is hsa-miR-6875-5p, miR-6857-5p is hsa-miR-6857-5p, miR-6726-5p is hsa-miR-6726-5p, miR-3188 is hsa-miR-3188, miR-8069 is hsa-miR-8069, miR-4257 is hsa-miR-4257, miR-1343-3p is hsa-miR-1343-3p, miR-7108-5p is hsa-miR-7108-5p, miR-6825-5p is hsa-miR-6825-5p, miR-7641 is hsa-miR-7641, miR-3185 is hsa-miR-3185, miR-4746-3p is hsa-miR-4746-3p, miR-6791-5p is hsa-miR-6791-5p, miR-6893-5p is hsa-miR-6893-5p, miR-4433b-3p is hsa-miR-4433b-3p, miR-3135b is hsa-miR-3135b, miR-6781-5p is hsa-miR-6781-5p, miR-1908-5p is hsa-miR-1908-5p, miR-4792 is hsa-miR-4792, miR-7845-5p is hsa-miR-7845-5p, miR-4417 is hsa-miR-4417, miR-3184-5p is hsa-miR-3184-5p, miR-1225-5p is hsa-miR-1225-5p, miR-1231 is hsa-miR-1231, miR-1225-3p is hsa-miR-1225-3p, miR-150-3p is hsa-miR-150-3p, miR-4433-3p is hsa-miR-4433-3p, miR-6125 is hsa-miR-6125, miR-4513 is hsa-miR-4513, miR-6787-5p is hsa-miR-6787-5p, miR-6784-5p is hsa-miR-6784-5p, miR-615-5p is hsa-miR-615-5p, miR-6765-3p is hsa-miR-6765-3p, miR-5572 is hsa-miR-5572, miR-6842-5p is hsa-miR-6842-5p, miR-8063 is hsa-miR-8063, miR-6780b-5p is hsa-miR-6780b-5p, miR-187-5p is hsa-miR-187-5p, miR-128-1-5p is hsa-miR-128-1-5p, miR-6729-5p is hsa-miR-6729-5p, miR-6741-5p is hsa-miR-6741-5p, miR-6757-5p is hsa-miR-6757-5p, miR-7110-5p is hsa-miR-7110-5p, miR-7975 is hsa-miR-7975, miR-1233-5p is hsa-miR-1233-5p, miR-6845-5p is hsa-miR-6845-5p, miR-3937 is hsa-miR-3937, miR-4467 is hsa-miR-4467, miR-7109-5p is hsa-miR-7109-5p, miR-6088 is hsa-miR-6088, miR-6782-5p is hsa-miR-6782-5p, miR-5195-3p is hsa-miR-5195-3p, miR-4454 is hsa-miR-4454, miR-6724-5p is hsa-miR-6724-5p, miR-8072 is hsa-miR-8072, miR-4516 is hsa-miR-4516, miR-6756-5p is hsa-miR-6756-5p, miR-4665-3p is hsa-miR-4665-3p, miR-6826-5p is hsa-miR-6826-5p, miR-6820-5p is hsa-miR-6820-5p, miR-6887-5p is hsa-miR-6887-5p, miR-3679-5p is hsa-miR-3679-5p, miR-7847-3p is hsa-miR-7847-3p, miR-6721-5p is hsa-miR-6721-5p, miR-3622a-5p is hsa-miR-3622a-5p, miR-939-5p is hsa-miR-939-5p, miR-602 is hsa-miR-602, miR-7977 is hsa-miR-7977, miR-6749-5p is hsa-miR-6749-5p, miR-1914-3p is hsa-miR-1914-3p, miR-4651 is hsa-miR-4651, miR-4695-5p is hsa-miR-4695-5p, miR-6848-5p is hsa-miR-6848-5p, miR-1228-3p is hsa-miR-1228-3p, miR-642b-3p is hsa-miR-642b-3p, miR-6746-5p is hsa-miR-6746-5p, miR-3620-5p is hsa-miR-3620-5p, miR-3131 is hsa-miR-3131, miR-6732-5p is hsa-miR-6732-5p, miR-7113-3p is hsa-miR-7113-3p, miR-23a-3p is hsa-miR-23a-3p, miR-3154 is hsa-miR-3154, miR-4723-5p is hsa-miR-4723-5p, miR-3663-3p is hsa-miR-3663-3p, miR-4734 is hsa-miR-4734, miR-6816-5p is hsa-miR-6816-5p, miR-4442 is hsa-miR-4442, miR-4476 is hsa-miR-4476, miR-423-5p is hsa-miR-423-5p, miR-1249 is hsa-miR-1249, miR-6515-3p is hsa-miR-6515-3p, miR-887-3p is hsa-miR-887-3p, miR-4741 is hsa-miR-4741, miR-6766-3p is hsa-miR-6766-3p, miR-4673 is hsa-miR-4673, miR-6779-5p is hsa-miR-6779-5p, miR-4706 is hsa-miR-4706, miR-1268b is hsa-miR-1268b, miR-4632-5p is hsa-miR-4632-5p, miR-3197 is hsa-miR-3197, miR-6798-5p is hsa-miR-6798-5p, miR-711 is hsa-miR-711, miR-6840-3p is hsa-miR-6840-3p, miR-6763-5p is hsa-miR-6763-5p, miR-6727-5p is hsa-miR-6727-5p, miR-371a-5p is hsa-miR-371a-5p, miR-6824-5p is hsa-miR-6824-5p, miR-4648 is hsa-miR-4648, miR-1227-5p is hsa-miR-1227-5p, miR-564 is hsa-miR-564, miR-3679-3p is hsa-miR-3679-3p, miR-2861 is hsa-miR-2861, miR-6737-5p is hsa-miR-6737-5p, miR-4725-3p is hsa-miR-4725-3p, miR-6716-5p is hsa-miR-6716-5p, miR-4675 is hsa-miR-4675, miR-1915-3p is hsa-miR-1915-3p, miR-671-5p is hsa-miR-671-5p, miR-3656 is hsa-miR-3656, miR-6722-3p is hsa-miR-6722-3p, miR-4707-5p is hsa-miR-4707-5p, miR-4449 is hsa-miR-4449, miR-1202 is hsa-miR-1202, miR-4649-5p is hsa-miR-4649-5p, miR-744-5p is hsa-miR-744-5p, miR-642a-3p is hsa-miR-642a-3p, miR-451a is hsa-miR-451a, miR-6870-5p is hsa-miR-6870-5p, miR-4443 is hsa-miR-4443, miR-6808-5p is hsa-miR-6808-5p, miR-4728-5p is hsa-miR-4728-5p, miR-937-5p is hsa-miR-937-5p, miR-135a-3p is hsa-miR-135a-3p, miR-663b is hsa-miR-663b, miR-1343-5p is hsa-miR-1343-5p, miR-6822-5p is hsa-miR-6822-5p, miR-6803-5p is hsa-miR-6803-5p, miR-6805-3p is hsa-miR-6805-3p, miR-128-2-5p is hsa-miR-128-2-5p, miR-4640-5p is hsa-miR-4640-5p, miR-1469 is hsa-miR-1469, miR-92a-2-5p is hsa-miR-92a-2-5p, miR-3940-5p is hsa-miR-3940-5p, miR-4281 is hsa-miR-4281, miR-1260b is hsa-miR-1260b, miR-4758-5p is hsa-miR-4758-5p, miR-1915-5p is hsa-miR-1915-5p, miR-5001-5p is hsa-miR-5001-5p, miR-4286 is hsa-miR-4286, miR-6126 is hsa-miR-6126, miR-6789-5p is hsa-miR-6789-5p, miR-4459 is hsa-miR-4459, miR-1268a is hsa-miR-1268a, miR-6752-5p is hsa-miR-6752-5p, miR-6131 is hsa-miR-6131, miR-6800-5p is hsa-miR-6800-5p, miR-4532 is hsa-miR-4532, miR-6872-3p is hsa-miR-6872-3p, miR-718 is hsa-miR-718, miR-6769a-5p is hsa-miR-6769a-5p, miR-4707-3p is hsa-miR-4707-3p, miR-6765-5p is hsa-miR-6765-5p, miR-4739 is hsa-miR-4739, miR-4525 is hsa-miR-4525, miR-4270 is hsa-miR-4270, miR-4534 is hsa-miR-4534, miR-6785-5p is hsa-miR-6785-5p, miR-6850-5p is hsa-miR-6850-5p, miR-4697-5p is hsa-miR-4697-5p, miR-1260a is hsa-miR-1260a, miR-4486 is hsa-miR-4486, miR-6880-5p is hsa-miR-6880-5p, miR-6802-5p is hsa-miR-6802-5p, miR-6861-5p is hsa-miR-6861-5p, miR-92b-5p is hsa-miR-92b-5p, miR-1238-5p is hsa-miR-1238-5p, miR-6851-5p is hsa-miR-6851-5p, miR-7704 is hsa-miR-7704, miR-149-3p is hsa-miR-149-3p, miR-4689 is hsa-miR-4689, miR-4688 is hsa-miR-4688, miR-125a-3p is hsa-miR-125a-3p, miR-23b-3p is hsa-miR-23b-3p, miR-614 is hsa-miR-614, miR-1913 is hsa-miR-1913, miR 5p is hsa-miR-16-5p, miR-6717-5p is hsa-miR-6717-5p, miR-3648 is hsa-miR-3648, miR-3162-5p is hsa-miR-3162-5p, miR-1909-3p is hsa-miR-1909-3p, miR-8073 is hsa-miR-8073, miR-6769b-5p is hsa-miR-6769b-5p, miR-6836-3p is hsa-miR-6836-3p, miR-4484 is hsa-miR-4484, miR-6819-5p is hsa-miR-6819-5p, and miR-6794-5p is hsa-miR-6794-5p.

(13) The device according to (11) or (12), wherein the nucleic acid(s) is/are polynucleotide(s) selected from the group consisting of the following polynucleotides (a) to (e):

(a) a polynucleotide consisting of a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 115, 117 to 189, and 666 to 675, (c) a polynucleotide consisting of a nucleotide sequence complementary to a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 115, 117 to 189, and 666 to 675 or a nucleotide sequence from the nucleotide sequence by the replacement of u with t, and (e) a polynucleotide hybridizing under stringent conditions to any of the polynucleotides (a) to (d).

(14) The device according to any of (11) to (13), wherein the device further comprises nucleic acid(s) capable of specifically binding to polynucleotide(s) selected from other esophageal cancer markers miR-575 and miR-24-3p.

(15) The device according to (14), wherein miR-575 is hsa-miR-575, and miR-24-3p is

(16) The device according to (14) or (15), wherein the nucleic acid(s) is/are polynucleotide(s) selected from the group consisting of the following polynucleotides (f) to (j):

(f) a polynucleotide consisting of a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 116 and 676, (h) a polynucleotide consisting of a nucleotide sequence complementary to a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 116 and 676 or a nucleotide sequence from the nucleotide sequence by the replacement of u with t, and (j) a polynucleotide hybridizing under stringent conditions to any of the polynucleotides (f) to (i).

(17) The device according to any of (11) to (16), wherein the device further comprises a nucleic acid capable of specifically binding to at least one polynucleotide selected from the group consisting of the following other esophageal cancer markers: miR-675-5p, miR-486-3p, miR-6777-5p, miR-4497, miR-296-3p, miR-6738-5p, miR-4731-5p, miR-6889-5p, miR-6786-5p, miR-92a-3p, miR-4294, miR-4763-3p, miR-6076, miR-663a, miR-760, miR-4667-5p, miR-6090, miR-4730, miR-7106-5p, miR-3196, miR-5698, miR-6087, miR-4665-5p, miR-8059, and miR-6879-5p.

(18) The device according to (17), wherein miR-675-5p is hsa-miR-675-5p, miR-486-3p is hsa-miR-486-3p, miR-6777-5p is hsa-miR-6777-5p, miR-4497 is hsa-miR-4497, miR 3p is hsa-miR-296-3p, miR-6738-5p is hsa-miR-6738-5p, miR-4731-5p is hsa-miR-4731-5p, miR-6889-5p is hsa-miR-6889-5p, miR-6786-5p is hsa-miR-6786-5p, miR-92a-3p is hsa-miR-92a-3p, miR-4294 is hsa-miR-4294, miR-4763-3p is hsa-miR-4763-3p, miR-6076 is hsa-miR-6076, miR-663a is hsa-miR-663a, miR-760 is hsa-miR-760, miR-4667-5p is hsa-miR-4667-5p, miR-6090 is hsa-miR-6090, miR-4730 is hsa-miR-4730, miR-7106-5p is hsa-miR-7106-5p, miR-3196 is hsa-miR-3196, miR-5698 is hsa-miR-5698, miR-6087 is hsa-miR-6087, miR-4665-5p is hsa-miR-4665-5p, miR-8059 is hsa-miR-8059, and miR-6879-5p is hsa-miR-6879-5p.

(19) The device according to (17) or (18), wherein the nucleic acid is a polynucleotide selected from the group consisting of the following polynucleotides (k) to (o):

(k) a polynucleotide consisting of a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 190 to 214, (m) a polynucleotide consisting of a nucleotide sequence complementary to a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 190 to 214 or a nucleotide sequence from the nucleotide sequence by the replacement of u with t, and (o) a polynucleotide hybridizing under stringent conditions to any of the polynucleotides (k) to (n).

(20) The device according to any one of (11) to (19), wherein the device is for measurement based on a hybridization technique.

(21) The device according to (20), wherein the hybridization technique is a nucleic acid array technique.

(22) The device according to any of (11) to (21), wherein the device comprises at least two nucleic acids capable of specifically binding to at least two polynucleotides, respectively, selected from all of the esophageal cancer markers according to (11) or (12).

(23) A method for detecting esophageal cancer, comprising measuring an expression level of a target nucleic acid in a sample of a subject using a kit according to any of (1) to (10) or a device according to any of (11) to (22), and evaluating the subject in vitro as having esophageal cancer or having no esophageal cancer using the measured expression level and a control expression level of a healthy subject measured in the same way as above.

(24) The method according to (23), wherein the subject is a human.

(25) The method according to (23) or (24), wherein the sample is blood, serum, or plasma.

Definition of Term

The terms used herein are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The aforementioned RNA includes any of total RNA, mRNA, rRNA, miRNA, siRNA, snoRNA, snRNA, non-coding RNA and synthetic RNA. Here, the "synthetic DNA" and the "synthetic RNA" refer to DNA and RNA artificially prepared using, for example, an automatic nucleic acid synthesizer, on the basis of predetermined nucleotide sequences (which may be any of natural and non-natural sequences). The "non-natural sequence" used herein is intended to be used in a broad sense and includes, for example, a sequence comprising substitution, deletion, insertion, and/or addition of one or more nucleotide(s) (i.e., a variant sequence) and a sequence comprising one or more modified nucleotide(s) (i.e., a modified sequence), which are different from the natural sequence. The term "polynucleotide" used herein is used interchangeably with the term "nucleic acid".

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus(+) strand (or a sense strand) or a complementary strand (or an antisense strand) that constitutes a duplex. The gene is not particularly limited by its length. Thus, the "gene" used herein includes any of double-stranded DNA including human genomic DNA, single-stranded DNA (plus strand), single-stranded DNA having a sequence complementary to the plus strand (complementary strand) including cDNA, microRNA (miRNA), and their fragments, and their transcripts, unless otherwise specified. The "gene" includes not only a "gene" represented by a particular nucleotide sequence (or SEQ ID NO) but also "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 700 or a nucleotide sequence from the nucleotide sequence by the replacement of u with t. Regardless whether or not there is a difference in functional region, the "gene" can comprise, for example, expression regulatory regions, coding regions, exons, or introns. The "gene" may be contained in a cell or may exist alone after being released from a cell. Alternatively, the "gene" may be in a state enclosed in a vesicle called exosome.

The term "exosome" used herein is a vesicle that is encapsulated by lipid bilayer and secreted from a cell. The exosome is derived from a multivesicular endosome and may incorporate biomaterials such as "genes" (e.g., RNA or DNA) or proteins when released into an extracellular environment. The exosome is known to be contained in a body fluid such as blood, serum, plasma or lymph.

The term "transcript" used herein refers to an RNA synthesized from the DNA sequence of a gene as a template. RNA polymerase binds to a site called a promoter located upstream of the gene and adds ribonucleotides complementary to the nucleotide sequence of the DNA to the 3' end to synthesize RNA. This RNA contains not only the gene itself but also the whole sequence from a transcription initiation site to the end of a polyA sequence, including expression regulatory regions, coding regions, exons, or introns.

Unless otherwise specified, the term "microRNA (miRNA)" used herein is intended to mean a 15- to 25-nucleotide non-coding RNA that is involved in the suppression of translation of mRNA, and that transcribed as an RNA precursor having a hairpin-like structure, cleaved by a dsRNA-cleaving enzyme which has RNase III cleavage activity, and integrated into a protein complex called RISC.

The term "miRNA" used herein includes not only a "miRNA" represented by a particular nucleotide sequence (or SEQ ID NO) but also a precursor of the "miRNA" (pre-miRNA or pri-miRNA), and miRNAs that have biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 700. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting RNA resulting from the expression of a gene or a polynucleotide from the RNA, and/or a polynucleotide complementary thereto.

The term "primer" used herein includes a polynucleotide that specifically recognizes and amplifies an RNA resulting from the expression of a gene or a polynucleotide from the RNA, and/or a polynucleotide complementary thereto. In this context, the complementary polynucleotide (complementary strand or reverse strand) means a polynucleotide in a complementary relationship of—A:T (U) and G:C base pairs with the full-length sequence of a polynucleotide consisting of a nucleotide sequence defined by any of SEQ ID NOs: 1 to 700 or a nucleotide sequence from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence that is 100% complementary to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 700 or a nucleotide sequence from the nucleotide sequence by the replacement of u with t, or a partial sequence thereof; a variant that exhibits identity of approximately 90% or higher, approximately 95% or higher, approximately 97% or higher, approximately 98% or higher, approximately 99% or higher to each of these nucleotide sequences or the partial sequence thereof; or a nucleic acid hybridizing under the stringent conditions defined above to a polynucleotide or an oligonucleotide comprising each of these nucleotide sequences or the partial sequence thereof.

The term "several" or "plurality" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "identity" used herein can be determined with or without an introduced gap, using a protein or gene search system based on BLAST or FASTA (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A., Vol. 85, p. 2444-2448).

The term "derivative" used herein is meant to include a unlimitedly modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) n.

The "nucleic acid" used herein capable of specifically binding to a polynucleotide selected from the esophageal cancer marker miRNAs described above is a synthesized or prepared nucleic acid and specifically includes a "nucleic acid probe" or a "primer". The "nucleic acid" is utilized directly or indirectly for detecting the presence or absence of esophageal cancer in a subject, for diagnosing the presence or absence of esophageal cancer the severity of esophageal cancer, the presence or absence of amelioration or the degree of amelioration of esophageal cancer, or the therapeutic sensitivity of esophageal cancer, or for screening for a candidate substance useful in the prevention, amelioration, or treatment of esophageal cancer. The "nucleic acid" includes a nucleotide, an oligonucleotide, and a polynucleotide capable of specifically recognizing and binding to a transcript represented by any of SEQ ID NOs: 1 to 700 or a synthetic cDNA nucleic acid thereof in vivo, particularly, in a sample such as a body fluid (e.g., blood or urine), in relation to the development of esophageal cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". The term "evaluation" used herein is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected, i.e., esophageal cancer.

The term "P" or "P value" used herein refers to a probability at which a more extreme statistic than that actually calculated from data under null hypothesis is observed in a statistical test. Thus, smaller "P" or "P value" s regarded as being a more significant difference between subjects to be compared.

The term "sensitivity" used herein means a value of (the number of true positives)/(the number of true positives+the number of false negatives). High sensitivity allows esophageal cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being esophageal cancer patients, leading to reduction in burden on patients and reduction in medical expense.

The term "accuracy" used herein means a value of (the number of true positives+the number of true negatives)/(the total number of cases). The accuracy indicates the ratio of samples that identified correctly in the discriminant results to all samples and serves as a primary index for evaluating detection performance.

The "sample" used herein that is subjected to determination, detection, or diagnosis refers to a tissue and a biological material in which the expression of the gene of the present invention varies as esophageal cancer develops, as esophageal cancer progresses, or as therapeutic effects on esophageal cancer are exerted. Specifically, the "sample" refers to an esophageal tissue, a periesophageal vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-204-3p gene" or "hsa-miR-204-3p" used herein includes the hsa-miR-204-3p gene (miRBase Accession No. MIMAT0022693) consisting of the nucleotide sequence represented by SEQ ID NO: 1, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 215) having a hairpin-like structure is known as a precursor of "hsa-miR-204-3p".

The term "hsa-miR-1247-3p gene" or "hsa-miR-1247-3p" used herein includes the hsa-miR-1247-3p gene (miRBase Accession No. MIMAT0022721) consisting of the nucleotide sequence represented by SEQ ID NO: 2, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 216) having a hairpin-like structure is known as a precursor of "hsa-miR-1247-3p".

The term "hsa-miR-6875-5p gene" or "hsa-miR-6875-5p" used herein includes the hsa-miR-6875-5p gene (miRBase Accession No. MIMAT0027650) consisting of the nucleotide sequence represented by SEQ ID NO: 3, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 217) having a hairpin-like structure is known as a precursor of "hsa-miR-6875-5p".

The term "hsa-miR-6857-5p gene" or "hsa-miR-6857-5p" used herein includes the hsa-miR-6857-5p gene (miRBase Accession No. MIMAT0027614) consisting of the nucleotide sequence represented by SEQ ID NO: 4, a homolog or an ortholog of a different organism species, and the like. The hsa-miR-6857-5p gene can be obtained by a method described in Ladewig E et al., 2012, Genome Res, Vol. 22, p. 1634-1645. Also, "hsa-mir-6857" (miRBase Accession No. MI0022703, SEQ ID NO: 218) having a hairpin-like structure is known as a precursor of "hsa-miR-6857-5p".

The term "hsa-miR-6726-5p gene" or "hsa-miR-6726-5p" used herein includes the hsa-miR-6726-5p gene (miRBase Accession No. MIMAT0027353) consisting of the nucleotide sequence represented by SEQ ID NO: 5, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 219) having a hairpin-like structure is known as a precursor of "hsa-miR-6726-5p".

The term "hsa-miR-3188 gene" or "hsa-miR-3188" used herein includes the hsa-miR-3188 gene (miRBase Accession No. MIMAT0015070) consisting of the nucleotide sequence represented by SEQ ID NO: 6, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 220) having a hairpin-like structure is known as a precursor of "hsa-miR-3188".

The term "hsa-miR-8069 gene" or "hsa-miR-8069" used herein includes the hsa-miR-8069 gene (miRBase Accession No. MIMAT0030996) consisting of the nucleotide sequence represented by SEQ ID NO: 7, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 221) having a hairpin-like structure is known as a precursor of "hsa-miR-8069".

The term "hsa-miR-4257 gene" or "hsa-miR-4257" used herein includes the hsa-miR-4257 gene (miRBase Accession No. MIMAT0016878) consisting of the nucleotide sequence represented by SEQ ID NO: 8, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 222) having a hairpin-like structure is known as a precursor of "hsa-miR-4257".

The term "hsa-miR-1343-3p gene" or "hsa-miR-1343-3p" used herein includes the hsa-miR-1343-3p gene (miRBase Accession No. MIMAT0019776) consisting of the nucleotide sequence represented by SEQ ID NO: 9, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 223) having a hairpin-like structure is known as a precursor of "hsa-miR-1343-3p".

The term "hsa-miR-7108-5p gene" or "hsa-miR-7108-5p" used herein includes the hsa-miR-7108-5p gene (miRBase Accession No. MIMAT0028113) consisting of the nucleotide sequence represented by SEQ ID NO: 10, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 224) having a hairpin-like structure is known as a precursor of "hsa-miR-7108-5p".

The term "hsa-miR-6825-5p gene" or "hsa-miR-6825-5p" used herein includes the hsa-miR-6825-5p gene (miRBase Accession No. MIMAT0027550) consisting of the nucleotide sequence represented by SEQ ID NO: 11, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 225) having a hairpin-like structure is known as a precursor of "hsa-miR-6825-5p".

The term "hsa-miR-7641 gene" or "hsa-miR-7641" used herein includes the hsa-miR-7641 gene (miRBase Accession No. MIMAT0029782) consisting of the nucleotide sequence represented by SEQ ID NO: 12, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NOs: 226 and 227) having a hairpin-like structure are known as precursors of "hsa-miR-7641".

The term "hsa-miR-3185 gene" or "hsa-miR-3185" used herein includes the hsa-miR-3185 gene (miRBase Accession No. MIMAT0015065) consisting of the nucleotide sequence represented by SEQ ID NO: 13, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 228) having a hairpin-like structure is known as a precursor of "hsa-miR-3185".

The term "hsa-miR-4746-3p gene" or "hsa-miR-4746-3p" used herein includes the hsa-miR-4746-3p gene (miRBase Accession No. MIMAT0019881) consisting of the nucleotide sequence represented by SEQ ID NO: 14, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 229) having a hairpin-like structure is known as a precursor of "hsa-miR-4746-3p".

The term "hsa-miR-6791-5p gene" or "hsa-miR-6791-5p" used herein includes the hsa-miR-6791-5p gene (miRBase Accession No. MIMAT0027482) consisting of the nucleotide sequence represented by SEQ ID NO: 15, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 230) having a hairpin-like structure is known as a precursor of "hsa-miR-6791-5p".

The term "hsa-miR-6893-5p gene" or "hsa-miR-6893-5p" used herein includes the hsa-miR-6893-5p gene (miRBase Accession No. MIMAT0027686) consisting of the nucleotide sequence represented by SEQ ID NO: 16, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 231) having a hairpin-like structure is known as a precursor of "hsa-miR-6893-5p".

The term "hsa-miR-4433b-3p gene" or "hsa-miR-4433b-3p" used herein includes the hsa-miR-4433b-3p gene (miRBase Accession No. MIMAT0030414) consisting of the nucleotide sequence represented by SEQ ID NO: 17, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 232) having a hairpin-like structure is known as a precursor of "hsa-miR-4433b-3p".

The term "hsa-miR-3135b gene" or "hsa-miR-3135b" used herein includes the hsa-miR-3135b gene (miRBase Accession No. MIMAT0018985) consisting of the nucleotide sequence represented by SEQ ID NO: 18, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 233) having a hairpin-like structure is known as a precursor of "hsa-miR-3135b".

The term "hsa-miR-6781-5p gene" or "hsa-miR-6781-5p" used herein includes the hsa-miR-6781-5p gene (miRBase Accession No. MIMAT0027462) consisting of the nucleotide sequence represented by SEQ ID NO: 19, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 234) having a hairpin-like structure is known as a precursor of "hsa-miR-6781-5p".

The term "hsa-miR-1908-5p gene" or "hsa-miR-1908-5p" used herein includes the hsa-miR-1908-5p gene (miRBase Accession No. MIMAT0007881) consisting of the nucleotide sequence represented by SEQ ID NO: 20, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 235) having a hairpin-like structure is known as a precursor of "hsa-miR-1908-5p".

The term "hsa-miR-4792 gene" or "hsa-miR-4792" used herein includes the hsa-miR-4792 gene (miRBase Accession No. MIMAT0019964) consisting of the nucleotide sequence represented by SEQ ID NO: 21, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 236) having a hairpin-like structure is known as a precursor of "hsa-miR-4792".

The term "hsa-miR-7845-5p gene" or "hsa-miR-7845-5p" used herein includes the hsa-miR-7845-5p gene (miRBase Accession No. MIMAT0030420) consisting of the nucleotide sequence represented by SEQ ID NO: 22, a homolog or an ortholog of a different organism species, and the like. The hsa-miR-7845-5p gene can be obtained by a method described in Plc H et al., 2012, PLoS One, Vol. 7, e50746. Also, "hsa-mir-7845" (miRBase Accession No. MI0025515, SEQ ID NO: 237) having a hairpin-like structure is known as a precursor of "hsa-miR-7845-5p".

The term "hsa-miR-4417 gene" or "hsa-miR-4417" used herein includes the hsa-miR-4417 gene (miRBase Accession No. MIMAT0018929) consisting of the nucleotide sequence represented by SEQ ID NO: 23, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 238) having a hairpin-like structure is known as a precursor of "hsa-miR-4417".

The term "hsa-miR-3184-5p gene" or "hsa-miR-3184-5p" used herein includes the hsa-miR-3184-5p gene (miRBase Accession No. MIMAT0015064) consisting of the nucleotide sequence represented by SEQ ID NO: 24, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 239) having a hairpin-like structure is known as a precursor of "hsa-miR-3184-5p".

The term "hsa-miR-1225-5p gene" or "hsa-miR-1225-5p" used herein includes the hsa-miR-1225-5p gene (miRBase Accession No. MIMAT0005572) consisting of the nucleotide sequence represented by SEQ ID NO: 25, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 240) having a hairpin-like structure is known as a precursor of "hsa-miR-1225-5p".

The term "hsa-miR-1231 gene" or "hsa-miR-1231" used herein includes the hsa-miR-1231 gene (miRBase Accession No. MIMAT0005586) consisting of the nucleotide sequence represented by SEQ ID NO: 26, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 241) having a hairpin-like structure is known as a precursor of "hsa-miR-1231".

The term "hsa-miR-1225-3p gene" or "hsa-miR-1225-3p" used herein includes the hsa-miR-1225-3p gene (miRBase Accession No. MIMAT0005573) consisting of the nucleotide sequence represented by SEQ ID NO: 27, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 240) having a hairpin-like structure is known as a precursor of "hsa-miR-1225-3p".

The term "hsa-miR-150-3p gene" or "hsa-miR-150-3p" used herein includes the hsa-miR-150-3p gene (miRBase Accession No. MIMAT0004610) consisting of the nucleotide sequence represented by SEQ ID NO: 28, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 242) having a hairpin-like structure is known as a precursor of "hsa-miR-150-3p".

The term "hsa-miR-4433-3p gene" or "hsa-miR-4433-3p" used herein includes the hsa-miR-4433-3p gene (miRBase Accession No. MIMAT0018949) consisting of the nucleotide sequence represented by SEQ ID NO: 29, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 243) having a hairpin-like structure is known as a precursor of "hsa-miR-4433-3p".

The term "hsa-miR-6125 gene" or "hsa-miR-6125" used herein includes the hsa-miR-6125 gene (miRBase Accession No. MIMAT0024598) consisting of the nucleotide sequence represented by SEQ ID NO: 30, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 244) having a hairpin-like structure is known as a precursor of "hsa-miR-6125".

The term "hsa-miR-4513 gene" or "hsa-miR-4513" used herein includes the hsa-miR-4513 gene (miRBase Accession No. MIMAT0019050) consisting of the nucleotide sequence represented by SEQ ID NO: 31, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 245) having a hairpin-like structure is known as a precursor of "hsa-miR-4513".

The term "hsa-miR-6787-5p gene" or "hsa-miR-6787-5p" used herein includes the hsa-miR-6787-5p gene (miRBase Accession No. MIMAT0027474) consisting of the nucleotide sequence represented by SEQ ID NO: 32, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 246) having a hairpin-like structure is known as a precursor of "hsa-miR-6787-5p".

The term "hsa-miR-6784-5p gene" or "hsa-miR-6784-5p" used herein includes the hsa-miR-6784-5p gene (miRBase Accession No. MIMAT0027468) consisting of the nucleotide sequence represented by SEQ ID NO: 33, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 247) having a hairpin-like structure is known as a precursor of "hsa-miR-6784-5p".

The term "hsa-miR-615-5p gene" or "hsa-miR-615-5p" used herein includes the hsa-miR-615-5p gene (miRBase Accession No. MIMAT0004804) consisting of the nucleotide sequence represented by SEQ ID NO: 34, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 248) having a hairpin-like structure is known as a precursor of "hsa-miR-615-5p".

The term "hsa-miR-6765-3p gene" or "hsa-miR-6765-3p" used herein includes the hsa-miR-6765-3p gene (miRBase Accession No. MIMAT0027431) consisting of the nucleotide sequence represented by SEQ ID NO: 35, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 249) having a hairpin-like structure is known as a precursor of "hsa-miR-6765-3p".

The term "hsa-miR-5572 gene" or "hsa-miR-5572" used herein includes the hsa-miR-5572 gene (miRBase Accession No. MIMAT0022260) consisting of the nucleotide sequence represented by SEQ ID NO: 36, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 250) having a hairpin-like structure is known as a precursor of "hsa-miR-5572".

The term "hsa-miR-6842-5p gene" or "hsa-miR-6842-5p" used herein includes the hsa-miR-6842-5p gene (miRBase Accession No. MIMAT0027586) consisting of the nucleotide sequence represented by SEQ ID NO: 37, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 251) having a hairpin-like structure is known as a precursor of "hsa-miR-6842-5p".

The term "hsa-miR-8063 gene" or "hsa-miR-8063" used herein includes the hsa-miR-8063 gene (miRBase Accession No. MIMAT0030990) consisting of the nucleotide sequence represented by SEQ ID NO: 38, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 252) having a hairpin-like structure is known as a precursor of "hsa-miR-8063".

The term "hsa-miR-6780b-5p gene" or "hsa-miR-6780b-5p" used herein includes the hsa-miR-6780b-5p gene (miRBase Accession No. MIMAT0027572) consisting of the nucleotide sequence represented by SEQ ID NO: 39, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 253) having a hairpin-like structure is known as a precursor of "hsa-miR-6780b-5p".

The term "hsa-miR-187-5p gene" or "hsa-miR-187-5p" used herein includes the hsa-miR-187-5p gene (miRBase Accession No. MIMAT0004561) consisting of the nucleotide sequence represented by SEQ ID NO: 40, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 254) having a hairpin-like structure is known as a precursor of "hsa-miR-187-5p".

The term "hsa-miR-128-1-5p gene" or "hsa-miR-128-1-5p" used herein includes the hsa-miR-128-1-5p gene (miRBase Accession No. MIMAT0026477) consisting of the nucleotide sequence represented by SEQ ID NO: 41, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 255) having a hairpin-like structure is known as a precursor of "hsa-miR-128-1-5p".

The term "hsa-miR-6729-5p gene" or "hsa-miR-6729-5p" used herein includes the hsa-miR-6729-5p gene (miRBase Accession No. MIMAT0027359) consisting of the nucleotide sequence represented by SEQ ID NO: 42, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 256) having a hairpin-like structure is known as a precursor of "hsa-miR-6729-5p".

The term "hsa-miR-6741-5p gene" or "hsa-miR-6741-5p" used herein includes the hsa-miR-6741-5p gene (miRBase Accession No. MIMAT0027383) consisting of the nucleotide sequence represented by SEQ ID NO: 43, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 257) having a hairpin-like structure is known as a precursor of "hsa-miR-6741-5p".

The term "hsa-miR-6757-5p gene" or "hsa-miR-6757-5p" used herein includes the hsa-miR-6757-5p gene (miRBase Accession No. MIMAT0027414) consisting of the nucleotide sequence represented by SEQ ID NO: 44, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 258) having a hairpin-like structure is known as a precursor of "hsa-miR-6757-5p".

The term "hsa-miR-7110-5p gene" or "hsa-miR-7110-5p" used herein includes the hsa-miR-7110-5p gene (miRBase Accession No. MIMAT0028117) consisting of the nucleotide sequence represented by SEQ ID NO: 45, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 259) having a hairpin-like structure is known as a precursor of "hsa-miR-7110-5p".

The term "hsa-miR-7975 gene" or "hsa-miR-7975" used herein includes the hsa-miR-7975 gene (miRBase Accession No. MIMAT0031178) consisting of the nucleotide sequence represented by SEQ ID NO: 46, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 260) having a hairpin-like structure is known as a precursor of "hsa-miR-7975".

The term "hsa-miR-1233-5p gene" or "hsa-miR-1233-5p" used herein includes the hsa-miR-1233-5p gene (miRBase Accession No. MIMAT0022943) consisting of the nucleotide sequence represented by SEQ ID NO: 47, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 261 and 262) having a hairpin-like structure are known as precursors of "hsa-miR-1233-5p".

The term "hsa-miR-6845-5p gene" or "hsa-miR-6845-5p" used herein includes the hsa-miR-6845-5p gene (miRBase Accession No. MIMAT0027590) consisting of the nucleotide sequence represented by SEQ ID NO: 48, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 263) having a hairpin-like structure is known as a precursor of "hsa-miR-6845-5p".

The term "hsa-miR-3937 gene" or "hsa-miR-3937" used herein includes the hsa-miR-3937 gene (miRBase Accession No. MIMAT0018352) consisting of the nucleotide sequence represented by SEQ ID NO: 49, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 264) having a hairpin-like structure is known as a precursor of "hsa-miR-3937".

The term "hsa-miR-4467 gene" or "hsa-miR-4467" used herein includes the hsa-miR-4467 gene (miRBase Accession No. MIMAT0018994) consisting of the nucleotide sequence represented by SEQ ID NO: 50, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 265) having a hairpin-like structure is known as a precursor of "hsa-miR-4467".

The term "hsa-miR-7109-5p gene" or "hsa-miR-7109-5p" used herein includes the hsa-miR-7109-5p gene (miRBase Accession No. MIMAT0028115) consisting of the nucleotide sequence represented by SEQ ID NO: 51, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 266) having a hairpin-like structure is known as a precursor of "hsa-miR-7109-5p".

The term "hsa-miR-6088 gene" or "hsa-miR-6088" used herein includes the hsa-miR-6088 gene (miRBase Accession No. MIMAT0023713) consisting of the nucleotide sequence represented by SEQ ID NO: 52, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 267) having a hairpin-like structure is known as a precursor of "hsa-miR-6088".

The term "hsa-miR-6782-5p gene" or "hsa-miR-6782-5p" used herein includes the hsa-miR-6782-5p gene (miRBase Accession No. MIMAT0027464) consisting of the nucleotide sequence represented by SEQ ID NO: 53, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 268) having a hairpin-like structure is known as a precursor of "hsa-miR-6782-5p".

The term "hsa-miR-5195-3p gene" or "hsa-miR-5195-3p" used herein includes the hsa-miR-5195-3p gene (miRBase Accession No. MIMAT0021127) consisting of the nucleotide sequence represented by SEQ ID NO: 54, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 269) having a hairpin-like structure is known as a precursor of "hsa-miR-5195-3p".

The term "hsa-miR-4454 gene" or "hsa-miR-4454" used herein includes the hsa-miR-4454 gene (miRBase Accession No. MIMAT0018976) consisting of the nucleotide sequence represented by SEQ ID NO: 55, a homolog or an ortholog of a different organism species, and the like. The hsa-miR- 4454 gene can be obtained by a method described in Jima D D et al., 2010, Blood, Vol. 116, e118-e127. Also, "hsa-mir-4454" (miRBase Accession No. MI0016800, SEQ ID NO: 270) having a hairpin-like structure is known as a precursor of "hsa-miR-4454".

The term "hsa-miR-6724-5p gene" or "hsa-miR-6724-5p" used herein includes the hsa-miR-6724-5p gene (miRBase Accession No. MIMAT0025856) consisting of the nucleotide sequence represented by SEQ ID NO: 56, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 271) having a hairpin-like structure is known as a precursor of "hsa-miR-6724-5p".

The term "hsa-miR-8072 gene" or "hsa-miR-8072" used herein includes the hsa-miR-8072 gene (miRBase Accession No. MIMAT0030999) consisting of the nucleotide sequence represented by SEQ ID NO: 57, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 272) having a hairpin-like structure is known as a precursor of "hsa-miR-8072".

The term "hsa-miR-4516 gene" or "hsa-miR-4516" used herein includes the hsa-miR-4516 gene (miRBase Accession No. MIMAT0019053) consisting of the nucleotide sequence represented by SEQ ID NO: 58, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 273) having a hairpin-like structure is known as a precursor of "hsa-miR-4516".

The term "hsa-miR-6756-5p gene" or "hsa-miR-6756-5p" used herein includes the hsa-miR-6756-5p gene (miRBase Accession No. MIMAT0027412) consisting of the nucleotide sequence represented by SEQ ID NO: 59, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 274) having a hairpin-like structure is known as a precursor of "hsa-miR-6756-5p".

The term "hsa-miR-4665-3p gene" or "hsa-miR-4665-3p" used herein includes the hsa-miR-4665-3p gene (miRBase Accession No. MIMAT0019740) consisting of the nucleotide sequence represented by SEQ ID NO: 60, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 275) having a hairpin-like structure is known as a precursor of "hsa-miR-4665-3p".

The term "hsa-miR-6826-5p gene" or "hsa-miR-6826-5p" used herein includes the hsa-miR-6826-5p gene (miRBase Accession No. MIMAT0027552) consisting of the nucleotide sequence represented by SEQ ID NO: 61, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 276) having a hairpin-like structure is known as a precursor of "hsa-miR-6826-5p".

The term "hsa-miR-6820-5p gene" or "hsa-miR-6820-5p" used herein includes the hsa-miR-6820-5p gene (miRBase Accession No. MIMAT0027540) consisting of the nucleotide sequence represented by SEQ ID NO: 62, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 277) having a hairpin-like structure is known as a precursor of "hsa-miR-6820-5p".

The term "hsa-miR-6887-5p gene" or "hsa-miR-6887-5p" used herein includes the hsa-miR-6887-5p gene (miRBase Accession No. MIMAT0027674) consisting of the nucleotide sequence represented by SEQ ID NO: 63, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 278) having a hairpin-like structure is known as a precursor of "hsa-miR-6887-5p".

The term "hsa-miR-3679-5p gene" or "hsa-miR-3679-5p" used herein includes the hsa-miR-3679-5p gene (miRBase Accession No. MIMAT0018104) consisting of the nucleotide sequence represented by SEQ ID NO: 64, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 279) having a hairpin-like structure is known as a precursor of "hsa-miR-3679-5p".

The term "hsa-miR-7847-3p gene" or "hsa-miR-7847-3p" used herein includes the hsa-miR-7847-3p gene (miRBase Accession No. MIMAT0030422) consisting of the nucleotide sequence represented by SEQ ID NO: 65, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 280) having a hairpin-like structure is known as a precursor of "hsa-miR-7847-3p".

The term "hsa-miR-6721-5p gene" or "hsa-miR-6721-5p" used herein includes the hsa-miR-6721-5p gene (miRBase Accession No. MIMAT0025852) consisting of the nucleotide sequence represented by SEQ ID NO: 66, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 281) having a hairpin-like structure is known as a precursor of "hsa-miR-6721-5p".

The term "hsa-miR-3622a-5p gene" or "hsa-miR-3622a-5p" used herein includes the hsa-miR-3622a-5p gene (miRBase Accession No. MIMAT0018003) consisting of the nucleotide sequence represented by SEQ ID NO: 67, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 282) having a hairpin-like structure is known as a precursor of "hsa-miR-3622a-5p".

The term "hsa-miR-939-5p gene" or "hsa-miR-939-5p" used herein includes the hsa-miR-939-5p gene (miRBase Accession No. MIMAT0004982) consisting of the nucleotide sequence represented by SEQ ID NO: 68, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No.

MI0005761, SEQ ID NO: 283) having a hairpin-like structure is known as a precursor of "hsa-miR-939-5p".

The term "hsa-miR-602 gene" or "hsa-miR-602" used herein includes the hsa-miR-602 gene (miRBase Accession No. MIMAT0003270) consisting of the nucleotide sequence represented by SEQ ID NO: 69, a homolog or an ortholog of a different organism species, and the like. The hsa-miR-602 gene can be obtained by a method described in Cummins J M et al., 2006, Proc Natl Acad Sci USA, Vol. 103, p. 3687-3692. Also, "hsa-mir-602" (miRBase Accession No. MI0003615, SEQ ID NO: 284) having a hairpin-like structure is known as a precursor of "hsa-miR-602".

The term "hsa-miR-7977 gene" or "hsa-miR-7977" used herein includes the hsa-miR-7977 gene (miRBase Accession No. MIMAT0031180) consisting of the nucleotide sequence represented by SEQ ID NO: 70, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 285) having a hairpin-like structure is known as a precursor of "hsa-miR-7977".

The term "hsa-miR-6749-5p gene" or "hsa-miR-6749-5p" used herein includes the hsa-miR-6749-5p gene (miRBase Accession No. MIMAT0027398) consisting of the nucleotide sequence represented by SEQ ID NO: 71, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 286) having a hairpin-like structure is known as a precursor of "hsa-miR-6749-5p".

The term "hsa-miR-1914-3p gene" or "hsa-miR-1914-3p" used herein includes the hsa-miR-1914-3p gene (miRBase Accession No. MIMAT0007890) consisting of the nucleotide sequence represented by SEQ ID NO: 72, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 287) having a hairpin-like structure is known as a precursor of "hsa-miR-1914-3p".

The term "hsa-miR-4651 gene" or "hsa-miR-4651" used herein includes the hsa-miR-4651 gene (miRBase Accession No. MIMAT0019715) consisting of the nucleotide sequence represented by SEQ ID NO: 73, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 288) having a hairpin-like structure is known as a precursor of "hsa-miR-4651".

The term "hsa-miR-4695-5p gene" or "hsa-miR-4695-5p" used herein includes the hsa-miR-4695-5p gene (miRBase Accession No. MIMAT0019788) consisting of the nucleotide sequence represented by SEQ ID NO: 74, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 289) having a hairpin-like structure is known as a precursor of "hsa-miR-4695-5p".

The term "hsa-miR-6848-5p gene" or "hsa-miR-6848-5p" used herein includes the hsa-miR-6848-5p gene (miRBase Accession No. MIMAT0027596) consisting of the nucleotide sequence represented by SEQ ID NO: 75, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 290) having a hairpin-like structure is known as a precursor of "hsa-miR-6848-5p".

The term "hsa-miR-1228-3p gene" or "hsa-miR-1228-3p" used herein includes the hsa-miR-1228-3p gene (miRBase Accession No. MIMAT0005583) consisting of the nucleotide sequence represented by SEQ ID NO: 76, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 291) having a hairpin-like structure is known as a precursor of "hsa-miR-1228-3p".

The term "hsa-miR-642b-3p gene" or "hsa-miR-642b-3p" used herein includes the hsa-miR-642b-3p gene (miRBase Accession No. MIMAT0018444) consisting of the nucleotide sequence represented by SEQ ID NO: 77, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 292) having a hairpin-like structure is known as a precursor of "hsa-miR-642b-3p".

The term "hsa-miR-6746-5p gene" or "hsa-miR-6746-5p" used herein includes the hsa-miR-6746-5p gene (miRBase Accession No. MIMAT0027392) consisting of the nucleotide sequence represented by SEQ ID NO: 78, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 293) having a hairpin-like structure is known as a precursor of "hsa-miR-6746-5p".

The term "hsa-miR-3620-5p gene" or "hsa-miR-3620-5p" used herein includes the hsa-miR-3620-5p gene (miRBase Accession No. MIMAT0022967) consisting of the nucleotide sequence represented by SEQ ID NO: 79, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 294) having a hairpin-like structure is known as a precursor of "hsa-miR-3620-5p".

The term "hsa-miR-3131 gene" or "hsa-miR-3131" used herein includes the hsa-miR-3131 gene (miRBase Accession No. MIMAT0014996) consisting of the nucleotide sequence represented by SEQ ID NO: 80, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 295) having a hairpin-like structure is known as a precursor of "hsa-miR-3131".

The term "hsa-miR-6732-5p gene" or "hsa-miR-6732-5p" used herein includes the hsa-miR-6732-5p gene (miRBase Accession No. MIMAT0027365) consisting of the nucleotide sequence represented by SEQ ID NO: 81, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 296) having a hairpin-like structure is known as a precursor of "hsa-miR-6732-5p".

The term "hsa-miR-7113-3p gene" or "hsa-miR-7113-3p" used herein includes the hsa-miR-7113-3p gene (miRBase Accession No. MIMAT0028124) consisting of the nucleotide sequence represented by SEQ ID NO: 82, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 297) having a hairpin-like structure is known as a precursor of "hsa-miR-7113-3p".

The term "hsa-miR-23a-3p gene" or "hsa-miR-23a-3p" used herein includes the hsa-miR-23a-3p gene (miRBase Accession No. MIMAT0000078) consisting of the nucleotide sequence represented by SEQ ID NO: 83, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 298) having a hairpin-like structure is known as a precursor of "hsa-miR-23a-3p".

The term "hsa-miR-3154 gene" or "hsa-miR-3154" used herein includes the hsa-miR-3154 gene (miRBase Accession No. MIMAT0015028) consisting of the nucleotide sequence represented by SEQ ID NO: 84, a homolog or an ortholog of a different organism species, and the like. The hsa-miR-3154 gene can be obtained by a method described in Berezikov E et al., 2006, Genome Res, Vol. 16, p. 1289-1298. Also, "hsa-mir-3154" (miRBase Accession No. MI0014182, SEQ ID NO: 299) having a hairpin-like structure is known as a precursor of "hsa-miR-3154".

The term "hsa-miR-4723-5p gene" or "hsa-miR-4723-5p" used herein includes the hsa-miR-4723-5p gene (miRBase Accession No. MIMAT0019838) consisting of the nucleotide sequence represented by SEQ ID NO: 85, a homolog or an ortholog of a different organism species, and the like. The hsa-miR-4723-5p gene can be obtained by a method described in Persson H et al., 2011, Cancer Res, Vol. 71, p. 78-86. Also, "hsa-mir-4723" (miRBase Accession No. MI0017359, SEQ ID NO: 300) having a hairpin-like structure is known as a precursor of "hsa-miR-4723-5p".

The term "hsa-miR-3663-3p gene" or "hsa-miR-3663-3p" used herein includes the hsa-miR-3663-3p gene (miRBase Accession No. MIMAT0018085) consisting of the nucleotide sequence represented by SEQ ID NO: 86, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 301) having a hairpin-like structure is known as a precursor of "hsa-miR-3663-3p".

The term "hsa-miR-4734 gene" or "hsa-miR-4734" used herein includes the hsa-miR-4734 gene (miRBase Accession No. MIMAT0019859) consisting of the nucleotide sequence represented by SEQ ID NO: 87, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 302) having a hairpin-like structure is known as a precursor of "hsa-miR-4734".

The term "hsa-miR-6816-5p gene" or "hsa-miR-6816-5p" used herein includes the hsa-miR-6816-5p gene (miRBase Accession No. MIMAT0027532) consisting of the nucleotide sequence represented by SEQ ID NO: 88, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 303) having a hairpin-like structure is known as a precursor of "hsa-miR-6816-5p".

The term "hsa-miR-4442 gene" or "hsa-miR-4442" used herein includes the hsa-miR-4442 gene (miRBase Accession No. MIMAT0018960) consisting of the nucleotide sequence represented by SEQ ID NO: 89, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 304) having a hairpin-like structure is known as a precursor of "hsa-miR-4442".

The term "hsa-miR-4476 gene" or "hsa-miR-4476" used herein includes the hsa-miR-4476 gene (miRBase Accession No. MIMAT0019003) consisting of the nucleotide sequence represented by SEQ ID NO: 90, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 305) having a hairpin-like structure is known as a precursor of "hsa-miR-4476".

The term "hsa-miR-423-5p gene" or "hsa-miR-423-5p" used herein includes the hsa-miR-423-5p gene (miRBase Accession No. MIMAT0004748) consisting of the nucleotide sequence represented by SEQ ID NO: 91, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 306) having a hairpin-like structure is known as a precursor of "hsa-miR-423-5p".

The term "hsa-miR-1249 gene" or "hsa-miR-1249" used herein includes the hsa-miR-1249 gene (miRBase Accession No. MIMAT0005901) consisting of the nucleotide sequence represented by SEQ ID NO: 92, a homolog or an ortholog of a different organism species, and the like. The hsa-miR-1249 gene can be obtained by a method described in Morin R D et al., 2008, Genome Res, Vol. 18, p. 610-621. Also, "hsa-mir-1249" (miRBase Accession No. MI0006384, SEQ ID NO: 307) having a hairpin-like structure is known as a precursor of "hsa-miR-1249".

The term "hsa-miR-6515-3p gene" or "hsa-miR-6515-3p" used herein includes the hsa-miR-6515-3p gene (miRBase Accession No. MIMAT0025487) consisting of the nucleotide sequence represented by SEQ ID NO: 93, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 308) having a hairpin-like structure is known as a precursor of "hsa-miR-6515-3p".

The term "hsa-miR-887-3p gene" or "hsa-miR-887-3p" used herein includes the hsa-miR-887-3p gene (miRBase Accession No. MIMAT0004951) consisting of the nucleotide sequence represented by SEQ ID NO: 94, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 309) having a hairpin-like structure is known as a precursor of "hsa-miR-887-3p".

The term "hsa-miR-4741 gene" or "hsa-miR-4741" used herein includes the hsa-miR-4741 gene (miRBase Accession No. MIMAT0019871) consisting of the nucleotide sequence represented by SEQ ID NO: 95, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 310) having a hairpin-like structure is known as a precursor of "hsa-miR-4741".

The term "hsa-miR-6766-3p gene" or "hsa-miR-6766-3p" used herein includes the hsa-miR-6766-3p gene (miRBase Accession No. MIMAT0027433) consisting of the nucleotide sequence represented by SEQ ID NO: 96, a homolog or an ortholog of a different organism species, and the like. The hsa-miR-6766-3p gene can be obtained by a method described in Ladewig E et al., 2012, Genome Res, Vol. 22, p. 1634-1645. Also, "hsa-mir-6766" (miRBase Accession No. MI0022611, SEQ ID NO: 311) having a hairpin-like structure is known as a precursor of "hsa-miR-6766-3p".

The term "hsa-miR-4673 gene" or "hsa-miR-4673" used herein includes the hsa-miR-4673 gene (miRBase Accession No. MIMAT0019755) consisting of the nucleotide sequence represented by SEQ ID NO: 97, a homolog or an ortholog of a different organism species, and the like. The hsa-miR-4673 gene can be obtained by a method described in Persson H et al., 2011, Cancer Res, Vol. 71, p. 78-86. Also, "hsa-mir-4673" (miRBase Accession No. MI0017304, SEQ ID NO: 312) having a hairpin-like structure is known as a precursor of "hsa-miR-4673".

The term "hsa-miR-6779-5p gene" or "hsa-miR-6779-5p" used herein includes the hsa-miR-6779-5p gene (miRBase Accession No. MIMAT0027458) consisting of the nucleotide sequence represented by SEQ ID NO: 98, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. MI0022624, SEQ ID NO: 313) having a hairpin-like structure is known as a precursor of "hsa-miR-6779-5p".

The term "hsa-miR-4706 gene" or "hsa-miR-4706" used herein includes the hsa-miR-4706 gene (miRBase Accession No. MIMAT0019806) consisting of the nucleotide sequence represented by SEQ ID NO: 99, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 314) having a hairpin-like structure is known as a precursor of "hsa-miR-4706".

The term "hsa-miR-1268b gene" or "hsa-miR-1268b" used herein includes the hsa-miR-1268b gene (miRBase Accession No. MIMAT0018925) consisting of the nucleotide sequence represented by SEQ ID NO: 100, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 315) having a hairpin-like structure is known as a precursor of "hsa-miR-1268b".

The term "hsa-miR-4632-5p gene" or "hsa-miR-4632-5p" used herein includes the hsa-miR-4632-5p gene (miRBase Accession No. MIMAT0022977) consisting of the nucleotide sequence represented by SEQ ID NO: 101, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 316) having a hairpin-like structure is known as a precursor of "hsa-miR-4632-5p".

The term "hsa-miR-3197 gene" or "hsa-miR-3197" used herein includes the hsa-miR-3197 gene (miRBase Accession No. MIMAT0015082) consisting of the nucleotide sequence represented by SEQ ID NO: 102, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 317) having a hairpin-like structure is known as a precursor of "hsa-miR-3197".

The term "hsa-miR-6798-5p gene" or "hsa-miR-6798-5p" used herein includes the hsa-miR-6798-5p gene (miRBase Accession No. MIMAT0027496) consisting of the nucleotide sequence represented by SEQ ID NO: 103, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 318) having a hairpin-like structure is known as a precursor of "hsa-miR-6798-5p".

The term "hsa-miR-711 gene" or "hsa-miR-711" used herein includes the hsa-miR-711 gene (miRBase Accession No. MIMAT0012734) consisting of the nucleotide sequence represented by SEQ ID NO: 104, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 319) having a hairpin-like structure is known as a precursor of "hsa-miR-711".

The term "hsa-miR-6840-3p gene" or "hsa-miR-6840-3p" used herein includes the hsa-miR-6840-3p gene (miRBase Accession No. MIMAT0027583) consisting of the nucleotide sequence represented by SEQ ID NO: 105, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 320) having a hairpin-like structure is known as a precursor of "hsa-miR-6840-3p".

The term "hsa-miR-6763-5p gene" or "hsa-miR-6763-5p" used herein includes the hsa-miR-6763-5p gene (miRBase Accession No. MIMAT0027426) consisting of the nucleotide sequence represented by SEQ ID NO: 106, a homolog or an ortholog of a different organism species, and the like. The hsa-miR-6763-5p gene can be obtained by a method described in Ladewig E et al., 2012, Genome Res, Vol. 22, p. 1634-1645. Also, "hsa-mir-6763" (miRBase Accession No. MI0022608, SEQ ID NO: 321) having a hairpin-like structure is known as a precursor of "hsa-miR-6763-5p".

The term "hsa-miR-6727-5p gene" or "hsa-miR-6727-5p" used herein includes the hsa-miR-6727-5p gene (miRBase Accession No. MIMAT0027355) consisting of the nucleotide sequence represented by SEQ ID NO: 107, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 322) having a hairpin-like structure is known as a precursor of "hsa-miR-6727-5p".

The term "hsa-miR-371a-5p gene" or "hsa-miR-371a-5p" used herein includes the hsa-miR-371a-5p gene (miRBase Accession No. MIMAT0004687) consisting of the nucleotide sequence represented by SEQ ID NO: 108, a homolog or an ortholog of a different organism species, and the like. The hsa-miR-371a-5p gene can be obtained by a method described in Suh M R et al., 2004, Dev Biol, Vol. 270, p.

488-498. Also, "hsa-mir-371a" (miRBase Accession No. MI0000779, SEQ ID NO: 323) having a hairpin-like structure is known as a precursor of "hsa-miR-371a-5p".

The term "hsa-miR-6824-5p gene" or "hsa-miR-6824-5p" used herein includes the hsa-miR-6824-5p gene (miRBase Accession No. MIMAT0027548) consisting of the nucleotide sequence represented by SEQ ID NO: 109, a homolog or an ortholog of a different organism species, and the like. The hsa-miR-6824-5p gene can be obtained by a method described in Ladewig E et al., 2012, Genome Res, Vol. 22, p. 1634-1645. Also, "hsa-mir-6824" (miRBase Accession No. MI0022669, SEQ ID NO: 324) having a hairpin-like structure is known as a precursor of "hsa-miR-6824-5p".

The term "hsa-miR-4648 gene" or "hsa-miR-4648" used herein includes the hsa-miR-4648 gene (miRBase Accession No. MIMAT0019710) consisting of the nucleotide sequence represented by SEQ ID NO: 110, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 325) having a hairpin-like structure is known as a precursor of "hsa-miR-4648".

The term "hsa-miR-1227-5p gene" or "hsa-miR-1227-5p" used herein includes the hsa-miR-1227-5p gene (miRBase Accession No. MIMAT0022941) consisting of the nucleotide sequence represented by SEQ ID NO: 111, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 326) having a hairpin-like structure is known as a precursor of "hsa-miR-1227-5p".

The term "hsa-miR-564 gene" or "hsa-miR-564" used herein includes the hsa-miR-564 gene (miRBase Accession No. MIMAT0003228) consisting of the nucleotide sequence represented by SEQ ID NO: 112, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 327) having a hairpin-like structure is known as a precursor of "hsa-miR-564".

The term "hsa-miR-3679-3p gene" or "hsa-miR-3679-3p" used herein includes the hsa-miR-3679-3p gene (miRBase Accession No. MIMAT0018105) consisting of the nucleotide sequence represented by SEQ ID NO: 113, a homolog or an ortholog of a different organism species, and the like. The hsa-miR-3679-3p gene can be obtained by a method described in Creighton C J et al., 2010, PLoS One, Vol. 5, e9637. Also, "hsa-mir-3679" (miRBase Accession No. MI0016080, SEQ ID NO: 279) having a hairpin-like structure is known as a precursor of "hsa-miR-3679-3p".

The term "hsa-miR-2861 gene" or "hsa-miR-2861" used herein includes the hsa-miR-2861 gene (miRBase Accession No. MIMAT0013802) consisting of the nucleotide sequence represented by SEQ ID NO: 114, a homolog or an ortholog of a different organism species, and the like. The hsa-miR-2861 gene can be obtained by a method described in Li H et al., 2009, J Clin Invest, Vol. 119, p. 3666-3677. Also, "hsa-mir-2861" (miRBase Accession No. MI0013006, SEQ ID NO: 328) having a hairpin-like structure is known as a precursor of "hsa-miR-2861".

The term "hsa-miR-6737-5p gene" or "hsa-miR-6737-5p" used herein includes the hsa-miR-6737-5p gene (miRBase Accession No. MIMAT0027375) consisting of the nucleotide sequence represented by SEQ ID NO: 115, a homolog or an ortholog of a different organism species, and the like. The hsa-miR-6737-5p gene can be obtained by a method described in Ladewig E et al., 2012, Genome Res, Vol. 22, p. 1634-1645. Also, "hsa-mir-6737" (miRBase Accession No. MI0022582, SEQ ID NO: 329) having a hairpin-like structure is known as a precursor of "hsa-miR-6737-5p".

The term "hsa-miR-575 gene" or "hsa-miR-575" used herein includes the hsa-miR-575 gene (miRBase Accession No. MIMAT0003240) consisting of the nucleotide sequence represented by SEQ ID NO: 116, a homolog or an ortholog of a different organism species, and the like. The hsa-miR-575 gene can be obtained by a method described in Cummins J M et al., 2006, Proc Natl Acad Sci USA, Vol. 103, p. 3687-3692. Also, "hsa-mir-575" (miRBase Accession No. MI0003582, SEQ ID NO: 330) having a hairpin-like structure is known as a precursor of "hsa-miR-575".

The term "hsa-miR-4725-3p gene" or "hsa-miR-4725-3p" used herein includes the hsa-miR-4725-3p gene (miRBase Accession No. MIMAT0019844) consisting of the nucleotide sequence represented by SEQ ID NO: 117, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 331) having a hairpin-like structure is known as a precursor of "hsa-miR-4725-3p".

The term "hsa-miR-6716-5p gene" or "hsa-miR-6716-5p" used herein includes the hsa-miR-6716-5p gene (miRBase Accession No. MIMAT0025844) consisting of the nucleotide sequence represented by SEQ ID NO: 118, a homolog or an ortholog of a different organism species, and the like. The hsa-miR-6716-5p gene can be obtained by a method described in Li Y et al., 2012, Gene, Vol. 497, p. 330-335. Also, "hsa-mir-6716" (miRBase Accession No. MI0022550, SEQ ID NO: 332) having a hairpin-like structure is known as a precursor of "hsa-miR-6716-5p".

The term "hsa-miR-4675 gene" or "hsa-miR-4675" used herein includes the hsa-miR-4675 gene (miRBase Accession No. MIMAT0019757) consisting of the nucleotide sequence represented by SEQ ID NO: 119, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 333) having a hairpin-like structure is known as a precursor of "hsa-miR-4675".

The term "hsa-miR-1915-3p gene" or "hsa-miR-1915-3p" used herein includes the hsa-miR-1915-3p gene (miRBase Accession No. MIMAT0007892) consisting of the nucleotide sequence represented by SEQ ID NO: 120, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 334) having a hairpin-like structure is known as a precursor of "hsa-miR-1915-3p".

The term "hsa-miR-671-5p gene" or "hsa-miR-671-5p" used herein includes the hsa-miR-671-5p gene (miRBase Accession No. MIMAT0003880) consisting of the nucleotide sequence represented by SEQ ID NO: 121, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. MI0003760, SEQ ID NO: 335) having a hairpin-like structure is known as a precursor of "hsa-miR-671-5p".

The term "hsa-miR-3656 gene" or "hsa-miR-3656" used herein includes the hsa-miR-3656 gene (miRBase Accession No. MIMAT0018076) consisting of the nucleotide sequence represented by SEQ ID NO: 122, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 336) having a hairpin-like structure is known as a precursor of "hsa-miR-3656".

The term "hsa-miR-6722-3p gene" or "hsa-miR-6722-3p" used herein includes the hsa-miR-6722-3p gene (miRBase Accession No. MIMAT0025854) consisting of the nucleotide sequence represented by SEQ ID NO: 123, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 337) having a hairpin-like structure is known as a precursor of "hsa-miR-6722-3p".

The term "hsa-miR-4707-5p gene" or "hsa-miR-4707-5p" used herein includes the hsa-miR-4707-5p gene (miRBase Accession No. MIMAT0019807) consisting of the nucleotide sequence represented by SEQ ID NO: 124, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 338) having a hairpin-like structure is known as a precursor of "hsa-miR-4707-5p".

The term "hsa-miR-4449 gene" or "hsa-miR-4449" used herein includes the hsa-miR-4449 gene (miRBase Accession No. MIMAT0018968) consisting of the nucleotide sequence represented by SEQ ID NO: 125, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No. MI0016792, SEQ ID NO: 339) having a hairpin-like structure is known as a precursor of "hsa-miR-4449".

The term "hsa-miR-1202 gene" or "hsa-miR-1202" used herein includes the hsa-miR-1202 gene (miRBase Accession No. MIMAT0005865) consisting of the nucleotide sequence represented by SEQ ID NO: 126, a homolog or an ortholog of a different organism species, and the like. The hsa-miR-1202 gene can be obtained by a method described in Marton S et al., 2008, Leukemia, Vol. 22, p. 330-338. Also, "hsa-mir-1202" (miRBase Accession No. MI0006334, SEQ ID NO: 340) having a hairpin-like structure is known as a precursor of "hsa-miR-1202".

The term "hsa-miR-4649-5p gene" or "hsa-miR-4649-5p" used herein includes the hsa-miR-4649-5p gene (miRBase Accession No. MIMAT0019711) consisting of the nucleotide sequence represented by SEQ ID NO: 127, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 341) having a hairpin-like structure is known as a precursor of "hsa-miR-4649-5p".

The term "hsa-miR-744-5p gene" or "hsa-miR-744-5p" used herein includes the hsa-miR-744-5p gene (miRBase Accession No. MIMAT0004945) consisting of the nucleotide sequence represented by SEQ ID NO: 128, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 342) having a hairpin-like structure is known as a precursor of "hsa-miR-744-5p".

The term "hsa-miR-642a-3p gene" or "hsa-miR-642a-3p" used herein includes the hsa-miR-642a-3p gene (miRBase Accession No. MIMAT0020924) consisting of the nucleotide sequence represented by SEQ ID NO: 129, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 343) having a hairpin-like structure is known as a precursor of "hsa-miR-642a-3p".

The term "hsa-miR-451a gene" or "hsa-miR-451a" used herein includes the hsa-miR-451a gene (miRBase Accession No. MIMAT0001631) consisting of the nucleotide sequence represented by SEQ ID NO: 130, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 344) having a hairpin-like structure is known as a precursor of "hsa-miR-451a".

The term "hsa-miR-6870-5p gene" or "hsa-miR-6870-5p" used herein includes the hsa-miR-6870-5p gene (miRBase Accession No. MIMAT0027640) consisting of the nucleotide sequence represented by SEQ ID NO: 131, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 345) having a hairpin-like structure is known as a precursor of "hsa-miR-6870-5p".

The term "hsa-miR-4443 gene" or "hsa-miR-4443" used herein includes the hsa-miR-4443 gene (miRBase Accession No. MIMAT0018961) consisting of the nucleotide sequence represented by SEQ ID NO: 132, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786, SEQ ID NO: 346) having a hairpin-like structure is known as a precursor of "hsa-miR-4443".

The term "hsa-miR-6808-5p gene" or "hsa-miR-6808-5p" used herein includes the hsa-miR-6808-5p gene (miRBase Accession No. MIMAT0027516) consisting of the nucleotide sequence represented by SEQ ID NO: 133, a homolog or an ortholog of a different organism species, and the like. The hsa-miR-6808-5p gene can be obtained by a method described in Ladewig E et al., 2012, Genome Res, Vol. 22, p. 1634-1645. Also, "hsa-mir-6808" (miRBase Accession No. MI0022653, SEQ ID NO: 347) having a hairpin-like structure is known as a precursor of "hsa-miR-6808-5p".

The term "hsa-miR-4728-5p gene" or "hsa-miR-4728-5p" used herein includes the hsa-miR-4728-5p gene (miRBase Accession No. MIMAT0019849) consisting of the nucleotide sequence represented by SEQ ID NO: 134, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 348) having a hairpin-like structure is known as a precursor of "hsa-miR-4728-5p".

The term "hsa-miR-937-5p gene" or "hsa-miR-937-5p" used herein includes the hsa-miR-937-5p gene (miRBase Accession No. MIMAT0022938) consisting of the nucleotide sequence represented by SEQ ID NO: 135, a homolog or an ortholog of a different organism species, and the like. The hsa-miR-937-5p gene can be obtained by a method described in Lui W O et al., 2007, Cancer Res, Vol. 67, p. 6031-6043. Also, "hsa-mir-937" (miRBase Accession No. MI0005759, SEQ ID NO: 349) having a hairpin-like structure is known as a precursor of "hsa-miR-937-5p".

The term "hsa-miR-135a-3p gene" or "hsa-miR-135a-3p" used herein includes the hsa-miR-135a-3p gene (miRBase Accession No. MIMAT0004595) consisting of the nucleotide sequence represented by SEQ ID NO: 136, a homolog or an ortholog of a different organism species, and the like. The hsa-miR-135a-3p gene can be obtained by a method described in Lagos-Quintana M et al., 2002, Curr Biol, Vol. 12, p. 735-739. Also, "hsa-mir-135a-1" (miRBase Accession No. MI0000452, SEQ ID NO: 350) having a hairpin-like structure is known as a precursor of "hsa-miR-135a-3p".

The term "hsa-miR-663b gene" or "hsa-miR-663b" used herein includes the hsa-miR-663b gene (miRBase Accession No. MIMAT0005867) consisting of the nucleotide sequence represented by SEQ ID NO: 137, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 351) having a hairpin-like structure is known as a precursor of "hsa-miR-663b".

The term "hsa-miR-1343-5p gene" or "hsa-miR-1343-5p" used herein includes the hsa-miR-1343-5p gene (miRBase Accession No. MIMAT0027038) consisting of the nucleotide sequence represented by SEQ ID NO: 138, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 223) having a hairpin-like structure is known as a precursor of "hsa-miR-1343-5p".

The term "hsa-miR-6822-5p gene" or "hsa-miR-6822-5p" used herein includes the hsa-miR-6822-5p gene (miRBase Accession No. MIMAT0027544) consisting of the nucleotide sequence represented by SEQ ID NO: 139, a homolog or an ortholog of a different organism species, and the like. The hsa-miR-6822-5p gene can be obtained by a method described in Ladewig E et al., 2012, Genome Res, Vol. 22, p. 1634-1645. Also, "hsa-mir-6822" (miRBase Accession No. MI0022667, SEQ ID NO: 352) having a hairpin-like structure is known as a precursor of "hsa-miR-6822-5p".

The term "hsa-miR-6803-5p gene" or "hsa-miR-6803-5p" used herein includes the hsa-miR-6803-5p gene (miRBase Accession No. MIMAT0027506) consisting of the nucleotide sequence represented by SEQ ID NO: 140, a homolog or an ortholog of a different organism species, and the like. The hsa-miR-6803-5p gene can be obtained by a method described in Ladewig E et al., 2012, Genome Res, Vol. 22, p. 1634-1645. Also, "hsa-mir-6803" (miRBase Accession No. MI0022648, SEQ ID NO: 353) having a hairpin-like structure is known as a precursor of "hsa-miR-6803-5p".

The term "hsa-miR-6805-3p gene" or "hsa-miR-6805-3p" used herein includes the hsa-miR-6805-3p gene (miRBase Accession No. MIMAT0027511) consisting of the nucleotide sequence represented by SEQ ID NO: 141, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 354) having a hairpin-like structure is known as a precursor of "hsa-miR-6805-3p".

The term "hsa-miR-128-2-5p gene" or "hsa-miR-128-2-5p" used herein includes the hsa-miR-128-2-5p gene (miRBase Accession No. MIMAT0031095) consisting of the nucleotide sequence represented by SEQ ID NO: 142, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 355) having a hairpin-like structure is known as a precursor of "hsa-miR-128-2-5p".

The term "hsa-miR-4640-5p gene" or "hsa-miR-4640-5p" used herein includes the hsa-miR-4640-5p gene (miRBase Accession No. MIMAT0019699) consisting of the nucleotide sequence represented by SEQ ID NO: 143, a homolog or an ortholog of a different organism species, and the like. The hsa-miR-4640-5p gene can be obtained by a method described in Persson H et al., 2011, Cancer Res, Vol. 71, p. 78-86. Also, "hsa-mir-4640" (miRBase Accession No. MI0017267, SEQ ID NO: 356) having a hairpin-like structure is known as a precursor of "hsa-miR-4640-5p".

The term "hsa-miR-1469 gene" or "hsa-miR-1469" used herein includes the hsa-miR-1469 gene (miRBase Accession No. MIMAT0007347) consisting of the nucleotide sequence represented by SEQ ID NO: 144, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 357) having a hairpin-like structure is known as a precursor of "hsa-miR-1469".

The term "hsa-miR-92a-2-5p gene" or "hsa-miR-92a-2-5p" used herein includes the hsa-miR-92a-2-5p gene (miRBase Accession No. MIMAT0004508) consisting of the nucleotide sequence represented by SEQ ID NO: 145, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 358) having a hairpin-like structure is known as a precursor of "hsa-miR-92a-2-5p".

The term "hsa-miR-3940-5p gene" or "hsa-miR-3940-5p" used herein includes the hsa-miR-3940-5p gene (miRBase Accession No. MIMAT0019229) consisting of the nucleotide sequence represented by SEQ ID NO: 146, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 359) having a hairpin-like structure is known as a precursor of "hsa-miR-3940-5p".

The term "hsa-miR-4281 gene" or "hsa-miR-4281" used herein includes the hsa-miR-4281 gene (miRBase Accession No. MIMAT0016907) consisting of the nucleotide sequence represented by SEQ ID NO: 147, a homolog or an ortholog of a different organism species, and the like. The hsa-miR-4281 gene can be obtained by a method described in Goff L A et al., 2009, PLoS One, Vol. 4, e7192. Also, "hsa-mir-4281" (miRBase Accession No. MI0015885, SEQ ID NO: 360) having a hairpin-like structure is known as a precursor of "hsa-miR-4281".

The term "hsa-miR-1260b gene" or "hsa-miR-1260b" used herein includes the hsa-miR-1260b gene (miRBase Accession No. MIMAT0015041) consisting of the nucleotide sequence represented by SEQ ID NO: 148, a homolog or an ortholog of a different organism species, and the like.

The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 361) having a hairpin-like structure is known as a precursor of "hsa-miR-1260b".

The term "hsa-miR-4758-5p gene" or "hsa-miR-4758-5p" used herein includes the hsa-miR-4758-5p gene (miRBase Accession No. MIMAT0019903) consisting of the nucleotide sequence represented by SEQ ID NO: 149, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 362) having a hairpin-like structure is known as a precursor of "hsa-miR-4758-5p".

The term "hsa-miR-1915-5p gene" or "hsa-miR-1915-5p" used herein includes the hsa-miR-1915-5p gene (miRBase Accession No. MIMAT0007891) consisting of the nucleotide sequence represented by SEQ ID NO: 150, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 334) having a hairpin-like structure is known as a precursor of "hsa-miR-1915-5p".

The term "hsa-miR-5001-5p gene" or "hsa-miR-5001-5p" used herein includes the hsa-miR-5001-5p gene (miRBase Accession No. MIMAT0021021) consisting of the nucleotide sequence represented by SEQ ID NO: 151, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 363) having a hairpin-like structure is known as a precursor of "hsa-miR-5001-5p".

The term "hsa-miR-4286 gene" or "hsa-miR-4286" used herein includes the hsa-miR-4286 gene (miRBase Accession No. MIMAT0016916) consisting of the nucleotide sequence represented by SEQ ID NO: 152, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 364) having a hairpin-like structure is known as a precursor of "hsa-miR-4286".

The term "hsa-miR-6126 gene" or "hsa-miR-6126" used herein includes the hsa-miR-6126 gene (miRBase Accession No. MIMAT0024599) consisting of the nucleotide sequence represented by SEQ ID NO: 153, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 365) having a hairpin-like structure is known as a precursor of "hsa-miR-6126".

The term "hsa-miR-6789-5p gene" or "hsa-miR-6789-5p" used herein includes the hsa-miR-6789-5p gene (miRBase Accession No. MIMAT0027478) consisting of the nucleotide sequence represented by SEQ ID NO: 154, a homolog or an ortholog of a different organism species, and the like. The hsa-miR-6789-5p gene can be obtained by a method described in Ladewig E et al., 2012, Genome Res, Vol. 22, p. 1634-1645. Also, "hsa-mir-6789" (miRBase Accession No. MI0022634, SEQ ID NO: 366) having a hairpin-like structure is known as a precursor of "hsa-miR-6789-5p".

The term "hsa-miR-4459 gene" or "hsa-miR-4459" used herein includes the hsa-miR-4459 gene (miRBase Accession No. MIMAT0018981) consisting of the nucleotide sequence represented by SEQ ID NO: 155, a homolog or an ortholog of a different organism species, and the like. The hsa-miR-4459 gene can be obtained by a method described in Jima D D et al., 2010, Blood, Vol. 116, e118-e127. Also, "hsa-mir-4459" (miRBase Accession No. MI0016805, SEQ ID NO: 367) having a hairpin-like structure is known as a precursor of "hsa-miR-4459".

The term "hsa-miR-1268a gene" or "hsa-miR-1268a" used herein includes the hsa-miR-1268a gene (miRBase Accession No. MIMAT0005922) consisting of the nucleotide sequence represented by SEQ ID NO: 156, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 368) having a hairpin-like structure is known as a precursor of "hsa-miR-1268a".

The term "hsa-miR-6752-5p gene" or "hsa-miR-6752-5p" used herein includes the hsa-miR-6752-5p gene (miRBase Accession No. MIMAT0027404) consisting of the nucleotide sequence represented by SEQ ID NO: 157, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 369) having a hairpin-like structure is known as a precursor of "hsa-miR-6752-5p".

The term "hsa-miR-6131 gene" or "hsa-miR-6131" used herein includes the hsa-miR-6131 gene (miRBase Accession No. MIMAT0024615) consisting of the nucleotide sequence represented by SEQ ID NO: 158, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 370) having a hairpin-like structure is known as a precursor of "hsa-miR-6131".

The term "hsa-miR-6800-5p gene" or "hsa-miR-6800-5p" used herein includes the hsa-miR-6800-5p gene (miRBase Accession No. MIMAT0027500) consisting of the nucleotide sequence represented by SEQ ID NO: 159, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 371) having a hairpin-like structure is known as a precursor of "hsa-miR-6800-5p".

The term "hsa-miR-4532 gene" or "hsa-miR-4532" used herein includes the hsa-miR-4532 gene (miRBase Accession No. MIMAT0019071) consisting of the nucleotide sequence represented by SEQ ID NO: 160, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 372) having a hairpin-like structure is known as a precursor of "hsa-miR-4532".

The term "hsa-miR-6872-3p gene" or "hsa-miR-6872-3p" used herein includes the hsa-miR-6872-3p gene (miRBase Accession No. MIMAT0027645) consisting of the nucleotide sequence represented by SEQ ID NO: 161, a homolog or an ortholog of a different organism species, and the like. The hsa-miR-6872-3p gene can be obtained by a method described in Ladewig E et al., 2012, Genome Res, Vol. 22, p. 1634-1645. Also, "hsa-mir-6872" (miRBase Accession No. MI0022719, SEQ ID NO: 373) having a hairpin-like structure is known as a precursor of "hsa-miR-6872-3p".

The term "hsa-miR-718 gene" or "hsa-miR-718" used herein includes the hsa-miR-718 gene (miRBase Accession No. MIMAT0012735) consisting of the nucleotide sequence represented by SEQ ID NO: 162, a homolog or an ortholog of a different organism species, and the like. The hsa-miR-718 gene can be obtained by a method described in Artzi S et al., 2008, BMC Bioinformatics, Vol. 9, p. 39. Also, "hsa-mir-718" (miRBase Accession No. MI0012489, SEQ ID NO: 374) having a hairpin-like structure is known as a precursor of "hsa-miR-718".

The term "hsa-miR-6769a-5p gene" or "hsa-miR-6769a-5p" used herein includes the hsa-miR-6769a-5p gene (miRBase Accession No. MIMAT0027438) consisting of the nucleotide sequence represented by SEQ ID NO: 163, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 375) having a hairpin-like structure is known as a precursor of "hsa-miR-6769a-5p".

The term "hsa-miR-4707-3p gene" or "hsa-miR-4707-3p" used herein includes the hsa-miR-4707-3p gene (miRBase Accession No. MIMAT0019808) consisting of the nucleotide sequence represented by SEQ ID NO: 164, a homolog or an ortholog of a different organism species, and the like. The hsa-miR-4707-3p gene can be obtained by a method described in Persson H et al., 2011, Cancer Res, Vol. 71, p. 78-86. Also, "hsa-mir-4707" (miRBase Accession No. MI0017340, SEQ ID NO: 338) having a hairpin-like structure is known as a precursor of "hsa-miR-4707-3p".

The term "hsa-miR-6765-5p gene" or "hsa-miR-6765-5p" used herein includes the hsa-miR-6765-5p gene (miRBase Accession No. MIMAT0027430) consisting of the nucleotide sequence represented by SEQ ID NO: 165, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 249) having a hairpin-like structure is known as a precursor of "hsa-miR-6765-5p".

The term "hsa-miR-4739 gene" or "hsa-miR-4739" used herein includes the hsa-miR-4739 gene (miRBase Accession No. MIMAT0019868) consisting of the nucleotide sequence represented by SEQ ID NO: 166, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 376) having a hairpin-like structure is known as a precursor of "hsa-miR-4739".

The term "hsa-miR-4525 gene" or "hsa-miR-4525" used herein includes the hsa-miR-4525 gene (miRBase Accession No. MIMAT0019064) consisting of the nucleotide sequence represented by SEQ ID NO: 167, a homolog or an ortholog of a different organism species, and the like. The hsa-miR-4525 gene can be obtained by a method described in Jima D D et al., 2010, Blood, Vol. 116, e118-e127. Also, "hsa-mir-4525" (miRBase Accession No. MI0016892, SEQ ID NO: 377) having a hairpin-like structure is known as a precursor of "hsa-miR-4525".

The term "hsa-miR-4270 gene" or "hsa-miR-4270" used herein includes the hsa-miR-4270 gene (miRBase Accession No. MIMAT0016900) consisting of the nucleotide sequence represented by SEQ ID NO: 168, a homolog or an ortholog of a different organism species, and the like. The hsa-miR-4270 gene can be obtained by a method described in Goff L A et al., 2009, PLoS One, Vol. 4, e7192. Also, "hsa-mir-4270" (miRBase Accession No. MI0015878, SEQ ID NO: 378) having a hairpin-like structure is known as a precursor of "hsa-miR-4270".

The term "hsa-miR-4534 gene" or "hsa-miR-4534" used herein includes the hsa-miR-4534 gene (miRBase Accession No. MIMAT0019073) consisting of the nucleotide sequence represented by SEQ ID NO: 169, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 379) having a hairpin-like structure is known as a precursor of "hsa-miR-4534".

The term "hsa-miR-6785-5p gene" or "hsa-miR-6785-5p" used herein includes the hsa-miR-6785-5p gene (miRBase Accession No. MIMAT0027470) consisting of the nucleotide sequence represented by SEQ ID NO: 170, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 380) having a hairpin-like structure is known as a precursor of "hsa-miR-6785-5p".

The term "hsa-miR-6850-5p gene" or "hsa-miR-6850-5p" used herein includes the hsa-miR-6850-5p gene (miRBase Accession No. MIMAT0027600) consisting of the nucleotide sequence represented by SEQ ID NO: 171, a homolog or an ortholog of a different organism species, and the like. The hsa-miR-6850-5p gene can be obtained by a method described in Ladewig E et al., 2012, Genome Res, Vol. 22, p. 1634-1645. Also, "hsa-mir-6850" (miRBase Accession No. MI0022696, SEQ ID NO: 381) having a hairpin-like structure is known as a precursor of "hsa-miR-6850-5p".

The term "hsa-miR-4697-5p gene" or "hsa-miR-4697-5p" used herein includes the hsa-miR-4697-5p gene (miRBase Accession No. MIMAT0019791) consisting of the nucleotide sequence represented by SEQ ID NO: 172, a homolog or an ortholog of a different organism species, and the like. The hsa-miR-4697-5p gene can be obtained by a method described in Persson H et al., 2011, Cancer Res, Vol. 71, p. 78-86. Also, "hsa-mir-4697" (miRBase Accession No. MI0017330, SEQ ID NO: 382) having a hairpin-like structure is known as a precursor of "hsa-miR-4697-5p".

The term "hsa-miR-1260a gene" or "hsa-miR-1260a" used herein includes the hsa-miR-1260a gene (miRBase Accession No. MIMAT0005911) consisting of the nucleotide sequence represented by SEQ ID NO: 173, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 383) having a hairpin-like structure is known as a precursor of "hsa-miR-1260a".

The term "hsa-miR-4486 gene" or "hsa-miR-4486" used herein includes the hsa-miR-4486 gene (miRBase Accession No. MIMAT0019020) consisting of the nucleotide sequence represented by SEQ ID NO: 174, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847, SEQ ID NO: 384) having a hairpin-like structure is known as a precursor of "hsa-miR-4486".

The term "hsa-miR-6880-5p gene" or "hsa-miR-6880-5p" used herein includes the hsa-miR-6880-5p gene (miRBase Accession No. MIMAT0027660) consisting of the nucleotide sequence represented by SEQ ID NO: 175, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 385) having a hairpin-like structure is known as a precursor of "hsa-miR-6880-5p".

The term "hsa-miR-6802-5p gene" or "hsa-miR-6802-5p" used herein includes the hsa-miR-6802-5p gene (miRBase Accession No. MIMAT0027504) consisting of the nucleotide sequence represented by SEQ ID NO: 176, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802" (miRBase Accession No. MI0022647, SEQ ID NO: 386) having a hairpin-like structure is known as a precursor of "hsa-miR-6802-5p".

The term "hsa-miR-6861-5p gene" or "hsa-miR-6861-5p" used herein includes the hsa-miR-6861-5p gene (miRBase Accession No. MIMAT0027623) consisting of the nucleotide sequence represented by SEQ ID NO: 177, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 387) having a hairpin-like structure is known as a precursor of "hsa-miR-6861-5p".

The term "hsa-miR-92b-5p gene" or "hsa-miR-92b-5p" used herein includes the hsa-miR-92b-5p gene (miRBase Accession No. MIMAT0004792) consisting of the nucleotide sequence represented by SEQ ID NO: 178, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 388) having a hairpin-like structure is known as a precursor of "hsa-miR-92b-5p".

The term "hsa-miR-1238-5p gene" or "hsa-miR-1238-5p" used herein includes the hsa-miR-1238-5p gene (miRBase Accession No. MIMAT0022947) consisting of the nucleotide sequence represented by SEQ ID NO: 179, a homolog or an ortholog of a different organism species, and the like. The hsa-miR-1238-5p gene can be obtained by a method described in Berezikov E et al., 2007, Mol Cell, Vol. 28, p. 328-336. Also, "hsa-mir-1238" (miRBase Accession No. MI0006328, SEQ ID NO: 389) having a hairpin-like structure is known as a precursor of "hsa-miR-1238-5p".

The term "hsa-miR-6851-5p gene" or "hsa-miR-6851-5p" used herein includes the hsa-miR-6851-5p gene (miRBase Accession No. MIMAT0027602) consisting of the nucleotide sequence represented by SEQ ID NO: 180, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697, SEQ ID NO: 390) having a hairpin-like structure is known as a precursor of "hsa-miR-6851-5p".

The term "hsa-miR-7704 gene" or "hsa-miR-7704" used herein includes the hsa-miR-7704 gene (miRBase Accession No. MIMAT0030019) consisting of the nucleotide sequence represented by SEQ ID NO: 181, a homolog or an ortholog of a different organism species, and the like. The hsa-miR-7704 gene can be obtained by a method described in Swaminathan S et al., 2013, Biochem Biophys Res Commun, Vol. 434, p. 228-234. Also, "hsa-mir-7704" (miRBase Accession No. MI0025240, SEQ ID NO: 391) having a hairpin-like structure is known as a precursor of "hsa-miR-7704".

The term "hsa-miR-149-3p gene" or "hsa-miR-149-3p" used herein includes the hsa-miR-149-3p gene (miRBase Accession No. MIMAT0004609) consisting of the nucleotide sequence represented by SEQ ID NO: 182, a homolog or an ortholog of a different organism species, and the like. The hsa-miR-149-3p gene can be obtained by a method described in Lagos-Quintana M et al., 2002, Curr Biol, Vol. 12, p. 735-739. Also, "hsa-mir-149" (miRBase Accession No. MI0000478, SEQ ID NO: 392) having a hairpin-like structure is known as a precursor of "hsa-miR-149-3p".

The term "hsa-miR-4689 gene" or "hsa-miR-4689" used herein includes the hsa-miR-4689 gene (miRBase Accession No. MIMAT0019778) consisting of the nucleotide sequence represented by SEQ ID NO: 183, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 393) having a hairpin-like structure is known as a precursor of "hsa-miR-4689".

The term "hsa-miR-4688 gene" or "hsa-miR-4688" used herein includes the hsa-miR-4688 gene (miRBase Accession No. MIMAT0019777) consisting of the nucleotide sequence represented by SEQ ID NO: 184, a homolog or an ortholog of a different organism species, and the like. The hsa-miR-4688 gene can be obtained by a method described in Persson H et al., 2011, Cancer Res, Vol. 71, p. 78-86. Also, "hsa-mir-4688" (miRBase Accession No. MI0017321, SEQ ID NO: 394) having a hairpin-like structure is known as a precursor of "hsa-miR-4688".

The term "hsa-miR-125a-3p gene" or "hsa-miR-125a-3p" used herein includes the hsa-miR-125a-3p gene (miRBase Accession No. MIMAT0004602) consisting of the nucleotide sequence represented by SEQ ID NO: 185, a homolog or an ortholog of a different organism species, and the like. The hsa-miR-125a-3p gene can be obtained by a method described in Lagos-Quintana Metal., 2002, Curr Biol, Vol. 12, p. 735-739. Also, "hsa-mir-125a" (miRBase Accession No. MI0000469, SEQ ID NO: 395) having a hairpin-like structure is known as a precursor of "hsa-miR-125a-3p".

The term "hsa-miR-23b-3p gene" or "hsa-miR-23b-3p" used herein includes the hsa-miR-23b-3p gene (miRBase Accession No. MIMAT0000418) consisting of the nucleotide sequence represented by SEQ ID NO: 186, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 396) having a hairpin-like structure is known as a precursor of "hsa-miR-23b-3p".

The term "hsa-miR-614 gene" or "hsa-miR-614" used herein includes the hsa-miR-614 gene (miRBase Accession No. MIMAT0003282) consisting of the nucleotide sequence represented by SEQ ID NO: 187, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 397) having a hairpin-like structure is known as a precursor of "hsa-miR-614".

The term "hsa-miR-1913 gene" or "hsa-miR-1913" used herein includes the hsa-miR-1913 gene (miRBase Accession No. MIMAT0007888) consisting of the nucleotide sequence represented by SEQ ID NO: 188, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 398) having a hairpin-like structure is known as a precursor of "hsa-miR-1913".

The term "hsa-miR-16-5p gene" or "hsa-miR-16-5p" used herein includes the hsa-miR-16-5p gene (miRBase Accession No. MIMAT0000069) consisting of the nucleotide sequence represented by SEQ ID NO: 189, a homolog or an ortholog of a different organism species, and the like. The hsa-miR-16-5p gene can be obtained by a method described in Lagos-Quintana M et al., 2001, Science, Vol. 294, p. 853-858. Also, "hsa-mir-16-1 and hsa-mir-16-2" (miRBase Accession Nos. MI0000070 and MI0000115, SEQ ID NOs: 399 and 400) having a hairpin-like structure are known as precursors of "hsa-miR-16-5p".

The term "hsa-miR-675-5p gene" or "hsa-miR-675-5p" used herein includes the hsa-miR-675-5p gene (miRBase Accession No. MIMAT0004284) consisting of the nucleotide sequence represented by SEQ ID NO: 190, a homolog or an ortholog of a different organism species, and the like. The hsa-miR-675-5p gene can be obtained by a method described in Cai X et al., 2007, RNA, Vol. 13, p. 313-316. Also, "hsa-mir-675" (miRBase Accession No. MI0005416, SEQ ID NO: 401) having a hairpin-like structure is known as a precursor of "hsa-miR-675-5p".

The term "hsa-miR-486-3p gene" or "hsa-miR-486-3p" used herein includes the hsa-miR-486-3p gene (miRBase Accession No. MIMAT0004762) consisting of the nucleotide sequence represented by SEQ ID NO: 191, a homolog or an ortholog of a different organism species, and the like. The hsa-miR-486-3p gene can be obtained by a method described in Fu H et al., 2005, FEBS Left, Vol. 579, p. 3849-3854. Also, "hsa-mir-486 and hsa-mir-486-2" (miRBase Accession Nos. MI0002470 and MI0023622, SEQ ID NOs: 402 and 403) having a hairpin-like structure are known as precursors of "hsa-miR-486-3p".

The term "hsa-miR-6777-5p gene" or "hsa-miR-6777-5p" used herein includes the hsa-miR-6777-5p gene (miRBase Accession No. MIMAT0027454) consisting of the nucleotide sequence represented by SEQ ID NO: 192, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 404) having a hairpin-like structure is known as a precursor of "hsa-miR-6777-5p".

The term "hsa-miR-4497 gene" or "hsa-miR-4497" used herein includes the hsa-miR-4497 gene (miRBase Accession No. MIMAT0019032) consisting of the nucleotide sequence represented by SEQ ID NO: 193, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 405) having a hairpin-like structure is known as a precursor of "hsa-miR-4497".

The term "hsa-miR-296-3p gene" or "hsa-miR-296-3p" used herein includes the hsa-miR-296-3p gene (miRBase Accession No. MIMAT0004679) consisting of the nucleotide sequence represented by SEQ ID NO: 194, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 406) having a hairpin-like structure is known as a precursor of "hsa-miR-296-3p".

The term "hsa-miR-6738-5p gene" or "hsa-miR-6738-5p" used herein includes the hsa-miR-6738-5p gene (miRBase Accession No. MIMAT0027377) consisting of the nucleotide sequence represented by SEQ ID NO: 195, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 407) having a hairpin-like structure is known as a precursor of "hsa-miR-6738-5p".

The term "hsa-miR-4731-5p gene" or "hsa-miR-4731-5p" used herein includes the hsa-miR-4731-5p gene (miRBase Accession No. MIMAT0019853) consisting of the nucleotide sequence represented by SEQ ID NO: 196, a homolog or an ortholog of a different organism species, and the like. The hsa-miR-4731-5p gene can be obtained by a method described in Persson H et al., 2011, Cancer Res, Vol. 71, p. 78-86. Also, "hsa-mir-4731" (miRBase Accession No. MI0017368, SEQ ID NO: 408) having a hairpin-like structure is known as a precursor of "hsa-miR-4731-5p".

The term "hsa-miR-6889-5p gene" or "hsa-miR-6889-5p" used herein includes the hsa-miR-6889-5p gene (miRBase Accession No. MIMAT0027678) consisting of the nucleotide sequence represented by SEQ ID NO: 197, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. MI0022736, SEQ ID NO: 409) having a hairpin-like structure is known as a precursor of "hsa-miR-6889-5p".

The term "hsa-miR-6786-5p gene" or "hsa-miR-6786-5p" used herein includes the hsa-miR-6786-5p gene (miRBase Accession No. MIMAT0027472) consisting of the nucleotide sequence represented by SEQ ID NO: 198, a homolog or an ortholog of a different organism species, and the like. The hsa-miR-6786-5p gene can be obtained by a method described in Ladewig E et al., 2012, Genome Res, Vol. 22, p. 1634-1645. Also, "hsa-mir-6786" (miRBase Accession No. MI0022631, SEQ ID NO: 410) having a hairpin-like structure is known as a precursor of "hsa-miR-6786-5p".

The term "hsa-miR-92a-3p gene" or "hsa-miR-92a-3p" used herein includes the hsa-miR-92a-3p gene (miRBase Accession No. MIMAT0000092) consisting of the nucleotide sequence represented by SEQ ID NO: 199, a homolog or an ortholog of a different organism species, and the like. The hsa-miR-92a-3p gene can be obtained by a method described in Mourelatos Z et al., 2002, Genes Dev, Vol. 16, p. 720-728. Also, "hsa-mir-92a-1 and hsa-mir-92a-2" (miRBase Accession Nos. MI0000093 and MI0000094, SEQ ID NOs: 411 and 358) having a hairpin-like structure are known as precursors of "hsa-miR-92a-3p".

The term "hsa-miR-4294 gene" or "hsa-miR-4294" used herein includes the hsa-miR-4294 gene (miRBase Accession No. MIMAT0016849) consisting of the nucleotide sequence represented by SEQ ID NO: 200, a homolog or an ortholog of a different organism species, and the like. The hsa-miR-4294 gene can be obtained by a method described in Goff L A et al., 2009, PLoS One, Vol. 4, e7192. Also, "hsa-mir-4294" (miRBase Accession No. MI0015827, SEQ ID NO: 412) having a hairpin-like structure is known as a precursor of "hsa-miR-4294".

The term "hsa-miR-4763-3p gene" or "hsa-miR-4763-3p" used herein includes the hsa-miR-4763-3p gene (miRBase Accession No. MIMAT0019913) consisting of the nucleotide sequence represented by SEQ ID NO: 201, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 413) having a hairpin-like structure is known as a precursor of "hsa-miR-4763-3p".

The term "hsa-miR-6076 gene" or "hsa-miR-6076" used herein includes the hsa-miR-6076 gene (miRBase Accession No. MIMAT0023701) consisting of the nucleotide sequence represented by SEQ ID NO: 202, a homolog or an ortholog of a different organism species, and the like. The hsa-miR-6076 gene can be obtained by a method described in Voellenkle C et al., 2012, RNA, Vol. 18, p. 472-484. Also, "hsa-mir-6076" (miRBase Accession No. MI0020353, SEQ ID NO: 414) having a hairpin-like structure is known as a precursor of "hsa-miR-6076".

The term "hsa-miR-663a gene" or "hsa-miR-663a" used herein includes the hsa-miR-663a gene (miRBase Accession No. MIMAT0003326) consisting of the nucleotide sequence represented by SEQ ID NO: 203, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 415) having a hairpin-like structure is known as a precursor of "hsa-miR-663a".

The term "hsa-miR-760 gene" or "hsa-miR-760" used herein includes the hsa-miR-760 gene (miRBase Accession No. MIMAT0004957) consisting of the nucleotide sequence represented by SEQ ID NO: 204, a homolog or an ortholog of a different organism species, and the like. The hsa-miR-760 gene can be obtained by a method described in Berezikov E et al., 2006, Genome Res, Vol. 16, p. 1289-1298. Also, "hsa-mir-760" (miRBase Accession No. MI0005567, SEQ ID NO: 416) having a hairpin-like structure is known as a precursor of "hsa-miR-760".

The term "hsa-miR-4667-5p gene" or "hsa-miR-4667-5p" used herein includes the hsa-miR-4667-5p gene (miRBase Accession No. MIMAT0019743) consisting of the nucleotide sequence represented by SEQ ID NO: 205, a homolog or an ortholog of a different organism species, and the like. The hsa-miR-4667-5p gene can be obtained by a method described in Persson H et al., 2011, Cancer Res, Vol. 71, p. 78-86. Also, "hsa-mir-4667" (miRBase Accession No. MI0017297, SEQ ID NO: 417) having a hairpin-like structure is known as a precursor of "hsa-miR-4667-5p".

The term "hsa-miR-6090 gene" or "hsa-miR-6090" used herein includes the hsa-miR-6090 gene (miRBase Accession No. MIMAT0023715) consisting of the nucleotide sequence represented by SEQ ID NO: 206, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 418) having a hairpin-like structure is known as a precursor of "hsa-miR-6090".

The term "hsa-miR-4730 gene" or "hsa-miR-4730" used herein includes the hsa-miR-4730 gene (miRBase Accession No. MIMAT0019852) consisting of the nucleotide sequence represented by SEQ ID NO: 207, a homolog or an ortholog of a different organism species, and the like. The hsa-miR-4730 gene can be obtained by a method described in Persson H et al., 2011, Cancer Res, Vol. 71, p. 78-86. Also, "hsa-mir-4730" (miRBase Accession No. MI0017367, SEQ ID NO: 419) having a hairpin-like structure is known as a precursor of "hsa-miR-4730".

The term "hsa-miR-7106-5p gene" or "hsa-miR-7106-5p" used herein includes the hsa-miR-7106-5p gene (miRBase Accession No. MIMAT0028109) consisting of the nucleotide sequence represented by SEQ ID NO: 208, a homolog or an ortholog of a different organism species, and the like. The hsa-miR-7106-5p gene can be obtained by a method described in Ladewig E et al., 2012, Genome Res, Vol. 22, p. 1634-1645. Also, "hsa-mir-7106" (miRBase Accession No. MI0022957, SEQ ID NO: 420) having a hairpin-like structure is known as a precursor of "hsa-miR-7106-5p".

The term "hsa-miR-3196 gene" or "hsa-miR-3196" used herein includes the hsa-miR-3196 gene (miRBase Accession No. MIMAT0015080) consisting of the nucleotide sequence represented by SEQ ID NO: 209, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 421) having a hairpin-like structure is known as a precursor of "hsa-miR-3196".

The term "hsa-miR-5698 gene" or "hsa-miR-5698" used herein includes the hsa-miR-5698 gene (miRBase Accession No. MIMAT0022491) consisting of the nucleotide sequence represented by SEQ ID NO: 210, a homolog or an ortholog of a different organism species, and the like. The hsa-miR-5698 gene can be obtained by a method described in Watahiki A et al., 2011, PLoS One, Vol. 6, e24950. Also, "hsa-mir-5698" (miRBase Accession No. MI0019305, SEQ ID NO: 422) having a hairpin-like structure is known as a precursor of "hsa-miR-5698".

The term "hsa-miR-6087 gene" or "hsa-miR-6087" used herein includes the hsa-miR-6087 gene (miRBase Accession No. MIMAT0023712) consisting of the nucleotide sequence represented by SEQ ID NO: 211, a homolog or an ortholog of a different organism species, and the like. The hsa-miR-6087 gene can be obtained by a method described in Yoo J K et al., 2012, Stem Cells Dev, Vol. 21, p. 2049-2057. Also, "hsa-mir-6087" (miRBase Accession No. MI0020364, SEQ ID NO: 423) having a hairpin-like structure is known as a precursor of "hsa-miR-6087".

The term "hsa-miR-4665-5p gene" or "hsa-miR-4665-5p" used herein includes the hsa-miR-4665-5p gene (miRBase Accession No. MIMAT0019739) consisting of the nucleotide sequence represented by SEQ ID NO: 212, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 275) having a hairpin-like structure is known as a precursor of "hsa-miR-4665-5p".

The term "hsa-miR-8059 gene" or "hsa-miR-8059" used herein includes the hsa-miR-8059 gene (miRBase Accession No. MIMAT0030986) consisting of the nucleotide sequence represented by SEQ ID NO: 213, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 424) having a hairpin-like structure is known as a precursor of "hsa-miR-8059".

The term "hsa-miR-6879-5p gene" or "hsa-miR-6879-5p" used herein includes the hsa-miR-6879-5p gene (miRBase Accession No. MIMAT0027658) consisting of the nucleotide sequence represented by SEQ ID NO: 214, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 425) having a hairpin-like structure is known as a precursor of "hsa-miR-6879-5p".

The term "hsa-miR-6717-5p gene" or "hsa-miR-6717-5p" used herein includes the hsa-miR-6717-5p gene (miRBase Accession No. MIMAT0025846) consisting of the nucleotide sequence represented by SEQ ID NO: 666, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 677) having a hairpin-like structure is known as a precursor of "hsa-miR-6717-5p".

The term "hsa-miR-3648 gene" or "hsa-miR-3648" used herein includes the hsa-miR-3648 gene (miRBase Accession No. MIMAT0018068) consisting of the nucleotide sequence represented by SEQ ID NO: 667, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648" (miRBase Accession No. MI0016048, SEQ ID NO: 678) having a hairpin-like structure is known as a precursor of "hsa-miR-3648".

The term "hsa-miR-3162-5p gene" or "hsa-miR-3162-5p" used herein includes the hsa-miR-3162-5p gene (miRBase Accession No. MIMAT0015036) consisting of the nucleotide sequence represented by SEQ ID NO: 668, a homolog or an ortholog of a different organism species, and the like. The hsa-miR-3162-5p gene can be obtained by a method described in Stark M S et al., 2010, PLoS One, Vol. 5, e9685. Also, "hsa-mir-3162" (miRBase Accession No. MI0014192, SEQ ID NO: 679) having a hairpin-like structure is known as a precursor of "hsa-miR-3162-5p".

The term "hsa-miR-1909-3p gene" or "hsa-miR-1909-3p" used herein includes the hsa-miR-1909-3p gene (miRBase Accession No. MIMAT0007883) consisting of the nucleotide sequence represented by SEQ ID NO: 669, a homolog or an ortholog of a different organism species, and the like. The hsa-miR-1909-3p gene can be obtained by a method described in Bar M et al., 2008, Stem Cells, Vol. 26, p. 2496-2505. Also, "hsa-mir-1909" (miRBase Accession No. MI0008330, SEQ ID NO: 680) having a hairpin-like structure is known as a precursor of "hsa-miR-1909-3p".

The term "hsa-miR-8073 gene" or "hsa-miR-8073" used herein includes the hsa-miR-8073 gene (miRBase Accession No. MIMAT0031000) consisting of the nucleotide sequence represented by SEQ ID NO: 670, a homolog or an ortholog of a different organism species, and the like. The hsa-miR-8073 gene can be obtained by a method described in Wang H J et al., 2013, Shock, Vol. 39, p. 480-487. Also, "hsa-mir-8073" (miRBase Accession No. MI0025909, SEQ ID NO: 681) having a hairpin-like structure is known as a precursor of "hsa-miR-8073".

The term "hsa-miR-6769b-5p gene" or "hsa-miR-6769b-5p" used herein includes the hsa-miR-6769b-5p gene (miRBase Accession No. MIMAT0027620) consisting of the nucleotide sequence represented by SEQ ID NO: 671, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 682) having a hairpin-like structure is known as a precursor of "hsa-miR-6769b-5p".

The term "hsa-miR-6836-3p gene" or "hsa-miR-6836-3p" used herein includes the hsa-miR-6836-3p gene (miRBase Accession No. MIMAT0027575) consisting of the nucleotide sequence represented by SEQ ID NO: 672, a homolog or an ortholog of a different organism species, and the like. The hsa-miR-6836-3p gene can be obtained by a method described in Ladewig E et al., 2012, Genome Res, Vol. 22, p. 1634-1645. Also, "hsa-mir-6836" (miRBase Accession No. MI0022682, SEQ ID NO: 683) having a hairpin-like structure is known as a precursor of "hsa-miR-6836-3p".

The term "hsa-miR-4484 gene" or "hsa-miR-4484" used herein includes the hsa-miR-4484 gene (miRBase Accession No. MIMAT0019018) consisting of the nucleotide sequence represented by SEQ ID NO: 673, a homolog or an ortholog of a different organism species, and the like. The hsa-miR-4484 gene can be obtained by a method described in Jima D D et al., 2010, Blood, Vol. 116, e118-e127. Also, "hsa-mir-4484" (miRBase Accession No. MI0016845, SEQ ID NO: 684) having a hairpin-like structure is known as a precursor of "hsa-miR-4484".

The term "hsa-miR-6819-5p gene" or "hsa-miR-6819-5p" used herein includes the hsa-miR-6819-5p gene (miRBase Accession No. MIMAT0027538) consisting of the nucleotide sequence represented by SEQ ID NO: 674, a homolog or an ortholog of a different organism species, and the like. The hsa-miR-6819-5p gene can be obtained by a method described in Ladewig E et al., 2012, Genome Res, Vol. 22, p. 1634-1645. Also, "hsa-mir-6819" (miRBase Accession No. MI0022664, SEQ ID NO: 685) having a hairpin-like structure is known as a precursor of "hsa-miR-6819-5p".

The term "hsa-miR-6794-5p gene" or "hsa-miR-6794-5p" used herein includes the hsa-miR-6794-5p gene (miRBase Accession No. MIMAT0027488) consisting of the nucleotide sequence represented by SEQ ID NO: 675, a homolog or an ortholog of a different organism species, and the like. The hsa-miR-6794-5p gene can be obtained by a method described in Ladewig E et al., 2012, Genome Res, Vol. 22, p. 1634-1645. Also, "hsa-mir-6794" (miRBase Accession No. MI0022639, SEQ ID NO: 686) having a hairpin-like structure is known as a precursor of "hsa-miR-6794-5p".

The term "hsa-miR-24-3p gene" or "hsa-miR-24-3p" used herein includes the hsa-miR-24-3p gene (miRBase Accession No. MIMAT0000080) consisting of the nucleotide sequence represented by SEQ ID NO: 676, a homolog or an ortholog of a different organism species, and the like. The hsa-miR-24-3p gene can be obtained by a method described in Lagos-Quintana M et al., 2001, Science, Vol. 294, p. 853-858. Also, "hsa-mir-24-1 and hsa-mir-24-2" (miRBase Accession Nos. MI0000080 and MI0000081, SEQ ID NOs: 687 and 688) having a hairpin-like structure are known as precursors of "hsa-miR-24-3p".

A mature miRNA may become a variant due to the sequence cleaved shorter or longer by one to several flanking nucleotides or due to substitution of nucleotides when cut out as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 214 and 666 to 676 as well as a large number of the nucleotide sequence variants and fragments represented by SEQ ID NOs: 426 to 665 and 689 to 700, called isomiRs. These variants can also be obtained as miRNAs that have a nucleotide sequence represented by any of SEQ ID NOs: 1 to 214 and 666 to 676.

Specifically, among the variants of polynucleotides consisting of a nucleotide sequence represented by any of SEQ ID NOs: 1, 2, 6, 9, 13, 18, 20, 21, 23, 28, 29, 30, 31, 34, 36, 40, 41, 46, 47, 50, 52, 54, 55, 56, 58, 64, 66, 67, 68, 72, 73, 74, 76, 77, 79, 80, 83, 84, 85, 87, 89, 90, 91, 92, 93, 94, 95, 97, 99, 100, 101, 102, 104, 108, 110, 112, 113, 114, 117, 118, 120, 121, 122, 124, 125, 126, 127, 128, 129, 130, 132, 134, 135, 136, 137, 142, 143, 145, 146, 147, 148, 149, 150, 151, 152, 153, 155, 156, 158, 160, 162, 164, 166, 167, 173, 174, 178, 182, 183, 184, 185, 186, 187, 188, 189, 190, 191, 193, 194, 196, 199, 201, 203, 204, 205, 207, 209, 210, 211, 212, 666, 667, 668, 669, 673, and 676 or a nucleotide sequence from the nucleotide sequence by the replacement of u with t according to the present invention, examples of the longest variants registered in miRBase Release 20 include polynucleotides represented by SEQ ID NOs: 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 689, 691, 693, 695, 697, and 699, respectively. Also, among the variants of polynucleotides consisting of the nucleotide sequence represented by any of SEQ ID NOs: 1, 2, 6, 9, 13, 18, 20, 21, 23, 28, 29, 30, 31, 34, 36, 40, 41, 46, 47, 50, 52, 54, 55, 56, 58, 64, 66, 67, 68, 72, 73, 74, 76, 77, 79, 80, 83, 84, 85, 87, 89, 90, 91, 92, 93, 94, 95, 97, 99, 100, 101, 102, 104, 108, 110, 112, 113, 114, 117, 118, 120, 121, 122, 124, 125, 126, 127, 128, 129, 130, 132, 134, 135, 136, 137, 142, 143, 145, 146, 147, 148, 149, 150, 151, 152, 153, 155, 156, 158, 160, 162, 164, 166, 167, 173, 174, 178, 182, 183, 184, 185, 186, 187, 188, 189, 190, 191, 193, 194, 196, 199, 201, 203, 204, 205, 207, 209, 210, 211, 212, 666, 667, 668, 669, 673, and 676 or a nucleotide sequence derived from the nucleotide sequence by the replacement of u with t according to the present invention, examples of shortest variants registered in the miRBase Release 20 include polynucleotides having sequences represented by SEQ ID NOs: 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 690, 692, 694, 696, 698, and 700, respectively. In addition to these variants and fragments, examples thereof include a large number of isomiR polynucleotides consisting of a nucleotide sequence represented by SEQ ID NOs: 1 to 214 and 666 to 676 registered in the miRBase. Examples of the polynucleotide comprising a nucleotide sequence represented by any of SEQ ID NOs: 1 to 214 and 666 to 676 include a polynucleotide represented by any of SEQ ID NOs: 215 to 425 and 677 to 688, which are their respective precursors.

The names and miRBase Accession Nos. (registration numbers) of the genes consisting of a nucleotide sequence represented by SEQ ID NOs: 1 to 700 are shown in Table 1.

The term "capable of specifically binding" used herein means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-204-3p | MIMAT0022693 |
| 2 | hsa-miR-1247-3p | MIMAT0022721 |
| 3 | hsa-miR-6875-5p | MIMAT0027650 |
| 4 | hsa-miR-6857-5p | MIMAT0027614 |
| 5 | hsa-miR-6726-5p | MIMAT0027353 |
| 6 | hsa-miR-3188 | MIMAT0015070 |
| 7 | hsa-miR-8069 | MIMAT0030996 |
| 8 | hsa-miR-4257 | MIMAT0016878 |
| 9 | hsa-miR-1343-3p | MIMAT0019776 |
| 10 | hsa-miR-7108-5p | MIMAT0028113 |
| 11 | hsa-miR-6825-5p | MIMAT0027550 |
| 12 | hsa-miR-7641 | MIMAT0029782 |
| 13 | hsa-miR-3185 | MIMAT0015065 |
| 14 | hsa-miR-4746-3p | MIMAT0019881 |
| 15 | hsa-miR-6791-5p | MIMAT0027482 |
| 16 | hsa-miR-6893-5p | MIMAT0027686 |
| 17 | hsa-miR-4433b-3p | MIMAT0030414 |
| 18 | hsa-miR-3135b | MIMAT0018985 |
| 19 | hsa-miR-6781-5p | MIMAT0027462 |
| 20 | hsa-miR-1908-5p | MIMAT0007881 |
| 21 | hsa-miR-4792 | MIMAT0019964 |
| 22 | hsa-miR-7845-5p | MIMAT0030420 |
| 23 | hsa-miR-4417 | MIMAT0018929 |
| 24 | hsa-miR-3184-5p | MIMAT0015064 |
| 25 | hsa-miR-1225-5p | MIMAT0005572 |
| 26 | hsa-miR-1231 | MIMAT0005586 |
| 27 | hsa-miR-1225-3p | MIMAT0005573 |
| 28 | hsa-miR-150-3p | MIMAT0004610 |
| 29 | hsa-miR-4433-3p | MIMAT0018949 |
| 30 | hsa-miR-6125 | MIMAT0024598 |
| 31 | hsa-miR-4513 | MIMAT0019050 |
| 32 | hsa-miR-6787-5p | MIMAT0027474 |
| 33 | hsa-miR-6784-5p | MIMAT0027468 |
| 34 | hsa-miR-615-5p | MIMAT0004804 |
| 35 | hsa-miR-6765-3p | MIMAT0027431 |
| 36 | hsa-miR-5572 | MIMAT0022260 |
| 37 | hsa-miR-6842-5p | MIMAT0027586 |
| 38 | hsa-miR-8063 | MIMAT0030990 |
| 39 | hsa-miR-6780b-5p | MIMAT0027572 |
| 40 | hsa-miR-187-5p | MIMAT0004561 |
| 41 | hsa-miR-128-1-5p | MIMAT0026477 |
| 42 | hsa-miR-6729-5p | MIMAT0027359 |
| 43 | hsa-miR-6741-5p | MIMAT0027383 |
| 44 | hsa-miR-6757-5p | MIMAT0027414 |
| 45 | hsa-miR-7110-5p | MIMAT0028117 |
| 46 | hsa-miR-7975 | MIMAT0031178 |
| 47 | hsa-miR-1233-5p | MIMAT0022943 |
| 48 | hsa-miR-6845-5p | MIMAT0027590 |
| 49 | hsa-miR-3937 | MIMAT0018352 |
| 50 | hsa-miR-4467 | MIMAT0018994 |
| 51 | hsa-miR-7109-5p | MIMAT0028115 |
| 52 | hsa-miR-6088 | MIMAT0023713 |
| 53 | hsa-miR-6782-5p | MIMAT0027464 |
| 54 | hsa-miR-5195-3p | MIMAT0021127 |
| 55 | hsa-miR-4454 | MIMAT0018976 |
| 56 | hsa-miR-6724-5p | MIMAT0025856 |
| 57 | hsa-miR-8072 | MIMAT0030999 |
| 58 | hsa-miR-4516 | MIMAT0019053 |
| 59 | hsa-miR-6756-5p | MIMAT0027412 |
| 60 | hsa-miR-4665-3p | MIMAT0019740 |
| 61 | hsa-miR-6826-5p | MIMAT0027552 |
| 62 | hsa-miR-6820-5p | MIMAT0027540 |
| 63 | hsa-miR-6887-5p | MIMAT0027674 |
| 64 | hsa-miR-3679-5p | MIMAT0018104 |
| 65 | hsa-miR-7847-3p | MIMAT0030422 |
| 66 | hsa-miR-6721-5p | MIMAT0025852 |
| 67 | hsa-miR-3622a-5p | MIMAT0018003 |
| 68 | hsa-miR-939-5p | MIMAT0004982 |
| 69 | hsa-miR-602 | MIMAT0003270 |
| 70 | hsa-miR-7977 | MIMAT0031180 |
| 71 | hsa-miR-6749-5p | MIMAT0027398 |
| 72 | hsa-miR-1914-3p | MIMAT0007890 |
| 73 | hsa-miR-4651 | MIMAT0019715 |
| 74 | hsa-miR-4695-5p | MIMAT0019788 |
| 75 | hsa-miR-6848-5p | MIMAT0027596 |
| 76 | hsa-miR-1228-3p | MIMAT0005583 |
| 77 | hsa-miR-642b-3p | MIMAT0018444 |

TABLE 1-continued

| SEQ ID NO: | Gene name | miRBase registration No. |
|---|---|---|
| 78 | hsa-miR-6746-5p | MIMAT0027392 |
| 79 | hsa-miR-3620-5p | MIMAT0022967 |
| 80 | hsa-miR-3131 | MIMAT0014996 |
| 81 | hsa-miR-6732-5p | MIMAT0027365 |
| 82 | hsa-miR-7113-3p | MIMAT0028124 |
| 83 | hsa-miR-23a-3p | MIMAT0000078 |
| 84 | hsa-miR-3154 | MIMAT0015028 |
| 85 | hsa-miR-4723-5p | MIMAT0019838 |
| 86 | hsa-miR-3663-3p | MIMAT0018085 |
| 87 | hsa-miR-4734 | MIMAT0019859 |
| 88 | hsa-miR-6816-5p | MIMAT0027532 |
| 89 | hsa-miR-4442 | MIMAT0018960 |
| 90 | hsa-miR-4476 | MIMAT0019003 |
| 91 | hsa-miR-423-5p | MIMAT0004748 |
| 92 | hsa-miR-1249 | MIMAT0005901 |
| 93 | hsa-miR-6515-3p | MIMAT0025487 |
| 94 | hsa-miR-887-3p | MIMAT0004951 |
| 95 | hsa-miR-4741 | MIMAT0019871 |
| 96 | hsa-miR-6766-3p | MIMAT0027433 |
| 97 | hsa-miR-4673 | MIMAT0019755 |
| 98 | hsa-miR-6779-5p | MIMAT0027458 |
| 99 | hsa-miR-4706 | MIMAT0019806 |
| 100 | hsa-miR-1268b | MIMAT0018925 |
| 101 | hsa-miR-4632-5p | MIMAT0022977 |
| 102 | hsa-miR-3197 | MIMAT0015082 |
| 103 | hsa-miR-6798-5p | MIMAT0027496 |
| 104 | hsa-miR-711 | MIMAT0012734 |
| 105 | hsa-miR-6840-3p | MIMAT0027583 |
| 106 | hsa-miR-6763-5p | MIMAT0027426 |
| 107 | hsa-miR-6727-5p | MIMAT0027355 |
| 108 | hsa-miR-371a-5p | MIMAT0004687 |
| 109 | hsa-miR-6824-5p | MIMAT0027548 |
| 110 | hsa-miR-4648 | MIMAT0019710 |
| 111 | hsa-miR-1227-5p | MIMAT0022941 |
| 112 | hsa-miR-564 | MIMAT0003228 |
| 113 | hsa-miR-3679-3p | MIMAT0018105 |
| 114 | hsa-miR-2861 | MIMAT0013802 |
| 115 | hsa-miR-6737-5p | MIMAT0027375 |
| 116 | hsa-miR-575 | MIMAT0003240 |
| 117 | hsa-miR-4725-3p | MIMAT0019844 |
| 118 | hsa-miR-6716-5p | MIMAT0025844 |
| 119 | hsa-miR-4675 | MIMAT0019757 |
| 120 | hsa-miR-1915-3p | MIMAT0007892 |
| 121 | hsa-miR-671-5p | MIMAT0003880 |
| 122 | hsa-miR-3656 | MIMAT0018076 |
| 123 | hsa-miR-6722-3p | MIMAT0025854 |
| 124 | hsa-miR-4707-5p | MIMAT0019807 |
| 125 | hsa-miR-4449 | MIMAT0018968 |
| 126 | hsa-miR-1202 | MIMAT0005865 |
| 127 | hsa-miR-4649-5p | MIMAT0019711 |
| 128 | hsa-miR-744-5p | MIMAT0004945 |
| 129 | hsa-miR-642a-3p | MIMAT0020924 |
| 130 | hsa-miR-451a | MIMAT0001631 |
| 131 | hsa-miR-6870-5p | MIMAT0027640 |
| 132 | hsa-miR-4443 | MIMAT0018961 |
| 133 | hsa-miR-6808-5p | MIMAT0027516 |
| 134 | hsa-miR-4728-5p | MIMAT0019849 |
| 135 | hsa-miR-937-5p | MIMAT0022938 |
| 136 | hsa-miR-135a-3p | MIMAT0004595 |
| 137 | hsa-miR-663b | MIMAT0005867 |
| 138 | hsa-miR-1343-5p | MIMAT0027038 |
| 139 | hsa-miR-6822-5p | MIMAT0027544 |
| 140 | hsa-miR-6803-5p | MIMAT0027506 |
| 141 | hsa-miR-6805-3p | MIMAT0027511 |
| 142 | hsa-miR-128-2-5p | MIMAT0031095 |
| 143 | hsa-miR-4640-5p | MIMAT0019699 |
| 144 | hsa-miR-1469 | MIMAT0007347 |
| 145 | hsa-miR-92a-2-5p | MIMAT0004508 |
| 146 | hsa-miR-3940-5p | MIMAT0019229 |
| 147 | hsa-miR-4281 | MIMAT0016907 |
| 148 | hsa-miR-1260b | MIMAT0015041 |
| 149 | hsa-miR-4758-5p | MIMAT0019903 |
| 150 | hsa-miR-1915-5p | MIMAT0007891 |
| 151 | hsa-miR-5001-5p | MIMAT0021021 |
| 152 | hsa-miR-4286 | MIMAT0016916 |
| 153 | hsa-miR-6126 | MIMAT0024599 |
| 154 | hsa-miR-6789-5p | MIMAT0027478 |
| 155 | hsa-miR-4459 | MIMAT0018981 |
| 156 | hsa-miR-1268a | MIMAT0005922 |
| 157 | hsa-miR-6752-5p | MIMAT0027404 |
| 158 | hsa-miR-6131 | MIMAT0024615 |
| 159 | hsa-miR-6800-5p | MIMAT0027500 |
| 160 | hsa-miR-4532 | MIMAT0019071 |
| 161 | hsa-miR-6872-3p | MIMAT0027645 |
| 162 | hsa-miR-718 | MIMAT0012735 |
| 163 | hsa-miR-6769a-5p | MIMAT0027438 |
| 164 | hsa-miR-4707-3p | MIMAT0019808 |
| 165 | hsa-miR-6765-5p | MIMAT0027430 |
| 166 | hsa-miR-4739 | MIMAT0019868 |
| 167 | hsa-miR-4525 | MIMAT0019064 |
| 168 | hsa-miR-4270 | MIMAT0016900 |
| 169 | hsa-miR-4534 | MIMAT0019073 |
| 170 | hsa-miR-6785-5p | MIMAT0027470 |
| 171 | hsa-miR-6850-5p | MIMAT0027600 |
| 172 | hsa-miR-4697-5p | MIMAT0019791 |
| 173 | hsa-miR-1260a | MIMAT0005911 |
| 174 | hsa-miR-4486 | MIMAT0019020 |
| 175 | hsa-miR-6880-5p | MIMAT0027660 |
| 176 | hsa-miR-6802-5p | MIMAT0027504 |
| 177 | hsa-miR-6861-5p | MIMAT0027623 |
| 178 | hsa-miR-92b-5p | MIMAT0004792 |
| 179 | hsa-miR-1238-5p | MIMAT0022947 |
| 180 | hsa-miR-6851-5p | MIMAT0027602 |
| 181 | hsa-miR-7704 | MIMAT0030019 |
| 182 | hsa-miR-149-3p | MIMAT0004609 |
| 183 | hsa-miR-4689 | MIMAT0019778 |
| 184 | hsa-miR-4688 | MIMAT0019777 |
| 185 | hsa-miR-125a-3p | MIMAT0004602 |
| 186 | hsa-miR-23b-3p | MIMAT0000418 |
| 187 | hsa-miR-614 | MIMAT0003282 |
| 188 | hsa-miR-1913 | MIMAT0007888 |
| 189 | hsa-miR-16-5p | MIMAT0000069 |
| 190 | hsa-miR-675-5p | MIMAT0004284 |
| 191 | hsa-miR-486-3p | MIMAT0004762 |
| 192 | hsa-miR-6777-5p | MIMAT0027454 |
| 193 | hsa-miR-4497 | MIMAT0019032 |
| 194 | hsa-miR-296-3p | MIMAT0004679 |
| 195 | hsa-miR-6738-5p | MIMAT0027377 |
| 196 | hsa-miR-4731-5p | MIMAT0019853 |
| 197 | hsa-miR-6889-5p | MIMAT0027678 |
| 198 | hsa-miR-6786-5p | MIMAT0027472 |
| 199 | hsa-miR-92a-3p | MIMAT0000092 |
| 200 | hsa-miR-4294 | MIMAT0016849 |
| 201 | hsa-miR-4763-3p | MIMAT0019913 |
| 202 | hsa-miR-6076 | MIMAT0023701 |
| 203 | hsa-miR-663a | MIMAT0003326 |
| 204 | hsa-miR-760 | MIMAT0004957 |
| 205 | hsa-miR-4667-5p | MIMAT0019743 |
| 206 | hsa-miR-6090 | MIMAT0023715 |
| 207 | hsa-miR-4730 | MIMAT0019852 |
| 208 | hsa-miR-7106-5p | MIMAT0028109 |
| 209 | hsa-miR-3196 | MIMAT0015080 |
| 210 | hsa-miR-5698 | MIMAT0022491 |
| 211 | hsa-miR-6087 | MIMAT0023712 |
| 212 | hsa-miR-4665-5p | MIMAT0019739 |
| 213 | hsa-miR-8059 | MIMAT0030986 |
| 214 | hsa-miR-6879-5p | MIMAT0027658 |
| 215 | hsa-mir-204 | MI0000284 |
| 216 | hsa-mir-1247 | MI0006382 |
| 217 | hsa-mir-6875 | MI0022722 |
| 218 | hsa-mir-6857 | MI0022703 |
| 219 | hsa-mir-6726 | MI0022571 |
| 220 | hsa-mir-3188 | MI0014232 |
| 221 | hsa-mir-8069 | MI0025905 |
| 222 | hsa-mir-4257 | MI0015856 |
| 223 | hsa-mir-1343 | MI0017320 |
| 224 | hsa-mir-7108 | MI0022959 |
| 225 | hsa-mir-6825 | MI0022670 |
| 226 | hsa-mir-7641-1 | MI0024975 |
| 227 | hsa-mir-7641-2 | MI0024976 |
| 228 | hsa-mir-3185 | MI0014227 |
| 229 | hsa-mir-4746 | MI0017385 |
| 230 | hsa-mir-6791 | MI0022636 |
| 231 | hsa-mir-6893 | MI0022740 |

TABLE 1-continued

| SEQ ID NO: | Gene name | miRBase registration No. |
|---|---|---|
| 232 | hsa-mir-4433b | MI0025511 |
| 233 | hsa-mir-3135b | MI0016809 |
| 234 | hsa-mir-6781 | MI0022626 |
| 235 | hsa-mir-1908 | MI0008329 |
| 236 | hsa-mir-4792 | MI0017439 |
| 237 | hsa-mir-7845 | MI0025515 |
| 238 | hsa-mir-4417 | MI0016753 |
| 239 | hsa-mir-3184 | MI0014226 |
| 240 | hsa-mir-1225 | MI0006311 |
| 241 | hsa-mir-1231 | MI0006321 |
| 242 | hsa-mir-150 | MI0000479 |
| 243 | hsa-mir-4433 | MI0016773 |
| 244 | hsa-mir-6125 | MI0021259 |
| 245 | hsa-mir-4513 | MI0016879 |
| 246 | hsa-mir-6787 | MI0022632 |
| 247 | hsa-mir-6784 | MI0022629 |
| 248 | hsa-mir-615 | MI0003628 |
| 249 | hsa-mir-6765 | MI0022610 |
| 250 | hsa-mir-5572 | MI0019117 |
| 251 | hsa-mir-6842 | MI0022688 |
| 252 | hsa-mir-8063 | MI0025899 |
| 253 | hsa-mir-6780b | MI0022681 |
| 254 | hsa-mir-187 | MI0000274 |
| 255 | hsa-mir-128-1 | MI0000447 |
| 256 | hsa-mir-6729 | MI0022574 |
| 257 | hsa-mir-6741 | MI0022586 |
| 258 | hsa-mir-6757 | MI0022602 |
| 259 | hsa-mir-7110 | MI0022961 |
| 260 | hsa-mir-7975 | MI0025751 |
| 261 | hsa-mir-1233-1 | MI0006323 |
| 262 | hsa-mir-1233-2 | MI0015973 |
| 263 | hsa-mir-6845 | MI0022691 |
| 264 | hsa-mir-3937 | MI0016593 |
| 265 | hsa-mir-4467 | MI0016818 |
| 266 | hsa-mir-7109 | MI0022960 |
| 267 | hsa-mir-6088 | MI0020365 |
| 268 | hsa-mir-6782 | MI0022627 |
| 269 | hsa-mir-5195 | MI0018174 |
| 270 | hsa-mir-4454 | MI0016800 |
| 271 | hsa-mir-6724 | MI0022559 |
| 272 | hsa-mir-8072 | MI0025908 |
| 273 | hsa-mir-4516 | MI0016882 |
| 274 | hsa-mir-6756 | MI0022601 |
| 275 | hsa-mir-4665 | MI0017295 |
| 276 | hsa-mir-6826 | MI0022671 |
| 277 | hsa-mir-6820 | MI0022665 |
| 278 | hsa-mir-6887 | MI0022734 |
| 279 | hsa-mir-3679 | MI0016080 |
| 280 | hsa-mir-7847 | MI0025517 |
| 281 | hsa-mir-6721 | MI0022556 |
| 282 | hsa-mir-3622a | MI0016013 |
| 283 | hsa-mir-939 | MI0005761 |
| 284 | hsa-mir-602 | MI0003615 |
| 285 | hsa-mir-7977 | MI0025753 |
| 286 | hsa-mir-6749 | MI0022594 |
| 287 | hsa-mir-1914 | MI0008335 |
| 288 | hsa-mir-4651 | MI0017279 |
| 289 | hsa-mir-4695 | MI0017328 |
| 290 | hsa-mir-6848 | MI0022694 |
| 291 | hsa-mir-1228 | MI0006318 |
| 292 | hsa-mir-642b | MI0016685 |
| 293 | hsa-mir-6746 | MI0022591 |
| 294 | hsa-mir-3620 | MI0016011 |
| 295 | hsa-mir-3131 | MI0014151 |
| 296 | hsa-mir-6732 | MI0022577 |
| 297 | hsa-mir-7113 | MI0022964 |
| 298 | hsa-mir-23a | MI0000079 |
| 299 | hsa-mir-3154 | MI0014182 |
| 300 | hsa-mir-4723 | MI0017359 |
| 301 | hsa-mir-3663 | MI0016064 |
| 302 | hsa-mir-4734 | MI0017371 |
| 303 | hsa-mir-6816 | MI0022661 |
| 304 | hsa-mir-4442 | MI0016785 |
| 305 | hsa-mir-4476 | MI0016828 |
| 306 | hsa-mir-423 | MI0001445 |
| 307 | hsa-mir-1249 | MI0006384 |
| 308 | hsa-mir-6515 | MI0022227 |
| 309 | hsa-mir-887 | MI0005562 |
| 310 | hsa-mir-4741 | MI0017379 |
| 311 | hsa-mir-6766 | MI0022611 |
| 312 | hsa-mir-4673 | MI0017304 |
| 313 | hsa-mir-6779 | MI0022624 |
| 314 | hsa-mir-4706 | MI0017339 |
| 315 | hsa-mir-1268b | MI0016748 |
| 316 | hsa-mir-4632 | MI0017259 |
| 317 | hsa-mir-3197 | MI0014245 |
| 318 | hsa-mir-6798 | MI0022643 |
| 319 | hsa-mir-711 | MI0012488 |
| 320 | hsa-mir-6840 | MI0022686 |
| 321 | hsa-mir-6763 | MI0022608 |
| 322 | hsa-mir-6727 | MI0022572 |
| 323 | hsa-mir-371a | MI0000779 |
| 324 | hsa-mir-6824 | MI0022669 |
| 325 | hsa-mir-4648 | MI0017275 |
| 326 | hsa-mir-1227 | MI0006316 |
| 327 | hsa-mir-564 | MI0003570 |
| 328 | hsa-mir-2861 | MI0013006 |
| 329 | hsa-mir-6737 | MI0022582 |
| 330 | hsa-mir-575 | MI0003582 |
| 331 | hsa-mir-4725 | MI0017362 |
| 332 | hsa-mir-6716 | MI0022550 |
| 333 | hsa-mir-4675 | MI0017306 |
| 334 | hsa-mir-1915 | MI0008336 |
| 335 | hsa-mir-671 | MI0003760 |
| 336 | hsa-mir-3656 | MI0016056 |
| 337 | hsa-mir-6722 | MI0022557 |
| 338 | hsa-mir-4707 | MI0017340 |
| 339 | hsa-mir-4449 | MI0016792 |
| 340 | hsa-mir-1202 | MI0006334 |
| 341 | hsa-mir-4649 | MI0017276 |
| 342 | hsa-mir-744 | MI0005559 |
| 343 | hsa-mir-642a | MI0003657 |
| 344 | hsa-mir-451a | MI0001729 |
| 345 | hsa-mir-6870 | MI0022717 |
| 346 | hsa-mir-4443 | MI0016786 |
| 347 | hsa-mir-6808 | MI0022653 |
| 348 | hsa-mir-4728 | MI0017365 |
| 349 | hsa-mir-937 | MI0005759 |
| 350 | hsa-mir-135a-1 | MI0000452 |
| 351 | hsa-mir-663b | MI0006336 |
| 352 | hsa-mir-6822 | MI0022667 |
| 353 | hsa-mir-6803 | MI0022648 |
| 354 | hsa-mir-6805 | MI0022650 |
| 355 | hsa-mir-128-2 | MI0000727 |
| 356 | hsa-mir-4640 | MI0017267 |
| 357 | hsa-mir-1469 | MI0007074 |
| 358 | hsa-mir-92a-2 | MI0000094 |
| 359 | hsa-mir-3940 | MI0016597 |
| 360 | hsa-mir-4281 | MI0015885 |
| 361 | hsa-mir-1260b | MI0014197 |
| 362 | hsa-mir-4758 | MI0017399 |
| 363 | hsa-mir-5001 | MI0017867 |
| 364 | hsa-mir-4286 | MI0015894 |
| 365 | hsa-mir-6126 | MI0021260 |
| 366 | hsa-mir-6789 | MI0022634 |
| 367 | hsa-mir-4459 | MI0016805 |
| 368 | hsa-mir-1268a | MI0006405 |
| 369 | hsa-mir-6752 | MI0022597 |
| 370 | hsa-mir-6131 | MI0021276 |
| 371 | hsa-mir-6800 | MI0022645 |
| 372 | hsa-mir-4532 | MI0016899 |
| 373 | hsa-mir-6872 | MI0022719 |
| 374 | hsa-mir-718 | MI0012489 |
| 375 | hsa-mir-6769a | MI0022614 |
| 376 | hsa-mir-4739 | MI0017377 |
| 377 | hsa-mir-4525 | MI0016892 |
| 378 | hsa-mir-4270 | MI0015878 |
| 379 | hsa-mir-4534 | MI0016901 |
| 380 | hsa-mir-6785 | MI0022630 |
| 381 | hsa-mir-6850 | MI0022696 |
| 382 | hsa-mir-4697 | MI0017330 |
| 383 | hsa-mir-1260a | MI0006394 |
| 384 | hsa-mir-4486 | MI0016847 |
| 385 | hsa-mir-6880 | MI0022727 |

TABLE 1-continued

| SEQ ID NO: | Gene name | miRBase registration No. |
|---|---|---|
| 386 | hsa-mir-6802 | MI0022647 |
| 387 | hsa-mir-6861 | MI0022708 |
| 388 | hsa-mir-92b | MI0003560 |
| 389 | hsa-mir-1238 | MI0006328 |
| 390 | hsa-mir-6851 | MI0022697 |
| 391 | hsa-mir-7704 | MI0025240 |
| 392 | hsa-mir-149 | MI0000478 |
| 393 | hsa-mir-4689 | MI0017322 |
| 394 | hsa-mir-4688 | MI0017321 |
| 395 | hsa-mir-125a | MI0000469 |
| 396 | hsa-mir-23b | MI0000439 |
| 397 | hsa-mir-614 | MI0003627 |
| 398 | hsa-mir-1913 | MI0008334 |
| 399 | hsa-mir-16-1 | MI0000070 |
| 400 | hsa-mir-16-2 | MI0000115 |
| 401 | hsa-mir-675 | MI0005416 |
| 402 | hsa-mir-486 | MI0002470 |
| 403 | hsa-mir-486-2 | MI0023622 |
| 404 | hsa-mir-6777 | MI0022622 |
| 405 | hsa-mir-4497 | MI0016859 |
| 406 | hsa-mir-296 | MI0000747 |
| 407 | hsa-mir-6738 | MI0022583 |
| 408 | hsa-mir-4731 | MI0017368 |
| 409 | hsa-mir-6889 | MI0022736 |
| 410 | hsa-mir-6786 | MI0022631 |
| 411 | hsa-mir-92a-1 | MI0000093 |
| 412 | hsa-mir-4294 | MI0015827 |
| 413 | hsa-mir-4763 | MI0017404 |
| 414 | hsa-mir-6076 | MI0020353 |
| 415 | hsa-mir-663a | MI0003672 |
| 416 | hsa-mir-760 | MI0005567 |
| 417 | hsa-mir-4667 | MI0017297 |
| 418 | hsa-mir-6090 | MI0020367 |
| 419 | hsa-mir-4730 | MI0017367 |
| 420 | hsa-mir-7106 | MI0022957 |
| 421 | hsa-mir-3196 | MI0014241 |
| 422 | hsa-mir-5698 | MI0019305 |
| 423 | hsa-mir-6087 | MI0020364 |
| 424 | hsa-mir-8059 | MI0025895 |
| 425 | hsa-mir-6879 | MI0022726 |
| 426 | isomiR example 1 of SEQ ID NO: 1 | — |
| 427 | isomiR example 2 of SEQ ID NO: 1 | — |
| 428 | isomiR example 1 of SEQ ID NO: 2 | — |
| 429 | isomiR example 2 of SEQ ID NO: 2 | — |
| 430 | isomiR example 1 of SEQ ID NO: 6 | — |
| 431 | isomiR example 2 of SEQ ID NO: 6 | — |
| 432 | isomiR example 1 of SEQ ID NO: 9 | — |
| 433 | isomiR example 2 of SEQ ID NO: 9 | — |
| 434 | isomiR example 1 of SEQ ID NO: 13 | — |
| 435 | isomiR example 2 of SEQ ID NO: 13 | — |
| 436 | isomiR example 1 of SEQ ID NO: 18 | — |
| 437 | isomiR example 2 of SEQ ID NO: 18 | — |
| 438 | isomiR example 1 of SEQ ID NO: 20 | — |
| 439 | isomiR example 2 of SEQ ID NO: 20 | — |
| 440 | isomiR example 1 of SEQ ID NO: 21 | — |
| 441 | isomiR example 2 of SEQ ID NO: 21 | — |
| 442 | isomiR example 1 of SEQ ID NO: 23 | — |
| 443 | isomiR example 2 of SEQ ID NO: 23 | — |
| 444 | isomiR example 1 of SEQ ID NO: 28 | — |
| 445 | isomiR example 2 of SEQ ID NO: 28 | — |
| 446 | isomiR example 1 of SEQ ID NO: 29 | — |
| 447 | isomiR example 2 of SEQ ID NO: 29 | — |
| 448 | isomiR example 1 of SEQ ID NO: 30 | — |
| 449 | isomiR example 2 of SEQ ID NO: 30 | — |
| 450 | isomiR example 1 of SEQ ID NO: 31 | — |
| 451 | isomiR example 2 of SEQ ID NO: 31 | — |
| 452 | isomiR example 1 of SEQ ID NO: 34 | — |
| 453 | isomiR example 2 of SEQ ID NO: 34 | — |
| 454 | isomiR example 1 of SEQ ID NO: 36 | — |
| 455 | isomiR example 2 of SEQ ID NO: 36 | — |
| 456 | isomiR example 1 of SEQ ID NO: 40 | — |
| 457 | isomiR example 2 of SEQ ID NO: 40 | — |
| 458 | isomiR example 1 of SEQ ID NO: 41 | — |
| 459 | isomiR example 2 of SEQ ID NO: 41 | — |
| 460 | isomiR example 1 of SEQ ID NO: 46 | — |
| 461 | isomiR example 2 of SEQ ID NO: 46 | — |
| 462 | isomiR example 1 of SEQ ID NO: 47 | — |
| 463 | isomiR example 2 of SEQ ID NO: 47 | — |
| 464 | isomiR example 1 of SEQ ID NO: 50 | — |
| 465 | isomiR example 2 of SEQ ID NO: 50 | — |
| 466 | isomiR example 1 of SEQ ID NO: 52 | — |
| 467 | isomiR example 2 of SEQ ID NO: 52 | — |
| 468 | isomiR example 1 of SEQ ID NO: 54 | — |
| 469 | isomiR example 2 of SEQ ID NO: 54 | — |
| 470 | isomiR example 1 of SEQ ID NO: 55 | — |
| 471 | isomiR example 2 of SEQ ID NO: 55 | — |
| 472 | isomiR example 1 of SEQ ID NO: 56 | — |
| 473 | isomiR example 2 of SEQ ID NO: 56 | — |
| 474 | isomiR example 1 of SEQ ID NO: 58 | — |
| 475 | isomiR example 2 of SEQ ID NO: 58 | — |
| 476 | isomiR example 1 of SEQ ID NO: 64 | — |
| 477 | isomiR example 2 of SEQ ID NO: 64 | — |
| 478 | isomiR example 1 of SEQ ID NO: 66 | — |
| 479 | isomiR example 2 of SEQ ID NO: 66 | — |
| 480 | isomiR example 1 of SEQ ID NO: 67 | — |
| 481 | isomiR example 2 of SEQ ID NO: 67 | — |
| 482 | isomiR example 1 of SEQ ID NO: 68 | — |
| 483 | isomiR example 2 of SEQ ID NO: 68 | — |
| 484 | isomiR example 1 of SEQ ID NO: 72 | — |
| 485 | isomiR example 2 of SEQ ID NO: 72 | — |
| 486 | isomiR example 1 of SEQ ID NO: 73 | — |
| 487 | isomiR example 2 of SEQ ID NO: 73 | — |
| 488 | isomiR example 1 of SEQ ID NO: 74 | — |
| 489 | isomiR example 2 of SEQ ID NO: 74 | — |
| 490 | isomiR example 1 of SEQ ID NO: 76 | — |
| 491 | isomiR example 2 of SEQ ID NO: 76 | — |
| 492 | isomiR example 1 of SEQ ID NO: 77 | — |
| 493 | isomiR example 2 of SEQ ID NO: 77 | — |
| 494 | isomiR example 1 of SEQ ID NO: 79 | — |
| 495 | isomiR example 2 of SEQ ID NO: 79 | — |
| 496 | isomiR example 1 of SEQ ID NO: 80 | — |
| 497 | isomiR example 2 of SEQ ID NO: 80 | — |
| 498 | isomiR example 1 of SEQ ID NO: 83 | — |
| 499 | isomiR example 2 of SEQ ID NO: 83 | — |
| 500 | isomiR example 1 of SEQ ID NO: 84 | — |
| 501 | isomiR example 2 of SEQ ID NO: 84 | — |
| 502 | isomiR example 1 of SEQ ID NO: 85 | — |
| 503 | isomiR example 2 of SEQ ID NO: 85 | — |
| 504 | isomiR example 1 of SEQ ID NO: 87 | — |
| 505 | isomiR example 2 of SEQ ID NO: 87 | — |
| 506 | isomiR example 1 of SEQ ID NO: 89 | — |
| 507 | isomiR example 2 of SEQ ID NO: 89 | — |
| 508 | isomiR example 1 of SEQ ID NO: 90 | — |
| 509 | isomiR example 2 of SEQ ID NO: 90 | — |
| 510 | isomiR example 1 of SEQ ID NO: 91 | — |
| 511 | isomiR example 2 of SEQ ID NO: 91 | — |
| 512 | isomiR example 1 of SEQ ID NO: 92 | — |
| 513 | isomiR example 2 of SEQ ID NO: 92 | — |
| 514 | isomiR example 1 of SEQ ID NO: 93 | — |
| 515 | isomiR example 2 of SEQ ID NO: 93 | — |
| 516 | isomiR example 1 of SEQ ID NO: 94 | — |
| 517 | isomiR example 2 of SEQ ID NO: 94 | — |
| 518 | isomiR example 1 of SEQ ID NO: 95 | — |
| 519 | isomiR example 2 of SEQ ID NO: 95 | — |
| 520 | isomiR example 1 of SEQ ID NO: 97 | — |
| 521 | isomiR example 2 of SEQ ID NO: 97 | — |
| 522 | isomiR example 1 of SEQ ID NO: 99 | — |
| 523 | isomiR example 2 of SEQ ID NO: 99 | — |
| 524 | isomiR example 1 of SEQ ID NO: 100 | — |
| 525 | isomiR example 2 of SEQ ID NO: 100 | — |
| 526 | isomiR example 1 of SEQ ID NO: 101 | — |
| 527 | isomiR example 2 of SEQ ID NO: 101 | — |
| 528 | isomiR example 1 of SEQ ID NO: 102 | — |
| 529 | isomiR example 2 of SEQ ID NO: 102 | — |
| 530 | isomiR example 1 of SEQ ID NO: 104 | — |
| 531 | isomiR example 2 of SEQ ID NO: 104 | — |
| 532 | isomiR example 1 of SEQ ID NO: 108 | — |
| 533 | isomiR example 2 of SEQ ID NO: 108 | — |
| 534 | isomiR example 1 of SEQ ID NO: 110 | — |
| 535 | isomiR example 2 of SEQ ID NO: 110 | — |
| 536 | isomiR example 1 of SEQ ID NO: 112 | — |
| 537 | isomiR example 2 of SEQ ID NO: 112 | — |
| 538 | isomiR example 1 of SEQ ID NO: 113 | — |
| 539 | isomiR example 2 of SEQ ID NO: 113 | — |

TABLE 1-continued

| SEQ ID NO: | Gene name | miRBase registration No. |
|---|---|---|
| 540 | isomiR example 1 of SEQ ID NO: 114 | — |
| 541 | isomiR example 2 of SEQ ID NO: 114 | — |
| 542 | isomiR example 1 of SEQ ID NO: 117 | — |
| 543 | isomiR example 2 of SEQ ID NO: 117 | — |
| 544 | isomiR example 1 of SEQ ID NO: 118 | — |
| 545 | isomiR example 2 of SEQ ID NO: 118 | — |
| 546 | isomiR example 1 of SEQ ID NO: 120 | — |
| 547 | isomiR example 2 of SEQ ID NO: 120 | — |
| 548 | isomiR example 1 of SEQ ID NO: 121 | — |
| 549 | isomiR example 2 of SEQ ID NO: 121 | — |
| 550 | isomiR example 1 of SEQ ID NO: 122 | — |
| 551 | isomiR example 2 of SEQ ID NO: 122 | — |
| 552 | isomiR example 1 of SEQ ID NO: 124 | — |
| 553 | isomiR example 2 of SEQ ID NO: 124 | — |
| 554 | isomiR example 1 of SEQ ID NO: 125 | — |
| 555 | isomiR example 2 of SEQ ID NO: 125 | — |
| 556 | isomiR example 1 of SEQ ID NO: 126 | — |
| 557 | isomiR example 2 of SEQ ID NO: 126 | — |
| 558 | isomiR example 1 of SEQ ID NO: 127 | — |
| 559 | isomiR example 2 of SEQ ID NO: 127 | — |
| 560 | isomiR example 1 of SEQ ID NO: 128 | — |
| 561 | isomiR example 2 of SEQ ID NO: 128 | — |
| 562 | isomiR example 1 of SEQ ID NO: 129 | — |
| 563 | isomiR example 2 of SEQ ID NO: 129 | — |
| 564 | isomiR example 1 of SEQ ID NO: 130 | — |
| 565 | isomiR example 2 of SEQ ID NO: 130 | — |
| 566 | isomiR example 1 of SEQ ID NO: 132 | — |
| 567 | isomiR example 2 of SEQ ID NO: 132 | — |
| 568 | isomiR example 1 of SEQ ID NO: 134 | — |
| 569 | isomiR example 2 of SEQ ID NO: 134 | — |
| 570 | isomiR example 1 of SEQ ID NO: 135 | — |
| 571 | isomiR example 2 of SEQ ID NO: 135 | — |
| 572 | isomiR example 1 of SEQ ID NO: 136 | — |
| 573 | isomiR example 2 of SEQ ID NO: 136 | — |
| 574 | isomiR example 1 of SEQ ID NO: 137 | — |
| 575 | isomiR example 2 of SEQ ID NO: 137 | — |
| 576 | isomiR example 1 of SEQ ID NO: 142 | — |
| 577 | isomiR example 2 of SEQ ID NO: 142 | — |
| 578 | isomiR example 1 of SEQ ID NO: 143 | — |
| 579 | isomiR example 2 of SEQ ID NO: 143 | — |
| 580 | isomiR example 1 of SEQ ID NO: 145 | — |
| 581 | isomiR example 2 of SEQ ID NO: 145 | — |
| 582 | isomiR example 1 of SEQ ID NO: 146 | — |
| 583 | isomiR example 2 of SEQ ID NO: 146 | — |
| 584 | isomiR example 1 of SEQ ID NO: 147 | — |
| 585 | isomiR example 2 of SEQ ID NO: 147 | — |
| 586 | isomiR example 1 of SEQ ID NO: 148 | — |
| 587 | isomiR example 2 of SEQ ID NO: 148 | — |
| 588 | isomiR example 1 of SEQ ID NO: 149 | — |
| 589 | isomiR example 2 of SEQ ID NO: 149 | — |
| 590 | isomiR example 1 of SEQ ID NO: 150 | — |
| 591 | isomiR example 2 of SEQ ID NO: 150 | — |
| 592 | isomiR example 1 of SEQ ID NO: 151 | — |
| 593 | isomiR example 2 of SEQ ID NO: 151 | — |
| 594 | isomiR example 1 of SEQ ID NO: 152 | — |
| 595 | isomiR example 2 of SEQ ID NO: 152 | — |
| 596 | isomiR example 1 of SEQ ID NO: 153 | — |
| 597 | isomiR example 2 of SEQ ID NO: 153 | — |
| 598 | isomiR example 1 of SEQ ID NO: 155 | — |
| 599 | isomiR example 2 of SEQ ID NO: 155 | — |
| 600 | isomiR example 1 of SEQ ID NO: 156 | — |
| 601 | isomiR example 2 of SEQ ID NO: 156 | — |
| 602 | isomiR example 1 of SEQ ID NO: 158 | — |
| 603 | isomiR example 2 of SEQ ID NO: 158 | — |
| 604 | isomiR example 1 of SEQ ID NO: 160 | — |
| 605 | isomiR example 2 of SEQ ID NO: 160 | — |
| 606 | isomiR example 1 of SEQ ID NO: 162 | — |
| 607 | isomiR example 2 of SEQ ID NO: 162 | — |
| 608 | isomiR example 1 of SEQ ID NO: 164 | — |
| 609 | isomiR example 2 of SEQ ID NO: 164 | — |
| 610 | isomiR example 1 of SEQ ID NO: 166 | — |
| 611 | isomiR example 2 of SEQ ID NO: 166 | — |
| 612 | isomiR example 1 of SEQ ID NO: 167 | — |
| 613 | isomiR example 2 of SEQ ID NO: 167 | — |
| 614 | isomiR example 1 of SEQ ID NO: 173 | — |
| 615 | isomiR example 2 of SEQ ID NO: 173 | — |
| 616 | isomiR example 1 of SEQ ID NO: 174 | — |
| 617 | isomiR example 2 of SEQ ID NO: 174 | — |
| 618 | isomiR example 1 of SEQ ID NO: 178 | — |
| 619 | isomiR example 2 of SEQ ID NO: 178 | — |
| 620 | isomiR example 1 of SEQ ID NO: 182 | — |
| 621 | isomiR example 2 of SEQ ID NO: 182 | — |
| 622 | isomiR example 1 of SEQ ID NO: 183 | — |
| 623 | isomiR example 2 of SEQ ID NO: 183 | — |
| 624 | isomiR example 1 of SEQ ID NO: 184 | — |
| 625 | isomiR example 2 of SEQ ID NO: 184 | — |
| 626 | isomiR example 1 of SEQ ID NO: 185 | — |
| 627 | isomiR example 2 of SEQ ID NO: 185 | — |
| 628 | isomiR example 1 of SEQ ID NO: 186 | — |
| 629 | isomiR example 2 of SEQ ID NO: 186 | — |
| 630 | isomiR example 1 of SEQ ID NO: 187 | — |
| 631 | isomiR example 2 of SEQ ID NO: 187 | — |
| 632 | isomiR example 1 of SEQ ID NO: 188 | — |
| 633 | isomiR example 2 of SEQ ID NO: 188 | — |
| 634 | isomiR example 1 of SEQ ID NO: 189 | — |
| 635 | isomiR example 2 of SEQ ID NO: 189 | — |
| 636 | isomiR example 1 of SEQ ID NO: 190 | — |
| 637 | isomiR example 2 of SEQ ID NO: 190 | — |
| 638 | isomiR example 1 of SEQ ID NO: 191 | — |
| 639 | isomiR example 2 of SEQ ID NO: 191 | — |
| 640 | isomiR example 1 of SEQ ID NO: 193 | — |
| 641 | isomiR example 2 of SEQ ID NO: 193 | — |
| 642 | isomiR example 1 of SEQ ID NO: 194 | — |
| 643 | isomiR example 2 of SEQ ID NO: 194 | — |
| 644 | isomiR example 1 of SEQ ID NO: 196 | — |
| 645 | isomiR example 2 of SEQ ID NO: 196 | — |
| 646 | isomiR example 1 of SEQ ID NO: 199 | — |
| 647 | isomiR example 2 of SEQ ID NO: 199 | — |
| 648 | isomiR example 1 of SEQ ID NO: 201 | — |
| 649 | isomiR example 2 of SEQ ID NO: 201 | — |
| 650 | isomiR example 1 of SEQ ID NO: 203 | — |
| 651 | isomiR example 2 of SEQ ID NO: 203 | — |
| 652 | isomiR example 1 of SEQ ID NO: 204 | — |
| 653 | isomiR example 2 of SEQ ID NO: 204 | — |
| 654 | isomiR example 1 of SEQ ID NO: 205 | — |
| 655 | isomiR example 2 of SEQ ID NO: 205 | — |
| 656 | isomiR example 1 of SEQ ID NO: 207 | — |
| 657 | isomiR example 2 of SEQ ID NO: 207 | — |
| 658 | isomiR example 1 of SEQ ID NO: 209 | — |
| 659 | isomiR example 2 of SEQ ID NO: 209 | — |
| 660 | isomiR example 1 of SEQ ID NO: 210 | — |
| 661 | isomiR example 2 of SEQ ID NO: 210 | — |
| 662 | isomiR example 1 of SEQ ID NO: 211 | — |
| 663 | isomiR example 2 of SEQ ID NO: 211 | — |
| 664 | isomiR example 1 of SEQ ID NO: 212 | — |
| 665 | isomiR example 2 of SEQ ID NO: 212 | — |
| 666 | hsa-miR-6717-5p | MIMAT0025846 |
| 667 | hsa-miR-3648 | MIMAT0018068 |
| 668 | hsa-miR-3162-5p | MIMAT0015036 |
| 669 | hsa-miR-1909-3p | MIMAT0007883 |
| 670 | hsa-miR-8073 | MIMAT0031000 |
| 671 | hsa-miR-6769b-5p | MIMAT0027620 |
| 672 | hsa-miR-6836-3p | MIMAT0027575 |
| 673 | hsa-miR-4484 | MIMAT0019018 |
| 674 | hsa-miR-6819-5p | MIMAT0027538 |
| 675 | hsa-miR-6794-5p | MIMAT0027488 |
| 676 | hsa-miR-24-3p | MIMAT0000080 |
| 677 | hsa-mir-6717 | MI0022551 |
| 678 | hsa-mir-3648 | MI0016048 |
| 679 | hsa-mir-3162 | MI0014192 |
| 680 | hsa-mir-1909 | MI0008330 |
| 681 | hsa-mir-8073 | MI0025909 |
| 682 | hsa-mir-6769b | MI0022706 |
| 683 | hsa-mir-6836 | MI0022682 |
| 684 | hsa-mir-4484 | MI0016845 |
| 685 | hsa-mir-6819 | MI0022664 |
| 686 | hsa-mir-6794 | MI0022639 |
| 687 | hsa-mir-24-1 | MI0000080 |
| 688 | hsa-mir-24-2 | MI0000081 |
| 689 | isomiR example 1 of SEQ ID NO: 666 | — |
| 690 | isomiR example 2 of SEQ ID NO: 666 | — |
| 691 | isomiR example 1 of SEQ ID NO: 667 | — |
| 692 | isomiR example 2 of SEQ ID NO: 667 | — |
| 693 | isomiR example 1 of SEQ ID NO: 668 | — |

TABLE 1-continued

| SEQ ID NO: | Gene name | miRBase registration No. |
|---|---|---|
| 694 | isomiR example 2 of SEQ ID NO: 668 | — |
| 695 | isomiR example 1 of SEQ ID NO: 669 | — |
| 696 | isomiR example 2 of SEQ ID NO: 669 | — |
| 697 | isomiR example 1 of SEQ ID NO: 673 | — |
| 698 | isomiR example 2 of SEQ ID NO: 673 | — |
| 699 | isomiR example 1 of SEQ ID NO: 676 | — |
| 700 | isomiR example 2 of SEQ ID NO: 676 | — |

The present specification encompasses the contents described in the specifications and/or drawings of Japanese Patent Application No. 2014-125036 and No. 2015-070379 from which the present application claims priority.

Advantageous Effect of Invention

According to the present invention, esophageal cancer can be detected easily and high accuracy. For example, the presence or absence of esophageal cancer in a patient can be easily detected by using, as indicators, the determined expression levels of several miRNAs in blood, serum, and/or plasma of the patients, which can be collected with limited invasiveness.

BRIEF DESCRIPTION OF DRAWINGS

FIGS. 4A-4B: FIG. 4A: a discriminant (−2.65×hsa-miR-4739-3.01×hsa-miR-1343-5p+0.69×hsa-miR-204-3p+0.95×hsa-miR-4723-5p−0.56×hsa-miR-6726-5p−0.99×hsa-miR-6717-5p+57.33) was prepared by use of Fisher's discriminant analysis from the expression level measurement values of hsa-miR-204-3p (SEQ ID NO: 1), hsa-miR-6726-5p (SEQ ID NO: 5), hsa-miR-4723-5p (SEQ ID NO: 85), hsa-miR-1343-5p (SEQ ID NO: 138), hsa-miR-4739 (SEQ ID NO: 166), and hsa-miR-6717-5p (SEQ ID NO: 666) in 34 esophageal cancer patients, 103 healthy subjects, 69 pancreatic cancer patients, 66 bile duct cancer patients, 30 colorectal cancer patients, 33 stomach cancer patients, 32 liver cancer patients, and 15 benign pancreaticobiliary disease patients selected as training cohorts, and discriminant scores obtained from the discriminant were plotted on the ordinate against the sample groups on the abscissa. The dotted line in the diagram depicts a discrimination boundary that offered a discriminant score of 0 and discriminated between the groups. FIG. 4B: discriminant scores obtained from the discriminant prepared for the training cohort as to the expression level measurement values of hsa-miR-204-3p (SEQ ID NO: 1), hsa-miR-6726-5p (SEQ ID NO: 5), hsa-miR-4723-5p (SEQ ID NO: 85), hsa-miR-1343-5p (SEQ ID NO: 138), hsa-miR-4739 (SEQ ID NO: 166), and hsa-miR-6717-5p (SEQ ID NO: 666) in 16 esophageal cancer patients, 47 healthy subjects, 30 pancreatic cancer patients, 33 bile duct cancer patients, 20 colorectal cancer patients, 17 stomach cancer patients, 20 liver cancer patients, and 6 benign pancreaticobiliary disease patients selected as validation cohort were plotted on the ordinate against the sample groups on the abscissa. The dotted line in the diagram depicts the discriminant boundary that offered a discriminant score of 0 and discriminated between both of the groups.

DESCRIPTION OF EMBODIMENTS

Figure 1:
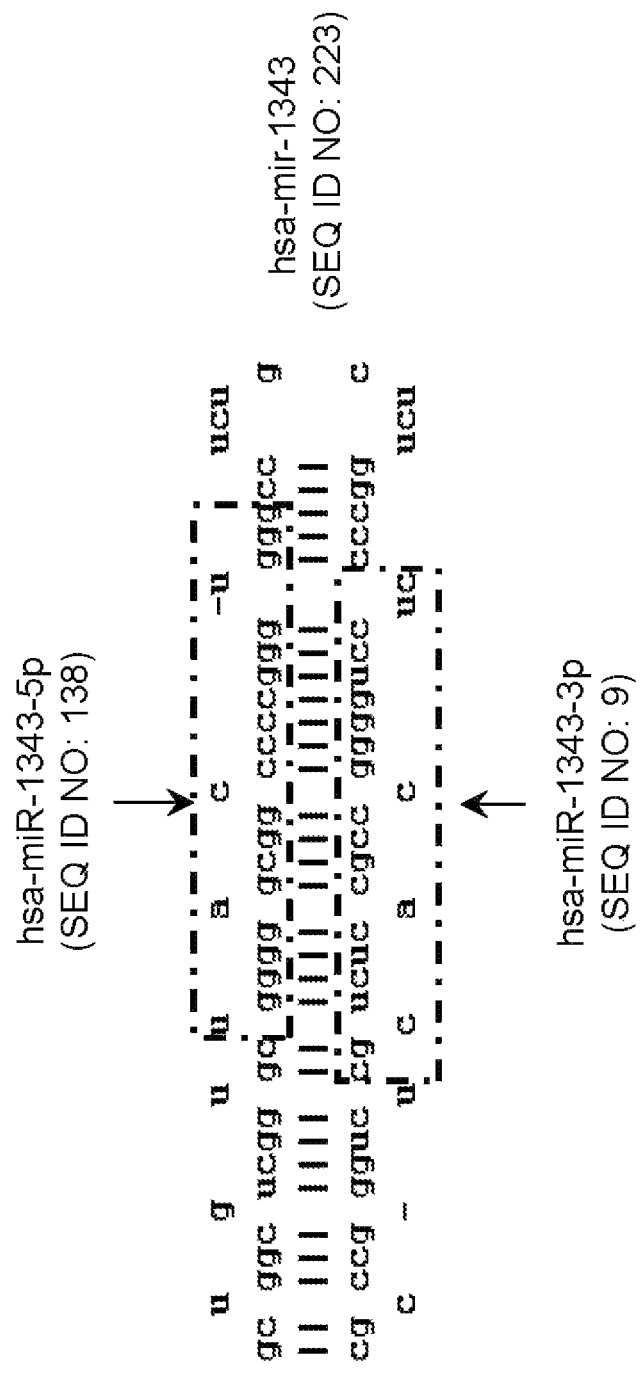
FIG. 1 This figure shows the relationship between hsa-miR-1343-3p consisting of a nucleotide sequence represented by SEQ ID NO: 9 and hsa-miR-1343-5p consisting of a nucleotide sequence represented by SEQ ID NO: 138, which are produced from a precursor hsa-mir-1343 consisting of a nucleotide sequence represented by SEQ ID NO: 223.

Hereinafter, the present invention will be further described in detail specifically.

1. Target Nucleic Acid for Esophageal Cancer

Primary target nucleic acids that can be used as esophageal cancer markers for detecting the presence and/or absence of esophageal cancer or esophageal cancer cells using the nucleic acid probe or the primer for the detection of esophageal cancer defined above according to the present invention is at least one miRNAs selected from the group consisting of the following miRNAs: hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR- 8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p, and hsa-miR-6794-5p. Furthermore, miRNAs selected from other esophageal cancer markers that can be combined with these miRNAs, i.e., hsa-miR-575 and hsa-miR-24-3p, can also be preferably used as a target nucleic acid. Moreover, at least one miRNA selected from the group consisting of the following other esophageal cancer markers that can be combined with these miRNAs, i.e., hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059 and hsa-miR-6879-5p can also be preferably used as target nucleic acids.

These miRNAs include, for example, a human gene comprising a nucleotide sequence represented by any of SEQ ID NOs: 1 to 214 and 666 to 676 (i.e., hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p, hsa-miR-6794-5p hsa-miR-575, hsa-miR-24-3p, hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059 and hsa-miR-6879-5p, respectively), a congener thereof, a transcript thereof, and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 700 or a transcript thereof, more preferably the transcript, i.e., a miRNA or its precursor RNA (pri-miRNA or pre-miRNA).

The first target gene is the hsa-miR-204-3p gene, a congener thereof, a transcript thereof, or a variant or a derivative thereof. None of the previously known reports show that change in the expression of the gene or the transcript thereof can serve as a marker for esophageal cancer.

The second target gene is the hsa-miR-1247-3p gene, a congener thereof, a transcript thereof, or a variant or a derivative thereof. None of the previously known reports show that change in the expression of the gene or the transcript thereof can serve as a marker for esophageal cancer.

The third target gene is the hsa-miR-6875-5p gene, a congener thereof, a transcript thereof, or a variant or a derivative thereof. None of the previously known reports show that change in the expression of the gene or the transcript thereof can serve as a marker for esophageal cancer.

The fourth target gene is the hsa-miR-6857-5p gene, a congener thereof, a transcript thereof, or a variant or a derivative thereof. None of the previously known reports show that change in the expression of the gene or the transcript thereof can serve as a marker for esophageal cancer.

The fifth target gene is the hsa-miR-6726-5p gene, a congener thereof, a transcript thereof, or a variant or a derivative thereof. None of the previously known reports show that change in the expression of the gene or the transcript thereof can serve as a marker for esophageal cancer.

The sixth target gene is the hsa-miR-3188 gene, a congener thereof, a transcript thereof, or a variant or a derivative thereof. None of the previously known reports show that change in the expression of the gene or the transcript thereof can serve as a marker for esophageal cancer.

The seventh target gene is the hsa-miR-8069 gene, a congener thereof, a transcript thereof, or a variant or a derivative thereof. None of the previously known reports show that change in the expression of the gene or the transcript thereof can serve as a marker for esophageal cancer.

The eighth target gene is the hsa-miR-4257 gene, a congener thereof, a transcript thereof, or a variant or a derivative thereof. None of the previously known reports show that change in the expression of the gene or the transcript thereof can serve as a marker for esophageal cancer.

The ninth target gene is the hsa-miR-1343-3p gene, a congener thereof, a transcript thereof, or a variant or a derivative thereof. None of the previously known reports show that change in the expression of the gene or the transcript thereof can serve as a marker for esophageal cancer.

The 10th target gene is the hsa-miR-7108-5p gene, a congener thereof, a transcript thereof, or a variant or a derivative thereof. None of the previously known reports show that change in the expression of the gene or the transcript thereof can serve as a marker for esophageal cancer.

The 11th target gene is the hsa-miR-6825-5p gene, a congener thereof, a transcript thereof, or a variant or a derivative thereof. None of the previously known reports show that change in the expression of the gene or the transcript thereof can serve as a marker for esophageal cancer.

The 12th target gene is the hsa-miR-7641 gene, a congener thereof, a transcript thereof, or a variant or a derivative thereof. None of the previously known reports show that change in the expression of the gene or the transcript thereof can serve as a marker for esophageal cancer.

The 13th target gene is the hsa-miR-3185 gene, a congener thereof, a transcript thereof, or a variant or a derivative thereof. None of the previously known reports show that change in the expression of the gene or the transcript thereof can serve as a marker for esophageal cancer.

The 14th target gene is the hsa-miR-4746-3p gene, a congener thereof, a transcript thereof, or a variant or a derivative thereof. None of the previously known reports show that change in the expression of the gene or the transcript thereof can serve as a marker for esophageal cancer.

The 15th target gene is the hsa-miR-6791-5p gene, a congener thereof, a transcript thereof, or a variant or a derivative thereof. None of the previously known reports show that change in the expression of the gene or the transcript thereof can serve as a marker for esophageal cancer.

The 16th target gene is the hsa-miR-6893-5p gene, a congener thereof, a transcript thereof, or a variant or a derivative thereof. None of the previously known reports show that change in the expression of the gene or the transcript thereof can serve as a marker for esophageal cancer.

The 17th target gene is the hsa-miR-4433b-3p gene, a congener thereof, a transcript thereof, or a variant or a derivative thereof. None of the previously known reports show that change in the expression of the gene or the transcript thereof can serve as a marker for esophageal cancer.

The 18th target gene is the hsa-miR-3135b gene, a congener thereof, a transcript thereof, or a variant or a derivative thereof. None of the previously known reports show that change in the expression of the gene or the transcript thereof can serve as a marker for esophageal cancer.

The 19th target gene is the hsa-miR-6781-5p gene, a congener thereof, a transcript thereof, or a variant or a derivative thereof. None of the previously known reports show that change in the expression of the gene or the transcript thereof can serve as a marker for esophageal cancer.

The 20th target gene is the hsa-miR-1908-5p gene, a congener thereof, a transcript thereof, or a variant or a derivative thereof. None of the previously known reports show that change in the expression of the gene or the transcript thereof can serve as a marker for esophageal cancer.

The 21st target gene is the hsa-miR-4792 gene, a congener thereof, a transcript thereof, or a variant or a derivative thereof. None of the previously known reports show that change in the expression of the gene or the transcript thereof can serve as a marker for esophageal cancer.

The 22nd target gene is the hsa-miR-7845-5p gene, a congener thereof, a transcript thereof, or a variant or a derivative thereof. None of the previously known reports show that change in the expression of the gene or the transcript thereof can serve as a marker for esophageal cancer.

The 23rd target gene is the hsa-miR-4417 gene, a congener thereof, a transcript thereof, or a variant or a derivative thereof. None of the previously known reports show that change in the expression of the gene or the transcript thereof can serve as a marker for esophageal cancer.

The 24th target gene is the hsa-miR-3184-5p gene, a congener thereof, a transcript thereof, or a variant or a derivative thereof. None of the previously known reports show that change in the expression of the gene or the transcript thereof can serve as a marker for esophageal cancer.

The 25th target gene is the hsa-miR-1225-5p gene, a congener thereof, a transcript thereof, or a variant or a derivative thereof. None of the previously known reports show that change in the expression of the gene or the transcript thereof can serve as a marker for esophageal cancer.

The 26th target gene is the hsa-miR-1231 gene, a congener thereof, a transcript thereof, or a variant or a derivative thereof. None of the previously known reports show that change in the expression of the gene or the transcript thereof can serve as a marker for esophageal cancer.

The 27th target gene is the hsa-miR-1225-3p gene, a congener thereof, a transcript thereof, or a variant or a derivative thereof. None of the previously known reports show that change in the expression of the gene or the transcript thereof can serve as a marker for esophageal cancer.

The 28th target gene is the hsa-miR-150-3p gene, a congener thereof, a transcript thereof, or a variant or a derivative thereof. None of the previously known reports show that change in the expression of the gene or the transcript thereof can serve as a marker for esophageal cancer.

The 29th target gene is the hsa-miR-4433-3p gene, a congener thereof, a transcript thereof, or a variant or a derivative thereof. None of the previously known reports show that change in the expression of the gene or the transcript thereof can serve as a marker for esophageal cancer.

The 30th target gene is the hsa-miR-6125 gene, a congener thereof, a transcript thereof, or a variant or a derivative thereof. None of the previously known reports show that change in the expression of the gene or the transcript thereof can serve as a marker for esophageal cancer.

The 31st target gene is the hsa-miR-4513 gene, a congener thereof, a transcript thereof, or a variant or a derivative thereof. None of the previously known reports show that change in the expression of the gene or the transcript thereof can serve as a marker for esophageal cancer.

The 32nd target gene is the hsa-miR-6787-5p gene, a congener thereof, a transcript thereof, or a variant or a derivative thereof. None of the previously known reports show that change in the expression of the gene or the transcript thereof can serve as a marker for esophageal cancer.

The 33rd target gene is the hsa-miR-6784-5p gene, a congener thereof, a transcript thereof, or a variant or a derivative thereof. None of the previously known reports show that change in the expression of the gene or the transcript thereof can serve as a marker for esophageal cancer.

The 34th target gene is the hsa-miR-615-5p gene, a congener thereof, a transcript thereof, or a variant or a derivative thereof. None of the previously known reports show that change in the expression of the gene or the transcript thereof can serve as a marker for esophageal cancer.

The 35th target gene is the hsa-miR-6765-3p gene, a congener thereof, a transcript thereof, or a variant or a derivative thereof. None of the previously known reports show that change in the expression of the gene or the transcript thereof can serve as a marker for esophageal cancer.

The 36th target gene is the hsa-miR-5572 gene, a congener thereof, a transcript thereof, or a variant or a derivative thereof. None of the previously known reports show that change in the expression of the gene or the transcript thereof can serve as a marker for esophageal cancer.

The 37th target gene is the hsa-miR-6842-5p gene, a congener thereof, a transcript thereof, or a variant or a derivative thereof. None of the previously known reports show that change in the expression of the gene or the transcript thereof can serve as a marker for esophageal cancer.

The 38th target gene is the hsa-miR-8063 gene, a congener thereof, a transcript thereof, or a variant or a derivative thereof. None of the previously known reports show that change in the expression of the gene or the transcript thereof can serve as a marker for esophageal cancer.

The 39th target gene is the hsa-miR-6780b-5p gene, a congener thereof, a transcript thereof, or a variant or a derivative thereof. None of the previously known reports show that change in the expression of the gene or the transcript thereof can serve as a marker for esophageal cancer.

The 40th target gene is the hsa-miR-187-5p gene, a congener thereof, a transcript thereof, or a variant or a derivative thereof. None of the previously known reports show that change in the expression of the gene or the transcript thereof can serve as a marker for esophageal cancer.

The 41st target gene is the hsa-miR-128-1-5p gene, a congener thereof, a transcript thereof, or a variant or a derivative thereof. None of the previously known reports show that change in the expression of the gene or the transcript thereof can serve as a marker for esophageal cancer.

The 42nd target gene is the hsa-miR-6729-5p gene, a congener thereof, a transcript thereof, or a variant or a derivative thereof. None of the previously known reports show that change in the expression of the gene or the transcript thereof can serve as a marker for esophageal cancer.

The 43rd target gene is the hsa-miR-6741-5p gene, a congener thereof, a transcript thereof, or a variant or a derivative thereof. None of the previously known reports show that change in the expression of the gene or the transcript thereof can serve as a marker for esophageal cancer.

The 44th target gene is the hsa-miR-6757-5p gene, a congener thereof, a transcript thereof, or a variant or a derivative thereof. None of the previously known reports show that change in the expression of the gene or the transcript thereof can serve as a marker for esophageal cancer.

The 45th target gene is the hsa-miR-7110-5p gene, a congener thereof, a transcript thereof, or a variant or a derivative thereof. None of the previously known reports show that change in the expression of the gene or the transcript thereof can serve as a marker for esophageal cancer.

The 46th target gene is the hsa-miR-7975 gene, a congener thereof, a transcript thereof, or a variant or a derivative thereof. None of the previously known reports show that change in the expression of the gene or the transcript thereof can serve as a marker for esophageal cancer.

The 47th target gene is the hsa-miR-1233-5p gene, a congener thereof, a transcript thereof, or a variant or a derivative thereof. None of the previously known reports show that change in the expression of the gene or the transcript thereof can serve as a marker for esophageal cancer.

The 48th target gene is the hsa-miR-6845-5p gene, a congener thereof, a transcript thereof, or a variant or a derivative thereof. None of the previously known reports show that change in the expression of the gene or the transcript thereof can serve as a marker for esophageal cancer.

The 49th target gene is the hsa-miR-3937 gene, a congener thereof, a transcript thereof, or a variant or a derivative thereof. None of the previously known reports show that change in the expression of the gene or the transcript thereof can serve as a marker for esophageal cancer.

The 50th target gene is the hsa-miR-4467 gene, a congener thereof, a transcript thereof, or a variant or a derivative thereof. None of the previously known reports show that change in the expression of the gene or the transcript thereof can serve as a marker for esophageal cancer.

The 51st target gene is the hsa-miR-7109-5p gene, a congener thereof, a transcript thereof, or a variant or a derivative thereof. None of the previously known reports show that change in the expression of the gene or the transcript thereof can serve as a marker for esophageal cancer.

The 52nd target gene is the hsa-miR-6088 gene, a congener thereof, a transcript thereof, or a variant or a derivative thereof. None of the previously known reports show that change in the expression of the gene or the transcript thereof can serve as a marker for esophageal cancer.

The 53rd target gene is the hsa-miR-6782-5p gene, a congener thereof, a transcript thereof, or a variant or a derivative thereof. None of the previously known reports show that change in the expression of the gene or the transcript thereof can serve as a marker for esophageal cancer.

The 54th target gene is the hsa-miR-5195-3p gene, a congener thereof, a transcript thereof, or a variant or a derivative thereof. None of the previously known reports show that change in the expression of the gene or the transcript thereof can serve as a marker for esophageal cancer.

The 55th target gene is the hsa-miR-4454 gene, a congener thereof, a transcript thereof, or a variant or a derivative thereof. None of the previously known reports show that change in the expression of the gene or the transcript thereof can serve as a marker for esophageal cancer.

The 56th target gene is the hsa-miR-6724-5p gene, a congener thereof, a transcript thereof, or a variant or a derivative thereof. None of the previously known reports show that change in the expression of the gene or the transcript thereof can serve as a marker for esophageal cancer.

The 57th target gene is the hsa-miR-8072 gene, a congener thereof, a transcript thereof, or a variant or a derivative thereof. None of the previously known reports show that change in the expression of the gene or the transcript thereof can serve as a marker for esophageal cancer.

The 58th target gene is the hsa-miR-4516 gene, a congener thereof, a transcript thereof, or a variant or a derivative thereof. None of the previously known reports show that change in the expression of the gene or the transcript thereof can serve as a marker for esophageal cancer.

The 59th target gene is the hsa-miR-6756-5p gene, a congener thereof, a transcript thereof, or a variant or a derivative thereof. None of the previously known reports show that change in the expression of the gene or the transcript thereof can serve as a marker for esophageal cancer.

The 60th target gene is the hsa-miR-4665-3p gene, a congener thereof, a transcript thereof, or a variant or a derivative thereof. None of the previously known reports show that change in the expression of the gene or the transcript thereof can serve as a marker for esophageal cancer.

The 61st target gene is the hsa-miR-6826-5p gene, a congener thereof, a transcript thereof, or a variant or a derivative thereof. None of the previously known reports show that change in the expression of the gene or the transcript thereof can serve as a marker for esophageal cancer.

The 62nd target gene is the hsa-miR-6820-5p gene, a congener thereof, a transcript thereof, or a variant or a derivative thereof. None of the previously known reports show that change in the expression of the gene or the transcript thereof can serve as a marker for esophageal cancer.

The 63rd target gene is the hsa-miR-6887-5p gene, a congener thereof, a transcript thereof, or a variant or a derivative thereof. None of the previously known reports show that change in the expression of the gene or the transcript thereof can serve as a marker for esophageal cancer.

The 64th target gene is the hsa-miR-3679-5p gene, a congener thereof, a transcript thereof, or a variant or a derivative thereof. None of the previously known reports show that change in the expression of the gene or the transcript thereof can serve as a marker for esophageal cancer.

The 65th target gene is the hsa-miR-7847-3p gene, a congener thereof, a transcript thereof, or a variant or a derivative thereof. None of the previously known reports show that change in the expression of the gene or the transcript thereof can serve as a marker for esophageal cancer.

The 66th target gene is the hsa-miR-6721-5p gene, a congener thereof, a transcript thereof, or a variant or a derivative thereof. None of the previously known reports show that change in the expression of the gene or the transcript thereof can serve as a marker for esophageal cancer.

The 67th target gene is the hsa-miR-3622a-5p gene, a congener thereof, a transcript thereof, or a variant or a derivative thereof. None of the previously known reports show that change in the expression of the gene or the transcript thereof can serve as a marker for esophageal cancer.

The 68th target gene is the hsa-miR-939-5p gene, a congener thereof, a transcript thereof, or a variant or a derivative thereof. None of the previously known reports show that change in the expression of the gene or the transcript thereof can serve as a marker for esophageal cancer.

The 69th target gene is the hsa-miR-602 gene, a congener thereof, a transcript thereof, or a variant or a derivative thereof. None of the previously known reports show that change in the expression of the gene or the transcript thereof can serve as a marker for esophageal cancer.

The 70th target gene is the hsa-miR-7977 gene, a congener thereof, a transcript thereof, or a variant or a derivative thereof. None of the previously known reports show that change in the expression of the gene or the transcript thereof can serve as a marker for esophageal cancer.

The 71st target gene is the hsa-miR-6749-5p gene, a congener thereof, a transcript thereof, or a variant or a derivative thereof. None of the previously known reports show that change in the expression of the gene or the transcript thereof can serve as a marker for esophageal cancer.

The 72nd target gene is the hsa-miR-1914-3p gene, a congener thereof, a transcript thereof, or a variant or a derivative thereof. None of the previously known reports show that change in the expression of the gene or the transcript thereof can serve as a marker for esophageal cancer.

The 73rd target gene is the hsa-miR-4651 gene, a congener thereof, a transcript thereof, or a variant or a derivative thereof. None of the previously known reports show that change in the expression of the gene or the transcript thereof can serve as a marker for esophageal cancer.

The 74th target gene is the hsa-miR-4695-5p gene, a congener thereof, a transcript thereof, or a variant or a derivative thereof. None of the previously known reports show that change in the expression of the gene or the transcript thereof can serve as a marker for esophageal cancer.

The 75th target gene is the hsa-miR-6848-5p gene, a congener thereof, a transcript thereof, or a variant or a derivative thereof. None of the previously known reports show that change in the expression of the gene or the transcript thereof can serve as a marker for esophageal cancer.

The 76th target gene is the hsa-miR-1228-3p gene, a congener thereof, a transcript thereof, or a variant or a derivative thereof. None of the previously known reports show that change in the expression of the gene or the transcript thereof can serve as a marker for esophageal cancer.

The 77th target gene is the hsa-miR-642b-3p gene, a congener thereof, a transcript thereof, or a variant or a derivative thereof. None of the previously known reports show that change in the expression of the gene or the transcript thereof can serve as a marker for esophageal cancer.

The 78th target gene is the hsa-miR-6746-5p gene, a congener thereof, a transcript thereof, or a variant or a derivative thereof. None of the previously known reports show that change in the expression of the gene or the transcript thereof can serve as a marker for esophageal cancer.

The 79th target gene is the hsa-miR-3620-5p gene, a congener thereof, a transcript thereof, or a variant or a derivative thereof. None of the previously known reports show that change in the expression of the gene or the transcript thereof can serve as a marker for esophageal cancer.

The 80th target gene is the hsa-miR-3131 gene, a congener thereof, a transcript thereof, or a variant or a derivative thereof. None of the previously known reports show that change in the expression of the gene or the transcript thereof can serve as a marker for esophageal cancer.

The 81st target gene is the hsa-miR-6732-5p gene, a congener thereof, a transcript thereof, or a variant or a derivative thereof. None of the previously known reports show that change in the expression of the gene or the transcript thereof can serve as a marker for esophageal cancer.

The 82nd target gene is the hsa-miR-7113-3p gene, a congener thereof, a transcript thereof, or a variant or a derivative thereof. None of the previously known reports show that change in the expression of the gene or the transcript thereof can serve as a marker for esophageal cancer.

The 83rd target gene is the hsa-miR-23a-3p gene, a congener thereof, a transcript thereof, or a variant or a derivative thereof. None of the previously known reports show that change in the expression of the gene or the transcript thereof can serve as a marker for esophageal cancer.

The 84th target gene is the hsa-miR-3154 gene, a congener thereof, a transcript thereof, or a variant or a derivative thereof. None of the previously known reports show that change in the expression of the gene or the transcript thereof can serve as a marker for esophageal cancer.

The 85th target gene is the hsa-miR-4723-5p gene, a congener thereof, a transcript thereof, or a variant or a derivative thereof. None of the previously known reports show that change in the expression of the gene or the transcript thereof can serve as a marker for esophageal cancer.

The 86th target gene is the hsa-miR-3663-3p gene, a congener thereof, a transcript thereof, or a variant or a derivative thereof. None of the previously known reports show that change in the expression of the gene or the transcript thereof can serve as a marker for esophageal cancer.

The 87th target gene is the hsa-miR-4734 gene, a congener thereof, a transcript thereof, or a variant or a derivative thereof. None of the previously known reports show that change in the expression of the gene or the transcript thereof can serve as a marker for esophageal cancer.

The 88th target gene is the hsa-miR-6816-5p gene, a congener thereof, a transcript thereof, or a variant or a derivative thereof. None of the previously known reports show that change in the expression of the gene or the transcript thereof can serve as a marker for esophageal cancer.

The 89th target gene is the hsa-miR-4442 gene, a congener thereof, a transcript thereof, or a variant or a derivative thereof. None of the previously known reports show that change in the expression of the gene or the transcript thereof can serve as a marker for esophageal cancer.

The 90th target gene is the hsa-miR-4476 gene, a congener thereof, a transcript thereof, or a variant or a derivative thereof. None of the previously known reports show that change in the expression of the gene or the transcript thereof can serve as a marker for esophageal cancer.

The 91st target gene is the hsa-miR-423-5p gene, a congener thereof, a transcript thereof, or a variant or a derivative thereof. None of the previously known reports show that change in the expression of the gene or the transcript thereof can serve as a marker for esophageal cancer.

The 92nd target gene is the hsa-miR-1249 gene, a congener thereof, a transcript thereof, or a variant or a derivative thereof. None of the previously known reports show that change in the expression of the gene or the transcript thereof can serve as a marker for esophageal cancer.

The 93rd target gene is the hsa-miR-6515-3p gene, a congener thereof, a transcript thereof, or a variant or a derivative thereof. None of the previously known reports show that change in the expression of the gene or the transcript thereof can serve as a marker for esophageal cancer.

The 94th target gene is the hsa-miR-887-3p gene, a congener thereof, a transcript thereof, or a variant or a derivative thereof. None of the previously known reports show that change in the expression of the gene or the transcript thereof can serve as a marker for esophageal cancer.

The 95th target gene is the hsa-miR-4741 gene, a congener thereof, a transcript thereof, or a variant or a derivative thereof. None of the previously known reports show that change in the expression of the gene or the transcript thereof can serve as a marker for esophageal cancer.

The 96th target gene is the hsa-miR-6766-3p gene, a congener thereof, a transcript thereof, or a variant or a derivative thereof. None of the previously known reports show that change in the expression of the gene or the transcript thereof can serve as a marker for esophageal cancer.

The 97th target gene is the hsa-miR-4673 gene, a congener thereof, a transcript thereof, or a variant or a derivative thereof. None of the previously known reports show that change in the expression of the gene or the transcript thereof can serve as a marker for esophageal cancer.

The 98th target gene is the hsa-miR-6779-5p gene, a congener thereof, a transcript thereof, or a variant or a derivative thereof. None of the previously known reports show that change in the expression of the gene or the transcript thereof can serve as a marker for esophageal cancer.

The 99th target gene is the hsa-miR-4706 gene, a congener thereof, a transcript thereof, or a variant or a derivative thereof. None of the previously known reports show that change in the expression of the gene or the transcript thereof can serve as a marker for esophageal cancer.

The 100th target gene is the hsa-miR-1268b gene, a congener thereof, a transcript thereof, or a variant or a derivative thereof. None of the previously known reports show that change in the expression of the gene or the transcript thereof can serve as a marker for esophageal cancer.

The 101st target gene is the hsa-miR-4632-5p gene, a congener thereof, a transcript thereof, or a variant or a derivative thereof. None of the previously known reports show that change in the expression of the gene or the transcript thereof can serve as a marker for esophageal cancer.

The 102nd target gene is the hsa-miR-3197 gene, a congener thereof, a transcript thereof, or a variant or a derivative thereof. None of the previously known reports show that change in the expression of the gene or the transcript thereof can serve as a marker for esophageal cancer.

The 103rd target gene is the hsa-miR-6798-5p gene, a congener thereof, a transcript thereof, or a variant or a derivative thereof. None of the previously known reports show that change in the expression of the gene or the transcript thereof can serve as a marker for esophageal cancer.

The 104th target gene is the hsa-miR-711 gene, a congener thereof, a transcript thereof, or a variant or a derivative thereof. None of the previously known reports show that change in the expression of the gene or the transcript thereof can serve as a marker for esophageal cancer.

The 105th target gene is the hsa-miR-6840-3p gene, a congener thereof, a transcript thereof, or a variant or a derivative thereof. None of the previously known reports show that change in the expression of the gene or the transcript thereof can serve as a marker for esophageal cancer.

The 106th target gene is the hsa-miR-6763-5p gene, a congener thereof, a transcript thereof, or a variant or a derivative thereof. None of the previously known reports show that change in the expression of the gene or the transcript thereof can serve as a marker for esophageal cancer.

The 107th target gene is the hsa-miR-6727-5p gene, a congener thereof, a transcript thereof, or a variant or a derivative thereof. None of the previously known reports show that change in the expression of the gene or the transcript thereof can serve as a marker for esophageal cancer.

The 108th target gene is the hsa-miR-371a-5p gene, a congener thereof, a transcript thereof, or a variant or a derivative thereof. None of the previously known reports show that change in the expression of the gene or the transcript thereof can serve as a marker for esophageal cancer.

The 109th target gene is the hsa-miR-6824-5p gene, a congener thereof, a transcript thereof, or a variant or a derivative thereof. None of the previously known reports show that change in the expression of the gene or the transcript thereof can serve as a marker for esophageal cancer.

The 110th target gene is the hsa-miR-4648 gene, a congener thereof, a transcript thereof, or a variant or a derivative thereof. None of the previously known reports show that change in the expression of the gene or the transcript thereof can serve as a marker for esophageal cancer.

The 111th target gene is the hsa-miR-1227-5p gene, a congener thereof, a transcript thereof, or a variant or a derivative thereof. None of the previously known reports show that change in the expression of the gene or the transcript thereof can serve as a marker for esophageal cancer.

The 112th target gene is the hsa-miR-564 gene, a congener thereof, a transcript thereof, or a variant or a derivative thereof. None of the previously known reports show that change in the expression of the gene or the transcript thereof can serve as a marker for esophageal cancer.

The 113th target gene is the hsa-miR-3679-3p gene, a congener thereof, a transcript thereof, or a variant or a derivative thereof. None of the previously known reports show that change in the expression of the gene or the transcript thereof can serve as a marker for esophageal cancer.

The 114th target gene is the hsa-miR-2861 gene, a congener thereof, a transcript thereof, or a variant or a derivative thereof. None of the previously known reports show that change in the expression of the gene or the transcript thereof can serve as a marker for esophageal cancer.

The 115th target gene is the hsa-miR-6737-5p gene, a congener thereof, a transcript thereof, or a variant or a derivative thereof. None of the previously known reports show that change in the expression of the gene or the transcript thereof can serve as a marker for esophageal cancer.

The 116th target gene is the hsa-miR-575 gene, a congener thereof, a transcript thereof, or a variant or a derivative thereof. The previously known report shows that change in the expression of the gene or the transcript thereof can serve as a marker for esophageal cancer (Patent Literature 1).

The 117th target gene is the hsa-miR-4725-3p gene, a congener thereof, a transcript thereof, or a variant or a derivative thereof. None of the previously known reports show that change in the expression of the gene or the transcript thereof can serve as a marker for esophageal cancer.

The 118th target gene is the hsa-miR-6716-5p gene, a congener thereof, a transcript thereof, or a variant or a derivative thereof. None of the previously known reports show that change in the expression of the gene or the transcript thereof can serve as a marker for esophageal cancer.

The 119th target gene is the hsa-miR-4675 gene, a congener thereof, a transcript thereof, or a variant or a derivative thereof. None of the previously known reports show that change in the expression of the gene or the transcript thereof can serve as a marker for esophageal cancer.

The 120th target gene is the hsa-miR-1915-3p gene, a congener thereof, a transcript thereof, or a variant or a derivative thereof. None of the previously known reports show that change in the expression of the gene or the transcript thereof can serve as a marker for esophageal cancer.

The 121st target gene is the hsa-miR-671-5p gene, a congener thereof, a transcript thereof, or a variant or a derivative thereof. None of the previously known reports show that change in the expression of the gene or the transcript thereof can serve as a marker for esophageal cancer.

The 122nd target gene is the hsa-miR-3656 gene, a congener thereof, a transcript thereof, or a variant or a derivative thereof. None of the previously known reports show that change in the expression of the gene or the transcript thereof can serve as a marker for esophageal cancer.

The 123rd target gene is the hsa-miR-6722-3p gene, a congener thereof, a transcript thereof, or a variant or a derivative thereof. None of the previously known reports show that change in the expression of the gene or the transcript thereof can serve as a marker for esophageal cancer.

The 124th target gene is the hsa-miR-4707-5p gene, a congener thereof, a transcript thereof, or a variant or a derivative thereof. None of the previously known reports show that change in the expression of the gene or the transcript thereof can serve as a marker for esophageal cancer.

The 125th target gene is the hsa-miR-4449 gene, a congener thereof, a transcript thereof, or a variant or a derivative thereof. None of the previously known reports show that change in the expression of the gene or the transcript thereof can serve as a marker for esophageal cancer.

The 126th target gene is the hsa-miR-1202 gene, a congener thereof, a transcript thereof, or a variant or a derivative thereof. None of the previously known reports show that change in the expression of the gene or the transcript thereof can serve as a marker for esophageal cancer.

The 127th target gene is the hsa-miR-4649-5p gene, a congener thereof, a transcript thereof, or a variant or a derivative thereof. None of the previously known reports show that change in the expression of the gene or the transcript thereof can serve as a marker for esophageal cancer.

The 128th target gene is the hsa-miR-744-5p gene, a congener thereof, a transcript thereof, or a variant or a derivative thereof. None of the previously known reports show that change in the expression of the gene or the transcript thereof can serve as a marker for esophageal cancer.

The 129th target gene is the hsa-miR-642a-3p gene, a congener thereof, a transcript thereof, or a variant or a derivative thereof. None of the previously known reports show that change in the expression of the gene or the transcript thereof can serve as a marker for esophageal cancer.

The 130th target gene is the hsa-miR-451a gene, a congener thereof, a transcript thereof, or a variant or a derivative thereof. None of the previously known reports show that change in the expression of the gene or the transcript thereof can serve as a marker for esophageal cancer.

The 131st target gene is the hsa-miR-6870-5p gene, a congener thereof, a transcript thereof, or a variant or a derivative thereof. None of the previously known reports show that change in the expression of the gene or the transcript thereof can serve as a marker for esophageal cancer.

The 132nd target gene is the hsa-miR-4443 gene, a congener thereof, a transcript thereof, or a variant or a derivative thereof. None of the previously known reports show that change in the expression of the gene or the transcript thereof can serve as a marker for esophageal cancer.

The 133rd target gene is the hsa-miR-6808-5p gene, a congener thereof, a transcript thereof, or a variant or a derivative thereof. None of the previously known reports show that change in the expression of the gene or the transcript thereof can serve as a marker for esophageal cancer.

The 134th target gene is the hsa-miR-4728-5p gene, a congener thereof, a transcript thereof, or a variant or a derivative thereof. None of the previously known reports show that change in the expression of the gene or the transcript thereof can serve as a marker for esophageal cancer.

The 135th target gene is the hsa-miR-937-5p gene, a congener thereof, a transcript thereof, or a variant or a derivative thereof. None of the previously known reports show that change in the expression of the gene or the transcript thereof can serve as a marker for esophageal cancer.

The 136th target gene is the hsa-miR-135a-3p gene, a congener thereof, a transcript thereof, or a variant or a derivative thereof. None of the previously known reports show that change in the expression of the gene or the transcript thereof can serve as a marker for esophageal cancer.

The 137th target gene is the hsa-miR-663b gene, a congener thereof, a transcript thereof, or a variant or a derivative thereof. None of the previously known reports show that change in the expression of the gene or the transcript thereof can serve as a marker for esophageal cancer.

The 138th target gene is the hsa-miR-1343-5p gene, a congener thereof, a transcript thereof, or a variant or a derivative thereof. None of the previously known reports show that change in the expression of the gene or the transcript thereof can serve as a marker for esophageal cancer.

The 139th target gene is the hsa-miR-6822-5p gene, a congener thereof, a transcript thereof, or a variant or a derivative thereof. None of the previously known reports show that change in the expression of the gene or the transcript thereof can serve as a marker for esophageal cancer.

The 140th target gene is the hsa-miR-6803-5p gene, a congener thereof, a transcript thereof, or a variant or a derivative thereof. None of the previously known reports show that change in the expression of the gene or the transcript thereof can serve as a marker for esophageal cancer.

The 141st target gene is the hsa-miR-6805-3p gene, a congener thereof, a transcript thereof, or a variant or a derivative thereof. None of the previously known reports show that change in the expression of the gene or the transcript thereof can serve as a marker for esophageal cancer.

The 142nd target gene is the hsa-miR-128-2-5p gene, a congener thereof, a transcript thereof, or a variant or a derivative thereof. None of the previously known reports show that change in the expression of the gene or the transcript thereof can serve as a marker for esophageal cancer.

The 143rd target gene is the hsa-miR-4640-5p gene, a congener thereof, a transcript thereof, or a variant or a derivative thereof. None of the previously known reports show that change in the expression of the gene or the transcript thereof can serve as a marker for esophageal cancer.

The 144th target gene is the hsa-miR-1469 gene, a congener thereof, a transcript thereof, or a variant or a derivative thereof. None of the previously known reports show that change in the expression of the gene or the transcript thereof can serve as a marker for esophageal cancer.

The 145th target gene is the hsa-miR-92a-2-5p gene, a congener thereof, a transcript thereof, or a variant or a derivative thereof. None of the previously known reports show that change in the expression of the gene or the transcript thereof can serve as a marker for esophageal cancer.

The 146th target gene is the hsa-miR-3940-5p gene, a congener thereof, a transcript thereof, or a variant or a derivative thereof. None of the previously known reports show that change in the expression of the gene or the transcript thereof can serve as a marker for esophageal cancer.

The 147th target gene is the hsa-miR-4281 gene, a congener thereof, a transcript thereof, or a variant or a derivative thereof. None of the previously known reports show that change in the expression of the gene or the transcript thereof can serve as a marker for esophageal cancer.

The 148th target gene is the hsa-miR-1260b gene, a congener thereof, a transcript thereof, or a variant or a derivative thereof. None of the previously known reports show that change in the expression of the gene or the transcript thereof can serve as a marker for esophageal cancer.

The 149th target gene is the hsa-miR-4758-5p gene, a congener thereof, a transcript thereof, or a variant or a derivative thereof. None of the previously known reports show that change in the expression of the gene or the transcript thereof can serve as a marker for esophageal cancer.

The 150th target gene is the hsa-miR-1915-5p gene, a congener thereof, a transcript thereof, or a variant or a derivative thereof. None of the previously known reports show that change in the expression of the gene or the transcript thereof can serve as a marker for esophageal cancer.

The 151st target gene is the hsa-miR-5001-5p gene, a congener thereof, a transcript thereof, or a variant or a derivative thereof. None of the previously known reports show that change in the expression of the gene or the transcript thereof can serve as a marker for esophageal cancer.

The 152nd target gene is the hsa-miR-4286 gene, a congener thereof, a transcript thereof, or a variant or a derivative thereof. None of the previously known reports show that change in the expression of the gene or the transcript thereof can serve as a marker for esophageal cancer.

The 153rd target gene is the hsa-miR-6126 gene, a congener thereof, a transcript thereof, or a variant or a derivative thereof. None of the previously known reports show that change in the expression of the gene or the transcript thereof can serve as a marker for esophageal cancer.

The 154th target gene is the hsa-miR-6789-5p gene, a congener thereof, a transcript thereof, or a variant or a derivative thereof. None of the previously known reports show that change in the expression of the gene or the transcript thereof can serve as a marker for esophageal cancer.

The 155th target gene is the hsa-miR-4459 gene, a congener thereof, a transcript thereof, or a variant or a derivative thereof. None of the previously known reports show that change in the expression of the gene or the transcript thereof can serve as a marker for esophageal cancer.

The 156th target gene is the hsa-miR-1268a gene, a congener thereof, a transcript thereof, or a variant or a derivative thereof. None of the previously known reports show that change in the expression of the gene or the transcript thereof can serve as a marker for esophageal cancer.

The 157th target gene is the hsa-miR-6752-5p gene, a congener thereof, a transcript thereof, or a variant or a derivative thereof. None of the previously known reports show that change in the expression of the gene or the transcript thereof can serve as a marker for esophageal cancer.

The 158th target gene is the hsa-miR-6131 gene, a congener thereof, a transcript thereof, or a variant or a derivative thereof. None of the previously known reports show that change in the expression of the gene or the transcript thereof can serve as a marker for esophageal cancer.

The 159th target gene is the hsa-miR-6800-5p gene, a congener thereof, a transcript thereof, or a variant or a derivative thereof. None of the previously known reports show that change in the expression of the gene or the transcript thereof can serve as a marker for esophageal cancer.

The 160th target gene is the hsa-miR-4532 gene, a congener thereof, a transcript thereof, or a variant or a derivative thereof. None of the previously known reports show that change in the expression of the gene or the transcript thereof can serve as a marker for esophageal cancer.

The 161st target gene is the hsa-miR-6872-3p gene, a congener thereof, a transcript thereof, or a variant or a derivative thereof. None of the previously known reports show that change in the expression of the gene or the transcript thereof can serve as a marker for esophageal cancer.

The 162nd target gene is the hsa-miR-718 gene, a congener thereof, a transcript thereof, or a variant or a derivative thereof. None of the previously known reports show that change in the expression of the gene or the transcript thereof can serve as a marker for esophageal cancer.

The 163rd target gene is the hsa-miR-6769a-5p gene, a congener thereof, a transcript thereof, or a variant or a derivative thereof. None of the previously known reports show that change in the expression of the gene or the transcript thereof can serve as a marker for esophageal cancer.

The 164th target gene is the hsa-miR-4707-3p gene, a congener thereof, a transcript thereof, or a variant or a derivative thereof. None of the previously known reports show that change in the expression of the gene or the transcript thereof can serve as a marker for esophageal cancer.

The 165th target gene is the hsa-miR-6765-5p gene, a congener thereof, a transcript thereof, or a variant or a derivative thereof. None of the previously known reports show that change in the expression of the gene or the transcript thereof can serve as a marker for esophageal cancer.

The 166th target gene is the hsa-miR-4739 gene, a congener thereof, a transcript thereof, or a variant or a derivative thereof. None of the previously known reports show that change in the expression of the gene or the transcript thereof can serve as a marker for esophageal cancer.

The 167th target gene is the hsa-miR-4525 gene, a congener thereof, a transcript thereof, or a variant or a derivative thereof. None of the previously known reports show that change in the expression of the gene or the transcript thereof can serve as a marker for esophageal cancer.

The 168th target gene is the hsa-miR-4270 gene, a congener thereof, a transcript thereof, or a variant or a derivative thereof. None of the previously known reports show that change in the expression of the gene or the transcript thereof can serve as a marker for esophageal cancer.

The 169th target gene is the hsa-miR-4534 gene, a congener thereof, a transcript thereof, or a variant or a derivative thereof. None of the previously known reports show that change in the expression of the gene or the transcript thereof can serve as a marker for esophageal cancer.

The 170th target gene is the hsa-miR-6785-5p gene, a congener thereof, a transcript thereof, or a variant or a derivative thereof. None of the previously known reports show that change in the expression of the gene or the transcript thereof can serve as a marker for esophageal cancer.

The 171st target gene is the hsa-miR-6850-5p gene, a congener thereof, a transcript thereof, or a variant or a derivative thereof. None of the previously known reports show that change in the expression of the gene or the transcript thereof can serve as a marker for esophageal cancer.

The 172nd target gene is the hsa-miR-4697-5p gene, a congener thereof, a transcript thereof, or a variant or a derivative thereof. None of the previously known reports show that change in the expression of the gene or the transcript thereof can serve as a marker for esophageal cancer.

The 173rd target gene is the hsa-miR-1260a gene, a congener thereof, a transcript thereof, or a variant or a derivative thereof. None of the previously known reports show that change in the expression of the gene or the transcript thereof can serve as a marker for esophageal cancer.

The 174th target gene is the hsa-miR-4486 gene, a congener thereof, a transcript thereof, or a variant or a derivative thereof. None of the previously known reports show that change in the expression of the gene or the transcript thereof can serve as a marker for esophageal cancer.

The 175th target gene is the hsa-miR-6880-5p gene, a congener thereof, a transcript thereof, or a variant or a derivative thereof. None of the previously known reports show that change in the expression of the gene or the transcript thereof can serve as a marker for esophageal cancer.

The 176th target gene is the hsa-miR-6802-5p gene, a congener thereof, a transcript thereof, or a variant or a derivative thereof. None of the previously known reports show that change in the expression of the gene or the transcript thereof can serve as a marker for esophageal cancer.

The 177th target gene is the hsa-miR-6861-5p gene, a congener thereof, a transcript thereof, or a variant or a derivative thereof. None of the previously known reports show that change in the expression of the gene or the transcript thereof can serve as a marker for esophageal cancer.

The 178th target gene is the hsa-miR-92b-5p gene, a congener thereof, a transcript thereof, or a variant or a derivative thereof. None of the previously known reports show that change in the expression of the gene or the transcript thereof can serve as a marker for esophageal cancer.

The 179th target gene is the hsa-miR-1238-5p gene, a congener thereof, a transcript thereof, or a variant or a derivative thereof. None of the previously known reports show that change in the expression of the gene or the transcript thereof can serve as a marker for esophageal cancer.

The 180th target gene is the hsa-miR-6851-5p gene, a congener thereof, a transcript thereof, or a variant or a derivative thereof. None of the previously known reports show that change in the expression of the gene or the transcript thereof can serve as a marker for esophageal cancer.

The 181st target gene is the hsa-miR-7704 gene, a congener thereof, a transcript thereof, or a variant or a derivative thereof. None of the previously known reports show that change in the expression of the gene or the transcript thereof can serve as a marker for esophageal cancer.

The 182nd target gene is the hsa-miR-149-3p gene, a congener thereof, a transcript thereof, or a variant or a derivative thereof. None of the previously known reports show that change in the expression of the gene or the transcript thereof can serve as a marker for esophageal cancer.

The 183rd target gene is the hsa-miR-4689 gene, a congener thereof, a transcript thereof, or a variant or a derivative thereof. None of the previously known reports show that change in the expression of the gene or the transcript thereof can serve as a marker for esophageal cancer.

The 184th target gene is the hsa-miR-4688 gene, a congener thereof, a transcript thereof, or a variant or a derivative thereof. None of the previously known reports show that change in the expression of the gene or the transcript thereof can serve as a marker for esophageal cancer.

The 185th target gene is the hsa-miR-125a-3p gene, a congener thereof, a transcript thereof, or a variant or a derivative thereof. None of the previously known reports show that change in the expression of the gene or the transcript thereof can serve as a marker for esophageal cancer.

The 186th target gene is the hsa-miR-23b-3p gene, a congener thereof, a transcript thereof, or a variant or a derivative thereof. None of the previously known reports show that change in the expression of the gene or the transcript thereof can serve as a marker for esophageal cancer.

The 187th target gene is the hsa-miR-614 gene, a congener thereof, a transcript thereof, or a variant or a derivative thereof. None of the previously known reports show that change in the expression of the gene or the transcript thereof can serve as a marker for esophageal cancer.

The 188th target gene is the hsa-miR-1913 gene, a congener thereof, a transcript thereof, or a variant or a derivative thereof. None of the previously known reports show that change in the expression of the gene or the transcript thereof can serve as a marker for esophageal cancer.

The 189th target gene is the hsa-miR-16-5p gene, a congener thereof, a transcript thereof, or a variant or a derivative thereof. None of the previously known reports show that change in the expression of the gene or the transcript thereof can serve as a marker for esophageal cancer.

The 190th target gene is the hsa-miR-675-5p gene, a congener thereof, a transcript thereof, or a variant or a derivative thereof. None of the previously known reports show that change in the expression of the gene or the transcript thereof can serve as a marker for esophageal cancer.

The 191st target gene is the hsa-miR-486-3p gene, a congener thereof, a transcript thereof, or a variant or a derivative thereof. None of the previously known reports show that change in the expression of the gene or the transcript thereof can serve as a marker for esophageal cancer.

The 192nd target gene is the hsa-miR-6777-5p gene, a congener thereof, a transcript thereof, or a variant or a derivative thereof. None of the previously known reports show that change in the expression of the gene or the transcript thereof can serve as a marker for esophageal cancer.

The 193rd target gene is the hsa-miR-4497 gene, a congener thereof, a transcript thereof, or a variant or a derivative thereof. None of the previously known reports show that change in the expression of the gene or the transcript thereof can serve as a marker for esophageal cancer.

The 194th target gene is the hsa-miR-296-3p gene, a congener thereof, a transcript thereof, or a variant or a derivative thereof. None of the previously known reports show that change in the expression of the gene or the transcript thereof can serve as a marker for esophageal cancer.

The 195th target gene is the hsa-miR-6738-5p gene, a congener thereof, a transcript thereof, or a variant or a derivative thereof. None of the previously known reports show that change in the expression of the gene or the transcript thereof can serve as a marker for esophageal cancer.

The 196th target gene is the hsa-miR-4731-5p gene, a congener thereof, a transcript thereof, or a variant or a derivative thereof. None of the previously known reports show that change in the expression of the gene or the transcript thereof can serve as a marker for esophageal cancer.

The 197th target gene is the hsa-miR-6889-5p gene, a congener thereof, a transcript thereof, or a variant or a derivative thereof. None of the previously known reports show that change in the expression of the gene or the transcript thereof can serve as a marker for esophageal cancer.

The 198th target gene is the hsa-miR-6786-5p gene, a congener thereof, a transcript thereof, or a variant or a derivative thereof. None of the previously known reports show that change in the expression of the gene or the transcript thereof can serve as a marker for esophageal cancer.

The 199th target gene is the hsa-miR-92a-3p gene, a congener thereof, a transcript thereof, or a variant or a derivative thereof. The previously known report shows that change in the expression of the gene or the transcript thereof can serve as a marker for esophageal cancer (Patent Literature 1).

The 200th target gene is the hsa-miR-4294 gene, a congener thereof, a transcript thereof, or a variant or a derivative thereof. None of the previously known reports show that change in the expression of the gene or the transcript thereof can serve as a marker for esophageal cancer.

The 201st target gene is the hsa-miR-4763-3p gene, a congener thereof, a transcript thereof, or a variant or a derivative thereof. None of the previously known reports show that change in the expression of the gene or the transcript thereof can serve as a marker for esophageal cancer.

The 202nd target gene is the hsa-miR-6076 gene, a congener thereof, a transcript thereof, or a variant or a derivative thereof. None of the previously known reports show that change in the expression of the gene or the transcript thereof can serve as a marker for esophageal cancer.

The 203rd target gene is the hsa-miR-663a gene, a congener thereof, a transcript thereof, or a variant or a derivative thereof. The previously known report shows that change in the expression of the gene or the transcript thereof can serve as a marker for esophageal cancer (Patent Literature 1).

The 204th target gene is the hsa-miR-760 gene, a congener thereof, a transcript thereof, or a variant or a derivative thereof. None of the previously known reports show that change in the expression of the gene or the transcript thereof can serve as a marker for esophageal cancer.

The 205th target gene is the hsa-miR-4667-5p gene, a congener thereof, a transcript thereof, or a variant or a derivative thereof. None of the previously known reports show that change in the expression of the gene or the transcript thereof can serve as a marker for esophageal cancer.

The 206th target gene is the hsa-miR-6090 gene, a congener thereof, a transcript thereof, or a variant or a derivative thereof. None of the previously known reports show that change in the expression of the gene or the transcript thereof can serve as a marker for esophageal cancer.

The 207th target gene is the hsa-miR-4730 gene, a congener thereof, a transcript thereof, or a variant or a derivative thereof. None of the previously known reports show that change in the expression of the gene or the transcript thereof can serve as a marker for esophageal cancer.

The 208th target gene is the hsa-miR-7106-5p gene, a congener thereof, a transcript thereof, or a variant or a derivative thereof. None of the previously known reports show that change in the expression of the gene or the transcript thereof can serve as a marker for esophageal cancer.

The 209th target gene is the hsa-miR-3196 gene, a congener thereof, a transcript thereof, or a variant or a derivative thereof. None of the previously known reports show that change in the expression of the gene or the transcript thereof can serve as a marker for esophageal cancer.

The 210th target gene is the hsa-miR-5698 gene, a congener thereof, a transcript thereof, or a variant or a derivative thereof. None of the previously known reports show that change in the expression of the gene or the transcript thereof can serve as a marker for esophageal cancer.

The 211th target gene is the hsa-miR-6087 gene, a congener thereof, a transcript thereof, or a variant or a derivative thereof. None of the previously known reports show that change in the expression of the gene or the transcript thereof can serve as a marker for esophageal cancer.

The 212th target gene is the hsa-miR-4665-5p gene, a congener thereof, a transcript thereof, or a variant or a derivative thereof. None of the previously known reports show that change in the expression of the gene or the transcript thereof can serve as a marker for esophageal cancer.

The 213th target gene is the hsa-miR-8059 gene, a congener thereof, a transcript thereof, or a variant or a derivative thereof. None of the previously known reports show that change in the expression of the gene or the transcript thereof can serve as a marker for esophageal cancer.

The 214th target gene is the hsa-miR-6879-5p gene, a congener thereof, a transcript thereof, or a variant or a derivative thereof. None of the previously known reports show that change in the expression of the gene or the transcript thereof can serve as a marker for esophageal cancer.

The 215th target gene is the hsa-miR-6717-5p gene, a congener thereof, a transcript thereof, or a variant or a derivative thereof. None of the previously known reports show that change in the expression of the gene or the transcript thereof can serve as a marker for esophageal cancer.

The 216th target gene is the hsa-miR-3648 gene, a congener thereof, a transcript thereof, or a variant or a derivative thereof. None of the previously known reports show that change in the expression of the gene or the transcript thereof can serve as a marker for esophageal cancer.

The 217th target gene is the hsa-miR-3162-5p gene, a congener thereof, a transcript thereof, or a variant or a derivative thereof. None of the previously known reports show that change in the expression of the gene or the transcript thereof can serve as a marker for colorectal esophageal cancer.

The 218th target gene is the hsa-miR-1909-3p gene, a congener thereof, a transcript thereof, or a variant or a derivative thereof. None of the previously known reports show that change in the expression of the gene or the transcript thereof can serve as a marker for esophageal cancer.

The 219th target gene is the hsa-miR-8073 gene, a congener thereof, a transcript thereof, or a variant or a derivative thereof. None of the previously known reports show that change in the expression of the gene or the transcript thereof can serve as a marker for esophageal cancer.

The 220th target gene is the hsa-miR-6769b-5p gene, a congener thereof, a transcript thereof, or a variant or a derivative thereof. None of the previously known reports show that change in the expression of the gene or the transcript thereof can serve as a marker for esophageal cancer.

The 221st target gene is the hsa-miR-6836-3p gene, a congener thereof, a transcript thereof, or a variant or a derivative thereof. None of the previously known reports show that change in the expression of the gene or the transcript thereof can serve as a marker for esophageal cancer.

The 222nd target gene is the hsa-miR-4484 gene, a congener thereof, a transcript thereof, or a variant or a derivative thereof. None of the previously known reports show that change in the expression of the gene or the transcript thereof can serve as a marker for esophageal cancer.

The 223rd target gene is the hsa-miR-6819-5p gene, a congener thereof, a transcript thereof, or a variant or a derivative thereof. None of the previously known reports show that change in the expression of the gene or the transcript thereof can serve as a marker for esophageal cancer.

The 224th target gene is the hsa-miR-6794-5p gene, a congener thereof, a transcript thereof, or a variant or a derivative thereof. None of the previously known reports show that change in the expression of the gene or the transcript thereof can serve as a marker for esophageal cancer.

The 225th target gene is the hsa-miR-24-3p gene, a congener thereof, a transcript thereof, or a variant or a derivative thereof. The previously known report shows that change in the expression of the gene or the transcript thereof can serve as a marker for esophageal cancer (Patent Literature 1).

2. Nucleic Acid Probe or Primer for Detection of Esophageal Cancer

In the present invention, a nucleic acid capable of specifically binding to any of the target nucleic acids as the esophageal cancer markers described above can be used as a nucleic acid, for example, a nucleic acid probe or a primer, for the detection or diagnosis of esophageal cancer.

In the present invention, the nucleic acid probes or the primers that can be used for detecting esophageal cancer or for diagnosing esophageal cancer enable qualitative and/or quantitative measurement of the presence, expression level, or existing amount (abundance) of any of the target nucleic acids as the esophageal cancer markers described above, for example, human-derived hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsamiR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p, and hsa-miR-6794-5p or a combination thereof: congeners thereof: transcripts thereof: or variants or derivatives thereof; and, optionally in combination therewith, hsa-miR-575, and hsa-miR-24-3p or a combination thereof: congeners thereof: transcripts thereof: or variants or derivatives thereof; and, optionally in combination therewith, hsa-miR-675-5p, hsa-miR 3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059, and hsa-miR-6879-5p or a combination thereof, congeners thereof, transcripts thereof, or variants or derivatives thereof.

The expression levels of the target nucleic acids described above are increased or decreased (hereinafter, referred to as "increased/decreased") depending on the types of the target nucleic acids in a subject having esophageal cancer as compared with healthy subjects. Hence, the nucleic acid of the present invention can be effectively used for measuring expression levels of the target nucleic acids described above in body fluids from a subject (e.g., humans) suspected of having esophageal cancer and body fluids from healthy subjects and thereby detecting esophageal cancer through the comparison thereof.

The nucleic acid probes or the primers that can be used in the present invention is a nucleic acid probe capable of specifically binding to a polynucleotide consisting of a nucleotide sequence represented by at least one of SEQ ID NOs: 1 to 115, 117 to 189, and 666 to 675, or a primer for amplifying a polynucleotide consisting of a nucleotide sequence represented by at least one of SEQ ID NOs: 1 to 115, 117 to 189, and 666 to 675.

The nucleic acid probes or the primers can be further used in the present invention can comprise a nucleic acid probe capable of specifically binding to a polynucleotide consisting of a nucleotide sequence represented by any of SEQ ID NOs: 116 and 676, or a primer for amplifying a polynucleotide consisting of a nucleotide sequence represented by SEQ ID NOs: 116 and 676.

The nucleic acid probes or the primers that can be used in the present invention may further comprise a nucleic acid probe capable of specifically binding to a polynucleotide consisting of a nucleotide sequence represented by at least one of SEQ ID NOs: 190 to 214, or a primer for amplifying a polynucleotide consisting of a nucleotide sequence represented by at least one of SEQ ID NOs: 190 to 214.

Specifically, these nucleic acid probes or primers comprise a combination of one or more polynucleotides selected from a group of polynucleotides comprising nucleotide sequences represented by any of SEQ ID NOs: 1 to 700 or nucleotide sequences from the nucleotide sequences by the replacement of u with t, and a complementary polynucleotide group thereof, a group of polynucleotides respectively hybridizing under stringent conditions (mentioned later) to DNAs consisting of nucleotide sequences complementary to these nucleotide sequences, and a complementary polynucleotide group thereof, and a group of polynucleotides comprising 15 or more, preferably 17 or more consecutive nucleotides that are from the nucleotide sequences of these polynucleotide groups. These polynucleotides can be used as nucleic acid probes and primers for detecting the esophageal cancer markers as target nucleic acids.

More specifically, examples of the nucleic acid probes or the primers that can be used in the present invention include one or more polynucleotide(s) selected from the group consisting of the following polynucleotides (a) to (e):

(a) a polynucleotide consisting of a nucleotide sequence represented by any of SEQ ID NOs: 1 to 115, 117 to 189, and 666 to 675, or a nucleotide sequence from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 115, 117 to 189, and 666 to 675, (c) a polynucleotide consisting of a nucleotide sequence complementary to a nucleotide sequence represented by any of SEQ ID NOs: 1 to 115, 117 to 189, and 666 to 675, or a nucleotide sequence from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 115, 117 to 189, and 666 to 675, or a nucleotide sequence from the nucleotide sequence by the replacement of u with t, and (e) a polynucleotide hybridizing under stringent conditions to any of the polynucleotides (a) to (d).

In addition to at least one polynucleotides selected from any of the group consisting of the polynucleotides (a) to (e), the nucleic acid probe or the primer that can be used in the present invention may further comprise a polynucleotide selected from the group consisting of the following polynucleotides (f) to (j);

(f) a polynucleotide consisting of a nucleotide sequence represented by SEQ ID NOs: 116 to 676 or a nucleotide sequence from the nucleotide sequence by the replacement of u with t, a variant thereof, a derivative thereof, or a fragment thereof comprising 15 or more consecutive nucleotides, (g) a polynucleotide comprising a nucleotide sequence represented by SEQ ID NOs: 116 to 676, (h) a polynucleotide consisting of a nucleotide sequence complementary to a nucleotide sequence represented by SEQ ID NOs: 116 to 676 or a nucleotide sequence from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by SEQ ID NOs: 116 to 676 or a nucleotide sequence from the nucleotide sequence by the replacement of u with t, and (j) a polynucleotide hybridizing under stringent conditions to any of the polynucleotides (f) to (i).

In addition to at least one polynucleotides selected from any of the group consisting of the polynucleotides (a) to (j), the nucleic acid probes or the primers that can be used in the present invention may further comprise a polynucleotide selected from the group consisting of the following polynucleotides (k) to (o):

(k) a polynucleotide consisting of a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 190 to 214, (m) a polynucleotide consisting of a nucleotide sequence complementary to a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 190 to 214 or a nucleotide sequence from the nucleotide sequence by the replacement of u with t, and (o) a polynucleotide hybridizing under stringent conditions to any of the polynucleotides (k) to (n).

For the above-mentioned polynucleotides, the "fragment thereof comprising 15 or more consecutive nucleotides" can comprise, but is not limited to, the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, or the like, and is from the nucleotide sequence of each polynucleotide.

These polynucleotides or fragments thereof used in the present invention may each be DNA or may each be RNA.

The polynucleotides that can be used in the present invention can be prepared by use of a general technique such as a DNA recombination technique, a PCR method, or a method using an automatic DNA/RNA synthesizer.

The DNA recombination technique and the PCR method may employ techniques described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-575, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p, hsa-miR-6794-5phsa-miR-675-5p, hsa-miR-24-3p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR- 7106-5p, hsa-miR-3196, hsa-miR-5698, hsa-miR-6087, hsa-miR-4665-5p, hsa-miR-8059 and hsa-miR-6879-5p represented by SEQ ID NOs: 1 to 214 and 666 to 676 are known in the art, and their acquisition methods are also known as mentioned above. Therefore, each polynucleotide that can be used as a nucleic acid probe or a primer in the present invention can be prepared by cloning the gene.

Such nucleic acid probes or primers can be chemically synthesized using an automatic DNA synthesizer. In general, the phosphoramidite method is used in this synthesis, and single-stranded DNA up to approximately 100 nucleotides can be automatically synthesized by this method. The automatic DNA synthesizer is commercially available from, for example, Polygen GmbH, ABI, or Applied Biosystems, Inc.

Alternatively, the polynucleotides of the present invention can also be prepared by cDNA cloning methods. The cDNA cloning technique may employ, for example, microRNA Cloning Kit Wako.

In this context, the sequences of the nucleic acid probes and the primers for detecting the polynucleotide consisting of a nucleotide sequence represented by any of SEQ ID NOs: 1 to 214 and 666 to 676 do not exist as miRNAs or precursors thereof in the living body or in vivo. For example, the nucleotide sequences represented by SEQ ID NO: 9 and SEQ ID NO: 138 are produced from the precursor represented by SEQ ID NO: 223. This precursor has a hairpin-like structure as shown in FIG. 1, and the nucleotide sequences represented by SEQ ID NO: 9 and SEQ ID NO: 138 have mismatch sequences with each other. Likewise, a nucleotide sequence completely complementary to the nucleotide sequence represented by SEQ ID NO: 9 or SEQ ID NO: 138 is not naturally produced in vivo. As such, the nucleic acid probe and the primer for detecting the nucleotide sequence represented by any of SEQ ID NOs: 1 to 214 and 666 to 676 have artificial nucleotide sequences that do not exist in the living body or in vivo.

3. Kit or Device for Detection of Esophageal Cancer

The present invention also provides a kit or a device for the detection of esophageal cancer, comprising one or more polynucleotides (which may include a variant, a fragment, or a derivative thereof; hereinafter, also referred to as a polynucleotide for detection) that can be used as nucleic acid probes or primers in the present invention for measuring target nucleic acids as esophageal cancer markers.

The target nucleic acids as esophageal cancer markers according to the present invention are selected from the following group A:

(Group A) hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p and hsa-miR-6794-5p.

Additional target nucleic acids that may be optionally used in the measurement are selected from the following group B:

(Group B) hsa-miR-575 and hsa-miR-24-3p.

Additional target nucleic acids that may be further optionally used in the measurement are selected from the following group C:

(Group C) hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059 and hsa-miR-6879-5p.

The kit or the device of the present invention comprises one or more nucleic acid(s) capable of specifically binding to any of the target nucleic acids as the esophageal cancer markers described above, preferably one or more polynucleotide(s) selected from the polynucleotides described in the preceding Section 2, or variant(s) thereof, etc.

Specifically, the kit or the device of the present invention can comprise at least one polynucleotide comprising (or consisting of) a nucleotide sequence represented by any of SEQ ID NOs: 1 to 115, 117 to 189, and 666 to 675 or a nucleotide sequence from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotides comprising (or consisting of) a nucleotide sequence represented by SEQ ID NOs: 116 and 676 or a nucleotide sequence from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 190 to 214 or a nucleotide sequence from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment(s) that can be comprised in the kit or the device of the present invention is/are, for example, one or more polynucleotides, preferably two or more polynucleotides selected from the group consisting of the following polynucleotides (1) to (3):

(1) a polynucleotide comprising 15 or more consecutive nucleotides that are from a nucleotide sequence derived from a nucleotide sequence represented by any of SEQ ID NOs: 1 to 115, 117 to 189, and 666 to 675 by the replacement of u with t, or a complementary sequence thereof;

(2) a polynucleotide comprising 15 or more consecutive nucleotides that are from a nucleotide sequence derived from a nucleotide sequence represented by SEQ ID NOs: 116 and 676 by the replacement of u with t, or a complementary sequence thereof; and (3) a polynucleotide comprising 15 or more consecutive nucleotides that are from a nucleotide sequence derived from a nucleotide sequence represented by any of SEQ ID NOs: 190 to 214 by the replacement of u with t, or a complementary sequence thereof.

In a preferred embodiment, the polynucleotide is a polynucleotide consisting of a nucleotide sequence represented by any of SEQ ID NOs: 1 to 115, 117 to 189, and 666 to 675 or a nucleotide sequence from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 116 and 676 or a nucleotide sequence from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 190 to 214 or a nucleotide sequence from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range of from, for example, 15 consecutive nucleotides to less than the total number of nucleotides of the sequence, from 17 consecutive nucleotides to less than the total number of nucleotides of the sequence, or 19 consecutive nucleotides to less than the total number of nucleotides of the sequence, in the nucleotide sequence of each polynucleotide.

Specific examples of the combination of aforementioned polynucleotides constituting the kit or the device of the present invention can include a combination of 2, 3, 4, 5, 6, 7, 8, 9, 10 or more of the polynucleotides as relevant to the combinations of SEQ ID NOs: 1 to 214 and 666 to 676 shown in Table 1. However, these are given merely for illustrative purposes, and all of various other possible combinations are included in the present invention.

The aforementioned combination constituting the kit or the device for discriminating an esophageal cancer patient from a healthy subject according to the present invention is desirably, for example, a combination of two or more aforementioned polynucleotides consisting of the nucleotide sequences represented by SEQ ID NOs: 1 to 214 and 666 to 676 shown in Table 1. Usually, a combination of two of these polynucleotides can produce adequate performance.

The combination of two polynucleotides for specifically discriminating an esophageal cancer patient from a healthy subject is preferably a combination comprising at least one of newly found polynucleotides consisting of the nucleotide sequences represented by SEQ ID NOs: 1 to 115, 117 to 189 and 666 to 675, among the combinations constituted by two of the polynucleotides consisting of the nucleotide sequences represented by SEQ ID NOs: 1 to 214 and 666 to 676.

The combination of polynucleotides with cancer type specificity capable of discriminating an esophageal cancer patient not only from a healthy subject but also from other cancer patients is preferably, for example, a combination of two polynucleotides comprising at least one polynucleotide selected from the group consisting of polynucleotides consisting of the nucleotide sequences represented by SEQ ID NOs: 1, 2, 5, 8, 22, 32, 33, 35, 43, 44, 56, 85, 98, 106, 109, 115, 121, 126, 133, 138, 155, 157, 166, 177, 179, 185, 202, 212, 666, 667, 668, 669, 670, 671, 672, 673, 674, 675 and 676 (hereinafter, this group is referred to as "cancer type-specific polynucleotide group 1"); and any of the polynucleotides of the other SEQ ID NOs.

The combination of polynucleotides with cancer type specificity is more preferably a combination of multiple polynucleotides selected from cancer type-specific polynucleotide group 1.

The combination of polynucleotides with cancer type specificity is further preferably a combination comprising at least one polynucleotide selected from the group consisting of or more for polynucleotides consisting of the nucleotide sequences represented by SEQ ID NOs: 1, 22, 85, 109, 121, 126, 133, 138, 166, and 666 (hereinafter, this group is referred to as "cancer type-specific polynucleotide group 2") included in cancer type-specific polynucleotide group 1, among the combinations of multiple polynucleotides selected from the cancer type-specific polynucleotide group 1.

The number of the polynucleotides with cancer type specificity may be 1, 2, 3, 4, 5, 6, 7, 8, 9, 10 or more in the combination and is more preferably 6 or more in the combination. Usually, the combination of 6 polynucleotides of these polynucleotides can produce adequate performance.

Non-limiting examples of the combination of the polynucleotide consisting of the nucleotide sequence represented by SEQ ID NO: 1 or a complementary sequence thereof with polynucleotides consisting of nucleotide sequences represented by SEQ ID NOs of five polynucleotides selected from the cancer type-specific polynucleotide group 1 or complementary sequences thereof are listed below.

(1) a combination of polynucleotides consisting of the nucleotide sequences represented by SEQ ID NOs: 1, 85, 138, 166, 666, and 668 (markers: hsa-miR-4739, hsa-miR-1343-5p, hsa-miR-204-3p, hsa-miR-4723-5p, hsa-miR-3162-5p, and hsa-miR-6717-5p);

(2) a combination of polynucleotides consisting of the nucleotide sequences represented by SEQ ID NOs: 1, 85, 98, 138, 166, and 666 (markers: hsa-miR-4739, hsa-miR-1343-5p, hsa-miR-6779-5p, hsa-miR-204-3p, hsa-miR-4723-5p, and hsa-miR-6717-5p);

(3) a combination of polynucleotides consisting of the nucleotide sequences represented by SEQ ID NOs: 1, 85, 138, 155, 166, and 666 (markers: hsa-miR-4739, hsa-miR-1343-5p, hsa-miR-204-3p, hsa-miR-4723-5p, hsa-miR-4459, and hsa-miR-6717-5p);

(4) a combination of polynucleotides consisting of the nucleotide sequences represented by SEQ ID NOs: 1, 5, 85, 138, 166, and 666 (markers: hsa-miR-4739, hsa-miR-1343-5p, hsa-miR-204-3p, hsa-miR-4723-5p, hsa-miR-6726-5p, and hsa-miR-6717-5p); and (5) a combination of polynucleotides consisting of the nucleotide sequences represented by SEQ ID NOs: 1, 35, 85, 138, 166, and 666 (markers: hsa-miR-4739, hsa-miR-1343-5p, hsa-miR-204-3p, hsa-miR-4723-5p, hsa-miR-6765-3p, and hsa-miR-6717-5p).

Non-limiting examples of the combination of the polynucleotide consisting of the nucleotide sequence represented by SEQ ID NO: 22 or a complementary sequence thereof with polynucleotides consisting of nucleotide sequences represented by SEQ ID NOs of five polynucleotides selected from the cancer type-specific polynucleotide group 1 or complementary sequences thereof are further listed.

(1) a combination of SEQ ID NOs: 1, 22, 85, 138, 166 and 666 (markers: hsa-miR-4739, hsa-miR-1343-5p, hsa-miR-7845-5p, hsa-miR-204-3p, hsa-miR-4273-5p, and hsa-miR-6717-5p);

(2) a combination of polynucleotides consisting of the nucleotide sequences represented by SEQ ID NOs: 22, 32, 121, 133, 166, and 666 (markers: hsa-miR-4739, hsa-miR-7845-5p, hsa-miR-671-5p, hsa-miR-6787-5p, hsa-miR-6808-5p, and hsa-miR-6717-5p);

(3) a combination of polynucleotides consisting of the nucleotide sequences represented by SEQ ID NOs: 1, 22, 126, 138, 166, and 666 (markers: hsa-miR-4739, hsa-miR-1202, hsa-miR-1343-5p, hsa-miR-7845-5p, hsa-miR-204-3p, and hsa-miR-6717-5p);

(4) a combination of polynucleotides consisting of the nucleotide sequences represented by SEQ ID NOs: 1, 22, 121, 155, 166, and 666 (markers: hsa-miR-4739, hsa-miR-7845-5p, hsa-miR-671-5p, hsa-miR-204-3p, hsa-miR-4459, and hsa-miR-6717-5p); and (5) a combination of polynucleotides consisting of the nucleotide sequences represented by SEQ ID NOs: 22, 32, 109, 121, 666, and 667 (markers: hsa-miR-7845-5p, hsa-miR-671-5p, hsa-miR-3648, hsa-miR-6787-5p, hsa-miR-6824-5p, and hsa-miR-6717-5p).

Non-limiting examples of the combination of the polynucleotide consisting of the nucleotide sequence represented by SEQ ID NO: 85 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 85, 138, 166, 185, 666, and 669 (markers: miR-4739, miR-1343-5p, miR-125a-3p, miR-4723-5p, miR-1909-3p, and miR-6717-5p);

(2) a combination of polynucleotides consisting of the nucleotide sequences represented by SEQ ID NOs: 85, 138, 166, 185, 666, and 676 (markers: miR-4739, miR-1343-5p, miR-125a-3p, miR-4723-5p, miR-6717-5p, and miR-24-3p);

(3) a combination of polynucleotides consisting of the nucleotide sequences represented by SEQ ID NOs: 85, 138, 166, 177, 185, and 666 (markers: miR-4739, miR-1343-5p, miR-125a-3p, miR-4723-5p, miR-6861-5p, and miR-6717-5p);

(4) a combination of polynucleotides consisting of the nucleotide sequences represented by SEQ ID NOs: 85, 138, 166, 185, 666, and 667 (markers: miR-4739, miR-1343-5p, miR-3648, miR-125a-3p, miR-4723-5p, and miR-6717-5p); and (5) a combination of polynucleotides consisting of the nucleotide sequences represented by SEQ ID NOs: 33, 85, 138, 166, 185, and 666 (markers: miR-6784-5p, miR-4739, miR-1343-5p, miR-125a-3p, miR-4723-5p, and miR-6717-5p).

Non-limiting examples of the combination of the polynucleotide consisting of the nucleotide sequence represented by SEQ ID NO: 109 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 109, 121, 126, 138, 166, and 666 (markers: miR-4739, miR-1202, miR-1343-5p, miR-671-5p, miR-6824-5p, and miR-6717-5p);

(2) a combination of polynucleotides consisting of the nucleotide sequences represented by SEQ ID NOs: 1, 85, 109, 138, 166, and 666 (markers: miR-4739, miR-1343-5p, miR-204-3p, miR-4723-5p, miR-6824-5p, miR-6717-5p);

(3) a combination of polynucleotides consisting of the nucleotide sequences represented by SEQ ID NOs: 1, 109, 121, 138, 166, and 666 (markers: miR-4739, miR-1343-5p, miR-671-5p, miR-204-3p, miR-6824-5p, and miR-6717-5p);

(4) a combination of polynucleotides consisting of the nucleotide sequences represented by SEQ ID NOs: 109, 126, 138, 166, 666, and 676 (markers: miR-4739, miR-1202, miR-1343-5p, miR-6824-5p, miR-6717-5p, and miR-24-3p); and (5) a combination of polynucleotides consisting of the nucleotide sequences represented by SEQ ID NOs: 109, 126, 138, 166, 202, and 666 (markers: miR-4739, miR-1202, miR-1343-5p, miR-6824-5p, miR-6076, and miR-6717-5p).

Non-limiting examples of the combination of the polynucleotide consisting of the nucleotide sequence represented by SEQ ID NO: 121 or a complementary sequence thereof with polynucleotides consisting of nucleotide sequences represented by SEQ ID NOs of five polynucleotides selected from the cancer type-specific polynucleotide group 1 or complementary sequences thereof are further listed below.
(1) a combination of polynucleotides consisting of the nucleotide sequences represented by SEQ ID NOs: 1, 121, 138, 166, 666, and 668 (markers: miR-4739, miR-1343-5p, miR 5p, miR-204-3p, miR-3162-5p, and miR-6717-5p);
(2) a combination of polynucleotides consisting of the nucleotide sequences represented by SEQ ID NOs: 1, 33, 121, 138, 166, and 666 (markers: miR-6784-5p, miR-4739, miR-1343-5p, miR-671-5p, miR-204-3p, and miR-6717-5p);
(3) a combination of polynucleotides consisting of the nucleotide sequences represented by SEQ ID NOs: 1, 85, 121, 138, 166, and 666 (markers: miR-4739, miR-1343-5p, miR-671-5p, miR-204-3p, miR-4723-5p, and miR-6717-5p);
(4) a combination of polynucleotides consisting of the nucleotide sequences represented by SEQ ID NOs: 1, 121, 138, 166, 179, and 666 (markers: miR-4739, miR-1343-5p, miR-671-5p, miR-204-3p, miR-1238-5p, and miR-6717-5p); and
(5) a combination of polynucleotides consisting of the nucleotide sequences represented by SEQ ID NOs: 1, 121, 138, 166, 177, and 666 (markers: miR-4739, miR-1343-5p, miR-671-5p, miR-204-3p, miR-6861-5p, and miR-6717-5p).

Non-limiting examples of the combination of the polynucleotide consisting of the nucleotide sequence represented by SEQ ID NO: 126 or a complementary sequence thereof with polynucleotides consisting of nucleotide sequences represented by SEQ ID NOs of five polynucleotides selected from the cancer type-specific polynucleotide group 1 or complementary sequences thereof are further listed below.
(1) a combination of polynucleotides consisting of the nucleotide sequences represented by SEQ ID NOs: 32, 109, 126, 138, 166, and 666 (markers: miR-4739, miR-1202, miR-1343-5p, miR-6787-5p, miR-6824-5p, and miR-6717-5p);
(2) a combination of polynucleotides consisting of the nucleotide sequences represented by SEQ ID NOs: 1, 85, 126, 138, 166, and 666 (markers: miR-4739, miR-1202, miR-1343-5p, miR-204-3p, miR-4723-5p, and miR-6717-5p);
(3) a combination of polynucleotides consisting of the nucleotide sequences represented by SEQ ID NOs: 1, 109, 126, 138, 166, and 666 (markers: miR-4739, miR-1202, miR-1343-5p, miR-204-3p, miR-6824-5p, and miR-6717-5p);
(4) a combination of polynucleotides consisting of the nucleotide sequences represented by SEQ ID NOs: 22, 109, 126, 138, 166, and 666 (markers: miR-4739, miR-1202, miR-1343-5p, miR-7845-5p, miR-6824-5p, and miR-6717-5p); and
(5) a combination of SEQ ID NOs: 109, 126, 138, 157, 166, and 666 (markers: miR-4739, miR-1202, miR-6752-5p, miR-1343-5p, miR-6824-5p, and miR-6717-5p).

Non-limiting examples of the combination of the polynucleotide consisting of the nucleotide sequence represented by SEQ ID NO: 133 or a complementary sequence thereof with polynucleotides consisting of nucleotide sequences represented by SEQ ID NOs of five polynucleotides selected from the cancer type-specific polynucleotide group 1 or complementary sequences thereof are further listed below.
(1) a combination of polynucleotides consisting of the nucleotide sequences represented by SEQ ID NOs: 126, 133, 138, 166, 666, and 672 (markers: miR-4739, miR-1202, miR-1343-5p, miR-6808-5p, miR-6836-3p, and miR-6717-5p);
(2) a combination of polynucleotides consisting of the nucleotide sequences represented by SEQ ID NOs: 126, 133, 138, 166, 666 (markers: miR-4739, miR-1202, miR-1343-5p, miR-6808-5p, and miR-6717-5p);
(3) a combination of polynucleotides consisting of the nucleotide sequences represented by SEQ ID NOs: 109, 126, 133, 138, 166, and 666 (markers: miR-4739, miR-1202, miR-1343-5p, miR-6824-5p, miR-6808-5p, and miR-6717-5p);
(4) a combination of SEQ ID NOs: 126, 133, 138, 166, 666, and 673 (markers: miR-4739, miR-1202, miR-1343-5p, miR-4484, miR-6808-5p, and miR-6717-5p); and
(5) a combination of polynucleotides consisting of the nucleotide sequences represented by SEQ ID NOs: 126, 133, 138, 166, 666, and 675 (markers: miR-4739, miR-1202, miR-1343-5p, miR-6794-5p, miR-6808-5p, and miR-6717-5p).

Non-limiting examples of the combination of the polynucleotide consisting of the nucleotide sequence represented by SEQ ID NO: 138 or a complementary sequence thereof with polynucleotides consisting of nucleotide sequences represented by SEQ ID NOs of five polynucleotides selected from the cancer type-specific polynucleotide group 1 or complementary sequences thereof are further listed below.
(1) a combination of polynucleotides consisting of the nucleotide sequences represented by SEQ ID NOs: 1, 85, 138, 166, 666, and 669 (markers: miR-4739, miR-1343-5p, miR 3p, miR-4723-5p, miR-1909-3p, and miR-6717-5p);
(2) a combination of polynucleotides consisting of the nucleotide sequences represented by SEQ ID NOs: 8, 85, 138, 166, 185, and 666 (markers: miR-4739, miR-1343-5p, miR-125a-3p, miR-4723-5p, miR-4257, and miR-6717-5p);
(3) a combination of polynucleotides consisting of the nucleotide sequences represented by SEQ ID NOs: 1, 35, 121, 138, 166, and 666 (markers: miR-4739, miR-1343-5p, miR-671-5p, miR-204-3p, miR-6765-3p, and miR-6717-5p);
(4) a combination of polynucleotides consisting of the nucleotide sequences represented by SEQ ID NOs: 1, 121, 126, 138, 166, and 666 (markers: miR-4739, miR-1202, miR-1343-5p, miR-671-5p, miR-204-3p, and miR-6717-5p); and
(5) a combination of polynucleotides consisting of the nucleotide sequences represented by SEQ ID NOs: 1, 121, 138, 166, 666, and 672 (markers: miR-4739, miR-1343-5p, miR-671-5p, miR-204-3p, miR-6836-3p, and miR-6717-5p).

Non-limiting examples of the combination of the polynucleotide consisting of the nucleotide sequence represented by SEQ ID NO: 166 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 1, 85, 138, 166, 666, and 672 (markers: miR-4739, miR-1343-5p, miR-204-3p, miR-4723-5p, miR-6836-3p, and miR-6717-5p);

(2) a combination of polynucleotides consisting of the nucleotide sequences represented by SEQ ID NOs: 56, 85, 138, 166, 185, and 666 (markers: miR-4739, miR-1343-5p, miR-125a-3p, miR-6724-5p, miR-4723-5p, and miR-6717-5p);

(3) a combination of polynucleotides consisting of the nucleotide sequences represented by SEQ ID NOs: 1, 32, 121, 138, 166, and 666 (markers: miR-4739, miR-1343-5p, miR-671-5p, miR-204-3p, miR-6787-5p, and miR-6717-5p);

(4) a combination of polynucleotides consisting of the nucleotide sequences represented by SEQ ID NOs: 1, 22, 121, 138, 166, and 666 (markers: miR-4739, miR-1343-5p, miR-7845-5p, miR-671-5p, miR-204-3p, and miR-6717-5p); and (5) a combination of polynucleotides consisting of the nucleotide sequences represented by SEQ ID NOs: 5, 85, 138, 166, 185, and 666 (markers: miR-4739, miR-1343-5p, miR-125a-3p, miR-4723-5p, miR-6726-5p, and miR-6717-5p).

Non-limiting examples of the combination of the polynucleotide consisting of the nucleotide sequence represented by SEQ ID NO: 666 or a complementary sequence thereof with polynucleotides consisting of nucleotide sequences represented by SEQ ID NOs of five polynucleotides selected from the cancer type-specific polynucleotide group 1 or complementary sequences thereof are further listed below.

(1) a combination of polynucleotides consisting of the nucleotide sequences represented by SEQ ID NOs: 1, 121, 138, 157, 166, and 666 (markers: miR-4739, miR-6752-5p, miR-1343-5p, miR-671-5p, miR-204-3p, and miR-6717-5p);

(2) a combination of polynucleotides consisting of the nucleotide sequences represented by SEQ ID NOs: 1, 85, 133, 138, 166, and 666 (markers: miR-4739, miR-1343-5p, miR-204-3p, miR-4723-5p, miR-6808-5p, and miR-6717-5p);

(3) a combination of polynucleotides consisting of the nucleotide sequences represented by SEQ ID NOs: 1, 121, 138, 166, 185, and 666 (markers: miR-4739, miR-1343-5p, miR-671-5p, miR-204-3p, miR-125a-3p, and miR-6717-5p);

(4) a combination of polynucleotides consisting of the nucleotide sequences represented by SEQ ID NOs: 1, 121, 138, 166, 666, and 667 (markers: miR-4739, miR-1343-5p, miR-671-5p, miR-3648, miR-204-3p, and miR-6717-5p); and (5) a combination of SEQ ID NOs: 85, 138, 166, 185, and 666 (markers: miR-4739, miR-1343-5p, miR-125a-3p, miR-4723-5p, and miR-6717-5p).

The kit or the device of the present invention can also comprise a polynucleotide that is already known or that will be found in the future, to enable detection of esophageal cancer in addition to the polynucleotide(s) (which can include a variant, a fragment, and a derivative) according to the present invention.

The kit of the present invention can also comprise an antibody for measuring marker(s) for esophageal cancer examination known in the art, such as CEA or SCC, in addition to the polynucleotide(s), etc., according to the present invention described above.

These polynucleotides comprised in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one, preferably at least two, more preferably at least three, most preferably at least five to any of the esophageal cancer marker miRNAs, respectively, of the group 1 described above. The kit or the device of the present invention can optionally further comprise nucleic acids capable of specifically binding to the polynucleotides of at least one, preferably at least two, more preferably at least three, most preferably at least five to any of the esophageal cancer marker miRNAs, respectively, of the group 2 described above.

The kit or the device of the present invention can be used for detecting esophageal cancer as described in the Section 4 below.

4. Method for Detecting Esophageal Cancer

The present invention further provides a method for detecting esophageal cancer, comprising using the kit or the device of the present invention (comprising the above-mentioned nucleic acid(s) that can be used in the present invention) described in the preceding Section "3. Kit or device for detection of esophageal cancer" to measure expression levels of one or more esophageal cancer-derived genes represented by an expression level(s) of esophageal cancer-derived gene(s) selected from the following group 1 of miRNAs, i.e., hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913, hsa-miR-16-5p, hsa-miR-6717-5p, hsa-miR-3648, hsa-miR-3162-5p, hsa-miR-1909-3p, hsa-miR-8073, hsa-miR-6769b-5p, hsa-miR-6836-3p, hsa-miR-4484, hsa-miR-6819-5p, and hsa-miR-6794-5p; and optionally expression levels of esophageal cancer-derived gene(s) selected from the following group 2: i.e., hsa-miR-575 and hsa-miR-24-3p; and optionally expression levels of esophageal cancer-derived gene(s) selected from the following group 3: i.e., hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059, and hsa-miR-6879-5p in a sample in vitro, further comparing, for example, the expression level of the gene described above in the sample (e.g., blood, serum, or plasma) collected from a subject suspected of having esophageal cancer with a control expression level in the sample collected from a healthy subject (including a non-esophageal cancer patient), and evaluating the subject as having esophageal cancer when the expression level of the target nucleic acid is different between the samples.

This method of the present invention enables a limitedly invasive, early diagnosis of the cancer with high sensitivity and high specificity and thereby brings about early treatment and improved prognosis. In addition, exacerbation of the disease or the effectiveness of surgical, radiotherapeutic, and chemotherapeutic treatments can be monitored.

The method for extracting the esophageal cancer-derived gene(s) from the sample such as blood, serum, or plasma according to the present invention is/are particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizor™ (Life Technologies Corp.) may be used. The esophageal cancer-derived gene(s) may be prepared by the addition of a reagent for RNA extraction containing acidic phenol, such as Trizor™ (Life Technologies Corp.) or Isogen (Nippon Gene Co., Ltd.). Alternatively, a kit such as miRNeasy™ Mini Kit (Qiagen N.V.) may be used, though the method is not limited thereto.

The present invention also provides use of the kit or the device of the present invention for detecting in vitro an expression product(s) of an esophageal cancer-derived miRNA gene(s) in a sample from a subject.

In the method of the present invention, the kit or the device described above comprising a single polynucleotide or any possible combination of polynucleotides that can be used in the present invention as described above.

In the detection or (gentice) diagnosis of esophageal cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of esophageal cancer or the detection of the presence or absence of esophageal cancer. Specifically, the detection of esophageal cancer using the kit or the device can be performed by detecting in vitro expression level(s) of gene(s) using the nucleic acid probe(s) or the primer(s) contained in the kit or the device in a sample such as blood, serum, plasma, or urine from a subject suspected of having esophageal cancer. The subject suspected of having esophageal cancer can be evaluated as having esophageal cancer when the expression level(s) of target miRNA marker(s) measured using polynucleotide(s) (including variant(s), fragment(s), and derivative(s) thereof) consisting of a nucleotide sequence(s) represented by at least one of SEQ ID NOs: 1 to 115, 117 to 189, and 666 to 675 or a complementary sequence(s) thereof, and optionally nucleotide sequence(s) represented by one or more of SEQ ID NOs: 116 and 676 or a complementary sequence thereof, and optionally a nucleotide sequence(s) represented by one or more of SEQ ID NOs: 190 to 214 or a complementary sequence(s) thereof, in the sample such as blood, serum, plasma, or urine of the subject has a statistically significantly higher or lower than the expression level(s) thereof in the sample such as blood, serum, or plasma, or urine of a healthy subject.

The method of the present invention can be combined with a diagnostic imaging method such as esophagography, endoscopy, CT scan, MRI scan, endosonography, or ultrasonography. The method of the present invention is capable of specifically detecting esophageal cancer and can substantially discriminate esophageal cancer from the other cancers.

The method for detecting the absence of an expression product of esophageal cancer-derived gene(s) or the presence of the expression product(s) of esophageal cancer-derived gene(s) in a sample using the kit or the device of the present invention comprises collecting a body fluid such as blood, serum, plasma, or urine of a subject, and measuring the expression level(s) of the target gene(s) contained therein using one or more polynucleotides (including variant(s), fragment(s), and derivative(s)) selected from the polynucleotide group of the present invention, to evaluate the presence or absence of esophageal cancer or to detect esophageal cancer. Using the method for detecting esophageal cancer according to the present invention, for example, the presence or absence of amelioration of the disease or the degree of amelioration thereof in an esophageal cancer patient given a therapeutic drug for the amelioration of the disease can be also evaluated or diagnosed.

The method of the present invention can comprise, for example, the following steps (a), (b), and (c):
(a) a step of contacting in vitro a sample from a subject with polynucleotide(s) contained in the kit or the device of the present invention;
(b) a step of measuring expression level(s) of the target nucleic acid in the sample using the polynucleotide(s) as nucleic acid probe(s) or primer(s); and
(c) a step of evaluating the presence or absence of esophageal cancer (cells) in the subject on the basis of the measurement results in the step (b).

Specifically, the present invention provides a method for detecting esophageal cancer, comprising measuring expression level(s) of target nucleic acid(s) in a sample of a subject using a nucleic acid(s) capable of specifically binding to at least one (preferably at least two) polynucleotides selected from the group consisting of miR-204-3p, miR-1247-3p, miR-6875-5p, miR-6857-5p, miR-6726-5p, miR-3188, miR-8069, miR-4257, miR-1343-3p, miR-7108-5p, miR-6825-5p, miR-7641, miR-3185, miR-4746-3p, miR-6791-5p, miR-6893-5p, miR-4433b-3p, miR-3135b, miR-6781-5p, miR-1908-5p, miR-4792, miR-7845-5p, miR-4417, miR-3184-5p, miR-1225-5p, miR-1231, miR-1225-3p, miR-150-3p, miR-4433-3p, miR-6125, miR-4513, miR-6787-5p, miR-6784-5p, miR-615-5p, miR-6765-3p, miR-5572, miR-6842-5p, miR-8063, miR-6780b-5p, miR-187-5p, miR-128-1-5p, miR-6729-5p, miR-6741-5p, miR-6757-5p, miR-7110-5p, miR-7975, miR-1233-5p, miR-6845-5p, miR-3937, miR-4467, miR-7109-5p, miR-6088, miR-6782-5p, miR-5195-3p, miR-4454, miR-6724-5p, miR-8072, miR-4516, miR-6756-5p, miR-4665-3p, miR-6826-5p, miR-6820-5p, miR-6887-5p, miR-3679-5p, miR-7847-3p, miR-6721-5p, miR-3622a-5p, miR-939-5p, miR-602, miR-7977, miR-6749-5p, miR-1914-3p, miR-4651, miR-4695-5p, miR-6848-5p, miR-1228-3p, miR-642b-3p, miR-6746-5p, miR-3620-5p, miR-3131, miR-6732-5p, miR-7113-3p, miR-23a-3p, miR-3154, miR-4723-5p, miR-3663-3p, miR-4734, miR-6816-5p, miR-4442, miR-4476, miR-423-5p, miR-1249, miR-6515-3p, miR-887-3p, miR-4741, miR-6766-3p, miR-4673, miR-6779-5p, miR-4706, miR-1268b, miR-4632-5p, miR-3197, miR-6798-5p, miR-711, miR-6840-3p, miR-6763-5p, miR-6727-5p, miR-371a-5p, miR-6824-5p, miR-4648, miR-1227-5p, miR-564, miR-3679-3p, miR-2861, miR-6737-5p, miR-4725-3p, miR-6716-5p, miR-4675, miR-1915-3p, miR-671-5p, miR-3656, miR-6722-3p, miR-4707-5p, miR-4449, miR-1202, miR-4649-5p, miR-744-5p, miR-642a-3p, miR-451a, miR-6870-5p, miR-4443, miR-6808-5p, miR-4728-5p, miR-937-5p, miR-135a-3p, miR-663b, miR-1343-5p, miR-6822-5p, miR-6803-5p, miR-6805-3p, miR-128-2-5p, miR-4640-5p, miR-1469, miR-92a-2-5p, miR-3940-5p, miR-4281, miR-1260b, miR-4758-5p, miR-1915-5p, miR-5001-5p, miR-4286, miR-6126, miR-6789-5p, miR-4459, miR-1268a, miR-6752-5p, miR-6131, miR-6800-5p, miR-4532, miR-6872-3p, miR-718, miR-6769a-5p, miR-4707-3p, miR-6765-5p, miR-4739, miR-4525, miR-4270, miR-4534, miR-6785-5p, miR-6850-5p, miR-4697-5p, miR-1260a, miR-4486, miR-6880-5p, miR-6802-5p, miR-6861-5p, miR-92b-5p, miR-1238-5p, miR-6851-5p, miR-7704, miR-149-3p, miR-4689, miR-4688, miR-125a-3p, miR-23b-3p, miR-614, miR-1913, miR-16-5p, miR-6717-5p, miR-3648, miR-3162-5p, miR-1909-3p, miR-8073, miR-6769b-5p, miR-6836-3p, miR-4484, miR-6819-5p and miR-6794-5p; and evaluating in vitro whether or not the subject has esophageal cancer in the subject using the above-measured expression levels and a control expression level of healthy subject(s) measured in the same way as above.

The term "evaluation" used herein is evaluation support based on results of in vitro examination, not physician's judgment.

As described above, in a preferred embodiment of the method of the present invention, specifically, miR-204-3p is hsa-miR-204-3p, miR-1247-3p is hsa-miR-1247-3p, miR-6875-5p is hsa-miR-6875-5p, miR-6857-5p is hsa-miR-6857-5p, miR-6726-5p is hsa-miR-6726-5p, miR-3188 is hsa-miR-3188, miR-8069 is hsa-miR-8069, miR-4257 is hsa-miR-4257, miR-1343-3p is hsa-miR-1343-3p, miR-7108-5p is hsa-miR-7108-5p, miR-6825-5p is hsa-miR-6825-5p, miR-7641 is hsa-miR-7641, miR-3185 is hsa-miR-3185, miR-4746-3p is hsa-miR-4746-3p, miR-6791-5p is hsa-miR-6791-5p, miR-6893-5p is hsa-miR-6893-5p, miR-4433b-3p is hsa-miR-4433b-3p, miR-3135b is hsa-miR-3135b, miR-6781-5p is hsa-miR-6781-5p, miR-1908-5p is hsa-miR-1908-5p, miR-4792 is hsa-miR-4792, miR-7845-5p is hsa-miR-7845-5p, miR-4417 is hsa-miR-4417, miR-3184-5p is hsa-miR-3184-5p, miR-1225-5p is hsa-miR- 1225-5p, miR-1231 is hsa-miR-1231, miR-1225-3p is hsa-miR-1225-3p, miR-150-3p is hsa-miR-150-3p, miR-4433-3p is hsa-miR-4433-3p, miR-6125 is hsa-miR-6125, miR-4513 is hsa-miR-4513, miR-6787-5p is hsa-miR-6787-5p, miR-6784-5p is hsa-miR-6784-5p, miR-615-5p is hsa-miR-615-5p, miR-6765-3p is hsa-miR-6765-3p, miR-5572 is hsa-miR-5572, miR-6842-5p is hsa-miR-6842-5p, miR-8063 is hsa-miR-8063, miR-6780b-5p is hsa-miR-6780b-5p, miR-187-5p is hsa-miR-187-5p, miR-128-1-5p is hsa-miR-128-1-5p, miR-6729-5p is hsa-miR-6729-5p, miR-6741-5p is hsa-miR-6741-5p, miR-6757-5p is hsa-miR-6757-5p, miR-7110-5p is hsa-miR-7110-5p, miR-7975 is hsa-miR-7975, miR-1233-5p is hsa-miR-1233-5p, miR-6845-5p is hsa-miR-6845-5p, miR-3937 is hsa-miR-3937, miR-4467 is hsa-miR-4467, miR-7109-5p is hsa-miR-7109-5p, miR-6088 is hsa-miR-6088, miR-6782-5p is hsa-miR-6782-5p, miR-5195-3p is hsa-miR-5195-3p, miR-4454 is hsa-miR-4454, miR-6724-5p is hsa-miR-6724-5p, miR-8072 is hsa-miR-8072, miR-4516 is hsa-miR-4516, miR-6756-5p is hsa-miR-6756-5p, miR-4665-3p is hsa-miR-4665-3p, miR-6826-5p is hsa-miR-6826-5p, miR-6820-5p is hsa-miR-6820-5p, miR-6887-5p is hsa-miR-6887-5p, miR-3679-5p is hsa-miR-3679-5p, miR-7847-3p is hsa-miR-7847-3p, miR-6721-5p is hsa-miR-6721-5p, miR-3622a-5p is hsa-miR-3622a-5p, miR-939-5p is hsa-miR-939-5p, miR-602 is hsa-miR-602, miR-7977 is hsa-miR-7977, miR-6749-5p is hsa-miR-6749-5p, miR-1914-3p is hsa-miR-1914-3p, miR-4651 is hsa-miR-4651, miR-4695-5p is hsa-miR-4695-5p, miR-6848-5p is hsa-miR-6848-5p, miR-1228-3p is hsa-miR-1228-3p, miR-642b-3p is hsa-miR-642b-3p, miR-6746-5p is hsa-miR-6746-5p, miR-3620-5p is hsa-miR-3620-5p, miR-3131 is hsa-miR-3131, miR-6732-5p is hsa-miR-6732-5p, miR-7113-3p is hsa-miR-7113-3p, miR-23a-3p is hsa-miR-23a-3p, miR-3154 is hsa-miR-3154, miR-4723-5p is hsa-miR-4723-5p, miR-3663-3p is hsa-miR-3663-3p, miR-4734 is hsa-miR-4734, miR-6816-5p is hsa-miR-6816-5p, miR-4442 is hsa-miR-4442, miR-4476 is hsa-miR-4476, miR-423-5p is hsa-miR-423-5p, miR-1249 is hsa-miR-1249, miR-6515-3p is hsa-miR-6515-3p, miR-887-3p is hsa-miR-887-3p, miR-4741 is hsa-miR-4741, miR-6766-3p is hsa-miR-6766-3p, miR-4673 is hsa-miR-4673, miR-6779-5p is hsa-miR-6779-5p, miR-4706 is hsa-miR-4706, miR-1268b is hsa-miR-1268b, miR-4632-5p is hsa-miR-4632-5p, miR-3197 is hsa-miR-3197, miR-6798-5p is hsa-miR-6798-5p, miR-711 is hsa-miR-711, miR-6840-3p is hsa-miR-6840-3p, miR-6763-5p is hsa-miR-6763-5p, miR-6727-5p is hsa-miR-6727-5p, miR-371a-5p is hsa-miR-371a-5p, miR-6824-5p is hsa-miR-6824-5p, miR-4648 is hsa-miR-4648, miR-1227-5p is hsa-miR-1227-5p, miR-564 is hsa-miR-564, miR-3679-3p is hsa-miR-3679-3p, miR-2861 is hsa-miR-2861, miR-6737-5p is hsa-miR-6737-5p, miR-4725-3p is hsa-miR-4725-3p, miR-6716-5p is hsa-miR-6716-5p, miR-4675 is hsa-miR-4675, miR-1915-3p is hsa-miR-1915-3p, miR-671-5p is hsa-miR-671-5p, miR-3656 is hsa-miR-3656, miR-6722-3p is hsa-miR-6722-3p, miR-4707-5p is hsa-miR-4707-5p, miR-4449 is hsa-miR-4449, miR-1202 is hsa-miR-1202, miR-4649-5p is hsa-miR-4649-5p, miR-744-5p is hsa-miR-744-5p, miR-642a-3p is hsa-miR-642a-3p, miR-451a is hsa-miR-451a, miR-6870-5p is hsa-miR-6870-5p, miR-4443 is hsa-miR-4443, miR-6808-5p is hsa-miR-6808-5p, miR-4728-5p is hsa-miR-4728-5p, miR-937-5p is hsa-miR-937-5p, miR-135a-3p is hsa-miR-135a-3p, miR-663b is hsa-miR-663b, miR-1343-5p is hsa-miR-1343-5p, miR-6822-5p is hsa-miR-6822-5p, miR-6803-5p is hsa-miR-6803-5p, miR-6805-3p is hsa-miR-6805-3p, miR-128-2-5p is hsa-miR-128-2-5p, miR-4640-5p is hsa-miR-4640-5p, miR-1469 is hsa-miR-1469, miR-92a-2-5p is hsa-miR-92a-2-5p, miR-3940-5p is hsa-miR-3940-5p, miR-4281 is hsa-miR-4281, miR-1260b is hsa-miR-1260b, miR-4758-5p is hsa-miR-4758-5p, miR-1915-5p is hsa-miR-1915-5p, miR-5001-5p is hsa-miR-5001-5p, miR-4286 is hsa-miR-4286, miR-6126 is hsa-miR-6126, miR-6789-5p is hsa-miR-6789-5p, miR-4459 is hsa-miR-4459, miR-1268a is hsa-miR-1268a, miR-6752-5p is hsa-miR-6752-5p, miR-6131 is hsa-miR-6131, miR-6800-5p is hsa-miR-6800-5p, miR-4532 is hsa-miR-4532, miR-6872-3p is hsa-miR-6872-3p, miR-718 is hsa-miR-718, miR-6769a-5p is hsa-miR-6769a-5p, miR-4707-3p is hsa-miR-4707-3p, miR-6765-5p is hsa-miR-6765-5p, miR-4739 is hsa-miR-4739, miR-4525 is hsa-miR-4525, miR-4270 is hsa-miR-4270, miR-4534 is hsa-miR-4534, miR-6785-5p is hsa-miR-6785-5p, miR-6850-5p is hsa-miR-6850-5p, miR-4697-5p is hsa-miR-4697-5p, miR-1260a is hsa-miR-1260a, miR-4486 is hsa-miR-4486, miR-6880-5p is hsa-miR-6880-5p, miR-6802-5p is hsa-miR-6802-5p, miR-6861-5p is hsa-miR-6861-5p, miR-92b-5p is hsa-miR-92b-5p, miR-1238-5p is hsa-miR-1238-5p, miR-6851-5p is hsa-miR-6851-5p, miR-7704 is hsa-miR-7704, miR-149-3p is hsa-miR-149-3p, miR-4689 is hsa-miR-4689, miR-4688 is hsa-miR-4688, miR-125a-3p is hsa-miR-125a-3p, miR-23b-3p is hsa-miR-23b-3p, miR-614 is hsa-miR-614, miR-1913 is hsa-miR-1913, miR-16-5p is hsa-miR-16-5p, miR-6717-5p is hsa-miR-6717-5p, miR-3648 is hsa-miR-3648, miR-3162-5p is hsa-miR-3162-5p, miR-1909-3p is hsa-miR-1909-3p, miR-8073 is hsa-miR-8073, miR-6769b-5p is hsa-miR-6769b-5p, miR-6836-3p is hsa-miR-6836-3p, miR-4484 is hsa-miR-4484, miR-6819-5p is hsa-miR-6819-5p, and miR-6794-5p is hsa-miR-6794-5p.

In a preferred embodiment of the method of the present invention, specifically, the nucleic acid(s) (specifically, probe(s) or primer(s)) is selected from the group consisting of the following polynucleotides (a) to (e):

(a) a polynucleotide consisting of a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 115, 117 to 189, and 666 to 675, (c) a polynucleotide consisting of a nucleotide sequence complementary to a nucleotide sequence represented by any of SEQ ID NOs: 1 to 115, 117 to 189, and 666 to 675 or a nucleotide sequence from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 115, 117 to 189, and 666 to 675 or a nucleotide sequence from the nucleotide sequence by the replacement of u with t, and (e) a polynucleotide hybridizing under stringent conditions to any of the polynucleotides (a) to (d).

In the method of the present invention, a nucleic acid capable of specifically binding to a polynucleotide selected from miR-575 and miR-24-3p can be further used.

Specifically, miR-575 is hsa-miR-575, and miR-24-3p is hsa-miR-24-3p.

Specifically, the nucleic acid(s) is/are further selected from the group consisting of the following polynucleotides (f) to (j):
(f) a polynucleotide consisting of a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 116 and 676,
(h) a polynucleotide consisting of a nucleotide sequence complementary to a nucleotide sequence represented by any of SEQ ID NOs: 116 and 676 or a nucleotide sequence from the nucleotide sequence by the replacement of u with t, a variant thereof, a derivative thereof, or a fragment thereof comprising 15 or more consecutive nucleotides,
(i) a polynucleotide comprising a nucleotide sequence complementary to a nucleotide sequence represented by any of SEQ ID NOs: 116 and 676 or a nucleotide sequence from the nucleotide sequence by the replacement of u with t, and
(j) a polynucleotide hybridizing under stringent conditions to any of the polynucleotides (f) to (i).

The nucleic acid(s) in the method of the present invention can further comprise a nucleic acid capable of specifically binding to at least one polynucleotides selected from the following miRNAs: miR-675-5p, miR-486-3p, miR-6777-5p, miR-4497, miR-296-3p, miR-6738-5p, miR-4731-5p, miR-6889-5p, miR-6786-5p, miR-92a-3p, miR-4294, miR-4763-3p, miR-6076, miR-663a, miR-760, miR-4667-5p, miR-6090, miR-4730, miR-7106-5p, miR-3196, miR-5698, miR-6087, miR-4665-5p, miR-8059 and miR-6879-5p.

In a preferred embodiment, as for such nucleic acids, specifically, miR-675-5p is hsa-miR-675-5p, miR-486-3p is hsa-miR-486-3p, miR-6777-5p is hsa-miR-6777-5p, miR-4497 is hsa-miR-4497, miR-296-3p is hsa-miR-296-3p, miR-6738-5p is hsa-miR-6738-5p, miR-4731-5p is hsa-miR-4731-5p, miR-6889-5p is hsa-miR-6889-5p, miR-6786-5p is hsa-miR-6786-5p, miR-92a-3p is hsa-miR-92a-3p, miR-4294 is hsa-miR-4294, miR-4763-3p is hsa-miR-4763-3p, miR-6076 is hsa-miR-6076, miR-663a is hsa-miR-663a, miR-760 is hsa-miR-760, miR-4667-5p is hsa-miR-4667-5p, miR-6090 is hsa-miR-6090, miR-4730 is hsa-miR-4730, miR-7106-5p is hsa-miR-7106-5p, miR-3196 is hsa-miR-3196, miR-5698 is hsa-miR-5698, miR-6087 is hsa-miR-6087, miR-4665-5p is hsa-miR-4665-5p, miR-8059 is hsa-miR-8059, and miR-6879-5p is hsa-miR-6879-5p.

In a preferred embodiment, such nucleic acid(s) is specifically polynucleotide(s) selected from the group consisting of the following polynucleotides (k) to (o):
(k) a polynucleotide consisting of a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 190 to 214,
(m) a polynucleotide consisting of a nucleotide sequence complementary to a nucleotide sequence represented by any of SEQ ID NOs: 190 to 214 or a nucleotide sequence from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 190 to 214 or a nucleotide sequence from the nucleotide sequence by the replacement of u with t, and
(o) a polynucleotide hybridizing under stringent conditions to any of the polynucleotides (k) to (n).

Examples of the sample used in the method of the present invention can include samples prepared from living tissues (preferably esophageal tissues) or body fluids such as blood, serum, plasma, and urine from subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

The subject used herein refers to a mammal, for example, a human, a monkey, a mouse or a rat without any limitation, and is preferably a human.

The steps of the method of the present invention can be changed according to the type of the sample to be assayed.

In the case of using RNA as an analyte, the detection of esophageal cancer (cells) can comprise, for example, the following steps (a), (b), and (c):
(a) a step of binding RNA prepared from a sample from a subject or complementary polynucleotides (cDNAs) transcribed from the RNA to a polynucleotides in the kit or the device of the present invention;
(b) a step of measuring the sample-derived RNA or the cDNA(s) synthesized from the RNA, which is/are bound to the polynucleotide(s) by hybridization using the polynucleotide(s) as nucleic acid probe(s) or by quantitative RT-PCR using the polynucleotide(s) as primer(s); and
(c) a step of evaluating the presence or absence of esophageal cancer (or esophageal cancer-derived gene expression) on the basis of the measurement results of the step (b).

For example, various hybridization methods can be used for detecting, examining, evaluating, or diagnosing esophageal cancer (or esophageal cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe(s) that can be used in the present invention. Specific examples thereof can include a method which comprises labeling the nucleic acid probe (or a complementary strand) with a radioisotope ($^{32}P$, $^{33}P$, $^{35}S$, etc.), a fluorescent material, or the like, hybridizing the labeled product with the tissue-derived RNA from a subject, which is transferred to a nylon membrane or the like according to a routine method, and then detecting and measuring a signal from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises preparing cDNA from the tissue-derived RNA of a subject according to a routine method, hybridizing a pair of primers (consisting of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention is attached to a substrate (solid phase) is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes any of these arrays. 3D-Gene™ Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal from the label on the nucleic acid probes using an image detector (examples thereof can include Typhoon 9410 (GE Healthcare) and 3D-Gene' scanner (Toray Industries, Inc.)).

The "stringent conditions" used herein are, as mentioned above, conditions under which a nucleic acid probe hybridizes to its target sequence to a larger extent (e.g., a measurement value equal to or larger than "(a mean of background measurement values)+(a standard deviation of the background measurement values)×2") than that for other sequences.

The stringent conditions are defined by hybridization and subsequent washing conditions. Examples of the hybridization conditions include, but not limited to, 30° C. to 60° C. for 1 to 24 hours in a solution containing SSC, a surfactant, formamide, dextran sulfate, blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus (+) strand even by washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.); LNA™-based MicroRNA PCR (Exiqon); or Ncode™ miRNA qRT-PCT kit (Invitrogen Corp.) may be used.

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring target genes or gene expression levels in a sample from a subject using the polynucleotide, the kit, or the device (e.g., chip) for detection of the present invention, or a combination thereof, preparing a discriminant (discriminant function) with gene expression levels in a sample from an esophageal cancer patient and a sample from a healthy subject as supervising samples, and determining or evaluating the presence and/or absence of the esophageal cancer-derived genes in the sample.

Specifically, the present invention further provides the method comprising: a first step of measuring in vitro expression levels of target genes (target nucleic acid) in multiple samples that were known to be able to determine or evaluate the presence and/or absence of the esophageal cancer-derived gene in the samples, using the polynucleotides, the kit, or the device (e.g., chip) for detection of the present invention, or a combination thereof; a second step of constructing a discriminant with the measurement values of the expression levels of the target genes that was obtained in the first step as supervising samples; a third step of measuring in vitro expression levels of the target gene in a sample from a subject in the same way as in the first step; and a fourth step of assigning the measurement values of the expression levels of the target gene obtained in the third step into the discriminant obtained in the second step, and determining or evaluating the presence or absence of the esophageal cancer-derived gene in the sample on the basis of the results obtained from the discriminant, wherein the target gene can be detected using the polynucleotide or using a polynucleotide for the detection, that was contained in the polynucleotide, the kit or the device (e.g., chip). In this context, the discriminant can be prepared by use of Fisher's discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In this formula, x represents an explanatory variable, w represents a coefficient of the explanatory variable, and w0 represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, one type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer., 2002). In the Fisher's discriminant analysis, direction w of projection is determined so as to maximize Formula 2. In this formula, μ represents an average input, $n_g$ represents the number of data associate with class g, and $μ_g$ represents an average input of the data associate with class g. The numerator and the denominator are the interclass variance and the intraclass variance, respectively, when each data is projected in the direction of the vector w. Discriminant coefficient $w_i$ is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{xy_i=g} (w^T x_i - w^T \mu_g)(w^T x_i - w^T \mu_g)} \qquad \text{Formula 2}$$

$$\text{subject to } \mu = \sum_{i=1}^{n} \frac{x_i}{n}, \mu_g = \sum_{i: u_i = g}^{n} \frac{x_i}{n_g}$$

The Mahalanobis' distance is calculated according to Formula 3 in consideration of data correlation and can be used as nonlinear discriminant analysis for determining, a cluster in which a data point belongs to, based on a short Mahalanobis' distance from the data point to that cluster. In this formula, μ represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x, \mu) = \{(x-\mu)^t S^{-1}(x-\mu)\}^{\frac{1}{2}} \qquad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of data to be classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, comprises preparing a hyperplane by supervising a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., an esophageal cancer patient group and a healthy subject group. For example, esophageal tissue examination can be used for each subject to be confirmed either as an esophageal cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by using genes that were found to differ clearly in their gene expression levels between the two groups as explanatory variables and using this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a \quad \text{Formula 4}$$

subject to $y^T a = 0, 0 \leq a_i \leq C, i = 1, \ldots, l,$

Formula 5 is a finally obtained discriminant, and a group in which the data point belongs to can be determined on the basis of the sign of a value obtained according to the discriminant. In this formula, x represents a support vector, y represents a label indicating the association of a group, a represents the corresponding coefficient b represents a constant term, and K represents a kernel function.

$$f(x) = \text{sgn}\left(\sum_{i=1}^{l} y_i a_i K(x_i, x) + b\right) \quad \text{Formula 5}$$

For example, a RBF kernel defined by Formula 6 can be used as the kernel function. In this context, x represents a support vector, and γ represents a kernel parameter for adjusting the complexity of the hyperplane.

$$K(x_i, x_j) = \exp(-r\|x_i - x_j\|^2) r < 0 \quad \text{Formula 6}$$

In addition, an approach such as neural network, k-nearest neighbor algorithms, decision trees, or logistic regression analysis can be selected as a method for determining or evaluating the presence and/or absence of expression of an esophageal cancer-derived target gene in a sample from a subject, or for evaluating the expression level thereof by comparison with a control from a healthy subject.

The method of the present invention can comprise, for example, the following steps (a), (b), and (c):

(a) a step of measuring expression level(s) of target gene(s) in tissues containing esophageal cancer-derived genes from esophageal cancer patients and/or samples already known to be tissues containing no esophageal cancer-derived gene(s) from healthy subjects, using the polynucleotide, the kit, or the device (e.g., DNA chip) for detection according to the present invention;

(b) a step of preparing the discriminants of Formulas 1 to 3, 5, and 6 described above from the measurement values of the expression level measured in the step (a); and (c) a step of measuring an expression level of the target gene in a sample from a subject using the polynucleotide, the kit, or the device (e.g., DNA chip) for diagnosis (detection) according to the present invention, assigning the obtained measurement value(s) into the discriminants prepared in the step (b), and determining or evaluating the presence and/or absence of expression of the esophageal cancer-derived target gene in the sample, or evaluating the expression level thereof by comparison with a healthy subject-derived control, on the basis of the obtained results. In this context, in the discriminants of Formulas 1 to 3, 5, and 6, x represents an explanatory variable and includes a value obtained by measuring a polynucleotide selected from the polynucleotides described above in the Section 2 above, or a fragment thereof. Specifically, the explanatory variable for discriminating an esophageal cancer patient from a healthy subject according to the present invention is gene expression level(s) selected from, for example, the following expression levels (1) to (3):

(1) gene expression level(s) in the serum of an esophageal cancer patient or a healthy subject measured by any DNA comprising 15 or more consecutive nucleotides in a nucleotide sequence represented by any of SEQ ID NOs: 1 to 115, 117 to 189, and 666 to 675 or a complementary sequence thereof, (2) gene expression level(s) in the serum of an esophageal cancer patient or a healthy subject measured by any DNA comprising 15 or more consecutive nucleotides in a nucleotide sequence represented by SEQ ID NOs: 116 and 676 or a complementary sequence thereof, and (3) gene expression level(s) in the serum of an esophageal cancer patient or a healthy subject measured by any DNA comprising 15 or more consecutive nucleotides in a nucleotide sequence represented by any of SEQ ID NOs: 190 to 214 or a complementary sequence thereof.

As described above, for the method for determining or evaluating the presence and/or absence of esophageal cancer-derived gene(s) in a sample from a subject, the preparation of a discriminant requires a discriminant prepared in a training cohort. For enhancing the discrimination accuracy of the discriminant, it is necessary for the discriminant to use genes that show clear difference between two groups in the training cohort.

Each gene that is used for an explanatory variable in a discriminant is preferably determined as follows. First, comprehensive gene expression levels of an esophageal cancer patient group and comprehensive gene expression levels of a healthy subject group, both of which are in a training cohort, are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonfenoni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of an esophageal cancer patient group and gene expression levels of a healthy subject group may be calculated to select a gene that is used for an explanatory variable in a discriminant. Alternatively, ROC curves may be prepared using gene expression levels of an esophageal cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discriminant accuracy include a method of constructing a discriminant in every combination of genes that satisfy the significance level being P value, and a method of repetitively evaluating a discriminant while increasing the number of genes for use one by one in a descending order of difference in gene expression level (Furey T S. et al., 2000, Bioinformatics., Vol. 16, p. 906-14). A gene expression level of another independent esophageal cancer patient or healthy subject is assigned as an explanatory variable to this discriminant to calculate discriminant Specifically, the found gene set for diagnosis and the discriminant constructed using the gene set for diagnosis can be evaluated in an independent sample cohort to find a more universal gene set for diagnosis capable of detecting esophageal cancer and a more universal method for discriminating esophageal cancer.

Split-sample method is preferably used for evaluating the discriminant performance (generality). Specifically, a data set is divided into a training cohort andgenes in serum from a patient confirmed to be negative using CEA but finally found to have esophageal cancer by detailed examination such as computed tomography using a contrast medium, with genes expressed in serum from a patient having no esophageal cancer.

For example, the gene set for diagnosis is set to any combination selected from one or two or more of the polynucleotides based on a nucleotide sequence represented by any of SEQ ID NOs: 1 to 115, 177 to 189, and 666 to 675 or a complementary sequence thereof as described above; and optionally one or two or more of the polynucleotides based on a nucleotide sequence represented by SEQ ID NOs: 116 and 676 or a complementary sequence thereof, and optionally one or two or more of the polynucleotides based on a nucleotide sequence represented by any of SEQ ID NOs: 190 to 214 or a complementary sequence thereof. Further, a discriminant is constructed using expression levels of the gene set for diagnosis in samples from class I esophageal cancer patients as a result of tissue diagnosis and samples from class II healthy subjects as a result of tissue diagnosis. As a result, the presence or absence of esophageal cancer-derived genes in an unknown sample can be determined with 100% accuracy at the maximum by measuring expression levels of the gene set for diagnosis in an unknown sample.

EXAMPLES

Hereinafter, the present invention will be described further specifically with reference to Examples below. However, the scope of the present invention is not intended to be limited by these Examples.

Reference Example 1

<Collection of Samples from Esophageal Cancer Patient and Healthy Subject>

Sera were collected using VENOJECT II vacuum blood collecting tube VP-AS 109K60 (Terumo Corp.) from 100 healthy subjects and 34 esophageal cancer patients (3 cases with stage IB, 1 case with stage IIA, 5 cases with stage IIB, 4 cases with stage IIIA, 7 cases with stage IIIB, 2 cases with stage IIIC, and 1 case with yp stage IA, 3 cases with yp stage IIA, 2 cases with yp stage IIB, 5 cases with yp stage IIIA, and 1 case with yp stage IIIC as samples (yp) stage-classified by pathological examination after treatment) with no primary cancer found other than esophageal cancer after acquisition of informed consent, and used as a training cohort. Likewise, sera were collected using VENOJECT II vacuum blood collecting tube VP-AS109K60 (Terumo Corp.) from 50 healthy subjects and 16 esophageal cancer patients (3 cases with stage IIA, 2 cases with stage IIIA, 2 cases with stage IIIC, and 1 case with yp stage 0, 1 case with yp stage IA, 2 cases with yp stage IIA, 2 cases with yp stage IIIA, 1 case with yp stage IIIB, 1 case with yp stage IIIC, and 1 case with yp stage IV as samples (yp) stage-classified by pathological examination after treatment) with no primary cancer found other than esophageal cancer after acquisition of informed consent, and used as a validation cohort.

<Extraction of Total RNA>

Total RNA was obtained from 300 µL of the serum sample obtained from each of 200 persons in total of 150 healthy subjects and 50 esophageal cancer patients included in the training cohort and the validation cohort, using a reagent for RNA extraction in 3D-Gene™ RNA extraction reagent from liquid sample kit (Toray Industries, Inc.) according to the protocol provided by the manufacturer.

<Measurement of Gene Expression Level> miRNAs in the total RNA obtained from the serum samples of each of 200 persons in total of 150 healthy subjects and 50 esophageal cancer patients included in the training cohort and the validation cohort were fluorescently labeled using 3D-Gene™ miRNA Labeling kit (Toray Industries, Inc.) according to the protocol (ver 2.20) provided by the manufacturer. The oligo DNA chip used was 3D-Gene™ Human miRNA Oligo chip (Toray Industries, Inc.) with attached probes having sequences complementary to 2,555 miRNAs among the miRNAs registered in miRBase Release 20. Hybridization between the miRNAs in the total RNA and the probes on the DNA chip under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value having a nucleotide of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained for the 50 esophageal cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. &

Ripley, B. D. (2002) Modern Applied Statistics with S. Fourth Edition. Springer, New York. ISBN 0-387-95457-0).

Reference Example 2

<Collection of Samples of Cancers Other than Esophageal Cancer>

Serum was collected using VENOJECT II vacuum blood collecting tube VP-AS109K60 (Terumo Corp.) from each of 69 pancreatic cancer patients, 66 bile duct cancer patients, 30 colorectal cancer patients, 33 stomach cancer patients, 32 liver cancer patients, and 15 benign pancreaticobiliary disease patients confirmed to have no cancer in other organs after acquisition of informed consent, and used as a training cohort together with the samples of 34 esophageal cancer patients and 103 healthy subjects of Reference Example 1.

Likewise, Sera were collected using VENOJECT II vacuum blood collecting tube VP-AS109K60 (Terumo Corp.) from each of 30 pancreatic cancer patients, 33 bile duct cancer patients, 20 colorectal cancer patients, 17 stomach cancer patients, 20 liver cancer patients, and 6 benign pancreaticobiliary disease patients confirmed to have no cancer in other organs after acquisition of informed consent, and used as a validation cohort together with the samples of 16 esophageal cancer patients confirmed to have no cancer in organs other than the esophagus and 47 healthy subjects of Reference Example 1. Subsequent operations were conducted in the same way as in Reference Example 1.

Example 1

<Selection of Gene Markers Using Samples of Training Cohort, and Method for Evaluating Esophageal Cancer Discriminant Performance of the Single Gene Marker Using the Validation Cohort>

In this Example, a gene marker for discriminating an esophageal cancer patient from a healthy subject was selected from the training cohort and studied in samples of the validation cohort independent of the training cohort, for a method for evaluating the esophageal cancer discriminant performance of each selected gene marker alone.

Specifically, first, the miRNA expression levels of the training cohort and the validation cohort obtained in the preceding Reference Examples were combined and normalized by quantile normalization.

Next, genes for diagnosis were selected using the training cohort. Here, in order to acquire diagnostic markers with higher reliability, only genes having the expression level of $2^6$ or higher in 50% or more of the samples in either of the esophageal cancer patient group of the training cohort or the healthy subject group of the training cohort were selected. In order to further acquire statistically significant genes for discriminating an esophageal cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant. The result is described in Table 2 mentioned later.

In this way, hsa-miR-204-3p, hsa-miR-1247-3p, hsa-miR-6875-5p, hsa-miR-6857-5p, hsa-miR-6726-5p, hsa-miR-3188, hsa-miR-8069, hsa-miR-4257, hsa-miR-1343-3p, hsa-miR-7108-5p, hsa-miR-6825-5p, hsa-miR-7641, hsa-miR-3185, hsa-miR-4746-3p, hsa-miR-6791-5p, hsa-miR-6893-5p, hsa-miR-4433b-3p, hsa-miR-3135b, hsa-miR-6781-5p, hsa-miR-1908-5p, hsa-miR-4792, hsa-miR-7845-5p, hsa-miR-4417, hsa-miR-3184-5p, hsa-miR-1225-5p, hsa-miR-1231, hsa-miR-1225-3p, hsa-miR-150-3p, hsa-miR-4433-3p, hsa-miR-6125, hsa-miR-4513, hsa-miR-6787-5p, hsa-miR-6784-5p, hsa-miR-615-5p, hsa-miR-6765-3p, hsa-miR-5572, hsa-miR-6842-5p, hsa-miR-8063, hsa-miR-6780b-5p, hsa-miR-187-5p, hsa-miR-128-1-5p, hsa-miR-6729-5p, hsa-miR-6741-5p, hsa-miR-6757-5p, hsa-miR-7110-5p, hsa-miR-7975, hsa-miR-1233-5p, hsa-miR-6845-5p, hsa-miR-3937, hsa-miR-4467, hsa-miR-7109-5p, hsa-miR-6088, hsa-miR-6782-5p, hsa-miR-5195-3p, hsa-miR-4454, hsa-miR-6724-5p, hsa-miR-8072, hsa-miR-4516, hsa-miR-6756-5p, hsa-miR-4665-3p, hsa-miR-6826-5p, hsa-miR-6820-5p, hsa-miR-6887-5p, hsa-miR-3679-5p, hsa-miR-7847-3p, hsa-miR-6721-5p, hsa-miR-3622a-5p, hsa-miR-939-5p, hsa-miR-602, hsa-miR-7977, hsa-miR-6749-5p, hsa-miR-1914-3p, hsa-miR-4651, hsa-miR-4695-5p, hsa-miR-6848-5p, hsa-miR-1228-3p, hsa-miR-642b-3p, hsa-miR-6746-5p, hsa-miR-3620-5p, hsa-miR-3131, hsa-miR-6732-5p, hsa-miR-7113-3p, hsa-miR-23a-3p, hsa-miR-3154, hsa-miR-4723-5p, hsa-miR-3663-3p, hsa-miR-4734, hsa-miR-6816-5p, hsa-miR-4442, hsa-miR-4476, hsa-miR-423-5p, hsa-miR-1249, hsa-miR-6515-3p, hsa-miR-887-3p, hsa-miR-4741, hsa-miR-6766-3p, hsa-miR-4673, hsa-miR-6779-5p, hsa-miR-4706, hsa-miR-1268b, hsa-miR-4632-5p, hsa-miR-3197, hsa-miR-6798-5p, hsa-miR-711, hsa-miR-6840-3p, hsa-miR-6763-5p, hsa-miR-6727-5p, hsa-miR-371a-5p, hsa-miR-6824-5p, hsa-miR-4648, hsa-miR-1227-5p, hsa-miR-564, hsa-miR-3679-3p, hsa-miR-2861, hsa-miR-6737-5p, hsa-miR-575, hsa-miR-4725-3p, hsa-miR-6716-5p, hsa-miR-4675, hsa-miR-1915-3p, hsa-miR-671-5p, hsa-miR-3656, hsa-miR-6722-3p, hsa-miR-4707-5p, hsa-miR-4449, hsa-miR-1202, hsa-miR-4649-5p, hsa-miR-744-5p, hsa-miR-642a-3p, hsa-miR-451a, hsa-miR-6870-5p, hsa-miR-4443, hsa-miR-6808-5p, hsa-miR-4728-5p, hsa-miR-937-5p, hsa-miR-135a-3p, hsa-miR-663b, hsa-miR-1343-5p, hsa-miR-6822-5p, hsa-miR-6803-5p, hsa-miR-6805-3p, hsa-miR-128-2-5p, hsa-miR-4640-5p, hsa-miR-1469, hsa-miR-92a-2-5p, hsa-miR-3940-5p, hsa-miR-4281, hsa-miR-1260b, hsa-miR-4758-5p, hsa-miR-1915-5p, hsa-miR-5001-5p, hsa-miR-4286, hsa-miR-6126, hsa-miR-6789-5p, hsa-miR-4459, hsa-miR-1268a, hsa-miR-6752-5p, hsa-miR-6131, hsa-miR-6800-5p, hsa-miR-4532, hsa-miR-6872-3p, hsa-miR-718, hsa-miR-6769a-5p, hsa-miR-4707-3p, hsa-miR-6765-5p, hsa-miR-4739, hsa-miR-4525, hsa-miR-4270, hsa-miR-4534, hsa-miR-6785-5p, hsa-miR-6850-5p, hsa-miR-4697-5p, hsa-miR-1260a, hsa-miR-4486, hsa-miR-6880-5p, hsa-miR-6802-5p, hsa-miR-6861-5p, hsa-miR-92b-5p, hsa-miR-1238-5p, hsa-miR-6851-5p, hsa-miR-7704, hsa-miR-149-3p, hsa-miR-4689, hsa-miR-4688, hsa-miR-125a-3p, hsa-miR-23b-3p, hsa-miR-614, hsa-miR-1913 and hsa-miR-16-5p genes, and polynucleotides consisting of the nucleotide sequences represented by SEQ ID NOs: 1 to 189 related thereto were found.

Among them, genes newly found as markers for examining the presence or absence of esophageal cancer are polynucleotides consisting of the nucleotide sequences represented by SEQ ID NOs: 1 to 115 and 117 to 189.

A discriminant for determining the presence or absence of esophageal cancer was further prepared by Fisher's discriminant analysis with the expression levels of these genes as indicators. Specifically, any polynucleotide consisting of a nucleotide sequence represented by any of SEQ ID NOs: 1 to 189 found in the training cohort was apply for Formula 2 above to construct a discriminant. Calculated accuracy, sensitivity, and specificity are shown in Table 3 mentioned later. In this respect, a discriminant coefficient and a constant term are shown in Table 4.

In this context, for example, 42 polynucleotides consisting of the nucleotide sequences represented by SEQ ID NOs: 1, 3, 4, 5, 6, 9, 10, 13, 15, 17, 18, 19, 26, 28, 29, 30, 32, 33, 35, 40, 41, 43, 55, 58, 61, 63, 67, 68, 70, 76, 77, 80, 90, 92, 93, 95, 109, 116, 119, 122, 127 and 150 were selected as markers capable of determining esophageal cancer even in any of 3 stage I samples included in the training cohort.

Figure 2:
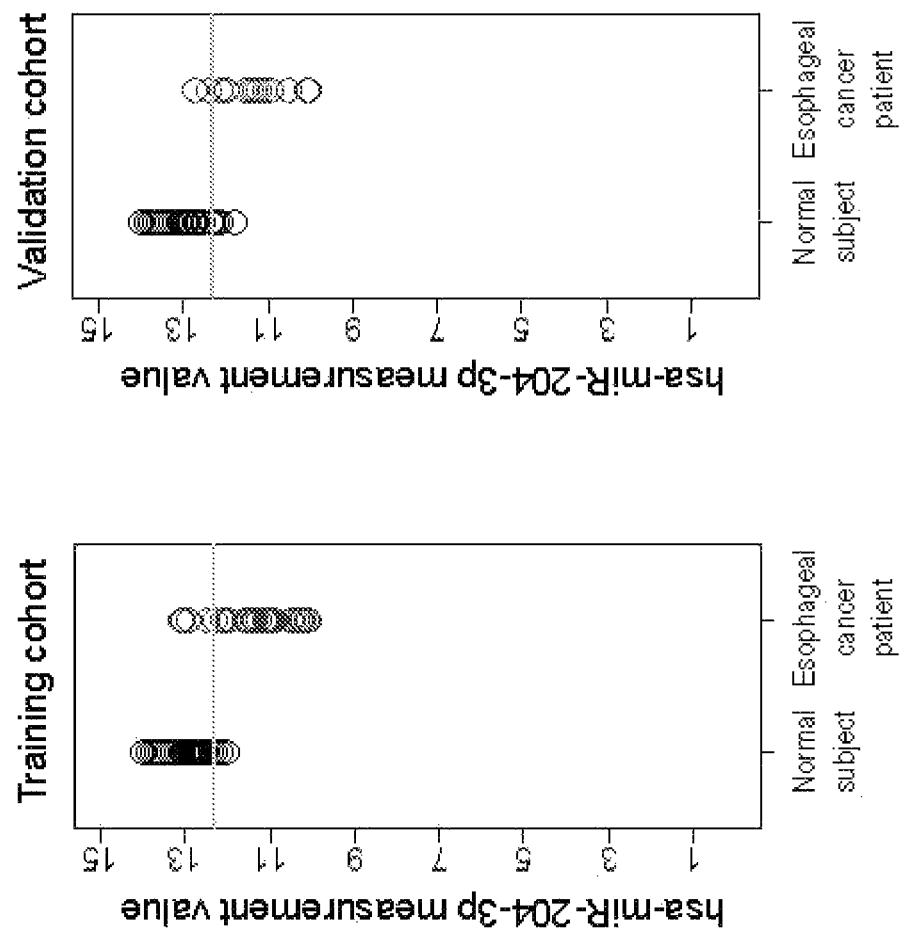
FIG. 2 Left diagram: the expression level measurement values of hsa-miR-204-3p (SEQ ID NO: 1) in healthy subjects (100 persons) and esophageal cancer patients (34 persons) selected as a training cohort were each plotted on the ordinate. The horizontal line in the diagram depicts a threshold (12.3) that was optimized by Fisher's discriminant analysis and discriminated between the two groups. Right diagram: the expression level measurement values of hsa-miR-204-3p (SEQ ID NO: 1) in healthy subjects (50 persons) and esophageal cancer patients (16 persons) selected as a validation cohort were each plotted on the ordinate. The horizontal line in the diagram depicts the threshold (12.3) that was set in the training cohort and discriminated between both of the groups.

Accuracy, sensitivity, and specificity for the validation cohort were calculated using the discriminant thus prepared, and the discriminant performance of the selected polynucleotides was validated using independent samples (Table 3). For example, the gene expression level measurement value of the nucleotide sequence represented by SEQ ID NO: 1 was compared between the healthy subjects (100 persons) and the esophageal cancer patients (34 persons) in the training cohort. As a result, the expression level measurement values were found to be significantly lower in the esophageal cancer patient group than in the healthy subject group (see the left diagram of FIG. 2). These results were also reproducible for the healthy subjects (50 persons) and the esophageal cancer patients (16 persons) in the validation cohort (see the right diagram of FIG. 2). Likewise, the results obtained about the other polynucleotides shown in SEQ ID NOs: 2 to 189 showed that the expression level measurement values were significantly lower (−) or higher (+) in the esophageal cancer patient group than in the healthy subject group (Table 2). These results were able to be validated in the validation cohort. For example, as for this nucleotide sequence represented by SEQ ID NO: 1, the number of correctly or incorrectly identified samples in the detection of esophageal cancer in the validation cohort was calculated using the threshold (12.3) that was set in the training cohort and discriminated between the two groups. As a result, 13 true positives, 48 true negatives, 2 false positives, and 3 false negatives were obtained. From these values, 92.4% accuracy, 81.2% sensitivity, and 96% specificity were obtained as detection performance. In this way, the detection performance was calculated as to any of the polynucleotides shown in SEQ ID NOs: 1 to 189, and described in Table 3. Likewise, 129 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 106, 107, 109, 110, 112, 113, 114, 115, 116, 117, 119, 120, 130, 131, 134, 139, 143, 151, 159, 173, 182, 185, 186, 187, 188 and 189 shown in Table 2 exhibited sensitivity of 81.2%, 87.5%, 93.8%, 100%, 87.5%, 87.5%, 81.2%, 75%, 87.5%, 100%, 100%, 87.5%, 81.2%, 75%, 87.5%, 87.5%, 81.2%, 93.8%, 93.8%, 81.2%, 100%, 87.5%, 68.8%, 87.5%, 81.2%, 75%, 87.5%, 81.2%, 81.2%, 87.5%, 75%, 68.8%, 81.2%, 75%, 68.8%, 100%, 68.8%, 87.5%, 87.5%, 81.2%, 68.8%, 75%, 75%, 87.5%, 68.8%, 62.5%, 93.8%, 75%, 81.2%, 62.5%, 56.2%, 56.2%, 56.2%, 75%, 68.8%, 62.5%, 62.5%, 62.5%, 68.8%, 68.8%, 68.8%, 56.2%, 56.2%, 56.2%, 81.2%, 56.2%, 50%, 68.8%, 75%, 56.2%, 56.2%, 56.2%, 62.5%, 43.8%, 50%, 56.2%, 56.2%, 68.8%, 62.5%, 62.5%, 68.8%, 56.2%, 43.8%, 62.5%, 56.2%, 43.8%, 43.8%, 75%, 56.2%, 56.2%, 62.5%, 56.2%, 87.5%, 43.8%, 50%, 43.8%, 50%, 56.2%, 43.8%, 50%, 43.8%, 68.8%, 62.5%, 56.2%, 43.8%, 43.8%, 56.2%, 56.2%, 62.5%, 56.2%, 62.5%, 50%, 68.8%, 56.2%, 43.8%, 62.5%, 43.8%, 43.8%, 43.8%, 43.8%, 50%, 56.2%, 43.8%, 43.8%, 75%, 62.5%, 43.8%, 50% and 62.5%, respectively, in the validation cohort (Table 3). As seen from Comparative Example mentioned later, the existing marker SCC for esophageal cancer had sensitivity of 37.5% in the validation cohort (Table 5-2), demonstrating that the 129 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 106, 107, 109, 110, 112, 113, 114, 115, 116, 117, 119, 120, 130, 131, 134, 139, 143, 151, 159, 173, 182, 185, 186, 187, 188 and 189 can discriminate, each alone, esophageal cancer in the validation cohort with sensitivity beyond SCC.

Thus, these polynucleotides can detect even early esophageal cancer and contribute to the early diagnosis of esophageal cancer.

Example 2

<Method for Evaluating Esophageal Cancer Discriminant Performance by Combination of Multiple Gene Markers Using Samples in the Validation Cohort>

In this Example, a method for evaluating esophageal cancer discriminant performance by a combination of the gene markers selected in Example 1 was studied. Specifically, Fisher's discriminant analysis was conducted as to 17,766 combinations of any two of the expression level measurement values of the newly found polynucleotides consisting of the nucleotide sequences represented by SEQ ID NOs: 1 to 115 and 117 to 189 among the polynucleotides consisting of the nucleotide sequences represented by SEQ ID NOs: 1 to 189 selected in Example 1, to construct a discriminant for determining the presence or absence of esophageal cancer. Next, accuracy, sensitivity, and specificity in the validation cohort were calculated using the discriminant thus prepared, and the discriminant performance of the selected polynucleotides was validated using the independent samples.

Figure 3:
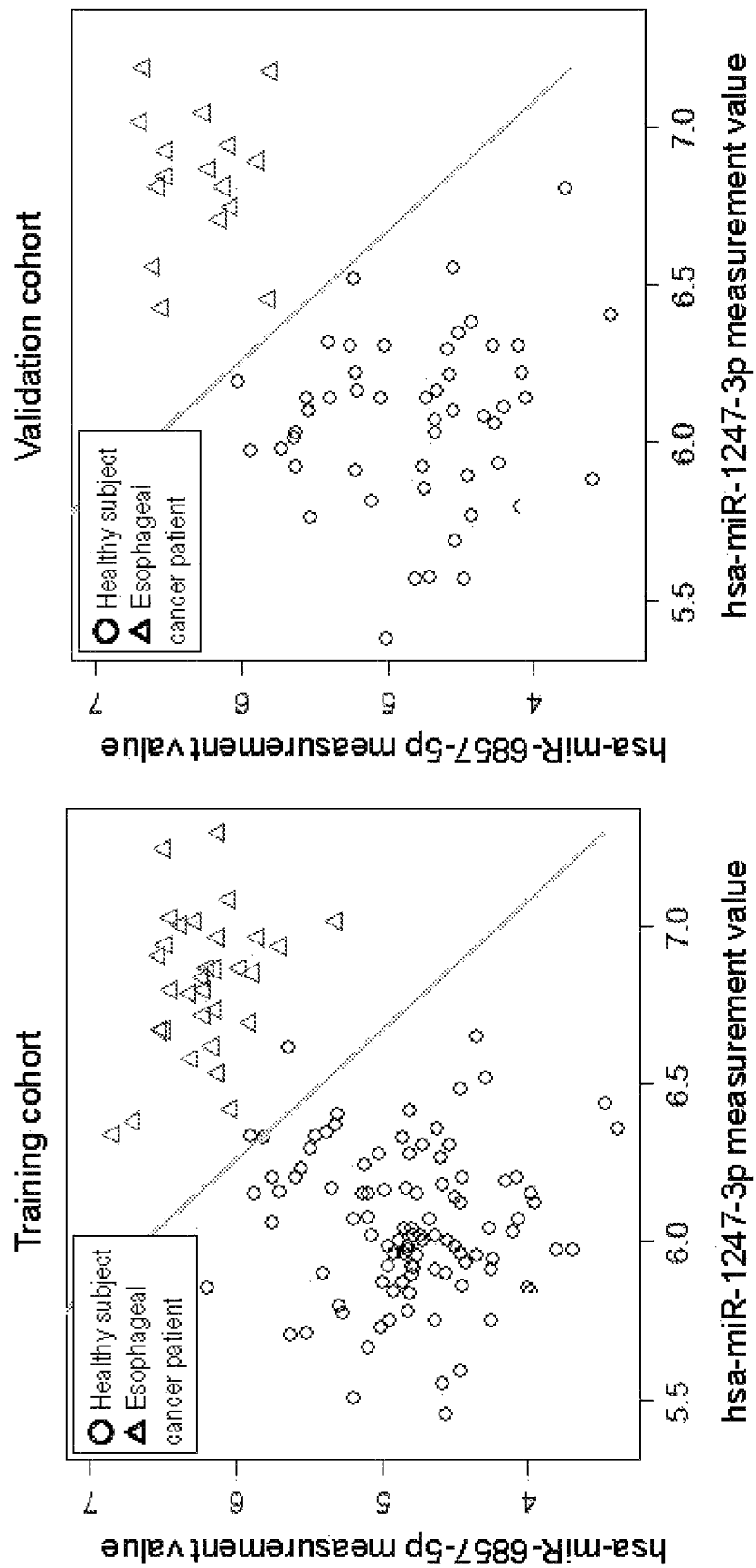
FIG. 3 Left diagram: the expression level measurement values of hsa-miR-1247-3p (SEQ ID NO: 2) in healthy subjects (100 persons, circles) and esophageal cancer patients (34 persons, triangles) selected as training cohort were each plotted on the abscissa against their expression level measurement values of hsa-miR-6857-5p (SEQ ID NO: 4) on the ordinate. The line in the diagram depicts a discriminant function (0=2.42x+y−21.17) that was optimized by Fisher's discriminant analysis and discriminated between both of the groups. Right diagram: the expression level measurement values of hsa-miR-1247-3p (SEQ ID NO: 2) in healthy subjects (50 persons, circles) and esophageal cancer patients (34 persons, triangles) selected as validation cohort were each plotted on the abscissa against their expression level measurement values of hsa-miR-6857-5p (SEQ ID NO: 4) on the ordinate. The line in the diagram depicts the threshold (0=2.42x+y−21.17) that was set in the training cohort and discriminated between both of the groups.

For example, the gene expression level measurement values of the nucleotide sequences represented by SEQ ID NO: 2 and SEQ ID NO: 4 were compared between the healthy subjects (100 persons) and the esophageal cancer patients (34 persons) in the training cohort. As a result, a variance diagram that significantly separated the measurement values of the esophageal cancer patient group from those of the healthy subject group was obtained (see the left diagram of FIG. 3). These results were also reproducible for the healthy subjects (50 persons) and the esophageal cancer patients (16 persons) in the validation cohort (see the right diagram of FIG. 3). Likewise, a variance diagram that significantly separated the measurement values of the esophageal cancer patient group from those of the healthy subject group was also obtained as to the other combinations of any two of the gene expression level measurement values of the newly found polynucleotides consisting of the nucleotide sequences represented by SEQ ID NOs: 1 to 115 and 117 to 189. These results were able to be validated in the validation cohort. As shown in FIG. 3, for example, as for these nucleotide sequences represented by SEQ ID NO: 2 and SEQ ID NO: 4, the number of samples that were correctly or incorrectly identified esophageal cancer was calculated using the function (0=2.42x+y−21.17) that was set in the training cohort and discriminated between the two groups. As a result, 15 true positives, 49 true negatives, 1 false positive, and 1 false negative were obtained. From these values, 97% accuracy, 93.8% sensitivity, and 98% specificity were obtained as the detection performance. In this way, the detection performance was calculated for the combinations of two of the polynucleotides consisting of the nucleotide sequences represented by SEQ ID NOs: 1 to 189. Among them, 188 combinations comprising the expression level measurement value of the polynucleotide consisting of the nucleotide sequence represented by SEQ ID NO: 1 and the detection performance thereof were described in Table 6 as an example. For example, any of combinations of the expression level measurement values of the polynucleotides consisting of the nucleotide sequences represented by SEQ ID NOs: 1 and 6, SEQ ID NOs: 1 and 9, SEQ ID NOs: 1 and 13, and SEQ ID NOs: 1 and 14 exhibited sensitivity of 100% in the validation cohort. Likewise, any of the remaining combinations of two polynucleotides consisting of the nucleotide sequences represented by SEQ ID NO: 1 and any of SEQ ID NOs: 2 to 189 also exhibited sensitivity of 81% or higher, which was beyond the sensitivity (37.5%) of the existing marker SCC for esophageal cancer (Table 5-2). The 17,096 combinations that showed sensitivity beyond SCC were obtained for the validation cohort. All of the nucleotide sequences 1 to 189 described in Table 2 obtained in Example 1 were employed at least once in these combinations. Thus, a combination of the expression level measurement values of two of the polynucleotides consisting of the nucleotide sequences represented by SEQ ID NOs: 1 to 189 also produced excellent esophageal cancer detection sensitivity.

Markers for the detection of esophageal cancer with better sensitivity are obtained by further combining 3, 4, 5, 6, 7, 8, 9, 10 or more of the expression level measurement values of the polynucleotides consisting of the nucleotide sequences represented by SEQ ID NOs: 1 to 189. For example, the newly found polynucleotides consisting of the nucleotide sequences represented by SEQ ID NOs: 1 to 115 and 117 to 189 among the polynucleotides consisting of the nucleotide sequences represented by SEQ ID NOs: 1 to 189 selected in Example 1 were measured to obtain their expression levels between the healthy subject group and the esophageal cancer group in the validation cohort. All of the polynucleotides were ranked in the descending order of their P values based on the Student's t-test which indicates statistical significance of difference between groups (i.e., one having the lowest P value was ranked in the first place), and esophageal cancer detection sensitivity was evaluated using combinations of one or more polynucleotides to which the polynucleotides were added one by one from the top to the bottom according to the rank. In short, the order in which the polynucleotides were combined in this evaluation is in reverse in terms of SEQ ID Nos from SEQ ID NO: 189 to SEQ ID NOs: 188, 187, . . . shown in Table 2. As a result, the sensitivity in the validation cohort was 31.2% for 1 polynucleotide (SEQ ID NO: 189), 56.2% for 2 polynucleotides (SEQ ID NOs: 188 and 189), 75.0% for 3 polynucleotides (SEQ ID NOs: 187 to 189), 93.8% for 5 polynucleotides (SEQ ID NOs: 185 to 189), 100% for 11 polynucleotides (SEQ ID NOs: 179 to 189), 100% for 30 polynucleotides (SEQ ID NOs: 160 to 189), 100% for 50 polynucleotides (SEQ ID NOs: 140 to 189), 100% for 100 polynucleotides (SEQ ID NOs: 89 to 115 and 117 to 189), 100% for 150 polynucleotides (SEQ ID NOs: 39 to 115 and 117 to 189), and 100% for 189 polynucleotides (SEQ ID NOs: 1 to 115 and 117 to 189).

These results demonstrated that a combination of multiple polynucleotides can produce higher esophageal cancer discriminant performance than that of each polynucleotide alone or a combination of a fewer number of polynucleotides. In this context, the combinations of multiple polynucleotides are not limited to the combinations of the polynucleotides added in the order of statistically significant difference as described above, and any combination of multiple polynucleotides can be used in the detection of esophageal cancer.

From these results, it can be concluded that all of the polynucleotides consisting of the nucleotide sequences represented by SEQ ID NOs: 1 to 189 serve as excellent markers for the detection of esophageal cancer.

TABLE 2

| SEQ ID NO: | Gene name | P value after Bonferroni correction | Expression level in esophageal cancer patient relative to healthy subject |
|---|---|---|---|
| 1 | hsa-miR-204-3p | 3.17E−32 | − |
| 2 | hsa-miR-1247-3p | 5.11E−32 | + |
| 3 | hsa-miR-6875-5p | 5.55E−29 | + |
| 4 | hsa-miR-6857-5p | 3.05E−27 | + |
| 5 | hsa-miR-6726-5p | 2.44E−26 | − |
| 6 | hsa-miR-3188 | 1.00E−24 | + |
| 7 | hsa-miR-8069 | 1.45E−24 | + |
| 8 | hsa-miR-4257 | 2.73E−23 | − |
| 9 | hsa-miR-1343-3p | 4.31E−23 | − |
| 10 | hsa-miR-7108-5p | 4.94E−23 | + |
| 11 | hsa-miR-6825-5p | 5.79E−23 | + |
| 12 | hsa-miR-7641 | 7.55E−23 | − |
| 13 | hsa-miR-3185 | 7.72E−22 | + |
| 14 | hsa-miR-4746-3p | 1.19E−21 | + |
| 15 | hsa-miR-6791-5p | 7.82E−21 | + |
| 16 | hsa-miR-6893-5p | 7.89E−21 | − |
| 17 | hsa-miR-4433b-3p | 8.03E−21 | + |
| 18 | hsa-miR-3135b | 1.34E−20 | − |
| 19 | hsa-miR-6781-5p | 2.01E−20 | + |
| 20 | hsa-miR-1908-5p | 2.19E−20 | + |
| 21 | hsa-miR-4792 | 2.39E−20 | + |
| 22 | hsa-miR-7845-5p | 3.30E−20 | + |
| 23 | hsa-miR-4417 | 7.21E−20 | + |
| 24 | hsa-miR-3184-5p | 1.29E−19 | + |
| 25 | hsa-miR-1225-5p | 1.55E−19 | + |
| 26 | hsa-miR-1231 | 3.51E−19 | + |
| 27 | hsa-miR-1225-3p | 3.85E−19 | + |
| 28 | hsa-miR-150-3p | 6.30E−19 | − |
| 29 | hsa-miR-4433-3p | 7.27E−19 | + |
| 30 | hsa-miR-6125 | 2.07E−18 | + |
| 31 | hsa-miR-4513 | 2.51E−18 | − |
| 32 | hsa-miR-6787-5p | 2.87E−18 | − |
| 33 | hsa-miR-6784-5p | 3.57E−18 | + |
| 34 | hsa-miR-615-5p | 8.70E−18 | − |
| 35 | hsa-miR-6765-3p | 1.34E−17 | − |
| 36 | hsa-miR-5572 | 1.62E−17 | + |
| 37 | hsa-miR-6842-5p | 2.45E−17 | + |
| 38 | hsa-miR-8063 | 2.69E−17 | − |
| 39 | hsa-miR-6780b-5p | 3.33E−17 | + |
| 40 | hsa-miR-187-5p | 9.41E−17 | − |
| 41 | hsa-miR-128-1-5p | 9.79E−17 | + |
| 42 | hsa-miR-6729-5p | 1.08E−16 | + |
| 43 | hsa-miR-6741-5p | 9.63E−16 | − |
| 44 | hsa-miR-6757-5p | 1.95E−15 | − |
| 45 | hsa-miR-7110-5p | 2.20E−15 | + |
| 46 | hsa-miR-7975 | 2.43E−15 | − |
| 47 | hsa-miR-1233-5p | 2.66E−15 | − |
| 48 | hsa-miR-6845-5p | 3.62E−15 | + |
| 49 | hsa-miR-3937 | 1.05E−14 | + |
| 50 | hsa-miR-4467 | 1.31E−14 | + |
| 51 | hsa-miR-7109-5p | 1.80E−14 | − |
| 52 | hsa-miR-6088 | 1.95E−14 | − |
| 53 | hsa-miR-6782-5p | 2.52E−14 | + |
| 54 | hsa-miR-5195-3p | 2.64E−14 | − |
| 55 | hsa-miR-4454 | 3.79E−14 | − |
| 56 | hsa-miR-6724-5p | 5.19E−14 | + |
| 57 | hsa-miR-8072 | 6.32E−14 | + |
| 58 | hsa-miR-4516 | 1.64E−13 | − |
| 59 | hsa-miR-6756-5p | 2.32E−13 | − |
| 60 | hsa-miR-4665-3p | 2.91E−13 | + |
| 61 | hsa-miR-6826-5p | 4.31E−13 | − |

TABLE 2-continued

| SEQ ID NO: | Gene name | P value after Bonferroni correction | Expression level in esophageal cancer patient relative to healthy subject |
|---|---|---|---|
| 62 | hsa-miR-6820-5p | 6.77E−13 | − |
| 63 | hsa-miR-6887-5p | 9.53E−13 | − |
| 64 | hsa-miR-3679-5p | 1.05E−12 | + |
| 65 | hsa-miR-7847-3p | 1.11E−12 | − |
| 66 | hsa-miR-6721-5p | 1.24E−12 | + |
| 67 | hsa-miR-3622a-5p | 2.38E−12 | − |
| 68 | hsa-miR-939-5p | 2.39E−12 | + |
| 69 | hsa-miR-602 | 3.03E−12 | + |
| 70 | hsa-miR-7977 | 5.99E−12 | − |
| 71 | hsa-miR-6749-5p | 8.45E−12 | − |
| 72 | hsa-miR-1914-3p | 8.68E−12 | − |
| 73 | hsa-miR-4651 | 9.05E−12 | − |
| 74 | hsa-miR-4695-5p | 9.79E−12 | + |
| 75 | hsa-miR-6848-5p | 1.17E−11 | + |
| 76 | hsa-miR-1228-3p | 1.56E−11 | + |
| 77 | hsa-miR-642b-3p | 1.71E−11 | + |
| 78 | hsa-miR-6746-5p | 2.34E−11 | − |
| 79 | hsa-miR-3620-5p | 2.79E−11 | + |
| 80 | hsa-miR-3131 | 2.99E−11 | − |
| 81 | hsa-miR-6732-5p | 3.68E−11 | + |
| 82 | hsa-miR-7113-3p | 5.38E−11 | + |
| 83 | hsa-miR-23a-3p | 5.53E−11 | − |
| 84 | hsa-miR-3154 | 6.89E−11 | + |
| 85 | hsa-miR-4723-5p | 9.65E−11 | − |
| 86 | hsa-miR-3663-3p | 3.45E−10 | − |
| 87 | hsa-miR-4734 | 3.66E−10 | + |
| 88 | hsa-miR-6816-5p | 4.49E−10 | + |
| 89 | hsa-miR-4442 | 5.02E−10 | − |
| 90 | hsa-miR-4476 | 5.16E−10 | − |
| 91 | hsa-miR-423-5p | 6.10E−10 | − |
| 92 | hsa-miR-1249 | 6.19E−10 | + |
| 93 | hsa-miR-6515-3p | 6.91E−10 | + |
| 94 | hsa-miR-887-3p | 7.28E−10 | + |
| 95 | hsa-miR-4741 | 9.08E−10 | + |
| 96 | hsa-miR-6766-3p | 1.13E−09 | + |
| 97 | hsa-miR-4673 | 2.76E−09 | + |
| 98 | hsa-miR-6779-5p | 2.82E−09 | − |
| 99 | hsa-miR-4706 | 3.75E−09 | − |
| 100 | hsa-miR-1268b | 5.40E−09 | + |
| 101 | hsa-miR-4632-5p | 5.60E−09 | + |
| 102 | hsa-miR-3197 | 6.35E−09 | + |
| 103 | hsa-miR-6798-5p | 9.47E−09 | + |
| 104 | hsa-miR-711 | 9.91E−09 | + |
| 105 | hsa-miR-6840-3p | 1.16E−08 | − |
| 106 | hsa-miR-6763-5p | 1.21E−08 | + |
| 107 | hsa-miR-6727-5p | 1.25E−08 | − |
| 108 | hsa-miR-371a-5p | 1.88E−08 | − |
| 109 | hsa-miR-6824-5p | 2.00E−08 | + |
| 110 | hsa-miR-4648 | 2.81E−08 | + |
| 111 | hsa-miR-1227-5p | 2.85E−08 | + |
| 112 | hsa-miR-564 | 5.06E−08 | − |
| 113 | hsa-miR-3679-3p | 5.14E−08 | + |
| 114 | hsa-miR-2861 | 6.22E−08 | − |
| 115 | hsa-miR-6737-5p | 6.48E−08 | + |
| 116 | hsa-miR-575 | 1.06E−07 | − |
| 117 | hsa-miR-4725-3p | 1.31E−07 | + |
| 118 | hsa-miR-6716-5p | 1.39E−07 | + |
| 119 | hsa-miR-4675 | 1.85E−07 | − |
| 120 | hsa-miR-1915-3p | 1.89E−07 | + |
| 121 | hsa-miR-671-5p | 1.89E−07 | − |
| 122 | hsa-miR-3656 | 2.14E−07 | + |
| 123 | hsa-miR-6722-3p | 2.15E−07 | + |
| 124 | hsa-miR-4707-5p | 2.32E−07 | + |
| 125 | hsa-miR-4449 | 2.73E−07 | + |
| 126 | hsa-miR-1202 | 4.73E−07 | − |
| 127 | hsa-miR-4649-5p | 1.23E−06 | − |
| 128 | hsa-miR-744-5p | 1.53E−06 | + |
| 129 | hsa-miR-642a-3p | 1.70E−06 | − |
| 130 | hsa-miR-451a | 2.39E−06 | − |
| 131 | hsa-miR-6870-5p | 2.74E−06 | + |
| 132 | hsa-miR-4443 | 3.08E−06 | + |
| 133 | hsa-miR-6808-5p | 3.57E−06 | + |
| 134 | hsa-miR-4728-5p | 4.15E−06 | − |
| 135 | hsa-miR-937-5p | 4.83E−06 | − |
| 136 | hsa-miR-135a-3p | 7.39E−06 | + |
| 137 | hsa-miR-663b | 8.35E−06 | − |
| 138 | hsa-miR-1343-5p | 9.72E−06 | + |
| 139 | hsa-miR-6822-5p | 1.03E−05 | + |
| 140 | hsa-miR-6803-5p | 1.05E−05 | + |
| 141 | hsa-miR-6805-3p | 1.86E−05 | + |
| 142 | hsa-miR-128-2-5p | 2.08E−05 | − |
| 143 | hsa-miR-4640-5p | 2.71E−05 | + |
| 144 | hsa-miR-1469 | 2.75E−05 | + |
| 145 | hsa-miR-92a-2-5p | 3.53E−05 | + |
| 146 | hsa-miR-3940-5p | 4.11E−05 | + |
| 147 | hsa-miR-4281 | 4.74E−05 | − |
| 148 | hsa-miR-1260b | 7.11E−05 | − |
| 149 | hsa-miR-4758-5p | 7.66E−05 | − |
| 150 | hsa-miR-1915-5p | 7.76E−05 | − |
| 151 | hsa-miR-5001-5p | 9.17E−05 | − |
| 152 | hsa-miR-4286 | 1.58E−04 | − |
| 153 | hsa-miR-6126 | 1.61E−04 | + |
| 154 | hsa-miR-6789-5p | 1.64E−04 | + |
| 155 | hsa-miR-4459 | 2.00E−04 | + |
| 156 | hsa-miR-1268a | 2.18E−04 | + |
| 157 | hsa-miR-6752-5p | 2.64E−04 | + |
| 158 | hsa-miR-6131 | 2.95E−04 | − |
| 159 | hsa-miR-6800-5p | 3.49E−04 | + |
| 160 | hsa-miR-4532 | 4.53E−04 | − |
| 161 | hsa-miR-6872-3p | 5.66E−04 | − |
| 162 | hsa-miR-718 | 6.77E−04 | + |
| 163 | hsa-miR-6769a-5p | 7.66E−04 | − |
| 164 | hsa-miR-4707-3p | 7.90E−04 | + |
| 165 | hsa-miR-6765-5p | 8.10E−04 | + |
| 166 | hsa-miR-4739 | 1.05E−03 | + |
| 167 | hsa-miR-4525 | 1.09E−03 | − |
| 168 | hsa-miR-4270 | 1.26E−03 | − |
| 169 | hsa-miR-4534 | 1.51E−03 | − |
| 170 | hsa-miR-6785-5p | 1.53E−03 | − |
| 171 | hsa-miR-6850-5p | 1.54E−03 | + |
| 172 | hsa-miR-4697-5p | 1.57E−03 | − |
| 173 | hsa-miR-1260a | 1.69E−03 | − |
| 174 | hsa-miR-4486 | 1.83E−03 | + |
| 175 | hsa-miR-6880-5p | 2.43E−03 | + |
| 176 | hsa-miR-6802-5p | 2.70E−03 | − |
| 177 | hsa-miR-6861-5p | 3.25E−03 | − |
| 178 | hsa-miR-92b-5p | 4.09E−03 | + |
| 179 | hsa-miR-1238-5p | 4.13E−03 | + |
| 180 | hsa-miR-6851-5p | 4.42E−03 | + |
| 181 | hsa-miR-7704 | 5.64E−03 | − |
| 182 | hsa-miR-149-3p | 5.75E−03 | − |
| 183 | hsa-miR-4689 | 6.06E−03 | − |
| 184 | hsa-miR-4688 | 9.69E−03 | − |
| 185 | hsa-miR-125a-3p | 2.00E−28 | − |
| 186 | hsa-miR-23b-3p | 7.47E−11 | − |
| 187 | hsa-miR-614 | 1.25E−08 | − |
| 188 | hsa-miR-1913 | 4.37E−08 | + |
| 189 | hsa-miR-16-5p | 3.26E−04 | − |

TABLE 3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 94 | 79.4 | 99 | 92.4 | 81.2 | 96 |
| 2 | 96.3 | 91.2 | 98 | 93.9 | 87.5 | 96 |
| 3 | 95.5 | 91.2 | 97 | 90.9 | 93.8 | 90 |
| 4 | 94 | 94.1 | 94 | 97 | 100 | 96 |
| 5 | 91 | 73.5 | 97 | 92.4 | 87.5 | 94 |
| 6 | 94 | 88.2 | 96 | 95.5 | 87.5 | 98 |
| 7 | 91.8 | 82.4 | 95 | 92.4 | 81.2 | 96 |
| 8 | 91.8 | 76.5 | 97 | 89.4 | 75 | 94 |
| 9 | 93.3 | 88.2 | 95 | 93.9 | 87.5 | 96 |
| 10 | 91 | 79.4 | 95 | 92.4 | 100 | 90 |

TABLE 3-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 11 | 88.8 | 82.4 | 91 | 93.9 | 100 | 92 |
| 12 | 89.6 | 79.4 | 93 | 93.9 | 87.5 | 96 |
| 13 | 92.5 | 88.2 | 94 | 92.4 | 81.2 | 96 |
| 14 | 92.5 | 88.2 | 94 | 90.9 | 75 | 96 |
| 15 | 90.3 | 88.2 | 91 | 95.5 | 87.5 | 98 |
| 16 | 91.8 | 73.5 | 98 | 93.9 | 87.5 | 96 |
| 17 | 90.3 | 79.4 | 94 | 83.3 | 81.2 | 84 |
| 18 | 97 | 97.1 | 97 | 97 | 93.8 | 98 |
| 19 | 91.8 | 73.5 | 98 | 92.4 | 93.8 | 92 |
| 20 | 91 | 85.3 | 93 | 90.9 | 81.2 | 94 |
| 21 | 91.8 | 85.3 | 94 | 98.5 | 100 | 98 |
| 22 | 94 | 85.3 | 97 | 90.9 | 87.5 | 92 |
| 23 | 92.5 | 79.4 | 97 | 87.9 | 68.8 | 94 |
| 24 | 91.8 | 88.2 | 93 | 92.4 | 87.5 | 94 |
| 25 | 93.3 | 85.3 | 96 | 90.9 | 81.2 | 94 |
| 26 | 89.6 | 76.5 | 94 | 87.9 | 75 | 92 |
| 27 | 93.3 | 85.3 | 96 | 97 | 87.5 | 100 |
| 28 | 88.8 | 76.5 | 93 | 86.4 | 81.2 | 88 |
| 29 | 88.1 | 82.4 | 90 | 89.4 | 81.2 | 92 |
| 30 | 93.3 | 91.2 | 94 | 93.9 | 87.5 | 96 |
| 31 | 88.8 | 67.6 | 96 | 90.9 | 75 | 96 |
| 32 | 91 | 76.5 | 96 | 87.9 | 68.8 | 94 |
| 33 | 86.6 | 79.4 | 89 | 86.4 | 81.2 | 88 |
| 34 | 90.3 | 76.5 | 95 | 92.4 | 75 | 98 |
| 35 | 89.6 | 70.6 | 96 | 89.4 | 68.8 | 96 |
| 36 | 87.3 | 82.4 | 89 | 92.4 | 100 | 90 |
| 37 | 89.6 | 73.5 | 95 | 89.4 | 68.8 | 96 |
| 38 | 86.6 | 76.5 | 90 | 92.4 | 87.5 | 94 |
| 39 | 88.1 | 67.6 | 95 | 97 | 87.5 | 100 |
| 40 | 89.6 | 82.4 | 92 | 92.4 | 81.2 | 96 |
| 41 | 88.1 | 76.5 | 92 | 81.8 | 68.8 | 86 |
| 42 | 89.6 | 64.7 | 98 | 92.4 | 75 | 98 |
| 43 | 91 | 73.5 | 97 | 87.9 | 75 | 92 |
| 44 | 85.8 | 70.6 | 91 | 97 | 87.5 | 100 |
| 45 | 84.3 | 64.7 | 91 | 84.8 | 68.8 | 90 |
| 46 | 88.1 | 64.7 | 96 | 84.8 | 62.5 | 92 |
| 47 | 88.1 | 67.6 | 95 | 93.9 | 93.8 | 94 |
| 48 | 88.1 | 64.7 | 96 | 86.4 | 75 | 90 |
| 49 | 87.3 | 67.6 | 94 | 92.4 | 81.2 | 96 |
| 50 | 83.6 | 73.5 | 87 | 87.9 | 62.5 | 96 |
| 51 | 83.6 | 64.7 | 90 | 81.8 | 56.2 | 90 |
| 52 | 83.6 | 61.8 | 91 | 83.3 | 56.2 | 92 |
| 53 | 88.8 | 73.5 | 94 | 84.8 | 56.2 | 94 |
| 54 | 89.6 | 76.5 | 94 | 90.9 | 75 | 96 |
| 55 | 86.6 | 67.6 | 93 | 87.9 | 68.8 | 94 |
| 56 | 87.3 | 73.5 | 92 | 81.8 | 62.5 | 88 |
| 57 | 88.1 | 64.7 | 96 | 80.3 | 62.5 | 86 |
| 58 | 88.1 | 64.7 | 96 | 87.9 | 62.5 | 96 |
| 59 | 89.6 | 70.6 | 96 | 81.8 | 68.8 | 86 |
| 60 | 87.3 | 70.6 | 93 | 83.3 | 68.8 | 88 |
| 61 | 85.1 | 58.8 | 94 | 92.4 | 68.8 | 100 |
| 62 | 91 | 69.7 | 98 | 81.8 | 56.2 | 90 |
| 63 | 85.1 | 58.8 | 94 | 84.8 | 56.2 | 94 |
| 64 | 84.3 | 58.8 | 93 | 86.4 | 56.2 | 96 |
| 65 | 81.3 | 55.9 | 90 | 87.9 | 81.2 | 90 |
| 66 | 84.3 | 67.6 | 90 | 77.3 | 56.2 | 84 |
| 67 | 86.6 | 55.9 | 97 | 84.8 | 50 | 96 |
| 68 | 79.1 | 61.8 | 85 | 83.3 | 68.8 | 88 |
| 69 | 84.3 | 58.8 | 93 | 89.4 | 75 | 94 |
| 70 | 85.8 | 52.9 | 97 | 84.8 | 56.2 | 94 |
| 71 | 83.6 | 61.8 | 91 | 86.4 | 56.2 | 96 |
| 72 | 85.1 | 61.8 | 93 | 80.3 | 56.2 | 88 |
| 73 | 84.3 | 50 | 96 | 89.4 | 62.5 | 98 |
| 74 | 79.9 | 52.9 | 89 | 81.8 | 43.8 | 94 |
| 75 | 84.3 | 58.8 | 93 | 78.8 | 50 | 88 |
| 76 | 86.6 | 64.7 | 94 | 81.8 | 56.2 | 90 |
| 77 | 85.1 | 58.8 | 94 | 87.9 | 56.2 | 98 |
| 78 | 81.3 | 55.9 | 90 | 86.4 | 68.8 | 92 |
| 79 | 84.3 | 58.8 | 93 | 84.8 | 62.5 | 92 |
| 80 | 82.8 | 55.9 | 92 | 89.4 | 62.5 | 98 |
| 81 | 82.8 | 64.7 | 89 | 80.3 | 68.8 | 84 |
| 82 | 81.3 | 58.8 | 89 | 83.3 | 56.2 | 92 |
| 83 | 85.8 | 55.9 | 96 | 78.8 | 43.8 | 90 |
| 84 | 85.8 | 58.8 | 95 | 83.3 | 62.5 | 90 |
| 85 | 83.6 | 50 | 95 | 81.8 | 56.2 | 90 |
| 86 | 79.1 | 32.4 | 95 | 83.3 | 43.8 | 96 |
| 87 | 76.9 | 26.5 | 94 | 81.8 | 43.8 | 94 |
| 88 | 85.1 | 70.6 | 90 | 87.9 | 75 | 92 |
| 89 | 81.3 | 52.9 | 91 | 83.3 | 56.2 | 92 |
| 90 | 85.8 | 52.9 | 97 | 84.8 | 56.2 | 94 |
| 91 | 83.6 | 58.8 | 92 | 71.2 | 31.2 | 84 |
| 92 | 80.5 | 41.2 | 93.9 | 83.3 | 62.5 | 90 |
| 93 | 79.1 | 38.2 | 93 | 75.8 | 56.2 | 82 |
| 94 | 79.1 | 50 | 89 | 87.9 | 87.5 | 88 |
| 95 | 85.1 | 55.9 | 95 | 81.8 | 43.8 | 94 |
| 96 | 85.8 | 58.8 | 95 | 80.3 | 50 | 90 |
| 97 | 85.8 | 55.9 | 96 | 83.3 | 43.8 | 96 |
| 98 | 76.9 | 38.2 | 90 | 86.4 | 50 | 98 |
| 99 | 82.8 | 50 | 94 | 84.8 | 56.2 | 94 |
| 100 | 77.6 | 44.1 | 89 | 74.2 | 43.8 | 84 |
| 101 | 85.8 | 52.9 | 97 | 86.4 | 50 | 98 |
| 102 | 85.8 | 64.7 | 93 | 81.8 | 43.8 | 94 |
| 103 | 80.6 | 52.9 | 90 | 80.3 | 68.8 | 84 |
| 104 | 85.8 | 61.8 | 94 | 89.4 | 62.5 | 98 |
| 105 | 79.1 | 38.2 | 93 | 78.8 | 31.2 | 94 |
| 106 | 79.9 | 50 | 90 | 83.3 | 56.2 | 92 |
| 107 | 83.6 | 55.9 | 93 | 84.8 | 43.8 | 98 |
| 108 | 79.9 | 44.1 | 92 | 72.7 | 31.2 | 86 |
| 109 | 84.3 | 47.1 | 97 | 83.3 | 43.8 | 96 |
| 110 | 79.1 | 41.2 | 92 | 89.4 | 56.2 | 100 |
| 111 | 79.9 | 38.2 | 94 | 75.8 | 31.2 | 90 |
| 112 | 85.1 | 50 | 97 | 87.9 | 56.2 | 98 |
| 113 | 82.1 | 47.1 | 94 | 83.3 | 62.5 | 90 |
| 114 | 80.6 | 44.1 | 93 | 86.4 | 56.2 | 96 |
| 115 | 79.9 | 50 | 90 | 83.3 | 62.5 | 90 |
| 116 | 88.1 | 55.9 | 99 | 84.8 | 50 | 96 |
| 117 | 82.8 | 61.8 | 90 | 86.4 | 68.8 | 92 |
| 118 | 82.1 | 47.1 | 94 | 77.3 | 31.2 | 92 |
| 119 | 79.1 | 38.2 | 93 | 89.4 | 56.2 | 100 |
| 120 | 78.4 | 29.4 | 95 | 81.8 | 43.8 | 94 |
| 121 | 80.6 | 41.2 | 94 | 77.3 | 31.2 | 92 |
| 122 | 79.9 | 38.2 | 94 | 78.8 | 18.8 | 98 |
| 123 | 80.6 | 44.1 | 93 | 78.8 | 37.5 | 92 |
| 124 | 79.9 | 50 | 90 | 77.3 | 37.5 | 90 |
| 125 | 79.1 | 32.4 | 95 | 81.8 | 37.5 | 96 |
| 126 | 81.3 | 35.3 | 97 | 80.3 | 37.5 | 94 |
| 127 | 78.4 | 44.1 | 90 | 81.8 | 37.5 | 96 |
| 128 | 80.6 | 38.2 | 95 | 83.3 | 37.5 | 98 |
| 129 | 74.6 | 26.5 | 91 | 72.7 | 18.8 | 90 |
| 130 | 84.3 | 47.1 | 97 | 86.4 | 62.5 | 94 |
| 131 | 79.9 | 32.4 | 96 | 86.4 | 43.8 | 100 |
| 132 | 82.8 | 47.1 | 95 | 80.3 | 31.2 | 96 |
| 133 | 80.6 | 35.3 | 96 | 72.7 | 12.5 | 92 |
| 134 | 76.9 | 32.4 | 92 | 80.3 | 43.8 | 92 |
| 135 | 79.9 | 35.3 | 95 | 80.3 | 31.2 | 96 |
| 136 | 79.9 | 44.1 | 92 | 71.2 | 31.2 | 84 |
| 137 | 74.6 | 23.5 | 92 | 80.3 | 18.8 | 100 |
| 138 | 81.3 | 44.1 | 94 | 81.8 | 37.5 | 96 |
| 139 | 76.9 | 26.5 | 94 | 84.8 | 43.8 | 98 |
| 140 | 76.9 | 35.3 | 91 | 69.7 | 25 | 84 |
| 141 | 76.9 | 35.3 | 91 | 80.3 | 31.2 | 96 |
| 142 | 79.1 | 29.4 | 96 | 83.3 | 31.2 | 100 |
| 143 | 79.1 | 29.4 | 96 | 86.4 | 43.8 | 100 |
| 144 | 77.6 | 26.5 | 95 | 74.2 | 25 | 90 |
| 145 | 78.4 | 32.4 | 94 | 78.8 | 37.5 | 92 |
| 146 | 76.9 | 29.4 | 93 | 77.3 | 31.2 | 92 |
| 147 | 75.4 | 23.5 | 93 | 78.8 | 25 | 96 |
| 148 | 81.3 | 38.2 | 96 | 80.3 | 37.5 | 94 |
| 149 | 82.8 | 38.2 | 98 | 78.8 | 18.8 | 98 |
| 150 | 79.1 | 29.4 | 96 | 78.8 | 31.2 | 94 |
| 151 | 80.6 | 38.2 | 95 | 81.8 | 50 | 92 |
| 152 | 76.1 | 23.5 | 94 | 77.3 | 31.2 | 92 |
| 153 | 73.9 | 23.5 | 91 | 75.8 | 12.5 | 96 |
| 154 | 73.1 | 11.8 | 94 | 75.8 | 31.2 | 90 |
| 155 | 81.3 | 38.2 | 96 | 80.3 | 25 | 98 |
| 156 | 73.1 | 26.5 | 89 | 71.2 | 31.2 | 84 |
| 157 | 73.9 | 17.6 | 93 | 66.7 | 6.2 | 86 |
| 158 | 79.9 | 35.3 | 95 | 80.3 | 31.2 | 96 |

TABLE 3-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 159 | 76.9 | 23.5 | 95 | 83.3 | 56.2 | 92 |
| 160 | 77.6 | 23.5 | 96 | 80.3 | 25 | 98 |
| 161 | 79.1 | 29.4 | 96 | 81.8 | 37.5 | 96 |
| 162 | 73.1 | 14.7 | 93 | 69.7 | 0 | 92 |
| 163 | 76.1 | 23.5 | 94 | 75.8 | 12.5 | 96 |
| 164 | 76.1 | 17.6 | 96 | 77.3 | 31.2 | 92 |
| 165 | 78.4 | 23.5 | 97 | 78.8 | 25 | 96 |
| 166 | 79.9 | 29.4 | 97 | 80.3 | 31.2 | 96 |
| 167 | 76.9 | 26.5 | 94 | 77.3 | 6.2 | 100 |
| 168 | 80.6 | 35.3 | 96 | 77.3 | 25 | 94 |
| 169 | 77.6 | 23.5 | 96 | 69.7 | 6.2 | 90 |
| 170 | 79.1 | 29.4 | 96 | 83.1 | 26.7 | 100 |
| 171 | 81.3 | 38.2 | 96 | 75.8 | 31.2 | 90 |
| 172 | 76.1 | 23.5 | 94 | 78.8 | 31.2 | 94 |
| 173 | 77.6 | 26.5 | 95 | 81.8 | 43.8 | 94 |
| 174 | 76.1 | 20.6 | 95 | 81.8 | 31.2 | 98 |
| 175 | 80.6 | 29.4 | 98 | 78.8 | 18.8 | 98 |
| 176 | 79.9 | 26.5 | 98 | 80.3 | 25 | 98 |
| 177 | 79.9 | 29.4 | 97 | 81.8 | 31.2 | 98 |
| 178 | 73.1 | 11.8 | 94 | 78.8 | 18.8 | 98 |
| 179 | 76.1 | 17.6 | 96 | 77.3 | 12.5 | 98 |
| 180 | 73.1 | 8.8 | 95 | 78.8 | 12.5 | 100 |
| 181 | 76.1 | 29.4 | 92 | 69.7 | 25 | 84 |
| 182 | 76.1 | 20.6 | 95 | 77.3 | 43.8 | 88 |
| 183 | 76.9 | 17.6 | 97 | 78.8 | 12.5 | 100 |
| 184 | 77.6 | 20.6 | 97 | 81.8 | 31.2 | 98 |
| 185 | 95.5 | 85.3 | 99 | 93.9 | 75 | 100 |
| 186 | 83.6 | 50 | 95 | 86.4 | 62.5 | 94 |
| 187 | 79.1 | 47.1 | 90 | 80.3 | 43.8 | 92 |
| 188 | 79.1 | 41.2 | 92 | 83.1 | 50 | 93.9 |
| 189 | 82.1 | 41.2 | 96 | 87.9 | 62.5 | 96 |

TABLE 4

| SEQ ID NO: | Discriminant coefficient | Constant term |
|---|---|---|
| 1 | 1.728 | 21.253 |
| 2 | 4.247 | 27.391 |
| 3 | 4.025 | 37.004 |
| 4 | 1.997 | 11.064 |
| 5 | 3.142 | 30.220 |
| 6 | 3.455 | 21.479 |
| 7 | 7.377 | 95.667 |
| 8 | 2.889 | 18.733 |
| 9 | 2.480 | 18.013 |
| 10 | 4.837 | 44.847 |
| 11 | 2.182 | 14.705 |
| 12 | 1.260 | 8.443 |
| 13 | 2.577 | 18.611 |
| 14 | 2.990 | 19.980 |
| 15 | 5.216 | 48.423 |
| 16 | 2.157 | 17.534 |
| 17 | 3.898 | 31.927 |
| 18 | 2.959 | 22.467 |
| 19 | 5.747 | 60.613 |
| 20 | 4.475 | 52.095 |
| 21 | 2.037 | 14.005 |
| 22 | 3.204 | 21.819 |
| 23 | 5.663 | 46.868 |
| 24 | 2.397 | 19.749 |
| 25 | 3.533 | 26.374 |
| 26 | 3.637 | 24.242 |
| 27 | 3.134 | 17.788 |
| 28 | 2.259 | 14.444 |
| 29 | 3.890 | 28.987 |
| 30 | 5.510 | 66.435 |
| 31 | 3.218 | 18.273 |
| 32 | 4.013 | 33.740 |
| 33 | 3.829 | 48.615 |
| 34 | 2.368 | 14.866 |
| 35 | 1.648 | 13.802 |
| 36 | 2.478 | 16.783 |
| 37 | 3.608 | 21.816 |
| 38 | 2.700 | 21.869 |
| 39 | 3.045 | 27.546 |
| 40 | 2.276 | 22.213 |
| 41 | 2.830 | 21.434 |
| 42 | 8.628 | 108.988 |
| 43 | 4.284 | 28.951 |
| 44 | 2.953 | 20.892 |
| 45 | 1.831 | 14.542 |
| 46 | 2.058 | 19.942 |
| 47 | 2.788 | 30.680 |
| 48 | 3.787 | 36.710 |
| 49 | 4.284 | 37.394 |
| 50 | 2.351 | 23.417 |
| 51 | 5.582 | 40.862 |
| 52 | 3.374 | 33.771 |
| 53 | 3.304 | 20.643 |
| 54 | 3.097 | 20.730 |
| 55 | 2.087 | 23.779 |
| 56 | 4.807 | 48.256 |
| 57 | 5.366 | 66.548 |
| 58 | 4.590 | 60.012 |
| 59 | 5.385 | 44.281 |
| 60 | 4.425 | 25.890 |
| 61 | 2.238 | 13.151 |
| 62 | 3.068 | 21.797 |
| 63 | 3.019 | 18.844 |
| 64 | 2.848 | 19.631 |
| 65 | 3.913 | 24.472 |
| 66 | 4.110 | 31.289 |
| 67 | 2.450 | 13.850 |
| 68 | 2.535 | 19.310 |
| 69 | 3.143 | 20.245 |
| 70 | 2.050 | 19.680 |
| 71 | 5.003 | 49.921 |
| 72 | 4.868 | 36.163 |
| 73 | 5.151 | 55.976 |
| 74 | 4.628 | 34.855 |
| 75 | 4.911 | 36.605 |
| 76 | 4.102 | 25.952 |
| 77 | 2.468 | 22.972 |
| 78 | 3.620 | 23.145 |
| 79 | 4.177 | 33.363 |
| 80 | 2.569 | 17.652 |
| 81 | 3.560 | 30.479 |
| 82 | 3.219 | 18.791 |
| 83 | 1.409 | 7.771 |
| 84 | 4.626 | 27.715 |
| 85 | 2.981 | 26.017 |
| 86 | 4.075 | 49.126 |
| 87 | 5.860 | 70.045 |
| 88 | 4.518 | 45.735 |
| 89 | 3.376 | 31.771 |
| 90 | 1.504 | 10.293 |
| 91 | 2.408 | 17.120 |
| 92 | 3.741 | 22.446 |
| 93 | 4.216 | 28.494 |
| 94 | 2.433 | 17.718 |
| 95 | 3.691 | 36.766 |
| 96 | 4.011 | 23.884 |
| 97 | 2.738 | 15.840 |
| 98 | 6.279 | 44.218 |
| 99 | 3.821 | 29.214 |
| 100 | 3.138 | 31.313 |
| 101 | 4.137 | 33.060 |
| 102 | 3.184 | 30.108 |
| 103 | 3.013 | 31.561 |
| 104 | 3.467 | 28.752 |
| 105 | 3.228 | 28.241 |
| 106 | 3.979 | 27.890 |
| 107 | 6.059 | 77.100 |
| 108 | 3.680 | 26.849 |
| 109 | 4.631 | 30.402 |
| 110 | 1.394 | 8.449 |
| 111 | 6.759 | 64.607 |

TABLE 4-continued

| SEQ ID NO: | Discriminant coefficient | Constant term |
|---|---|---|
| 112 | 1.409 | 7.968 |
| 113 | 3.162 | 19.071 |
| 114 | 5.990 | 73.977 |
| 115 | 5.334 | 38.106 |
| 116 | 1.456 | 8.354 |
| 117 | 4.005 | 39.314 |
| 118 | 3.960 | 26.029 |
| 119 | 2.965 | 22.212 |
| 120 | 4.191 | 46.456 |
| 121 | 3.073 | 19.231 |
| 122 | 4.802 | 55.520 |
| 123 | 6.630 | 56.690 |
| 124 | 4.376 | 32.100 |
| 125 | 3.860 | 25.003 |
| 126 | 2.820 | 18.115 |
| 127 | 2.803 | 28.773 |
| 128 | 2.467 | 17.131 |
| 129 | 2.799 | 21.018 |
| 130 | 1.014 | 8.569 |
| 131 | 3.279 | 24.306 |
| 132 | 2.463 | 15.756 |
| 133 | 5.281 | 36.256 |
| 134 | 4.856 | 33.829 |
| 135 | 4.127 | 34.385 |
| 136 | 2.446 | 18.351 |
| 137 | 3.464 | 30.213 |
| 138 | 3.758 | 39.142 |
| 139 | 3.002 | 17.723 |
| 140 | 6.638 | 74.011 |
| 141 | 2.417 | 18.061 |
| 142 | 2.771 | 29.864 |
| 143 | 4.044 | 31.341 |
| 144 | 5.475 | 55.815 |
| 145 | 1.996 | 18.798 |
| 146 | 4.966 | 60.960 |
| 147 | 3.897 | 45.041 |
| 148 | 2.189 | 18.504 |
| 149 | 5.725 | 48.947 |
| 150 | 1.479 | 9.192 |
| 151 | 4.007 | 30.769 |
| 152 | 2.375 | 17.501 |
| 153 | 3.148 | 34.147 |
| 154 | 4.614 | 45.732 |
| 155 | 3.496 | 28.749 |
| 156 | 3.223 | 36.168 |
| 157 | 3.880 | 43.759 |
| 158 | 2.161 | 22.836 |
| 159 | 4.249 | 36.373 |
| 160 | 3.372 | 40.014 |
| 161 | 2.156 | 12.836 |
| 162 | 3.830 | 25.976 |
| 163 | 4.148 | 26.395 |
| 164 | 3.013 | 19.353 |
| 165 | 4.848 | 51.132 |
| 166 | 3.658 | 41.969 |
| 167 | 2.809 | 19.310 |
| 168 | 5.360 | 42.861 |
| 169 | 3.044 | 20.270 |
| 170 | 2.349 | 21.153 |
| 171 | 5.182 | 58.972 |
| 172 | 4.905 | 38.453 |
| 173 | 2.327 | 16.003 |
| 174 | 2.883 | 20.522 |
| 175 | 2.041 | 15.621 |
| 176 | 4.697 | 39.475 |
| 177 | 3.841 | 27.790 |
| 178 | 3.535 | 28.077 |
| 179 | 3.283 | 21.183 |
| 180 | 4.096 | 26.607 |
| 181 | 7.491 | 103.673 |
| 182 | 5.921 | 55.473 |
| 183 | 3.240 | 30.496 |
| 184 | 3.873 | 27.506 |
| 185 | 1.385 | 7.776 |
| 186 | 1.393 | 7.911 |
| 187 | 1.816 | 11.959 |
| 188 | 3.362 | 20.857 |
| 189 | 1.031 | 6.129 |

TABLE 5-1

Training cohort

| Sample name | Cancer stage | CEA(ng/mL) | SCC(ng/mL) |
|---|---|---|---|
| EC03 | IIIB | 4 | 42.2 |
| EC04 | IIIB | 3.1 | 1 |
| EC05 | IB | 6.2 | 1.9 |
| EC06 | (yp) IIA | 3.3 | 1 |
| EC07 | IIB | 0.7 | 1 |
| EC09 | IIB | 2 | 14.7 |
| EC10 | (yp) IIB | 1.6 | 0.9 |
| EC12 | IIB | 3.3 | 1.2 |
| EC13 | IIIB | 1 | 6 |
| EC15 | IIIA | 2.7 | 2.4 |
| EC17 | IIIC | 4 | 2.1 |
| EC18 | IIIA | 4.6 | 3.2 |
| EC19 | IIIC | 1.3 | 3.8 |
| EC20 | IIIB | 2.5 | 1.5 |
| EC23 | (yp) IIIC | 4 | 0.7 |
| EC24 | IIIB | 5 | 1 |
| EC25 | IIA | なし | なし |
| EC26 | (yp) IIB | 1.4 | 0.9 |
| EC27 | (yp) IIIA | 4.8 | 2.1 |
| EC29 | (yp) IIIA | 3.1 | 0.8 |
| EC30 | IIIB | 3.6 | 0.6 |
| EC31 | IB | 4.7 | 0.9 |
| EC32 | (yp) IIIA | 0.5 | 1.3 |
| EC34 | IIIA | 3.6 | 0.7 |
| EC36 | IIIA | 4.1 | 1.2 |
| EC38 | (yp) IIA | 2.3 | 3.4 |
| EC40 | IIB | 6.6 | 1.6 |
| EC41 | (yp) IIIA | 14.2 | 1.3 |
| EC42 | IIB | 5.2 | 1.2 |
| EC45 | (yp) IA | 3.1 | 0.6 |
| EC47 | IIIB | 2.9 | 1 |
| EC48 | IB | 4 | 1.5 |
| EC49 | (yp) IIA | 1.8 | 8 |
| EC50 | (yp) IIIA | 1.7 | 1.2 |
| Sensitivity | | 12.1% | 36.4% |

TABLE 5-2

Validation cohort

| Sample name | Cancer stage | CEA(ng/mL) | SCC(ng/mL) |
|---|---|---|---|
| EC01 | (yp) IIA | 1.6 | 1.3 |
| EC02 | IIA | 1.3 | 2.4 |
| EC08 | IIIA | 2.1 | 1.1 |
| EC11 | (yp) IV | 1.8 | 1 |
| EC14 | IIA | 7.2 | 1.2 |
| EC16 | (yp) IIIA | 6.3 | 0.9 |
| EC21 | IIA | 3.2 | 2.4 |
| EC22 | (yp) IIA | 4.3 | 2.9 |
| EC28 | IIIA | 1.6 | 0.1 |
| EC33 | (yp) IIIC | 2.1 | 1.9 |
| EC35 | IIIC | 1.6 | 0.6 |
| EC37 | (yp) IIIA | 2.1 | 1 |
| EC39 | (yp) IA | 1.8 | 9.1 |

TABLE 5-2-continued

Validation cohort

| Sample name | Cancer stage | CEA(ng/mL) | SCC(ng/mL) |
|---|---|---|---|
| EC43 | IIIC | 6.6 | 1.3 |
| EC44 | (yp) IIIB | 2.2 | 11.2 |
| EC46 | (yp) 0 | 0.7 | 0.6 |
| | Sensitivity | 18.8% | 37.5% |

Each sample that exhibited a value equal to or higher than the reference value of each tumor marker (for CEA: 5 ng/mL, SCC: 1.5 ng/mL) was confirmed to be positive (+), and each sample that exhibited a value equal to or lower than the reference value was confirmed to be negative (−). The cancer stages were classified using samples collected before treatment, as a rule, except that samples stage-classified by pathological examination after treatment were represented by "yp".

TABLE 6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_2 | 98.5 | 94.1 | 100 | 98.5 | 93.8 | 100 |
| 1_3 | 96.3 | 88.2 | 99 | 92.4 | 87.5 | 94 |
| 1_4 | 95.5 | 85.3 | 99 | 93.9 | 93.8 | 94 |
| 1_5 | 95.5 | 88.2 | 98 | 93.9 | 87.5 | 96 |
| 1_6 | 95.5 | 82.4 | 100 | 98.5 | 100 | 98 |
| 1_7 | 96.3 | 85.3 | 100 | 93.9 | 93.8 | 94 |
| 1_8 | 99.3 | 97.1 | 100 | 93.9 | 93.8 | 94 |
| 1_9 | 98.5 | 100 | 98 | 95.5 | 100 | 94 |
| 1_10 | 96.3 | 88.2 | 99 | 97 | 93.8 | 98 |
| 1_11 | 97 | 88.2 | 100 | 97 | 93.8 | 98 |
| 1_12 | 94.8 | 82.4 | 99 | 93.9 | 87.5 | 96 |
| 1_13 | 94 | 82.4 | 98 | 95.5 | 100 | 94 |
| 1_14 | 96.3 | 88.2 | 99 | 97 | 100 | 96 |
| 1_15 | 94 | 82.4 | 98 | 95.5 | 93.8 | 96 |
| 1_16 | 94 | 79.4 | 99 | 93.9 | 87.5 | 96 |
| 1_17 | 96.3 | 85.3 | 100 | 92.4 | 87.5 | 94 |
| 1_18 | 97 | 88.2 | 100 | 95.5 | 87.5 | 98 |
| 1_19 | 96.3 | 85.3 | 100 | 95.5 | 93.8 | 96 |
| 1_20 | 96.3 | 88.2 | 99 | 97 | 93.8 | 98 |
| 1_21 | 97 | 88.2 | 100 | 98.5 | 93.8 | 100 |
| 1_22 | 98.5 | 94.1 | 100 | 92.4 | 93.8 | 92 |
| 1_23 | 96.3 | 85.3 | 100 | 92.4 | 87.5 | 94 |
| 1_24 | 96.3 | 85.3 | 100 | 93.9 | 87.5 | 96 |
| 1_25 | 95.5 | 82.4 | 100 | 92.4 | 87.5 | 94 |
| 1_26 | 94.8 | 82.4 | 99 | 92.4 | 87.5 | 94 |
| 1_27 | 95.5 | 85.3 | 99 | 95.5 | 93.8 | 96 |
| 1_28 | 93.3 | 76.5 | 99 | 93.9 | 87.5 | 96 |
| 1_29 | 94.8 | 79.4 | 100 | 92.4 | 87.5 | 94 |
| 1_30 | 97.8 | 91.2 | 100 | 95.5 | 93.8 | 96 |
| 1_31 | 95.5 | 85.3 | 99 | 92.4 | 87.5 | 94 |
| 1_32 | 95.5 | 85.3 | 99 | 93.9 | 87.5 | 96 |
| 1_33 | 95.5 | 82.4 | 100 | 89.4 | 87.5 | 90 |
| 1_34 | 97.8 | 91.2 | 100 | 97 | 87.5 | 100 |
| 1_35 | 96.3 | 85.3 | 100 | 93.9 | 87.5 | 96 |
| 1_36 | 94.8 | 82.4 | 99 | 93.9 | 87.5 | 96 |
| 1_37 | 95.5 | 85.3 | 99 | 93.9 | 87.5 | 96 |
| 1_38 | 95.5 | 85.3 | 99 | 93.9 | 93.8 | 94 |
| 1_39 | 97.8 | 94.1 | 99 | 95.5 | 87.5 | 98 |
| 1_40 | 99.3 | 97.1 | 100 | 98.5 | 93.8 | 100 |
| 1_41 | 94.8 | 82.4 | 99 | 93.9 | 87.5 | 96 |
| 1_42 | 94.8 | 85.3 | 98 | 95.5 | 87.5 | 98 |
| 1_43 | 94.8 | 85.3 | 98 | 93.9 | 93.8 | 94 |
| 1_44 | 97.8 | 91.2 | 100 | 97 | 93.8 | 98 |
| 1_45 | 95.5 | 85.3 | 99 | 92.4 | 87.5 | 94 |
| 1_46 | 95.5 | 82.4 | 100 | 95.5 | 87.5 | 98 |
| 1_47 | 97 | 88.2 | 100 | 93.9 | 87.5 | 96 |
| 1_48 | 95.5 | 82.4 | 100 | 93.9 | 87.5 | 96 |
| 1_49 | 94 | 79.4 | 99 | 95.5 | 87.5 | 98 |
| 1_50 | 95.5 | 85.3 | 99 | 92.4 | 93.8 | 92 |
| 1_51 | 95.5 | 82.4 | 100 | 92.4 | 87.5 | 94 |
| 1_52 | 95.5 | 82.4 | 100 | 95.5 | 93.8 | 96 |
| 1_53 | 97 | 88.2 | 100 | 90.9 | 87.5 | 92 |
| 1_54 | 96.3 | 88.2 | 99 | 95.5 | 87.5 | 98 |
| 1_55 | 95.5 | 82.4 | 100 | 95.5 | 87.5 | 98 |
| 1_56 | 96.3 | 88.2 | 99 | 93.9 | 93.8 | 94 |
| 1_57 | 95.5 | 85.3 | 99 | 89.4 | 93.8 | 88 |
| 1_58 | 97.8 | 94.1 | 99 | 97 | 100 | 96 |
| 1_59 | 96.3 | 85.3 | 100 | 95.5 | 100 | 94 |
| 1_60 | 94.8 | 82.4 | 99 | 87.9 | 81.2 | 90 |
| 1_61 | 97.8 | 91.2 | 100 | 98.5 | 93.8 | 100 |
| 1_62 | 95.5 | 84.8 | 99 | 93.9 | 87.5 | 96 |
| 1_63 | 96.3 | 88.2 | 99 | 93.9 | 87.5 | 96 |
| 1_64 | 97 | 88.2 | 100 | 93.9 | 87.5 | 96 |
| 1_65 | 97 | 91.2 | 99 | 92.4 | 93.8 | 92 |
| 1_66 | 94 | 79.4 | 99 | 90.9 | 87.5 | 92 |
| 1_67 | 94 | 79.4 | 99 | 92.4 | 81.2 | 96 |
| 1_68 | 94.8 | 82.4 | 99 | 92.4 | 87.5 | 94 |
| 1_69 | 96.3 | 85.3 | 100 | 92.4 | 87.5 | 94 |
| 1_70 | 94.8 | 79.4 | 100 | 95.5 | 87.5 | 98 |
| 1_71 | 96.3 | 88.2 | 99 | 95.5 | 93.8 | 96 |
| 1_72 | 94.8 | 85.3 | 98 | 90.9 | 93.8 | 90 |
| 1_73 | 94.8 | 85.3 | 98 | 92.4 | 87.5 | 94 |
| 1_74 | 94.8 | 82.4 | 99 | 93.9 | 93.8 | 94 |
| 1_75 | 94 | 82.4 | 98 | 92.4 | 87.5 | 94 |
| 1_76 | 94 | 79.4 | 99 | 95.5 | 93.8 | 96 |
| 1_77 | 96.3 | 85.3 | 100 | 90.9 | 87.5 | 92 |
| 1_78 | 95.5 | 85.3 | 99 | 93.9 | 93.8 | 94 |
| 1_79 | 94.8 | 79.4 | 100 | 89.4 | 87.5 | 90 |
| 1_80 | 96.3 | 85.3 | 100 | 93.9 | 87.5 | 96 |
| 1_81 | 94 | 79.4 | 99 | 89.4 | 87.5 | 90 |
| 1_82 | 94.8 | 85.3 | 98 | 92.4 | 93.8 | 92 |
| 1_83 | 94 | 79.4 | 99 | 95.5 | 87.5 | 98 |
| 1_84 | 94.8 | 82.4 | 99 | 93.9 | 87.5 | 96 |
| 1_85 | 96.3 | 85.3 | 100 | 92.4 | 87.5 | 94 |
| 1_86 | 96.3 | 88.2 | 99 | 95.5 | 93.8 | 96 |
| 1_87 | 95.5 | 82.4 | 100 | 90.9 | 81.2 | 94 |
| 1_88 | 95.5 | 82.4 | 100 | 93.9 | 87.5 | 96 |
| 1_89 | 95.5 | 85.3 | 99 | 90.9 | 87.5 | 92 |
| 1_90 | 94 | 79.4 | 99 | 93.9 | 87.5 | 96 |
| 1_91 | 94.8 | 79.4 | 100 | 93.9 | 87.5 | 96 |
| 1_92 | 93.2 | 76.5 | 99 | 92.4 | 87.5 | 94 |
| 1_93 | 94.8 | 82.4 | 99 | 92.4 | 87.5 | 94 |
| 1_94 | 94.8 | 79.4 | 100 | 89.4 | 87.5 | 90 |
| 1_95 | 96.3 | 85.3 | 100 | 90.9 | 87.5 | 92 |
| 1_96 | 94 | 79.4 | 99 | 92.4 | 81.2 | 96 |
| 1_97 | 96.3 | 85.3 | 100 | 93.9 | 87.5 | 96 |
| 1_98 | 95.5 | 82.4 | 100 | 95.5 | 93.8 | 96 |
| 1_99 | 95.5 | 85.3 | 99 | 93.9 | 93.8 | 94 |
| 1_100 | 94.8 | 79.4 | 100 | 92.4 | 87.5 | 94 |
| 1_101 | 95.5 | 85.3 | 99 | 95.5 | 93.8 | 96 |
| 1_102 | 95.5 | 82.4 | 100 | 92.4 | 93.8 | 92 |
| 1_103 | 96.3 | 85.3 | 100 | 89.4 | 93.8 | 88 |
| 1_104 | 96.3 | 85.3 | 100 | 97 | 93.8 | 98 |
| 1_105 | 95.5 | 88.2 | 98 | 92.4 | 87.5 | 94 |
| 1_106 | 94.8 | 82.4 | 99 | 92.4 | 87.5 | 94 |
| 1_107 | 95.5 | 85.3 | 99 | 90.9 | 81.2 | 94 |
| 1_108 | 95.5 | 85.3 | 99 | 89.4 | 93.8 | 88 |
| 1_109 | 96.3 | 85.3 | 100 | 93.9 | 87.5 | 96 |
| 1_110 | 94 | 79.4 | 99 | 95.5 | 93.8 | 96 |
| 1_111 | 94 | 79.4 | 99 | 90.9 | 81.2 | 94 |
| 1_112 | 94 | 79.4 | 99 | 93.9 | 87.5 | 96 |
| 1_113 | 93.3 | 79.4 | 98 | 93.9 | 87.5 | 96 |
| 1_114 | 97 | 88.2 | 100 | 93.9 | 87.5 | 96 |
| 1_115 | 95.5 | 82.4 | 100 | 90.9 | 87.5 | 92 |
| 1_116 | 94 | 79.4 | 99 | 92.4 | 81.2 | 96 |
| 1_117 | 94.8 | 82.4 | 99 | 93.9 | 87.5 | 96 |
| 1_118 | 94.8 | 82.4 | 99 | 93.9 | 87.5 | 96 |
| 1_119 | 95.5 | 85.3 | 99 | 95.5 | 93.8 | 96 |
| 1_120 | 94.8 | 82.4 | 99 | 95.5 | 93.8 | 96 |
| 1_121 | 94 | 79.4 | 99 | 90.9 | 87.5 | 92 |
| 1_122 | 94 | 79.4 | 99 | 92.4 | 87.5 | 94 |
| 1_123 | 94.8 | 79.4 | 100 | 93.9 | 87.5 | 96 |
| 1_124 | 94 | 79.4 | 99 | 93.9 | 87.5 | 96 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_125 | 94.8 | 82.4 | 99 | 92.4 | 87.5 | 94 |
| 1_126 | 96.3 | 85.3 | 100 | 93.9 | 87.5 | 96 |
| 1_127 | 96.3 | 85.3 | 100 | 92.4 | 93.8 | 92 |
| 1_128 | 96.3 | 88.2 | 99 | 92.4 | 87.5 | 94 |
| 1_129 | 95.5 | 82.4 | 100 | 89.4 | 81.2 | 92 |
| 1_130 | 94 | 79.4 | 99 | 92.4 | 87.5 | 94 |
| 1_131 | 94 | 79.4 | 99 | 95.5 | 87.5 | 98 |
| 1_132 | 95.5 | 82.4 | 100 | 93.9 | 93.8 | 94 |
| 1_133 | 94 | 79.4 | 99 | 95.5 | 87.5 | 98 |
| 1_134 | 97 | 91.2 | 99 | 93.9 | 87.5 | 96 |
| 1_135 | 94.8 | 82.4 | 99 | 93.9 | 87.5 | 96 |
| 1_136 | 95.5 | 82.4 | 100 | 95.5 | 87.5 | 98 |
| 1_137 | 97.8 | 91.2 | 100 | 92.4 | 87.5 | 94 |
| 1_138 | 96.3 | 85.3 | 100 | 97 | 93.8 | 98 |
| 1_139 | 95.5 | 82.4 | 100 | 90.9 | 81.2 | 94 |
| 1_140 | 94 | 79.4 | 99 | 92.4 | 81.2 | 96 |
| 1_141 | 94.8 | 82.4 | 99 | 92.4 | 87.5 | 94 |
| 1_142 | 95.5 | 85.3 | 99 | 90.9 | 87.5 | 92 |
| 1_143 | 95.5 | 82.4 | 100 | 92.4 | 87.5 | 94 |
| 1_144 | 94 | 79.4 | 99 | 92.4 | 81.2 | 96 |
| 1_145 | 94.8 | 82.4 | 99 | 95.5 | 87.5 | 98 |
| 1_146 | 94 | 79.4 | 99 | 92.4 | 87.5 | 94 |
| 1_147 | 95.5 | 85.3 | 99 | 93.9 | 93.8 | 94 |
| 1_148 | 94.8 | 79.4 | 100 | 93.9 | 87.5 | 96 |
| 1_149 | 94 | 79.4 | 99 | 95.5 | 87.5 | 98 |
| 1_150 | 96.3 | 85.3 | 100 | 90.9 | 81.2 | 94 |
| 1_151 | 95.5 | 82.4 | 100 | 93.9 | 87.5 | 96 |
| 1_152 | 93.3 | 79.4 | 98 | 93.9 | 87.5 | 96 |
| 1_153 | 96.3 | 88.2 | 99 | 95.5 | 87.5 | 98 |
| 1_154 | 94.8 | 82.4 | 99 | 89.4 | 81.2 | 92 |
| 1_155 | 97 | 88.2 | 100 | 98.5 | 93.8 | 100 |
| 1_156 | 94 | 79.4 | 99 | 90.9 | 81.2 | 94 |
| 1_157 | 93.3 | 79.4 | 98 | 90.9 | 87.5 | 92 |
| 1_158 | 94 | 82.4 | 98 | 95.5 | 87.5 | 98 |
| 1_159 | 94.8 | 79.4 | 100 | 92.4 | 87.5 | 94 |
| 1_160 | 95.5 | 82.4 | 100 | 93.9 | 93.8 | 92 |
| 1_161 | 94 | 79.4 | 99 | 93.9 | 87.5 | 96 |
| 1_162 | 94 | 79.4 | 99 | 93.9 | 87.5 | 96 |
| 1_163 | 94.8 | 82.4 | 99 | 93.9 | 87.5 | 96 |
| 1_164 | 94.8 | 82.4 | 99 | 92.4 | 87.5 | 94 |
| 1_165 | 95.5 | 82.4 | 100 | 93.9 | 87.5 | 96 |
| 1_166 | 94.8 | 79.4 | 100 | 95.5 | 87.5 | 98 |
| 1_167 | 96.3 | 85.3 | 100 | 93.9 | 81.2 | 98 |
| 1_168 | 94.8 | 79.4 | 100 | 92.4 | 87.5 | 94 |
| 1_169 | 96.3 | 85.3 | 100 | 92.4 | 81.2 | 96 |
| 1_170 | 96.3 | 88.2 | 99 | 92.3 | 86.7 | 94 |
| 1_171 | 94.8 | 82.4 | 99 | 92.4 | 81.2 | 96 |
| 1_172 | 95.5 | 85.3 | 99 | 95.5 | 87.5 | 98 |
| 1_173 | 94.8 | 79.4 | 100 | 92.4 | 81.2 | 96 |
| 1_174 | 95.5 | 85.3 | 99 | 95.5 | 93.8 | 96 |
| 1_175 | 95.5 | 82.4 | 100 | 90.9 | 81.2 | 94 |
| 1_176 | 94.8 | 82.4 | 99 | 93.9 | 93.8 | 94 |
| 1_177 | 95.5 | 82.4 | 100 | 93.9 | 93.8 | 94 |
| 1_178 | 94 | 79.4 | 99 | 92.4 | 81.2 | 96 |
| 1_179 | 94 | 79.4 | 99 | 92.4 | 87.5 | 94 |
| 1_180 | 94.8 | 82.4 | 99 | 92.4 | 81.2 | 96 |
| 1_181 | 94 | 79.4 | 99 | 93.9 | 87.5 | 96 |
| 1_182 | 94 | 85.3 | 98 | 92.4 | 87.5 | 94 |
| 1_183 | 94 | 79.4 | 99 | 95.5 | 93.8 | 96 |
| 1_184 | 94.8 | 79.4 | 100 | 93.9 | 87.5 | 96 |
| 1_185 | 95.5 | 85.3 | 99 | 97 | 87.5 | 100 |
| 1_186 | 94.8 | 79.4 | 100 | 95.5 | 87.5 | 98 |
| 1_187 | 94 | 79.4 | 99 | 93.9 | 87.5 | 96 |
| 1_188 | 94 | 79.4 | 99 | 93.8 | 93.8 | 93.9 |
| 1_189 | 94.8 | 79.4 | 100 | 93.9 | 87.5 | 96 |

Example 3

<Selection of Gene Markers Using all Samples and Method for Evaluating Esophageal Cancer Discriminant Performance of Acquired Gene Markers>

In this Example, the samples of the training cohort and the validation cohort used in Examples 1 and 2 were integrated, and selection of a gene marker and evaluation of its esophageal cancer discriminant performance were conducted using any of the samples.

Specifically, the miRNA expression levels in the sera of the 50 esophageal cancer patients and the 150 healthy subjects obtained in the preceding Reference Examples were normalized by quantile normalization. In order to acquire diagnosis markers with higher reliability, only genes having a gene expression level of $2^6$ or higher in 50% or more of the samples in either of the esophageal cancer patient group or the healthy subject group were selected in the gene marker selection. In order to further acquire statistical significance for discriminating an esophageal cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant and described in Table 7. In this way, hsa-miR-675-5p, hsa-miR-486-3p, hsa-miR-6777-5p, hsa-miR-4497, hsa-miR-296-3p, hsa-miR-6738-5p, hsa-miR-4731-5p, hsa-miR-6889-5p, hsa-miR-6786-5p, hsa-miR-92a-3p, hsa-miR-4294, hsa-miR-4763-3p, hsa-miR-6076, hsa-miR-663a, hsa-miR-760, hsa-miR-4667-5p, hsa-miR-6090, hsa-miR-4730, hsa-miR-7106-5p, hsa-miR-3196, hsa-miR-5698, hsa-miR-6087, hsa-miR-4665-5p, hsa-miR-8059 and hsa-miR-6879-5p genes, and the nucleotide sequences represented by SEQ ID NOs: 190 to 214 related thereto were found in addition to the genes described in Table 2. As with the nucleotide sequences of SEQ ID NOs: 1 to 189, the results obtained about the polynucleotides shown in the nucleotide sequences of SEQ ID NOs: 190 to 214 also showed that the gene measurement values were significantly lower (−) or higher (+) in the esophageal cancer patient group than in the healthy subject group (Table 7). These results were able to be validated in the validation cohort. Thus, the presence or absence of esophageal cancer in the newly obtained samples can be determined by the methods described in Examples 1 and 2 by using the gene expression level measurement values described in Table 7 either alone or in combination with the gene expression level measurement values described in Table 2.

TABLE 7

| SEQ ID NO: | Gene name | P value after Bonferroni correction | Expression level in esophageal cancer patient relative to healthy subject |
|---|---|---|---|
| 1 | hsa-miR-204-3p | 8.14E−45 | − |
| 2 | hsa-miR-1247-3p | 1.36E−45 | + |
| 3 | hsa-miR-6875-5p | 6.12E−37 | + |
| 4 | hsa-miR-6857-5p | 1.04E−39 | + |
| 5 | hsa-miR-6726-5p | 7.48E−40 | + |
| 6 | hsa-miR-3188 | 6.76E−39 | − |
| 7 | hsa-miR-8069 | 1.65E−29 | + |
| 8 | hsa-miR-4257 | 1.79E−35 | − |
| 9 | hsa-miR-1343-3p | 1.95E−36 | + |
| 10 | hsa-miR-7108-5p | 1.78E−35 | + |
| 11 | hsa-miR-6825-5p | 4.35E−36 | − |
| 12 | hsa-miR-7641 | 1.73E−34 | − |

TABLE 7-continued

| SEQ ID NO: | Gene name | P value after Bonferroni correction | Expression level in esophageal cancer patient relative to healthy subject |
|---|---|---|---|
| 13 | hsa-miR-3185 | 1.35E−33 | + |
| 14 | hsa-miR-4746-3p | 4.69E−34 | + |
| 15 | hsa-miR-6791-5p | 5.41E−32 | + |
| 16 | hsa-miR-6893-5p | 6.65E−32 | + |
| 17 | hsa-miR-4433b-3p | 7.92E−29 | + |
| 18 | hsa-miR-3135b | 9.14E−25 | − |
| 19 | hsa-miR-6781-5p | 1.02E−32 | + |
| 20 | hsa-miR-1908-5p | 1.06E−32 | + |
| 21 | hsa-miR-4792 | 7.47E−32 | + |
| 22 | hsa-miR-7845-5p | 6.13E−29 | + |
| 23 | hsa-miR-4417 | 1.23E−29 | + |
| 24 | hsa-miR-3184-5p | 1.98E−30 | + |
| 25 | hsa-miR-1225-5p | 1.13E−30 | + |
| 26 | hsa-miR-1231 | 1.73E−26 | + |
| 27 | hsa-miR-1225-3p | 4.81E−30 | + |
| 28 | hsa-miR-150-3p | 9.61E−24 | + |
| 29 | hsa-miR-4433-3p | 1.64E−27 | + |
| 30 | hsa-miR-6125 | 7.40E−28 | + |
| 31 | hsa-miR-4513 | 1.69E−23 | + |
| 32 | hsa-miR-6787-5p | 3.22E−27 | − |
| 33 | hsa-miR-6784-5p | 4.73E−27 | + |
| 34 | hsa-miR-615-5p | 9.34E−26 | − |
| 35 | hsa-miR-6765-3p | 7.95E−27 | + |
| 36 | hsa-miR-5572 | 1.59E−26 | − |
| 37 | hsa-miR-6842-5p | 2.94E−27 | − |
| 38 | hsa-miR-8063 | 1.48E−26 | + |
| 39 | hsa-miR-6780b-5p | 3.59E−29 | − |
| 40 | hsa-miR-187-5p | 8.52E−25 | − |
| 41 | hsa-miR-128-1-5p | 5.67E−21 | − |
| 42 | hsa-miR-6729-5p | 1.04E−26 | − |
| 43 | hsa-miR-6741-5p | 7.62E−23 | + |
| 44 | hsa-miR-6757-5p | 1.84E−26 | + |
| 45 | hsa-miR-7110-5p | 1.82E−24 | + |
| 46 | hsa-miR-7975 | 8.82E−24 | − |
| 47 | hsa-miR-1233-5p | 1.28E−26 | − |
| 48 | hsa-miR-6845-5p | 3.06E−24 | − |
| 49 | hsa-miR-3937 | 7.00E−24 | − |
| 50 | hsa-miR-4467 | 5.02E−23 | + |
| 51 | hsa-miR-7109-5p | 2.70E−17 | − |
| 52 | hsa-miR-6088 | 3.91E−22 | − |
| 53 | hsa-miR-6782-5p | 1.72E−19 | − |
| 54 | hsa-miR-5195-3p | 8.97E−24 | − |
| 55 | hsa-miR-4454 | 9.04E−23 | + |
| 56 | hsa-miR-6724-5p | 5.74E−19 | − |
| 57 | hsa-miR-8072 | 6.96E−19 | + |
| 58 | hsa-miR-4516 | 6.08E−22 | − |
| 59 | hsa-miR-6756-5p | 5.52E−19 | − |
| 60 | hsa-miR-4665-3p | 3.30E−20 | − |
| 61 | hsa-miR-6826-5p | 2.65E−21 | + |
| 62 | hsa-miR-6820-5p | 1.83E−18 | + |
| 63 | hsa-miR-6887-5p | 7.93E−19 | − |
| 64 | hsa-miR-3679-5p | 1.14E−21 | − |
| 65 | hsa-miR-7847-3p | 2.20E−20 | − |
| 66 | hsa-miR-6721-5p | 3.96E−16 | + |
| 67 | hsa-miR-3622a-5p | 1.78E−18 | + |
| 68 | hsa-miR-939-5p | 1.12E−17 | − |
| 69 | hsa-miR-602 | 9.30E−19 | + |
| 70 | hsa-miR-7977 | 4.08E−19 | − |
| 71 | hsa-miR-6749-5p | 2.11E−19 | − |
| 72 | hsa-miR-1914-3p | 3.49E−15 | − |
| 73 | hsa-miR-4651 | 9.97E−21 | − |
| 74 | hsa-miR-4695-5p | 1.01E−17 | + |
| 75 | hsa-miR-6848-5p | 1.96E−16 | + |
| 76 | hsa-miR-1228-3p | 1.45E−17 | + |
| 77 | hsa-miR-642b-3p | 3.30E−17 | + |
| 78 | hsa-miR-6746-5p | 2.40E−18 | − |
| 79 | hsa-miR-3620-5p | 3.16E−15 | + |
| 80 | hsa-miR-3131 | 1.67E−20 | − |
| 81 | hsa-miR-6732-5p | 3.23E−17 | + |
| 82 | hsa-miR-7113-3p | 6.47E−18 | + |
| 83 | hsa-miR-23a-3p | 1.75E−15 | + |
| 84 | hsa-miR-3154 | 3.86E−14 | + |
| 85 | hsa-miR-4723-5p | 4.11E−15 | − |
| 86 | hsa-miR-3663-3p | 6.62E−16 | − |
| 87 | hsa-miR-4734 | 9.47E−16 | + |
| 88 | hsa-miR-6816-5p | 1.28E−16 | − |
| 89 | hsa-miR-4442 | 9.49E−16 | + |
| 90 | hsa-miR-4476 | 9.75E−16 | − |
| 91 | hsa-miR-423-5p | 6.53E−13 | + |
| 92 | hsa-miR-1249 | 3.05E−15 | − |
| 93 | hsa-miR-6515-3p | 9.05E−12 | − |
| 94 | hsa-miR-887-3p | 1.74E−15 | + |
| 95 | hsa-miR-4741 | 9.67E−16 | + |
| 96 | hsa-miR-6766-3p | 2.28E−14 | − |
| 97 | hsa-miR-4673 | 2.15E−14 | − |
| 98 | hsa-miR-6779-5p | 3.15E−13 | + |
| 99 | hsa-miR-4706 | 8.59E−16 | + |
| 100 | hsa-miR-1268b | 1.75E−14 | + |
| 101 | hsa-miR-4632-5p | 4.72E−14 | − |
| 102 | hsa-miR-3197 | 6.20E−15 | + |
| 103 | hsa-miR-6798-5p | 1.13E−12 | + |
| 104 | hsa-miR-711 | 1.63E−16 | − |
| 105 | hsa-miR-6840-3p | 1.79E−12 | + |
| 106 | hsa-miR-6763-5p | 1.13E−12 | + |
| 107 | hsa-miR-6727-5p | 1.88E−15 | + |
| 108 | hsa-miR-371a-5p | 5.18E−12 | + |
| 109 | hsa-miR-6824-5p | 1.52E−13 | + |
| 110 | hsa-miR-4648 | 8.82E−15 | − |
| 111 | hsa-miR-1227-5p | 3.56E−11 | − |
| 112 | hsa-miR-564 | 4.80E−13 | − |
| 113 | hsa-miR-3679-3p | 1.57E−12 | − |
| 114 | hsa-miR-2861 | 7.34E−13 | + |
| 115 | hsa-miR-6737-5p | 5.72E−09 | + |
| 116 | hsa-miR-575 | 2.07E−11 | − |
| 117 | hsa-miR-4725-3p | 1.06E−13 | + |
| 118 | hsa-miR-6716-5p | 2.52E−11 | + |
| 119 | hsa-miR-4675 | 2.03E−14 | − |
| 120 | hsa-miR-1915-3p | 1.35E−13 | + |
| 121 | hsa-miR-671-5p | 1.87E−11 | + |
| 122 | hsa-miR-3656 | 7.58E−11 | − |
| 123 | hsa-miR-6722-3p | 9.17E−11 | + |
| 124 | hsa-miR-4707-5p | 1.41E−12 | − |
| 125 | hsa-miR-4449 | 4.22E−12 | + |
| 126 | hsa-miR-1202 | 1.28E−12 | − |
| 127 | hsa-miR-4649-5p | 8.69E−11 | − |
| 128 | hsa-miR-744-5p | 9.90E−11 | − |
| 129 | hsa-miR-642a-3p | 1.42E−09 | + |
| 130 | hsa-miR-451a | 3.46E−12 | + |
| 131 | hsa-miR-6870-5p | 2.08E−12 | + |
| 132 | hsa-miR-4443 | 5.77E−08 | − |
| 133 | hsa-miR-6808-5p | 9.18E−07 | + |
| 134 | hsa-miR-4728-5p | 2.27E−11 | + |
| 135 | hsa-miR-937-5p | 1.97E−08 | + |
| 136 | hsa-miR-135a-3p | 1.01E−07 | + |
| 137 | hsa-miR-663b | 1.89E−09 | + |
| 138 | hsa-miR-1343-5p | 1.68E−10 | + |
| 139 | hsa-miR-6822-5p | 2.82E−09 | − |
| 140 | hsa-miR-6803-5p | 8.05E−07 | − |
| 141 | hsa-miR-6805-3p | 6.65E−10 | − |
| 142 | hsa-miR-128-2-5p | 8.46E−10 | + |
| 143 | hsa-miR-4640-5p | 1.16E−10 | + |
| 144 | hsa-miR-1469 | 2.15E−07 | + |
| 145 | hsa-miR-92a-2-5p | 4.30E−10 | − |
| 146 | hsa-miR-3940-5p | 2.18E−07 | − |
| 147 | hsa-miR-4281 | 2.04E−08 | − |
| 148 | hsa-miR-1260b | 1.61E−08 | − |
| 149 | hsa-miR-4758-5p | 3.25E−08 | − |
| 150 | hsa-miR-1915-5p | 1.01E−07 | + |
| 151 | hsa-miR-5001-5p | 1.96E−08 | − |
| 152 | hsa-miR-4286 | 4.72E−07 | + |
| 153 | hsa-miR-6126 | 3.16E−09 | + |
| 154 | hsa-miR-6789-5p | 8.38E−08 | − |
| 155 | hsa-miR-4459 | 3.24E−08 | − |
| 156 | hsa-miR-1268a | 5.97E−07 | + |
| 157 | hsa-miR-6752-5p | 5.95E−06 | − |
| 158 | hsa-miR-6131 | 1.52E−07 | + |
| 159 | hsa-miR-6800-5p | 1.75E−07 | + |
| 160 | hsa-miR-4532 | 2.82E−05 | + |
| 161 | hsa-miR-6872-3p | 5.54E−07 | − |
| 162 | hsa-miR-718 | 3.56E−05 | − |

TABLE 7-continued

| SEQ ID NO: | Gene name | P value after Bonferroni correction | Expression level in esophageal cancer patient relative to healthy subject |
|---|---|---|---|
| 163 | hsa-miR-6769a-5p | 2.25E−06 | − |
| 164 | hsa-miR-4707-3p | 5.95E−07 | − |
| 165 | hsa-miR-6765-5p | 6.88E−07 | − |
| 166 | hsa-miR-4739 | 5.13E−06 | + |
| 167 | hsa-miR-4525 | 1.01E−06 | + |
| 168 | hsa-miR-4270 | 2.71E−05 | + |
| 169 | hsa-miR-4534 | 0.000121 | − |
| 170 | hsa-miR-6785-5p | 1.06E−06 | + |
| 171 | hsa-miR-6850-5p | 6.01E−05 | + |
| 172 | hsa-miR-4697-5p | 9.68E−08 | + |
| 173 | hsa-miR-1260a | 7.59E−07 | − |
| 174 | hsa-miR-4486 | 6.56E−06 | − |
| 175 | hsa-miR-6880-5p | 8.38E−07 | − |
| 176 | hsa-miR-6802-5p | 4.43E−06 | − |
| 177 | hsa-miR-6861-5p | 4.72E−06 | − |
| 178 | hsa-miR-92b-5p | 5.54E−05 | + |
| 179 | hsa-miR-1238-5p | 1.21E−05 | + |
| 180 | hsa-miR-6851-5p | 6.80E−06 | + |
| 182 | hsa-miR-149-3p | 4.63E−07 | − |
| 183 | hsa-miR-4689 | 6.67E−06 | + |
| 184 | hsa-miR-4688 | 4.38E−07 | + |
| 185 | hsa-miR-125a-3p | 7.44E−39 | − |
| 186 | hsa-miR-23b-3p | 4.37E−18 | − |
| 187 | hsa-miR-614 | 3.43E−14 | + |
| 188 | hsa-miR-1913 | 2.99E−12 | + |
| 189 | hsa-miR-16-5p | 1.45E−08 | + |
| 190 | hsa-miR-675-5p | 5.72E−07 | − |
| 191 | hsa-miR-486-3p | 2.23E−04 | − |
| 192 | hsa-miR-6777-5p | 3.28E−04 | − |
| 193 | hsa-miR-4497 | 3.90E−04 | − |
| 194 | hsa-miR-296-3p | 4.06E−04 | − |
| 195 | hsa-miR-6738-5p | 4.53E−04 | − |
| 196 | hsa-miR-4731-5p | 5.31E−04 | − |
| 197 | hsa-miR-6889-5p | 6.59E−04 | + |
| 198 | hsa-miR-6786-5p | 6.60E−04 | + |
| 199 | hsa-miR-92a-3p | 1.13E−03 | − |
| 200 | hsa-miR-4294 | 1.17E−03 | − |
| 201 | hsa-miR-4763-3p | 1.35E−03 | + |
| 202 | hsa-miR-6076 | 1.38E−03 | + |
| 203 | hsa-miR-663a | 1.52E−03 | + |
| 204 | hsa-miR-760 | 2.13E−03 | + |
| 205 | hsa-miR-4667-5p | 2.18E−03 | + |
| 206 | hsa-miR-6090 | 2.38E−03 | + |
| 207 | hsa-miR-4730 | 2.79E−03 | + |
| 208 | hsa-miR-7106-5p | 2.80E−03 | − |
| 209 | hsa-miR-3196 | 3.86E−03 | + |
| 210 | hsa-miR-5698 | 4.60E−03 | − |
| 211 | hsa-miR-6087 | 5.73E−03 | − |
| 212 | hsa-miR-4665-5p | 5.91E−03 | − |
| 213 | hsa-miR-8059 | 8.38E−03 | − |
| 214 | hsa-miR-6879-5p | 8.44E−03 | + |

Example 4

<Method for Evaluating Esophageal Cancer-Specific Discriminant Performance by Combination of Multiple Gene Markers Using Samples of Validation Cohort>

In this Example, gene markers for diagnosis were selected by comparing gene expression levels of miRNAs in serum of esophageal cancer patients with that of a control group consisting of healthy subjects, pancreatic cancer patients, bile duct cancer patients, colorectal cancer patients, stomach cancer patients, liver cancer patients, and benign pancreaticobiliary disease patients in the same way as the method described in Example 1 using the gene markers selected in Example 1 and targeting the training cohort described in Reference Example 2. The polynucleotides consisting of the nucleotide sequences represented by SEQ ID NOs: 666 to 676 thus newly selected were further combined with the polynucleotides consisting of the nucleotide sequences represented by SEQ ID NOs: 1 to 214 to study a method for evaluating esophageal cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted as to combinations of 1 to 6 expression level measurement values comprising at least one of the expression level measurement values of the polynucleotides consisting of the nucleotide sequences represented by SEQ ID NOs: 1 to 214 and 666 to 676, to construct a discriminant for determining the presence or absence of esophageal cancer. Next, accuracy, sensitivity, and specificity in the validation cohort were calculated using the discriminant thus prepared, with the esophageal cancer patient group as a positive sample group and, on the other hand, the healthy subject group, the pancreatic cancer patient group, the bile duct cancer patient group, the colorectal cancer patient group, the stomach cancer patient group, the liver cancer patient group, and the benign pancreaticobiliary disease patient group as a negative sample groups. The discriminant performance of the selected polynucleotides was validated using the independent samples.

Most of polynucleotides consisting of the nucleotide sequences represented by these SEQ ID NOs: 1 to 214 and 666 to 676 or complementary sequences thereof were able to provide relatively high accuracy, sensitivity, and specificity in the determination of the presence or absence of esophageal cancer, and furthermore, were able to specifically discriminate esophageal cancer from the other cancers. For example, at least one polynucleotide selected from the group consisting of polynucleotides consisting of the nucleotide sequences represented by SEQ ID NOs: 1, 2, 5, 8, 22, 32, 33, 35, 43, 44, 56, 85, 98, 106, 109, 115, 121, 126, 133, 138, 155, 157, 166, 177, 179, 185, 202, 212, 666, 667, 668, 669, 670, 671, 672, 673, 674, 675 and 676 or complementary sequences thereof (the cancer type-specific polynucleotide group 1) was able to specifically bind to the target marker.

Among the combinations of multiple polynucleotides selected from cancer type-specific polynucleotide group 1, particularly, combinations comprising at least one polynucleotide selected from the group consisting of polynucleotides consisting of the nucleotide sequences represented by SEQ ID NOs: 1, 22, 85, 109, 121, 126, 133, 138, 166, and 666 or complementary sequences thereof (the cancer type-specific polynucleotide group 2) were able to specifically discriminate esophageal cancer from the other cancers with high accuracy.

The number of the polynucleotides with cancer type specificity in the combination described above can be 1, 2, 3, 4, 5, 6, 7, 8, 9, 10 or more for the combination. The combinations of 6 or more of these polynucleotides were able to exhibit discriminant accuracy of 85% or higher. Specific results about the discrimination accuracy of the measurement using each polynucleotide in the cancer type-specific polynucleotide group 2 will be described below.

The discriminant accuracy of the measurement using the polynucleotide consisting of the nucleotide sequence represented by SEQ ID NO: 1 or a complementary sequence thereof is shown in Table 8-1. The measurement using one polynucleotide consisting of the nucleotide sequence represented by SEQ ID NO: 1 or a complementary sequence thereof exhibited accuracy of 65.4% in the training cohort and accuracy of 65.4% in the validation cohort. Also, for example, the measurement using the combinations of two polynucleotides comprising at least one polynucleotide consisting of the nucleotide sequence represented by SEQ ID NO: 1 or a complementary sequence thereof exhibited the highest accuracy of 78.3% in the training cohort and accuracy of 77.7% in the validation cohort. Furthermore, for example, the measurement using the combinations of three polynucleotides comprising at least one polynucleotide consisting of the nucleotide sequence represented by SEQ ID NO: 1 or a complementary sequence thereof exhibited the highest accuracy of 85.9% in the training cohort and accuracy of 79.8% in the validation cohort. Furthermore, for example, the measurement using the combinations of four polynucleotides comprising at least one polynucleotide consisting of the nucleotide sequence represented by SEQ ID NO: 1 or a complementary sequence thereof exhibited the highest accuracy of 89.2% in the training cohort and accuracy of 88.8% in the validation cohort. Furthermore, for example, the measurement using the combinations of five polynucleotides comprising at least one polynucleotide consisting of the nucleotide sequence represented by SEQ ID NO: 1 or a complementary sequence thereof exhibited the highest accuracy of 91.1% in the training cohort and accuracy of 90.4% in the validation cohort. Furthermore, for example, the measurement using the combinations of six polynucleotides comprising at least one polynucleotide consisting of the nucleotide sequence represented by SEQ ID NO: 1 or a complementary sequence thereof exhibited the highest accuracy of 92.7% in the training cohort and accuracy of 93.1% in the validation cohort.

The discriminant accuracy of the measurement using the polynucleotide consisting of the nucleotide sequence represented by SEQ ID NO: 22 or a complementary sequence thereof is shown in Table 8-2. The measurement using one polynucleotide consisting of the nucleotide sequence represented by SEQ ID NO: 22 or a complementary sequence thereof exhibited accuracy of 70.9% in the training cohort and accuracy of 69.1% in the validation cohort. Also, for example, the measurement using the combinations of two polynucleotides comprising at least one polynucleotide consisting of the nucleotide sequence represented by SEQ ID NO: 22 or a complementary sequence thereof exhibited the highest accuracy of 83.0% in the training cohort and accuracy of 77.7% in the validation cohort. Furthermore, for example, the measurement using the combinations of three polynucleotides comprising at least one polynucleotide consisting of the nucleotide sequence represented by SEQ ID NO: 22 or a complementary sequence thereof exhibited the highest accuracy of 86.9% in the training cohort and accuracy of 81.9% in the validation cohort. Furthermore, for example, the measurement using the combinations of four polynucleotides comprising at least one polynucleotide consisting of the nucleotide sequence represented by SEQ ID NO: 22 or a complementary sequence thereof exhibited the highest accuracy of 89.3% in the training cohort and accuracy of 87.2% in the validation cohort. Furthermore, for example, the measurement using the combinations of five polynucleotides comprising at least one polynucleotide consisting of the nucleotide sequence represented by SEQ ID NO: 22 or a complementary sequence thereof exhibited the highest accuracy of 91.4% in the training cohort and accuracy of 86.7% in the validation cohort. Furthermore, for example, the measurement using the combinations of six polynucleotides comprising at least one polynucleotide consisting of the nucleotide sequence represented by SEQ ID NO: 22 or a complementary sequence thereof exhibited the highest accuracy of 91.9% in the training cohort and accuracy of 90.4% in the validation cohort.

The discriminant accuracy of the measurement using the polynucleotide consisting of the nucleotide sequence represented by SEQ ID NO: 85 or a complementary sequence thereof is shown in Table 8-3. The measurement using one polynucleotide consisting of the nucleotide sequence represented by SEQ ID NO: 85 or a complementary sequence thereof exhibited accuracy of 65.2% in the training cohort and accuracy of 61.2% in the validation cohort. Also, for example, the measurement using the combinations of two polynucleotides comprising at least one polynucleotide consisting of the nucleotide sequence represented by SEQ ID NO: 85 or a complementary sequence thereof exhibited the highest accuracy of 79.1% in the training cohort and accuracy of 77.1% in the validation cohort. Furthermore, for example, the measurement using the combinations of three polynucleotides comprising at least one polynucleotide consisting of the nucleotide sequence represented by SEQ ID NO: 85 or a complementary sequence thereof exhibited the highest accuracy of 84.3% in the training cohort and accuracy of 78.1% in the validation cohort. Furthermore, for example, the measurement using the combinations of four polynucleotides comprising at least one polynucleotide consisting of the nucleotide sequence represented by SEQ ID NO: 85 or a complementary sequence thereof exhibited the highest accuracy of 88.5% in the training cohort and accuracy of 88.8% in the validation cohort. Furthermore, for example, the measurement using the combinations of five polynucleotides comprising at least one polynucleotide consisting of the nucleotide sequence represented by SEQ ID NO: 85 or a complementary sequence thereof exhibited the highest accuracy of 90.8% in the training cohort and accuracy of 91.0% in the validation cohort. Furthermore, for example, the measurement using the combinations of six polynucleotides comprising at least one polynucleotide consisting of the nucleotide sequence represented by SEQ ID NO: 85 or a complementary sequence thereof exhibited the highest accuracy of 91.6% in the training cohort and accuracy of 91.0% in the validation cohort.

The discriminant accuracy of the measurement using the polynucleotide consisting of the nucleotide sequence represented by SEQ ID NO: 109 or a complementary sequence thereof is shown in Table 8-4. The measurement using one polynucleotide consisting of the nucleotide sequence represented by SEQ ID NO: 109 or a complementary sequence thereof exhibited accuracy of 57.6% in the training cohort and accuracy of 54.8% in the validation cohort. Also, for example, the measurement using the combinations of two polynucleotides comprising at least one polynucleotide consisting of the nucleotide sequence represented by SEQ ID NO: 109 or a complementary sequence thereof exhibited the highest accuracy of 83.0% in the training cohort and accuracy of 76.1% in the validation cohort. Furthermore, for example, the measurement using the combinations of three polynucleotides comprising at least one polynucleotide consisting of the nucleotide sequence represented by SEQ ID NO: 109 or a complementary sequence thereof exhibited the highest accuracy of 85.9% in the training cohort and accuracy of 81.9% in the validation cohort. Furthermore, for example, the measurement using the combinations of four polynucleotides comprising at least one polynucleotide consisting of the nucleotide sequence represented by SEQ ID NO: 109 or a complementary sequence thereof exhibited the highest accuracy of 88.7% in the training cohort and accuracy of 84.5% in the validation cohort. Furthermore, for example, the measurement using the combinations of five polynucleotides comprising at least one polynucleotide consisting of the nucleotide sequence represented by SEQ ID NO: 109 or a complementary sequence thereof exhibited the highest accuracy of 91.1% in the training cohort and accuracy of 90.4% in the validation cohort. Furthermore, for example, the measurement using the combinations of six polynucleotides comprising at least one polynucleotide consisting of the nucleotide sequence represented by SEQ ID NO: 109 or a complementary sequence thereof exhibited the highest accuracy of 91.9% in the training cohort and accuracy of 90.4% in the validation cohort.

The discriminant accuracy of the measurement using the polynucleotide consisting of the nucleotide sequence represented by SEQ ID NO: 121 or a complementary sequence thereof is shown in Table 8-5. The measurement using one polynucleotide consisting of the nucleotide sequence represented by SEQ ID NO: 121 or a complementary sequence thereof exhibited accuracy of 72.3% in the training cohort and accuracy of 67.6% in the validation cohort. Also, for example, the measurement using the combinations of two polynucleotides comprising at least one polynucleotide consisting of the nucleotide sequence represented by SEQ ID NO: 121 or a complementary sequence thereof exhibited the highest accuracy of 81.9% in the training cohort and accuracy of 73.9% in the validation cohort. Furthermore, for example, the measurement using the combinations of three polynucleotides comprising at least one polynucleotide consisting of the nucleotide sequence represented by SEQ ID NO: 121 or a complementary sequence thereof exhibited the highest accuracy of 86.1% in the training cohort and accuracy of 79.7% in the validation cohort. Furthermore, for example, the measurement using the combinations of four polynucleotides comprising at least one polynucleotide consisting of the nucleotide sequence represented by SEQ ID NO: 121 or a complementary sequence thereof exhibited the highest accuracy of 89.0% in the training cohort and accuracy of 83.0% in the validation cohort. Furthermore, for example, the measurement using the combinations of five polynucleotides comprising at least one polynucleotide consisting of the nucleotide sequence represented by SEQ ID NO: 121 or a complementary sequence thereof exhibited the highest accuracy of 91.4% in the training cohort and accuracy of 86.2% in the validation cohort. Furthermore, for example, the measurement using the combinations of six polynucleotides comprising at least one polynucleotide consisting of the nucleotide sequence represented by SEQ ID NO: 121 or a complementary sequence thereof exhibited the highest accuracy of 91.6% in the training cohort and accuracy of 89.9% in the validation cohort.

The discriminant accuracy of the measurement using the polynucleotide consisting of the nucleotide sequence represented by SEQ ID NO: 126 or a complementary sequence thereof is shown in Table 8-6. The measurement using one polynucleotide consisting of the nucleotide sequence represented by SEQ ID NO: 126 or a complementary sequence thereof exhibited accuracy of 73.6% in the training cohort and accuracy of 66.0% in the validation cohort. Also, for example, the measurement using the combinations of two polynucleotides comprising at least one polynucleotide consisting of the nucleotide sequence represented by SEQ ID NO: 126 or a complementary sequence thereof exhibited the highest accuracy of 83.5% in the training cohort and accuracy of 76.1% in the validation cohort. Furthermore, for example, the measurement using the combinations of three polynucleotides comprising at least one polynucleotide consisting of the nucleotide sequence represented by SEQ ID NO: 126 or a complementary sequence thereof exhibited the highest accuracy of 88.5% in the training cohort and accuracy of 79.8% in the validation cohort. Furthermore, for example, the measurement using the combinations of four polynucleotides comprising at least one polynucleotide consisting of the nucleotide sequence represented by SEQ ID NO: 126 or a complementary sequence thereof exhibited the highest accuracy of 89.8% in the training cohort and accuracy of 84.0% in the validation cohort. Furthermore, for example, the measurement using the combinations of five polynucleotides comprising at least one polynucleotide consisting of the nucleotide sequence represented by SEQ ID NO: 126 or a complementary sequence thereof exhibited the highest accuracy of 91.1% in the training cohort and accuracy of 91.5% in the validation cohort. Furthermore, for example, the measurement using the combinations of six polynucleotides comprising at least one polynucleotide consisting of the nucleotide sequence represented by SEQ ID NO: 126 or a complementary sequence thereof exhibited the highest accuracy of 92.7% in the training cohort and accuracy of 90.4% in the validation cohort.

The discriminant accuracy of the measurement using the polynucleotide consisting of the nucleotide sequence represented by SEQ ID NO: 133 or a complementary sequence thereof is shown in Table 8-7. The measurement using one polynucleotide consisting of the nucleotide sequence represented by SEQ ID NO: 133 or a complementary sequence thereof exhibited accuracy of 52.9% in the training cohort and accuracy of 54.8% in the validation cohort. Also, for example, the measurement using the combinations of two polynucleotides comprising at least one polynucleotide consisting of the nucleotide sequence represented by SEQ ID NO: 133 or a complementary sequence thereof exhibited the highest accuracy of 81.7% in the training cohort and accuracy of 79.3% in the validation cohort. Furthermore, for example, the measurement using the combinations of three polynucleotides comprising at least one polynucleotide consisting of the nucleotide sequence represented by SEQ ID NO: 133 or a complementary sequence thereof exhibited the highest accuracy of 86.1% in the training cohort and accuracy of 83.5% in the validation cohort. Furthermore, for example, the measurement using the combinations of four polynucleotides comprising at least one polynucleotide consisting of the nucleotide sequence represented by SEQ ID NO: 133 or a complementary sequence thereof exhibited the highest accuracy of 89.0% in the training cohort and accuracy of 86.1% in the validation cohort. Furthermore, for example, the measurement using the combinations of five polynucleotides comprising at least one polynucleotide consisting of the nucleotide sequence represented by SEQ ID NO: 133 or a complementary sequence thereof exhibited the highest accuracy of 90.8% in the training cohort and accuracy of 89.4% in the validation cohort. Furthermore, for example, the measurement using the combinations of six polynucleotides comprising at least one polynucleotide consisting of the nucleotide sequence represented by SEQ ID NO: 133 or a complementary sequence thereof exhibited the highest accuracy of 91.3% in the training cohort and accuracy of 89.4% in the validation cohort.

The discriminant accuracy of the measurement using the polynucleotide consisting of the nucleotide sequence represented by SEQ ID NO: 138 or a complementary sequence thereof is shown in Table 8-8. The measurement using one polynucleotide consisting of the nucleotide sequence represented by SEQ ID NO: 138 or a complementary sequence thereof exhibited accuracy of 70.1% in the training cohort and accuracy of 68.1% in the validation cohort. Also, for example, the measurement using the combinations of two polynucleotides comprising at least one polynucleotide consisting of the nucleotide sequence represented by SEQ ID NO: 138 or a complementary sequence thereof exhibited the highest accuracy of 80.1% in the training cohort and accuracy of 77.7% in the validation cohort. Furthermore, for example, the measurement using the combinations of three polynucleotides comprising at least one polynucleotide consisting of the nucleotide sequence represented by SEQ ID NO: 138 or a complementary sequence thereof exhibited the highest accuracy of 85.8% in the training cohort and accuracy of 92.0% in the validation cohort. Furthermore, for example, the measurement using the combinations of four polynucleotides comprising at least one polynucleotide consisting of the nucleotide sequence represented by SEQ ID NO: 138 or a complementary sequence thereof exhibited the highest accuracy of 89.5% in the training cohort and accuracy of 88.8% in the validation cohort. Furthermore, for example, the measurement using the combinations of five polynucleotides comprising at least one polynucleotide consisting of the nucleotide sequence represented by SEQ ID NO: 138 or a complementary sequence thereof exhibited the highest accuracy of 91.6% in the training cohort and accuracy of 90.4% in the validation cohort. Furthermore, for example, the measurement using the combinations of six polynucleotides comprising at least one polynucleotide consisting of the nucleotide sequence represented by SEQ ID NO: 138 or a complementary sequence thereof exhibited the highest accuracy of 91.9% in the training cohort and accuracy of 90.4% in the validation cohort.

The discriminant accuracy of the measurement using the polynucleotide consisting of the nucleotide sequence represented by SEQ ID NO: 166 or a complementary sequence thereof is shown in Table 8-9. The measurement using one polynucleotide consisting of the nucleotide sequence represented by SEQ ID NO: 166 or a complementary sequence thereof exhibited accuracy of 71.7% in the training cohort and accuracy of 72.3% in the validation cohort. Also, for example, the measurement using the combinations of two polynucleotides comprising at least one polynucleotide consisting of the nucleotide sequence represented by SEQ ID NO: 166 or a complementary sequence thereof exhibited the highest accuracy of 80.9% in the training cohort and accuracy of 77.7% in the validation cohort. Furthermore, for example, the measurement using the combinations of three polynucleotides comprising at least one polynucleotide consisting of the nucleotide sequence represented by SEQ ID NO: 166 or a complementary sequence thereof exhibited the highest accuracy of 86.9% in the training cohort and accuracy of 81.9% in the validation cohort. Furthermore, for example, the measurement using the combinations of four polynucleotides comprising at least one polynucleotide consisting of the nucleotide sequence represented by SEQ ID NO: 166 or a complementary sequence thereof exhibited the highest accuracy of 90.1% in the training cohort and accuracy of 87.2% in the validation cohort. Furthermore, for example, the measurement using the combinations of five polynucleotides comprising at least one polynucleotide consisting of the nucleotide sequence represented by SEQ ID NO: 166 or a complementary sequence thereof exhibited the highest accuracy of 92.1% in the training cohort and accuracy of 90.4% in the validation cohort. Furthermore, for example, the measurement using the combinations of six polynucleotides comprising at least one polynucleotide consisting of the nucleotide sequence represented by SEQ ID NO: 166 or a complementary sequence thereof exhibited the highest accuracy of 91.6% in the training cohort and accuracy of 91.5% in the validation cohort.

The discriminant accuracy of the measurement using the polynucleotide consisting of the nucleotide sequence represented by SEQ ID NO: 666 or a complementary sequence thereof is shown in Table 8-10. The measurement using one polynucleotide consisting of the nucleotide sequence represented by SEQ ID NO: 666 or a complementary sequence thereof exhibited accuracy of 56.0% in the training cohort and accuracy of 53.2% in the validation cohort. Also, for example, the measurement using the combinations of two polynucleotides comprising at least one polynucleotide consisting of the nucleotide sequence represented by SEQ ID NO: 666 or a complementary sequence thereof exhibited the highest accuracy of 81.2% in the training cohort and accuracy of 78.2% in the validation cohort. Furthermore, for example, the measurement using the combinations of three polynucleotides comprising at least one polynucleotide consisting of the nucleotide sequence represented by SEQ ID NO: 666 or a complementary sequence thereof exhibited the highest accuracy of 85.9% in the training cohort and accuracy of 81.4% in the validation cohort. Furthermore, for example, the measurement using the combinations of four polynucleotides comprising at least one polynucleotide consisting of the nucleotide sequence represented by SEQ ID NO: 666 or a complementary sequence thereof exhibited the highest accuracy of 89.2% in the training cohort and accuracy of 89.9% in the validation cohort. Furthermore, for example, the measurement using the combinations of five polynucleotides comprising at least one polynucleotide consisting of the nucleotide sequence represented by SEQ ID NO: 666 or a complementary sequence thereof exhibited the highest accuracy of 91.3% in the training cohort and accuracy of 91.0% in the validation cohort. Furthermore, for example, the measurement using the combinations of six polynucleotides comprising at least one polynucleotide consisting of the nucleotide sequence represented by SEQ ID NO: 666 or a complementary sequence thereof exhibited the highest accuracy of 92.1% in the training cohort and accuracy of 91.5% in the validation cohort.

The expression level measurement values of the polynucleotides consisting of the nucleotide sequences represented by SEQ ID NOs: 1, 5, 85, 138, 166, and 666 were compared among 34 esophageal cancer patients, 103 healthy subjects, 69 pancreatic cancer patients, 66 bile duct cancer patients, 30 colorectal cancer patients, 33 stomach cancer patients, 32 liver cancer patients, and 15 benign pancreaticobiliary disease patients in the training cohort. As a result, a variance diagram that significantly separated the discriminant score of the esophageal cancer patient group from the discriminant scores of the other groups was obtained in the training cohort (see FIG. 4A). These results were also reproducible for the validation cohort (see FIG. 4B).

TABLE 8-1

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 1 | 65.4 | 76.5 | 64.4 | 65.4 | 62.5 | 65.7 |
| 1_22 | 78.3 | 85.3 | 77.6 | 77.7 | 87.5 | 76.7 |

TABLE 8-1-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1__22__126 | 85.9 | 100 | 84.5 | 79.8 | 87.5 | 79.1 |
| 1__138__166__666 | 89.2 | 94.1 | 88.8 | 88.8 | 81.2 | 89.5 |
| 1__121__138__166__666 | 91.1 | 94.1 | 90.8 | 90.4 | 87.5 | 90.7 |
| 1__85__138__166__666__668 | 90.6 | 94.1 | 90.2 | 91.5 | 81.2 | 92.4 |
| 1__85__98__138__166__666 | 90.8 | 97.1 | 90.2 | 92 | 87.5 | 92.4 |
| 1__85__138__155__166__666 | 91.9 | 97.1 | 91.4 | 91.5 | 81.2 | 92.4 |
| 1__5__85__138__166__666 | 92.7 | 91.2 | 92.8 | 93.1 | 81.2 | 94.2 |
| 1__35__85__138__166__666 | 90.8 | 97.1 | 90.2 | 91 | 81.2 | 91.9 |

TABLE 8-2

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 22 | 70.9 | 76.5 | 70.4 | 69.1 | 75 | 68.6 |
| 22__126 | 83 | 88.2 | 82.5 | 77.7 | 75 | 77.9 |
| 22__126__166 | 86.9 | 100 | 85.6 | 81.9 | 81.2 | 82 |
| 22__98__166__666 | 89.3 | 94.1 | 88.8 | 87.2 | 100 | 86 |
| 22__98__166__666__668 | 91.4 | 94.1 | 91.1 | 86.7 | 81.2 | 87.2 |
| 1__22__85__138__166__666 | 91.3 | 94.1 | 91.1 | 91.5 | 81.2 | 92.4 |
| 22__32__121__133__166__666 | 91.6 | 100 | 90.8 | 88.3 | 81.2 | 89 |
| 1__22__126__138__166__666 | 91.3 | 100 | 90.5 | 92 | 87.5 | 92.4 |
| 1__22__121__155__166__666 | 90.1 | 91.2 | 89.9 | 89.9 | 93.8 | 89.5 |
| 22__32__109__121__666__667 | 91.9 | 97.1 | 91.4 | 90.4 | 81.2 | 91.2 |

TABLE 8-3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 85 | 65.2 | 73.5 | 64.4 | 61.2 | 12.5 | 65.7 |
| 2__85 | 79.1 | 91.2 | 77.9 | 77.1 | 68.8 | 77.9 |
| 85__138__667 | 84.3 | 94.1 | 83.3 | 78.1 | 56.2 | 80.1 |
| 22__85__166__666 | 88.5 | 94.1 | 87.9 | 88.8 | 81.2 | 89.5 |
| 1__85__138__166__666 | 90.8 | 97.1 | 90.2 | 91 | 81.2 | 91.9 |
| 85__138__166__185__666__669 | 91.1 | 97.1 | 90.5 | 90.4 | 75 | 91.9 |
| 85__138__166__185__666__676 | 91.3 | 97.1 | 90.8 | 91 | 87.5 | 91.3 |
| 85__138__166__177__185__666 | 91.3 | 97.1 | 90.8 | 89.9 | 75 | 91.3 |
| 85__138__166__185__666__667 | 91.6 | 97.1 | 91.1 | 89.8 | 75 | 91.2 |
| 33__85__138__166__185__666 | 91.6 | 97.1 | 91.1 | 91 | 81.2 | 91.9 |

TABLE 8-4

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 109 | 57.6 | 64.7 | 56.9 | 54.8 | 56.2 | 54.7 |
| 33__109 | 83 | 100 | 81.3 | 76.1 | 81.2 | 75.6 |
| 22__109__126 | 85.9 | 94.1 | 85.1 | 81.9 | 75 | 82.6 |
| 33__109__121__667 | 88.7 | 94.1 | 88.2 | 84.5 | 81.2 | 84.8 |
| 109__126__138__166__666 | 91.1 | 97.1 | 90.5 | 90.4 | 81.2 | 91.3 |
| 109__121__126__138__166__666 | 91.6 | 97.1 | 91.1 | 90.4 | 87.5 | 90.7 |
| 1__85__109__138__166__666 | 91.1 | 97.1 | 90.5 | 91 | 81.2 | 91.9 |

TABLE 8-4-continued

|  | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1__109__121__138__166__666 | 90.8 | 91.2 | 90.8 | 89.9 | 87.5 | 90.1 |
| 109__126__138__166__666__676 | 91.9 | 100 | 91.1 | 90.4 | 81.2 | 91.3 |
| 109__126__138__166__202__666 | 91.1 | 97.1 | 90.5 | 90.4 | 81.2 | 91.3 |

TABLE 8-5

|  | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 121 | 72.3 | 73.5 | 72.1 | 67.6 | 43.8 | 69.8 |
| 2__121 | 81.9 | 91.2 | 81 | 73.9 | 75 | 73.8 |
| 22__121__667 | 86.1 | 94.1 | 85.3 | 79.7 | 87.5 | 78.9 |
| 22__109__121__126 | 89 | 91.2 | 88.8 | 83 | 81.2 | 83.1 |
| 22__32__109__121__666 | 91.4 | 100 | 90.5 | 86.2 | 68.8 | 87.8 |
| 1__121__138__166__666__668 | 90.3 | 91.2 | 90.2 | 89.9 | 75 | 91.3 |
| 1__33__121__138__166__666 | 91.6 | 100 | 90.8 | 89.9 | 87.5 | 90.1 |
| 1__85__121__138__166__666 | 90.6 | 94.1 | 90.2 | 92 | 87.5 | 92.4 |
| 1__121__138__166__179__666 | 90.6 | 94.1 | 90.2 | 91 | 87.5 | 91.3 |
| 1__121__138__166__177__666 | 91.1 | 94.1 | 90.8 | 91 | 87.5 | 91.3 |

TABLE 8-6

|  | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 126 | 73.6 | 76.5 | 73.3 | 66 | 25 | 69.8 |
| 126__138 | 83.5 | 88.2 | 83 | 76.1 | 43.8 | 79.1 |
| 109__126__138 | 88.5 | 94.1 | 87.9 | 79.8 | 68.8 | 80.8 |
| 22__126__166__202 | 89.8 | 100 | 88.8 | 84 | 81.2 | 84.3 |
| 1__126__138__166__666 | 91.1 | 97.1 | 90.5 | 91.5 | 87.5 | 91.9 |
| 32__109__126__138__166__666 | 91.9 | 100 | 91.1 | 92 | 87.5 | 92.4 |
| 1__85__126__138__166__666 | 90.8 | 97.1 | 90.2 | 91 | 81.2 | 91.9 |
| 1__109__126__138__166__666 | 92.7 | 100 | 91.9 | 90.4 | 81.2 | 91.3 |
| 22__109__126__138__166__666 | 91.3 | 100 | 90.5 | 89.9 | 81.2 | 90.7 |
| 109__126__138__157__166__666 | 91.1 | 97.1 | 90.5 | 90.4 | 81.2 | 91.3 |

TABLE 8-7

|  | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 133 | 52.9 | 50 | 53.2 | 54.8 | 56.2 | 54.7 |
| 33__133 | 81.7 | 94.1 | 80.5 | 79.3 | 81.2 | 79.1 |
| 22__126__133 | 86.1 | 94.1 | 85.3 | 83.5 | 93.8 | 82.6 |
| 22__126__133__667 | 89 | 100 | 87.9 | 86.1 | 93.8 | 85.4 |
| 126__133__138__166__666 | 90.8 | 97.1 | 90.2 | 89.4 | 87.5 | 89.5 |
| 126__133__138__166__666__672 | 90.8 | 97.1 | 90.2 | 89.4 | 87.5 | 89.5 |
| 126__133__138__166__666__ | 90.8 | 97.1 | 90.2 | 89.4 | 87.5 | 89.5 |
| 109__126__133__138__166__666 | 91.3 | 97.1 | 90.8 | 89.4 | 81.2 | 90.1 |
| 126__133__138__166__666__673 | 91.1 | 97.1 | 90.5 | 89.4 | 87.5 | 89.5 |
| 126__133__138__166__666__675 | 91.1 | 97.1 | 90.5 | 89.4 | 87.5 | 89.5 |

TABLE 8-8

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 138 | 70.1 | 70.6 | 70 | 68.1 | 68.8 | 68 |
| 33_138 | 80.1 | 94.1 | 78.7 | 77.7 | 75 | 77.9 |
| 138_166_666 | 85.8 | 94.1 | 85 | 92 | 93.8 | 91.9 |
| 138_166_185_666 | 89.5 | 97.1 | 88.8 | 88.8 | 93.8 | 88.4 |
| 85_138_166_185_666 | 91.6 | 97.1 | 91.1 | 90.4 | 75 | 91.9 |
| 1_85_138_166_666_669 | 90.8 | 97.1 | 90.2 | 91 | 81.2 | 91.9 |
| 8_85_138_166_185_666 | 91.6 | 97.1 | 91.1 | 91 | 81.2 | 91.9 |
| 1_35_121_138_166_666 | 91.9 | 97.1 | 91.4 | 90.4 | 87.5 | 90.7 |
| 1_121_126_138_166_666 | 90.8 | 97.1 | 90.2 | 90.4 | 87.5 | 90.7 |
| 1_121_138_166_666_672 | 91.3 | 94.1 | 91.1 | 89.9 | 87.5 | 90.1 |

TABLE 8-9

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 166 | 71.7 | 91.2 | 69.8 | 72.3 | 75 | 72.1 |
| 33_166 | 80.9 | 94.1 | 79.6 | 77.7 | 68.8 | 78.5 |
| 22_126_166 | 86.9 | 100 | 85.6 | 81.9 | 81.2 | 82 |
| 22_121_166_666 | 90.1 | 97.1 | 89.4 | 87.2 | 93.8 | 86.6 |
| 121_138_166_185_666 | 92.1 | 97.1 | 91.6 | 90.4 | 93.8 | 90.1 |
| 1_85_138_166_666_672 | 91.6 | 97.1 | 91.1 | 91.5 | 81.2 | 92.4 |
| 56_85_138_166_185_666 | 91.6 | 97.1 | 91.1 | 89.4 | 75 | 90.7 |
| 1_32_121_138_166_666 | 91.3 | 100 | 90.5 | 91 | 81.2 | 91.9 |
| 1_22_121_138_166_666 | 91.3 | 100 | 90.5 | 89.9 | 87.5 | 90.1 |
| 5_85_138_166_185_666 | 90.8 | 97.1 | 90.2 | 89.4 | 87.5 | 89.5 |

TABLE 8-10

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 666 | 56 | 41.2 | 57.5 | 53.2 | 75 | 51.2 |
| 33_666 | 81.2 | 85.3 | 80.7 | 78.2 | 62.5 | 79.7 |
| 2_32_666 | 85.9 | 97.1 | 84.8 | 81.4 | 68.8 | 82.6 |
| 98_138_166_666 | 89.2 | 91.2 | 89 | 89.9 | 87.5 | 90.1 |
| 98_138_166_666_668 | 91.3 | 91.2 | 91.4 | 91 | 87.5 | 91.3 |
| 1_121_138_157_166_666 | 90.8 | 94.1 | 90.5 | 90.4 | 87.5 | 90.7 |
| 1_85_133_138_166_666 | 92.1 | 97.1 | 91.6 | 91.5 | 81.2 | 92.4 |
| 1_121_138_166_185_666 | 91.3 | 100 | 90.5 | 91 | 87.5 | 91.3 |
| 1_121_138_166_666_667 | 91.1 | 97.1 | 90.5 | 90.4 | 87.5 | 90.6 |
| 85_138_166_185_666 | 91.6 | 97.1 | 91.1 | 90.4 | 75 | 91.9 |

Comparative Example 1

<Esophageal Cancer Discriminant Performance of Existing Tumor Marker in Blood>

The concentrations of the existing esophageal cancer tumor markers CEA and SCC in blood were measured in the training cohort and the validation cohort obtained in the preceding Reference Examples. When the concentrations of these tumor markers in blood are higher than the reference values described in Non-Patent Literature 3 above (CEA: 5 ng/mL, SCC: 1.5 ng/mL), subjects are suspected of having cancer, as a rule. Thus, whether or not the concentrations of CEA and SCC in blood exceeded their reference values was confirmed for each sample, and the results were assessed for the ability of these tumor markers to detect cancer in esophageal cancer patients. The sensitivity of each existing marker in the training cohort and the validation cohort was calculated. The results are shown in Table 5. The sensitivity of CEA was as low as 12.1% in the training cohort, and was as low as 18.8% in the validation cohort, whereas the sensitivity of SCC remained at 36.4% in the training cohort and 37.5% in the validation cohort, demonstrating that neither of the markers are useful in the detection of esophageal cancer (Tables 5-1 and 5-2).

On the other hand, as shown above in Tables 3 and 6 of Examples 1 and 2, it can be concluded that in all of the polynucleotides consisting of the nucleotide sequences represented by SEQ ID NOs: 1 to 189, combinations of 1 or 2 polynucleotides exhibiting sensitivity beyond the existing esophageal cancer markers are presented and thus such polynucleotides serve as excellent diagnosis markers.

As shown in these Examples and Comparative Example, the kit, etc., and the method of the present invention can detect esophageal cancer with higher sensitivity than the existing tumor markers and therefore permit early detection and treatment of esophageal cancer. As a result, survival rates can be improved, and a therapeutic option of endoscopic therapy or photo dynamic therapy, which places less burden on patients, can also be applied.

INDUSTRIAL APPLICABILITY

According to the present invention, esophageal cancer can be effectively detected by a simple and inexpensive method. This enables early detection, diagnosis and treatment of esophageal cancer. The method of the present invention can detect esophageal cancer with limited invasiveness using the blood of a patient and therefore allows esophageal cancer to be detected conveniently and rapidly.

All publications, patents, and patent applications cited herein are incorporated herein by reference in their entirety.

The invention claimed is:

1. A method for detecting esophageal cancer in a human subject, comprising:
measuring an expression level of hsa-miR-1233-5p in a blood, serum or plasma sample of the subject,
comparing the measured expression level of hsa-miR-1233-5p to a control expression level for a healthy subject;
detecting a decreased level of hsa-miR-1233-5p in the sample from the subject as compared to the control expression level;
wherein the decreased level of hsa-miR-1233-5p indicates that the subject has esophageal cancer; and
wherein the method further comprises treating the subject for the esophageal cancer or performing a diagnostic procedure on the subject with the esophageal cancer;
wherein the treatment comprises surgery, radiotherapy, chemotherapy or a combination thereof; and
wherein the diagnostic procedure comprises esophagography, endoscopy, CT scan, MRI scan, endosonography, or ultrasonography.

2. The method according to claim 1, comprising performing the diagnostic procedure on the subject.

3. The method according to claim 1, wherein the expression level of hsa-miR-1233-5p in the sample is measured by using a kit comprising a nucleic acid(s) that specifically binds to hsa-miR-1233-5p.

4. The method according to claim 3, wherein the kit further comprises at least one nucleic acid capable of specifically binding to at least one polynucleotide selected from the group consisting of other esophageal cancer markers: miR-1247-3p, miR-6875-5p, miR-6726-5p, miR-3188, miR-8069, miR-4257, miR-1343-3p, miR-7108-5p, miR-6825-5p, miR-7641, miR-3185, miR-4746-3p, miR-6791-5p, miR-6893-5p, miR-4433b-3p, miR-3135b, miR-6781-

5p, miR-1908-5p, miR-4792, miR-7845-5p, miR-4417, miR-3184-5p, miR-1225-5p, miR-1231, miR-1225-3p, miR-150-3p, miR-4433-3p, miR-6125, miR-4513, miR-6787-5p, miR-6784-5p, miR-615-5p, miR-6765-3p, miR-5572, miR-6842-5p, miR-8063, miR-6780b-5p, miR-187-5p, miR-128-1-5p, miR-6729-5p, miR-6741-5p, miR-6757-5p, miR-7110-5p, miR-7975, miR-6845-5p, miR-3937, miR-4467, miR-7109-5p, miR-6088, miR-6782-5p, miR-5195-3p, miR-4454, miR-6724-5p, miR-8072, miR-4516, miR-6756-5p, miR-4665-3p, miR-6826-5p, miR-6820-5p, miR-6887-5p, miR-3679-5p, miR-7847-3p, miR-6721-5p, miR-3622a-5p, miR-939-5p, miR-602, miR-7977, miR-6749-5p, miR-1914-3p, miR-4651, miR-4695-5p, miR-6848-5p, miR-1228-3p, miR-642b-3p, miR-6746-5p, miR-3620-5p, miR-3131, miR-6732-5p, miR-7113-3p, miR-23a-3p, miR-3154, miR-4723-5p, miR-3663-3p, miR-4734, miR-6816-5p, miR-4442, miR-4476, miR-423-5p, miR-1249, miR-6515-3p, miR-887-3p, miR-4741, miR-6766-3p, miR-4673, miR-6779-5p, miR-4706, miR-1268b, miR-4632-5p, miR-3197, miR-6798-5p, miR-711, miR-6840-3p, miR-6763-5p, miR-6727-5p, miR-371a-5p, miR-6824-5p, miR-4648, miR-1227-5p, miR-564, miR-3679-3p, miR-2861, miR-6737-5p, miR-4725-3p, miR-6716-5p, miR-4675, miR-1915-3p, miR-671-5p, miR-3656, miR-6722-3p, miR-4707-5p, miR-4449, miR-1202, miR-4649-5p, miR-744-5p, miR-642a-3p, miR-451a, miR-6870-5p, miR-4443, miR-6808-5p, miR-4728-5p, miR-937-5p, miR-135a-3p, miR-663b, miR-1343-5p, miR-6822-5p, miR-6803-5p, miR-6805-3p, miR-128-2-5p, miR-4640-5p, miR-1469, miR-92a-2-5p, miR-3940-5p, miR-4281, miR-1260b, miR-4758-5p, miR-1915-5p, miR-5001-5p, miR-4286, miR-6126, miR-6789-5p, miR-4459, miR-1268a, miR-6752-5p, miR-6131, miR-6800-5p, miR-4532, miR-6872-3p, miR-718, miR-6769a-5p, miR-4707-3p, miR-6765-5p, miR-4739, miR-4525, miR-4270, miR-4534, miR-6785-5p, miR-6850-5p, miR-4697-5p, miR-1260a, miR-4486, miR-6880-5p, miR-6802-5p, miR-6861-5p, miR-92b-5p, miR-1238-5p, miR-6851-5p, miR-7704, miR-149-3p, miR-4689, miR-4688, miR-125a-3p, miR-23b-3p, miR-614, miR-1913, miR-16-5p, miR-6717-5p, miR-3648, miR-3162-5p, miR-1909-3p, miR-8073, miR-6769b-5p, miR-6836-3p, miR-4484, miR-6819-5p, and miR-6794-5p, and/or miR-575, miR-24-3p, miR 5p, miR-486-3p, miR-6777-5p, miR-4497, miR-296-3p, miR-6738-5p, miR-4731-5p, miR-6889-5p, miR-6786-5p, miR-92a-3p, miR-4294, miR-4763-3p, miR-6076, miR-663a, miR-760, miR-4667-5p, miR-6090, miR-4730, miR-7106-5p, miR-3196, miR-5698, miR-6087, miR-4665-5p, miR-8059, and miR-6879-5p.

5. The method according to claim 1, wherein the expression level of hsa-miR-1233-5p in the sample is measured by using a device comprising a nucleic acid(s) that specifically binds to hsa-miR-1233-5p.

6. The method according to claim 5, wherein the device further comprises at least one nucleic acid capable of specifically binding to at least one polynucleotide selected from the group consisting of other esophageal cancer markers: miR-1247-3p, miR-6875-5p, miR-6726-5p, miR-3188, miR-8069, miR-4257, miR-1343-3p, miR-7108-5p, miR-6825-5p, miR-7641, miR-3185, miR-4746-3p, miR-6791-5p, miR-6893-5p, miR-4433b-3p, miR-3135b, miR-6781-5p, miR-1908-5p, miR-4792, miR-7845-5p, miR-4417, miR-3184-5p, miR-1225-5p, miR-1231, miR-1225-3p, miR-150-3p, miR-4433-3p, miR-6125, miR-4513, miR-6787-5p, miR-6784-5p, miR-615-5p, miR-6765-3p, miR-5572, miR-6842-5p, miR-8063, miR-6780b-5p, miR-187-5p, miR-128-1-5p, miR-6729-5p, miR-6741-5p, miR-6757-5p, miR-7110-5p, miR-7975, miR-6845-5p, miR-3937, miR-4467, miR-7109-5p, miR-6088, miR-6782-5p, miR-5195-3p, miR-4454, miR-6724-5p, miR-8072, miR-4516, miR-6756-5p, miR-4665-3p, miR-6826-5p, miR-6820-5p, miR-6887-5p, miR-3679-5p, miR-7847-3p, miR-6721-5p, miR-3622a-5p, miR-939-5p, miR-602, miR-7977, miR-6749-5p, miR-1914-3p, miR-4651, miR-4695-5p, miR-6848-5p, miR-1228-3p, miR-642b-3p, miR-6746-5p, miR-3620-5p, miR-3131, miR-6732-5p, miR-7113-3p, miR-23a-3p, miR-3154, miR-4723-5p, miR-3663-3p, miR-4734, miR-6816-5p, miR-4442, miR-4476, miR-423-5p, miR-1249, miR-6515-3p, miR-887-3p, miR-4741, miR-6766-3p, miR-4673, miR-6779-5p, miR-4706, miR-1268b, miR-4632-5p, miR-3197, miR-6798-5p, miR-711, miR-6840-3p, miR-6763-5p, miR-6727-5p, miR-371a-5p, miR-6824-5p, miR-4648, miR-1227-5p, miR-564, miR-3679-3p, miR-2861, miR-6737-5p, miR-4725-3p, miR-6716-5p, miR-4675, miR-1915-3p, miR-671-5p, miR-3656, miR-6722-3p, miR-4707-5p, miR-4449, miR-1202, miR-4649-5p, miR-744-5p, miR-642a-3p, miR-451a, miR-6870-5p, miR-4443, miR-6808-5p, miR-4728-5p, miR-937-5p, miR-135a-3p, miR-663b, miR-1343-5p, miR-6822-5p, miR-6803-5p, miR-6805-3p, miR-128-2-5p, miR-4640-5p, miR-1469, miR-92a-2-5p, miR-3940-5p, miR-4281, miR-1260b, miR-4758-5p, miR-1915-5p, miR-5001-5p, miR-4286, miR-6126, miR-6789-5p, miR-4459, miR-1268a, miR-6752-5p, miR-6131, miR-6800-5p, miR-4532, miR-6872-3p, miR-718, miR-6769a-5p, miR-4707-3p, miR-6765-5p, miR-4739, miR-4525, miR-4270, miR-4534, miR-6785-5p, miR-6850-5p, miR-4697-5p, miR-1260a, miR-4486, miR-6880-5p, miR-6802-5p, miR-6861-5p, miR-92b-5p, miR-1238-5p, miR-6851-5p, miR-7704, miR-149-3p, miR-4689, miR-4688, miR-125a-3p, miR-23b-3p, miR-614, miR-1913, miR-16-5p, miR-6717-5p, miR-3648, miR-3162-5p, miR-1909-3p, miR-8073, miR-6769b-5p, miR-6836-3p, miR-4484, miR-6819-5p, and miR-6794-5p, and/or miR-575, miR-24-3p, miR-675-5p, miR-486-3p, miR-6777-5p, miR-4497, miR-296-3p, miR-6738-5p, miR-4731-5p, miR-6889-5p, miR-6786-5p, miR-92a-3p, miR-4294, miR-4763-3p, miR-6076, miR-663a, miR-760, miR-4667-5p, miR-6090, miR-4730, miR-7106-5p, miR-3196, miR-5698, miR-6087, miR-4665-5p, miR-8059, and miR-6879-5p.

* * * * *